(12) United States Patent
Ogiwara et al.

(10) Patent No.: US 12,364,160 B2
(45) Date of Patent: Jul. 15, 2025

(54) ORGANIC ELECTROLUMINESCENT ELEMENT AND ELECTRONIC DEVICE

(71) Applicant: IDEMITSU KOSAN CO., LTD., Chiyoda-ku (JP)

(72) Inventors: Toshinari Ogiwara, Sodegaura (JP); Satomi Tasaki, Sodegaura (JP); Masahiro Kawamura, Sodegaura (JP); Keiji Okinaka, Sodegaura (JP); Yoshiaki Takahashi, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 789 days.

(21) Appl. No.: 14/908,031

(22) PCT Filed: Oct. 22, 2014

(86) PCT No.: PCT/JP2014/078108
§ 371 (c)(1),
(2) Date: Jan. 27, 2016

(87) PCT Pub. No.: WO2015/060352
PCT Pub. Date: Apr. 30, 2015

(65) Prior Publication Data
US 2016/0211466 A1    Jul. 21, 2016

(30) Foreign Application Priority Data

Oct. 24, 2013 (JP) ................................ 2013-221563
Mar. 19, 2014 (JP) ................................ 2014-056975

(51) Int. Cl.
H10K 85/60     (2023.01)
C07D 209/86    (2006.01)
(Continued)

(52) U.S. Cl.
CPC ....... *H10K 85/6572* (2023.02); *C07D 209/86* (2013.01); *C07D 235/08* (2013.01);
(Continued)

(58) Field of Classification Search
CPC .. C07D 487/14; C07D 493/04; C07D 307/91; C07D 333/76; C09K 11/06;
(Continued)

(56) References Cited

U.S. PATENT DOCUMENTS

2008/0145708 A1* 6/2008 Heil ................. C07C 39/17
                                                    570/183
2009/0072727 A1   3/2009 Takeda
(Continued)

FOREIGN PATENT DOCUMENTS

JP   2009-94486 A    4/2009
JP   2013-200939 A   10/2013
(Continued)

OTHER PUBLICATIONS

Masui, et al., Organic Electronics, 2013, vol. 14, pp. 2721-2726 (Year: 2013).*
(Continued)

*Primary Examiner* — Sadie White
(74) *Attorney, Agent, or Firm* — Oblon, McClelland, Maier & Neustadt, L.L.P.

(57) ABSTRACT

An organic electroluminescence device includes: an anode; an emitting layer; and a cathode, the emitting layer containing a first material and a second material represented by a formula (21) below. The first material has a singlet energy larger than a singlet energy of the second material.
(Continued)

(21)

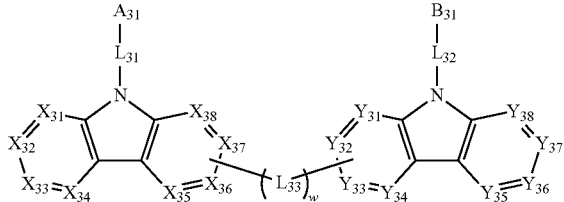

30 Claims, 5 Drawing Sheets

(51) Int. Cl.

| | | |
|---|---|---|
| *C07D 235/08* | (2006.01) | |
| *C07D 307/91* | (2006.01) | |
| *C07D 333/76* | (2006.01) | |
| *C07D 403/14* | (2006.01) | |
| *C07D 405/14* | (2006.01) | |
| *C07D 487/14* | (2006.01) | |
| *C07D 493/04* | (2006.01) | |
| *C09K 11/06* | (2006.01) | |
| *H10K 50/11* | (2023.01) | |
| *H10K 50/12* | (2023.01) | |
| *H10K 50/15* | (2023.01) | |
| *H10K 50/16* | (2023.01) | |
| *H10K 101/10* | (2023.01) | |

(52) U.S. Cl.
CPC ......... *C07D 307/91* (2013.01); *C07D 333/76* (2013.01); *C07D 403/14* (2013.01); *C07D 405/14* (2013.01); *C07D 487/14* (2013.01); *C07D 493/04* (2013.01); *C09K 11/06* (2013.01); *H10K 50/11* (2023.02); *H10K 50/121* (2023.02); *H10K 85/6574* (2023.02); *C09K 2211/1007* (2013.01); *C09K 2211/1011* (2013.01); *C09K 2211/1029* (2013.01); *C09K 2211/1088* (2013.01); *C09K 2211/1092* (2013.01); *H10K 50/15* (2023.02); *H10K 50/156* (2023.02); *H10K 50/16* (2023.02); *H10K 85/611* (2023.02); *H10K 85/615* (2023.02); *H10K 85/633* (2023.02); *H10K 85/654* (2023.02); *H10K 2101/10* (2023.02)

(58) Field of Classification Search
CPC ............... H01L 51/0052; H01L 51/006; H01L 51/5012; H10K 50/11; H10K 85/6572
See application file for complete search history.

(56) References Cited

U.S. PATENT DOCUMENTS

| | | | | |
|---|---|---|---|---|
| 2009/0167165 | A1* | 7/2009 | Otsu | C07D 209/86 |
| | | | | 313/504 |
| 2009/0302743 | A1* | 12/2009 | Kato | H05B 33/14 |
| | | | | 313/504 |
| 2011/0266528 | A1* | 11/2011 | Langer | C07F 7/0814 |
| | | | | 252/301.16 |
| 2012/0045862 | A1* | 2/2012 | Thompson | C23C 14/12 |
| | | | | 257/E51.026 |
| 2012/0138914 | A1* | 6/2012 | Kawamura | C07D 307/79 |
| | | | | 257/E51.026 |
| 2012/0241732 | A1 | 9/2012 | Endo et al. | |
| 2013/0092913 | A1 | 4/2013 | Nishimura et al. | |
| 2013/0126835 | A1* | 5/2013 | Takaku | H01L 51/0058 |
| | | | | 257/40 |
| 2013/0234119 | A1 | 9/2013 | Mizuki et al. | |
| 2014/0151647 | A1* | 6/2014 | Mizuki | H05B 33/20 |
| | | | | 257/40 |

FOREIGN PATENT DOCUMENTS

| | | |
|---|---|---|
| WO | 2011/070963 A1 | 6/2011 |
| WO | 2013/145923 A1 | 10/2013 |
| WO | 2014/166572 A1 | 10/2014 |

OTHER PUBLICATIONS

Nakanotani, et al., Scientific Reports, 2013, vol. 3, article 2127 (Year: 2013).*
Uoyama, et al., Nature, 2012, vol. 492, pp. 234-240 (Year: 2012).*
Dhayalan, et al., Eur. J. Org. Chem., 2009, 531-546 (Year: 2009).*
Ooyama, et al., Org. Biomol. Chem., 2007, 5, 2046-2054 (Year: 2007).*
Zhao, et al., Organic Electronics, 2009, 10, 925-931 (Year: 2009).*
Mazetyte, et al. Optical Materials, 2013, 35, 604-608 (Year: 2013).*
Du, et al., Chem. Eur. J. 2009, 15, 8275-8282 (Year: 2009).*
Ho (Year: 2012).*
Hiroki Uoyama, et al., "Highly efficient organic light-emitting diodes from delayed fluorescence," Nature, vol. 492, Dec. 13, 2012, pp. 234-238.
Chihaya Adachi, et al., "Expression of Highly-Efficient Thermally Activated Delayed-Fluorescence and Application Thereof to OLED," Organic EL Symposium, proceeding for the tenth meeting edited S2-5, 2010, 6 pages (With English translation).
Katsumi Tokumaru, "Organic Photochemical Reaction Theory," Tokyo Kagaku Dojin Co., Ltd., 1973, 9 pages (With English translation).
International Search Report Issued Jan. 20, 2015 in PCT/JP14/78108 Filed Oct. 22, 2014.

* cited by examiner

F I G . 4
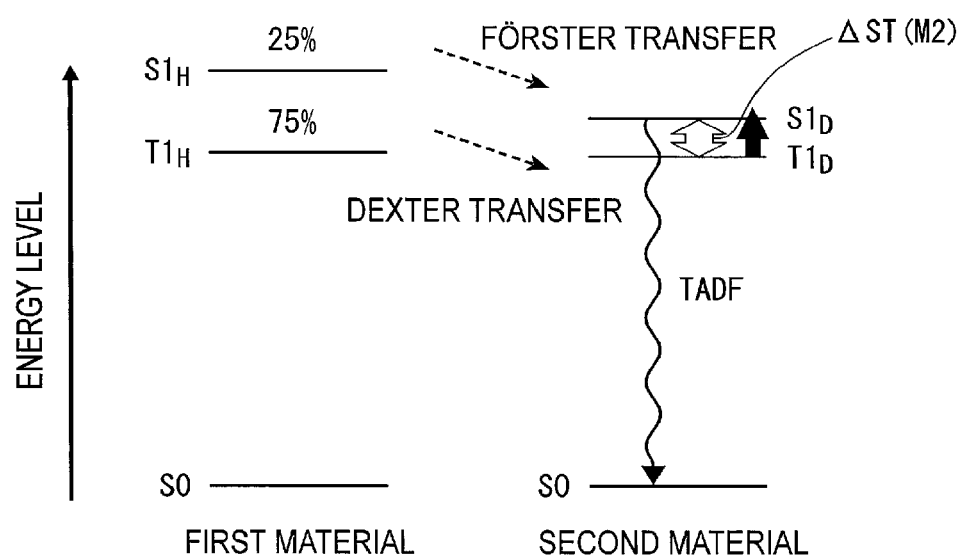

ORGANIC ELECTROLUMINESCENT ELEMENT AND ELECTRONIC DEVICE

TECHNICAL FIELD

The present invention relates to an organic electroluminescence device and an electronic device.

BACKGROUND ART

When a voltage is applied to an organic electroluminescence device (hereinafter, occasionally referred to as an organic EL device), holes are injected from an anode into an emitting layer and electrons are injected from a cathode into the emitting layer. The injected electrons and holes are recombined in an emitting layer to form excitons. Here, according to the electron spin statistics theory, singlet excitons and triplet excitons are generated at a ratio of 25%:75%. In the classification according to the emission principle, in a fluorescent EL device which uses emission caused by singlet excitons, the limited value of an internal quantum efficiency of the organic EL device is believed to be 25%. On the other hand, in a phosphorescent EL device which uses emission caused by triplet excitons, it has been known that the internal quantum efficiency can be improved up to 100% when intersystem crossing efficiently occurs from the singlet excitons.

A technology for extending a lifetime of a fluorescent organic EL device has recently been improved and applied to a full-color display of a mobile phone, TV and the like. However, an efficiency of a fluorescent EL device is required to be improved.

Based on such a background, a highly efficient fluorescent organic EL device using delayed fluorescence has been proposed and developed. For instance, an organic EL device using TTF (Triplet-Triplet Fusion) mechanism that is one of mechanisms for delayed fluorescence has been proposed. The TTF mechanism utilizes a phenomenon in which singlet excitons are generated by collision between two triplet excitons.

By using delayed fluorescence by the TTF mechanism, it is considered that an internal quantum efficiency can be theoretically raised up to 40% even in fluorescent emission. However, as compared with phosphorescent emission, the organic EL device providing the fluorescent emission using delayed fluorescence still has a problem on improving efficiency. Accordingly, in order to enhance the internal quantum efficiency, an organic EL device using another delayed fluorescence mechanism has been studied.

For instance, TADF (Thermally Activated Delayed Fluorescence) mechanism is used. The TADF mechanism utilizes a phenomenon in which inverse intersystem crossing from triplet excitons to singlet excitons is generated by using a material having a small energy gap ($\Delta ST$) between the singlet level and the triplet level. An organic EL device using the TADF mechanism is disclosed in, for instance, non-Patent Literature 1.

The non-Patent Literature 1 discloses carbazolyl dicyanobenzene (CDCB) as a TADF luminescent material. Moreover, the non-Patent Literature 1 discloses an organic EL device in which the CDCB is used as a dopant material and CBP is used as a host material.

CITATION LIST

Non-Patent Literature

Non-Patent Literature 1: "NATURE" vol. 492, p. 234-238, Dec. 13, 2012, written by Hiroki Uoyama et al

SUMMARY OF THE INVENTION

Problems to be Solved by the Invention

A material functioning as the luminescent material using the TADF mechanism is limitative and requires an advanced molecular design technique.

An object of the invention is to find an organic material functioning as a luminescent material using a TADF mechanism and to provide an organic electroluminescence device using the organic material. Another object of the invention is to provide an organic electroluminescence device having an improved luminous efficiency and a longer lifetime. Still another object of the invention is to provide an electronic device including the above-described organic electroluminescence device.

Means for Solving the Problems

According to an aspect of the invention, an organic electroluminescence device includes: an anode; an emitting layer; and a cathode, in which the emitting layer includes a first material and a second material, the first material has a partial structure represented by a formula (1) below, and the second material has a partial structure represented by a formula (2) below and a partial structure represented by a formula (3) below in one molecule.

[Formula 1]

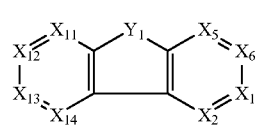

(1)

In the formula (1), $X_1$, $X_2$, $X_5$, $X_6$ and $X_{11}$ to $X_{14}$ each independently represent a nitrogen atom or a carbon atom to be bonded to another atom in a molecule of the first material, with a proviso that 0 set to 4 sets among a set of $X_1$ and $X_2$, a set of $X_5$ and $X_6$, a set of $X_1$ and $X_6$, a set of $X_{11}$ and $X_{12}$, a set of $X_{13}$ and $X_{14}$, and a set of $X_{12}$ and $X_{13}$ are carbon atoms to be bonded to a structure represented by a formula (1a) below. $Y_1$ represents a sulfur atom, an oxygen atom or a carbon atom.

[Formula 2]

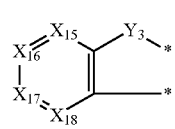

(1a)

In the formula (1a), $X_{15}$ to $X_{18}$ each independently represent a nitrogen atom or a carbon atom to be bonded to another atom in the molecule of the first material.

$Y_3$ represents a sulfur atom, an oxygen atom, a nitrogen atom or a carbon atom.

\* shows a bonding position to the carbon atom in the set selected from the set of $X_1$ and $X_2$, the set of $X_5$ and $X_6$, the set of $X_1$ and $X_6$, the set of $X_{11}$ and $X_{12}$, the set of $X_{13}$ and $X_{14}$, and the set of $X_{12}$ and $X_{13}$ in the formula (1).

$Y_1$ and $Y_3$ are optionally mutually the same or different and a plurality of $Y_3$ are optionally mutually the same or different.

[Formula 3]

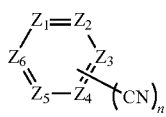

(2)

In the formula (2), CN is a cyano group; n is an integer of 1 or more.

$Z_1$ to $Z_6$ each independently represent a nitrogen atom, a carbon atom bonded to CN, or a carbon atom bonded to another atom in the molecule of the second material. a six-membered ring structure represented by the formula (2) is optionally provided in any position.

[Formula 4]

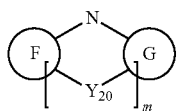

(3)

In the formula (3), F and G each independently represent a ring structure. m is 0 or 1. When m is 1, $Y_{20}$ is a single bond, oxygen atom, sulfur atom, selenium atom, carbon atom, silicon atom or germanium atom.

According to another aspect of the invention, an organic electroluminescence device includes: an anode; an emitting layer; and a cathode, in which the emitting layer contains a first material and a second material represented by a formula (21) below, and the first material has a singlet energy larger than a singlet energy of the second material.

[Formula 5]

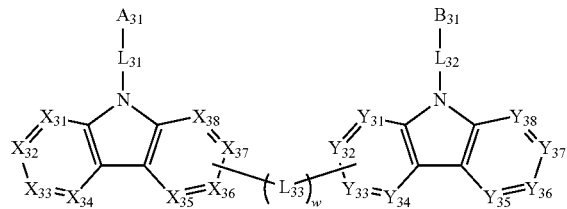

(21)

In the formula (21), $A_{31}$ and $B_{31}$ each independently represent a substituted or unsubstituted aromatic hydrocarbon group having 6 to 30 ring carbon atoms, or substituted or unsubstituted heterocyclic group having 5 to 30 ring atoms.

$X_{31}$ to $X_{38}$ and $Y_{31}$ to $Y_{38}$ each independently represent a nitrogen atom, a carbon atom to be bonded to $R^D$, or a carbon atom to be bonded to $L_{33}$. However, at least one of $X_{35}$ to $X_{38}$ is a carbon atom to be bonded to $L_{33}$ and at least one of $Y_{31}$ to $Y_{34}$ is a carbon atom to be bonded to $L_{33}$.

$R^D$ each independently represents a hydrogen atom, halogen atom, substituted or unsubstituted aromatic hydrocarbon group having 6 to 30 ring carbon atoms, substituted or unsubstituted heterocyclic group having 5 to 30 ring atoms, substituted or unsubstituted alkyl group having 1 to 30 carbon atoms, or substituted or unsubstituted silyl group.

$L_{31}$ and $L_{32}$ each independently represent a single bond or a linking group. The linking group for $L_{31}$ and $L_{32}$ is any one of a substituted or unsubstituted aromatic hydrocarbon group having 6 to 30 ring carbon atoms, substituted or unsubstituted heterocyclic group having 5 to 30 ring atoms, multiple linking group including 2 to 4 groups selected from the above aromatic hydrocarbon groups, multiple linking group including bonded 2 to 4 groups selected from the above heterocyclic groups, and multiple linking group including bonded 2 to 4 groups selected from the above aromatic hydrocarbon groups and heterocyclic groups.

$L_{33}$ represents a substituted or unsubstituted monocyclic hydrocarbon group having 6 or less ring carbon atoms or a substituted or unsubstituted monocyclic heterocyclic group having 6 or less ring atoms.

w is an integer of 0 to 3. When w is 0, at least one of $X_{35}$ to $X_{38}$ is directly bonded to at least one of $Y_{31}$ to $Y_{34}$.

However, at least one of $A_{31}$ and $B_{31}$ is a cyano-substituted aromatic hydrocarbon group having 6 to 30 ring carbon atoms or a cyano-substituted heterocyclic group having 6 to 30 ring atoms.

According to still another aspect of the invention, an organic electroluminescence device includes: an anode; an emitting layer; and a cathode, in which the emitting layer contains a first material and a second material represented by a formula (31) below, and the first material has a singlet energy larger than a singlet energy of the second material.

[Formula 6]

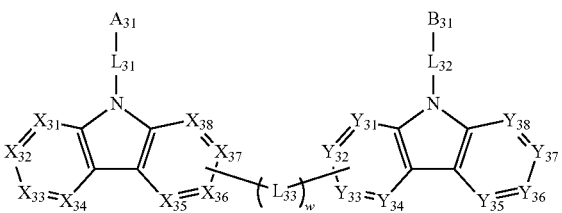

(31)

In the formula (31), $A_{31}$ and $B_{31}$ each independently represent a substituted or unsubstituted aromatic hydrocarbon group having 6 to 30 ring carbon atoms, or substituted or unsubstituted heterocyclic group having 5 to 30 ring atoms.

$X_{31}$ to $X_{38}$ and $Y_{31}$ to $Y_{38}$ each independently represent a nitrogen atom, a carbon atom to be bonded to $R^E$, or a carbon atom to be bonded to $L_{33}$. However, at least one of $X_{35}$ to $X_{38}$ is a carbon atom to be bonded to $L_{33}$ and at least one of $Y_{31}$ to $Y_{34}$ is a carbon atom to be bonded to $L_{33}$.

$R^E$ is each independently selected from the group consisting of a hydrogen atom, cyano group, substituted or unsubstituted amino group, and substituted or unsubstituted alkoxy group; when a plurality of $R^E$ are present, at least one of the plurality of $R^E$ is selected from the group consisting of a cyano group, substituted or unsubstituted amino group, and substituted or unsubstituted alkoxy group.

$L_{31}$ and $L_{32}$ each independently represent a single bond or a linking group. The linking group for $L_{31}$ and $L_{32}$ is any one of a substituted or unsubstituted aromatic hydrocarbon group having 6 to 30 ring carbon atoms, substituted or unsubstituted heterocyclic group having 5 to 30 ring atoms, multiple linking group including 2 to 4 groups selected from the above aromatic hydrocarbon groups, multiple linking group including bonded 2 to 4 groups selected from the above heterocyclic groups, and multiple linking group including bonded 2 to 4 groups selected from the above aromatic hydrocarbon groups and heterocyclic groups.

$L_{33}$ represents a substituted or unsubstituted monocyclic hydrocarbon group having 6 or less ring carbon atoms or a substituted or unsubstituted monocyclic heterocyclic group having 6 or less ring atoms.

w is an integer of 0 to 3. When w is 0, at least one of $X_{35}$ to $X_{38}$ is directly bonded to at least one of $Y_{31}$ to $Y_{34}$.

However, at least one of $A_{31}$ and $B_{31}$ is a cyano-substituted aromatic hydrocarbon group having 6 to 30 ring carbon atoms or a cyano-substituted heterocyclic group having 6 to 30 ring atoms.

According to a further aspect of the invention, an electronic device includes the organic electroluminescence device according to the above aspects of the invention.

According to the above aspects of the invention, an organic electroluminescence device configured to emit TADF and an electronic device including the organic electroluminescence device can be provided. According to the above aspects of the invention, an organic electroluminescence device having an improved luminous efficiency and a prolonged lifetime, and an electronic device including the organic electroluminescence device can be provided.

BRIEF DESCRIPTION OF DRAWINGS

FIG. 4 shows a relationship between energy levels of a first material and a second material and an energy transfer between the first material and the second material in an emitting layer.

DESCRIPTION OF EMBODIMENT(S)

First Exemplary Embodiment

Arrangement(s) of Organic EL Device

Figure 1:
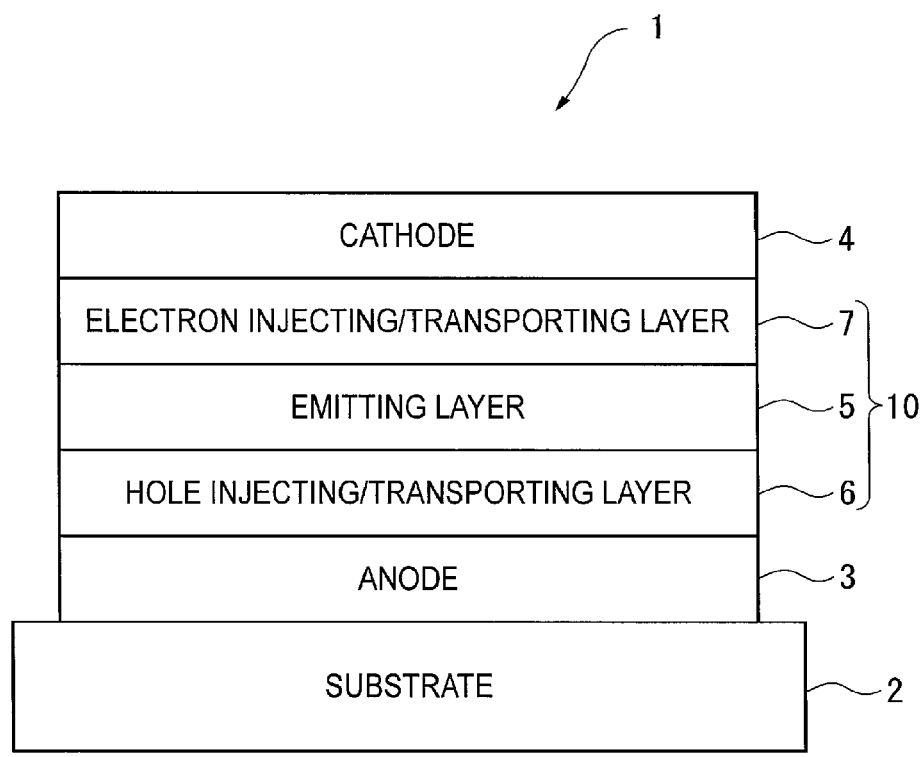
FIG. 1 schematically shows an exemplary arrangement of an organic electroluminescence device according to an exemplary embodiment of the invention.

An organic EL device according to a first exemplary embodiment will be described below.

The organic EL device includes a pair of electrodes and an organic layer between the pair of electrodes. The organic layer includes at least one layer formed of an organic compound. The organic layer may further include an inorganic compound.

In the organic EL device according to the exemplary embodiment, at least one layer of the organic layer(s) is an emitting layer. Accordingly, the organic layer may be provided by a single emitting layer. Alternatively, the organic layer may be provided by layers applied in a known organic EL device such as a hole injecting layer, a hole transporting layer, an electron injecting layer, an electron transporting layer, a hole blocking layer and an electron blocking layer.

The following are representative arrangement examples of the organic EL device:

(a) anode/emitting layer/cathode;
(b) anode/hole injecting·transporting layer/emitting layer/cathode;
(c) anode/emitting layer/electron injecting-transporting layer/cathode;
(d) anode/hole injecting-transporting layer/emitting layer/electron injecting transporting layer/cathode;
(e) anode/hole injecting·transporting layer/first emitting layer/second emitting layer/electron injecting·transporting layer/cathode; and
(f) anode/hole injecting·transporting layer/emitting layer/blocking layer/electron injecting·transporting layer/cathode.

While the arrangement (d) is preferably used among the above arrangements, the arrangement of the invention is not limited to the above arrangements.

The "hole injecting/transporting layer (or hole injecting·transporting layer) means "at least one of a hole injecting layer and a hole transporting layer while the "electron injecting/transporting layer (or electron injecting·transporting layer) means "at least one of" an electron injecting layer and an electron transporting layer. Herein, when the hole injecting layer and the hole transporting layer are provided, the hole injecting layer is preferably closer to the anode. When the electron injecting layer and the electron transporting layer are provided, the electron injecting layer is preferably closer to the cathode. Moreover, each of the hole injecting layer, the hole transporting layer, the electron transporting layer and the electron injecting layer may be provided by a single layer or by a laminate of a plurality of layers.

In the exemplary embodiment, the electron transporting layer means an organic layer having the highest electron mobility among organic layer(s) providing an electron transporting zone existing between the emitting layer and the cathode. When the electron transporting zone is provided by a single layer, the single layer is the electron transporting layer. Moreover, a blocking layer having an electron mobility that is not always high may be provided as shown in the arrangement (f) between the emitting layer and the electron transporting layer in order to prevent diffusion of excitation energy generated in the emitting layer. Thus, the organic layer adjacent to the emitting layer is not always an electron transporting layer.

FIG. 1 schematically shows an arrangement of the organic EL device according to the exemplary embodiment.

An organic EL device 1 includes a light-transmissive substrate 2, an anode 3, a cathode 4 and an organic layer 10 disposed between the anode 3 and the cathode 4.

The organic layer 10 includes an emitting layer 5. The organic layer 10 also includes a hole injecting/transporting layer 6 between the emitting layer 5 and the anode 3. The organic layer 10 further includes an electron injecting/transporting layer 7 between the emitting layer 5 and the cathode 4.

Emitting Layer

In the organic electroluminescence device in the exemplary embodiment, the emitting layer contains a first material and a second material. The first material is a compound having a different structure from that of the second material.

First Material

The first material in the exemplary embodiment has a partial structure represented by a formula (1) below.

[Formula 7]

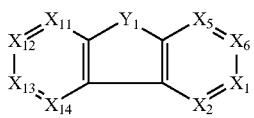

(1)

In the formula (1), $X_1$, $X_2$, $X_5$, $X_6$ and $X_{11}$ to $X_{14}$ are each independently a nitrogen atom or a carbon atom to be bonded to another atom in a molecule of the first material, with a proviso that 0 set to 4 sets among a set of $X_1$ and $X_2$, a set of $X_5$ and $X_6$, a set of $X_1$ and $X_6$, a set of $X_{11}$ and $X_{12}$, a set of $X_{13}$ and $X_{14}$, and a set of $X_{12}$ and $X_{13}$ are carbon atoms to be bonded to a structure represented by a formula (1a) below. $Y_1$ is a sulfur atom, an oxygen atom or a carbon atom.

[Formula 8]

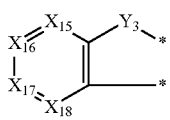

(1a)

In formula (1a), $X_{15}$ to $X_{18}$ are each independently a nitrogen atom or a carbon atom to be bonded to another atom in the molecule of the first material.

$Y_3$ is a sulfur atom, an oxygen atom, a nitrogen atom or a carbon atom.

* shows a bonding position to the carbon atom in the set selected from the set of $X_1$ and $X_2$, the set of $X_5$ and $X_6$, the set of $X_1$ and $X_6$, the set of $X_{11}$ and $X_{12}$, the set of $X_{13}$ and $X_{14}$, and the set of $X_{12}$ and $X_{13}$ in the formula (1).

$Y_1$ and $Y_3$ may be mutually the same or different. A plurality of $Y_3$ may be mutually the same or different.

In the exemplary embodiment, the first material is preferably represented by a formula (10) below.

[Formula 9]

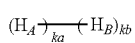

(10)

In the formula (10), ka and kb are each independently an integer of 1 to 4, preferably an integer of 1 to 3.

$H_A$ represents a structure represented by the formula (1).

In the formula (1), $X_1$, $X_2$, $X_5$, $X_6$ and $X_{11}$ to $X_{14}$ are each independently a nitrogen atom, a carbon atom to be bonded to $R^A$, or a carbon atom to be bonded to $H_B$, with a proviso that 0 set to 4 sets among the set of $X_1$ and $X_2$, the set of $X_5$ and $X_6$, the set of $X_1$ and $X_6$, the set of $X_{11}$ and $X_{12}$, the set of $X_{13}$ and $X_{14}$, and the set of $X_{12}$ and $X_{13}$ are carbon atoms to be bonded to the structure represented by the formula (1a).

In the formula (1a), $X_{15}$ to $X_{18}$ are each independently a nitrogen atom, a carbon atom to be bonded to $R^A$, or a carbon atom to be bonded to $H_B$.

$Y_1$ is a sulfur atom, an oxygen atom or $CR^XR^Y$.

$Y_3$ is a sulfur atom, an oxygen atom, $NR^B$ or $CR^XR^Y$.

* shows a bonding position to the carbon atom in the set selected from the set of $X_1$ and $X_2$, the set of $X_5$ and $X_6$, the set of $X_1$ and $X_6$, the set of $X_{11}$ and $X_{12}$, the set of $X_{13}$ and $X_{14}$, and the set of $X_{12}$ and $X_{13}$ in the formula (1).

$Y_1$ and $Y_3$ may be mutually the same or different. A plurality of $Y_3$ may be mutually the same or different.

$R^A$, $R^B$, $R^X$ and $R^Y$ are each independently a hydrogen atom, halogen atom, cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aryl group having 6 to 30 ring carbon atoms, or substituted or unsubstituted heterocyclic group having 5 to 30 ring atoms.

A plurality of $R^A$ may be mutually the same or different. A plurality of $R^B$ may be mutually the same or different.

In the formula (10), $H_B$ is a substituted or unsubstituted aryl group having 6 to 30 ring carbon atoms, a substituted or unsubstituted heterocyclic group having 5 to 30 ring atoms, a group derived from the structure $H_A$, or a group formed by bonding any 2 to 4 groups selected from these groups.

In the exemplary embodiment, the first material is preferably represented by a formula (11) below.

[Formula 10]

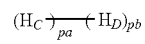

(11)

In the formula (11), pa and pb are each independently an integer of 1 to 4, preferably an integer of 1 to 3. $H_C$ represents structures represented by formulae (110) to (118) below.

[Formula 11]

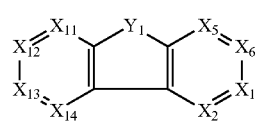

(110)

The structure represented by the formula (111) below corresponds to a case where the set of $X_5$ and $X_6$ in the

[Formula 12]

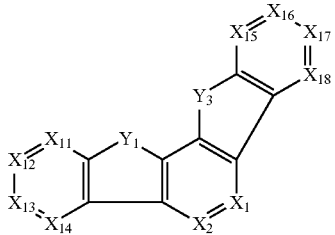

(111)

The structure represented by the formula (112) below corresponds to a case where the set of $X_5$ and $X_6$ in the formula (1) are carbon atoms to be bonded to the structure represented by the formula (1a).

[Formula 13]

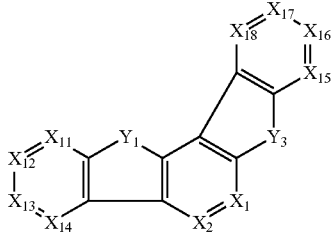

(112)

The structure represented by the formula (113) below corresponds to a case where the set of $X_1$ and $X_2$ in the formula (1) are carbon atoms to be bonded to the structure represented by the formula (1a).

[Formula 14]

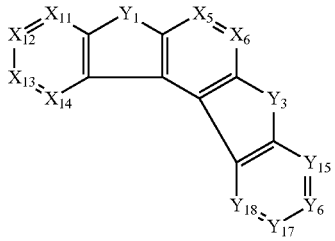

(113)

The structure represented by the formula (114) below corresponds to a case where the set of $X_1$ and $X_2$ in the formula (1) are carbon atoms to be bonded to the structure represented by the formula (1a).

[Formula 15]

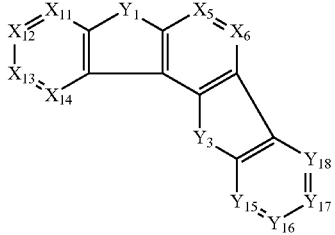

(114)

The structure represented by the formula (115) below corresponds to a case where the set of $X_1$ and $X_6$ in the formula (1) are carbon atoms to be bonded to the structure represented by the formula (1a).

[Formula 16]

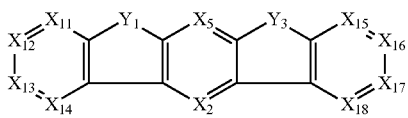

(115)

The structure represented by the formula (116) below corresponds to a case where the set of $X_1$ and $X_6$ in the formula (1) are carbon atoms to be bonded to the structure represented by the formula (1a).

[Formula 17]

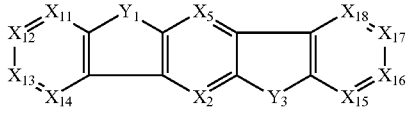

(116)

The structures represented by the formulae (117) and (118) below correspond to a case where the set of $X_1$ and $X_2$ and the set of $X_5$ and $X_6$ in the formula (1) are carbon atoms to be bonded to the structure represented by the formula (1a)

[Formula 18]

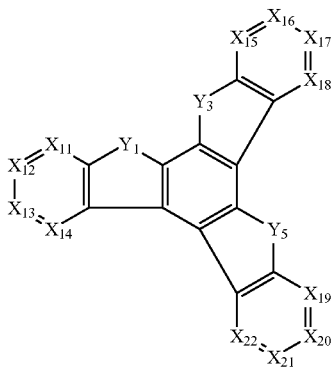

(117)

[Formula 19]

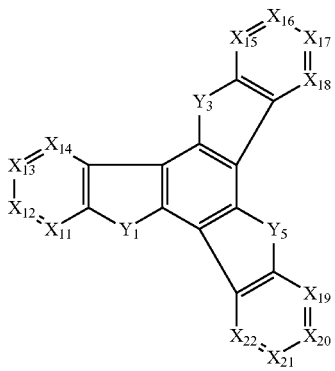

(118)

In the formulae (110) to (118), $X_1$, $X_2$, $X_5$, $X_6$, $X_{11}$ to $X_{14}$, $X_{15}$ to $X_{18}$, and $X_{19}$ to $X_{22}$ are each independently a nitrogen atom, a carbon atom to be bonded to $R^A$, or a carbon atom to be bonded to $H_D$. $Y_1$ is a sulfur atom, an oxygen atom or $CR^X R^Y$. $Y_3$ and $Y_5$ are each independently a sulfur atom, an oxygen atom, $NR^B$ or $CR^X R^Y$. $Y_1$, $Y_3$ and $Y_5$ may be mutually the same or different.

$R^A$, $R^B$, $R^X$ and $R^Y$ are each independently a hydrogen atom, halogen atom, cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aryl group having 6 to 30 ring carbon atoms, or substituted or unsubstituted heterocyclic group having 5 to 30 ring atoms.

A plurality of $R^A$ may be mutually the same or different. A plurality of $R^B$ may be mutually the same or different.

In the formula (11), $H_D$ is a substituted or unsubstituted aryl group having 6 to 30 ring carbon atoms, a substituted or unsubstituted heterocyclic group having 5 to 30 ring atoms, a group derived from the structure $H_C$, or a group formed by bonding any 2 to 4 groups selected from these groups.

The formula (10) is preferably represented by formulae (10a) and (10b). The formula (11) is preferably represented by formulae (11a) and (11b) below.

[Formula 20]

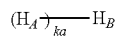 (10a)

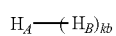 (10b)

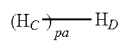 (11a)

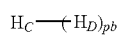 (11b)

In the formulae (10a) and (10b), $H_A$ and $H_B$ respectively represent the same as $H_A$ and $H_B$ in the formula (10). In the formula (10a), ka is preferably from 2 to 4. In the formula (10b), kb is preferably from 2 to 4.

In the formulae (11a) and (11b), $H_C$ and $H_D$ respectively represent the same as $H_C$ and $H_D$ in the formula (11). In the formula (11a), pa is preferably from 2 to 4. In the formula (11b), pb is preferably from 2 to 4.

The formula (10) is occasionally represented by formulae (10c) and (10d). The formula (11) is occasionally represented by formulae (11c) and (11d) below.

[Formula 21]

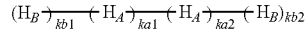 (10c)

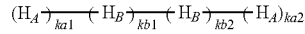 (10d)

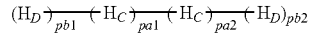 (11c)

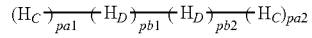 (11d)

In the formulae (10c) and (10d), $H_A$ and $H_B$ respectively represent the same as $H_A$ and $H_B$ in the formula (10). ka1 and ka2 are each independently an integer of 1 to 3 with a proviso of $2 \le ka1+ka2 \le 4$. kb1 and kb2 are each independently an integer of 1 to 3 with a proviso of $2 \le kb1+kb2 \le 4$. A plurality of $H_A$ may be mutually the same or different. A plurality of $H_B$ may be mutually the same or different. In the formulae (11c) and (11d), $H_C$ and $H_D$ respectively represent the same as $H_C$ and $H_D$ in the formula (11). pa1 and pa2 are each independently an integer of 1 to 3 with a proviso of $2 \le pa1+pa2 \le 4$. pb1 and pb2 are each independently an integer of 1 to 3 with a proviso of $2 \le pb1+pb2 \le 4$. A plurality of $H_C$ may be mutually the same or different. A plurality of $H_D$ may be mutually the same or different.

In the exemplary embodiment, preferably, $X_1$, $X_2$, $X_5$, $X_6$ and $X_{11}$ to $X_{14}$ are each independently a carbon atom to be bonded to $R^A$ or a carbon atom to be bonded to $H_B$.

In the exemplary embodiment, preferably, $X_1$, $X_2$, $X_5$, $X_6$, $X_{11}$ to $X_{14}$, $X_{15}$ to $X_{18}$ and $X_{19}$ to $X_{22}$ are each independently a carbon atom to be bonded to $R^A$ or a carbon atom to be bonded to $H_D$.

In the exemplary embodiment, preferably, $Y_1$ and $Y_3$ are each independently a sulfur atom or an oxygen atom.

In the exemplary embodiment, preferably, $Y_1$, $Y_3$ and $Y_5$ are each independently a sulfur atom or an oxygen atom.

In the exemplary embodiment, at least one of $X_1$, $X_2$, $X_5$, $X_6$, $X_{11}$ to $X_{14}$ and $X_{15}$ to $X_{18}$ is preferably a carbon atom to be bonded to $R^A$. The $R^A$ is preferably represented by a formula (1b) below.

[Formula 22]

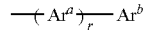 (1b)

In the formula (1b), r is an integer of 0 to 5, preferably an integer of 0 to 2. In the above formula (1b), $Ar^a$ is a substituted or unsubstituted arylene group having 6 to 15 ring carbon atoms or a substituted or unsubstituted heteroarylene group having 5 to 15 ring atoms. A plurality of $Ar^a$ may be mutually the same or different. $Ar^b$ is a substituted or unsubstituted aryl group having 6 to 20 ring carbon atoms or a substituted or unsubstituted heterocyclic having 5 to 20 ring atoms.

In the exemplary embodiment, at least one of $X_1$, $X_2$, $X_5$, $X_6$, $X_{11}$ to $X_{14}$, $X_{15}$ to $X_{18}$ and $X_{19}$ to $X_{22}$ is preferably a carbon atom to be bonded to $R^A$. $R^A$ is preferably represented by the formula (1b).

In the exemplary embodiment, $Ar^a$ in the formula (1) is preferably a substituted or unsubstituted arylene group having 6 to 15 ring carbon atoms, more preferably a phenylene group.

In the exemplary embodiment, the structure $H_B$ or the structure $H_D$ is preferably represented by a formula (1c) below.

[Formula 23]

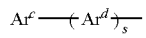
(1c)

In the formula (1c), s is an integer of 0 to 5, preferably an integer of 0 to 2. $Ar^c$ is a substituted or unsubstituted aryl group having 6 to 20 ring carbon atoms or a substituted or unsubstituted heterocyclic group having 5 to 20 ring atoms. $Ar^d$ is a substituted or unsubstituted arylene group having 6 to 15 ring carbon atoms or a substituted or unsubstituted heteroarylene group having 5 to 15 ring atoms. A plurality of $Ar^d$ may be mutually the same or different.

In the exemplary embodiment, the structure $H_A$ or the structure $H_C$ is preferably represented by any one of formulae (121) to (127) below.

[Formula 24]

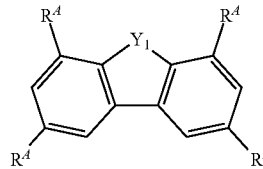
(121)

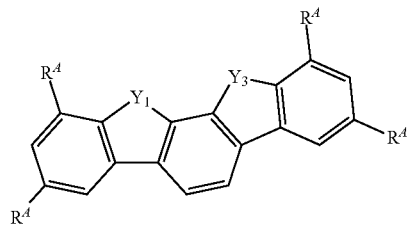
(122)

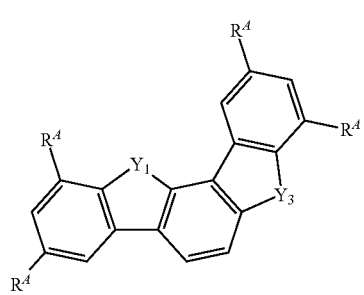
(123)

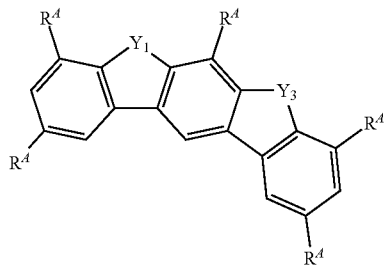
(124)

[Formula 25]

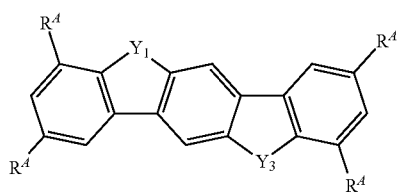
(125)

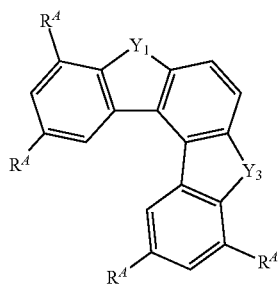
(126)

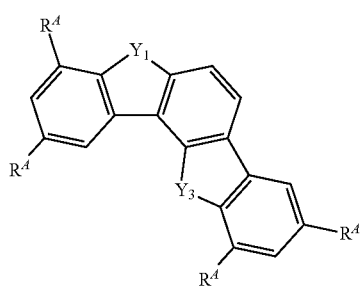
(127)

In each of the formulae (121) to (127), $Y_1$ is a sulfur atom, an oxygen atom or $CR^X R^Y$. $Y_3$ represents a sulfur atom, an oxygen atom, $NR^R$ or $CR^X R^Y$. At least one of a plurality of $R^A$ is a single bond to the structure $H_B$ or the structure $H_D$. At least one of the plurality of $R^A$ is represented by the formula (1b). The rest of the plurality of $R^A$ each independently is a hydrogen atom, halogen atom, cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aryl group having 6 to 30 ring carbon atoms, substituted or unsubstituted heterocyclic group having 5 to 30 ring atoms, or a single bond to the structure $H_A$ or the structure $H_C$.

In the exemplary embodiment, the structure $H_A$ or the structure $H_C$ is preferably represented by the formula (121).

Examples of the partial structure represented by the formula (1), the structure $H_A$ in the formula (10) or the structure $H_C$ in the formula (11) are shown below. Each of the structures is bonded to at least one selected from another atom, $R^A$, the structure $H_B$ and the structure $H_D$ in the molecule of the first material. It should be noted that these specific examples of the partial structures in the first material in the exemplary embodiment are not exhaustive.

[Formula 26]

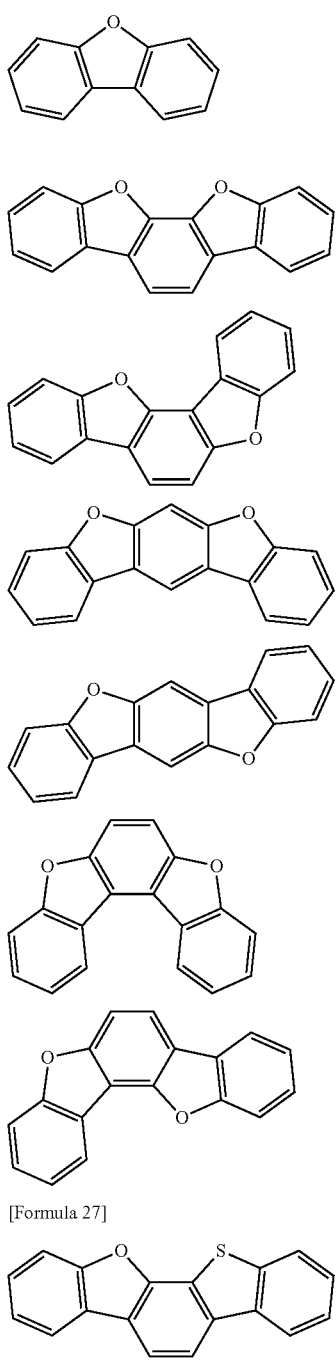

[Formula 27]

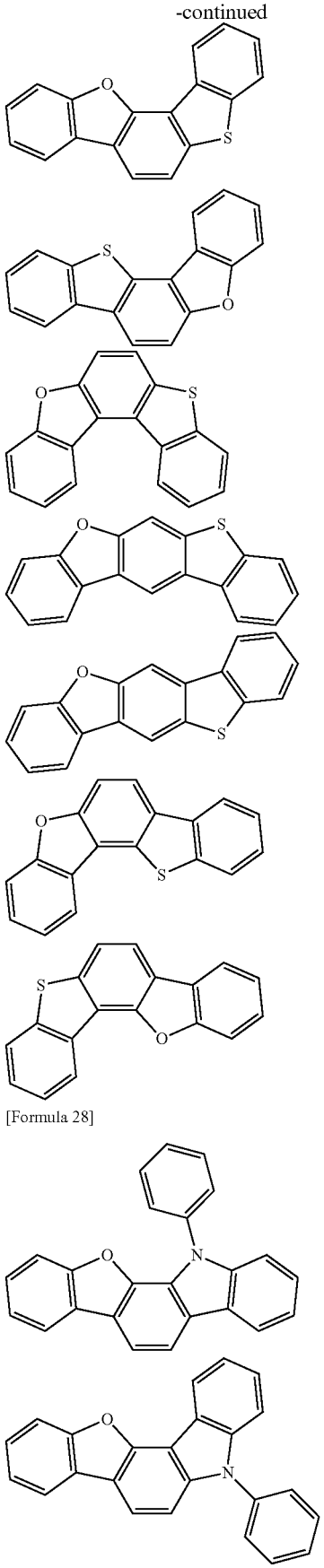

[Formula 28]

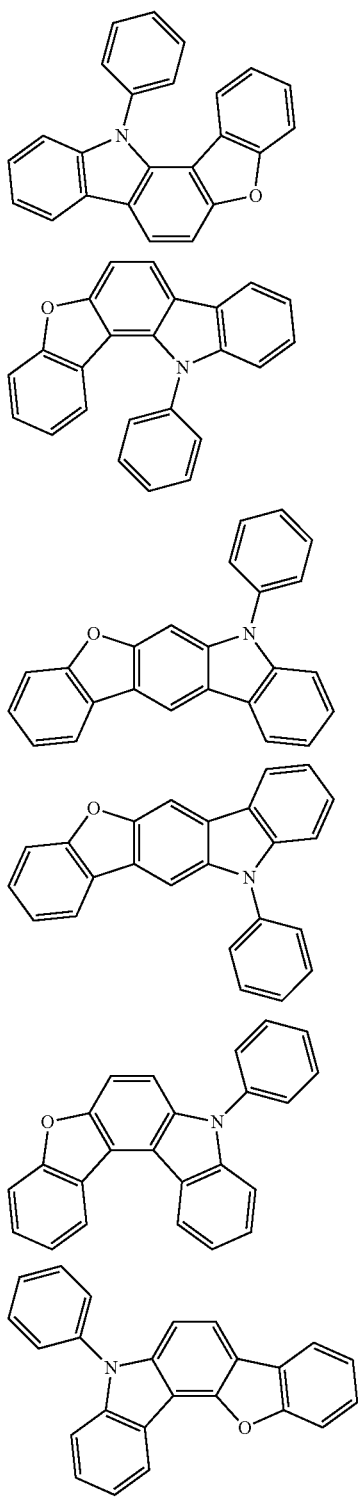

[Formula 29]

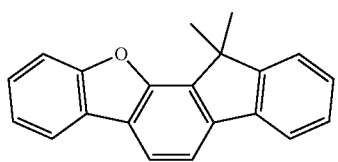

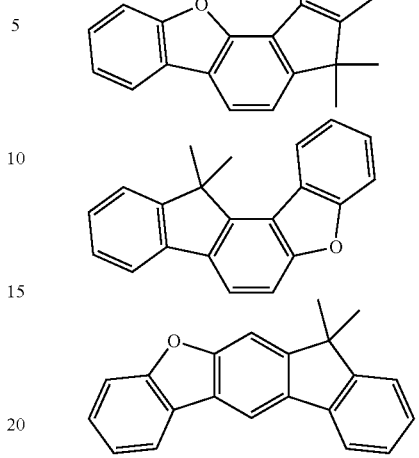

Examples of the structure $H_B$ in the formula (10), the structure $H_D$ in the formula (11), $R^A$ represented by the formula (1b) and the structure $H_B$ and the structure $H_D$ that are represented by the formula (1c) are shown below. Each of the structures is bonded to the partial structure represented by the formula (1), $R^A$, $H_A$, $H_C$ and the like in the molecule of the first material. In the following examples of the structures, * represents a bonding position to another structure. It should be noted that these specific examples of the structures in the first material in the exemplary embodiment are not exhaustive.

[Formula 30]

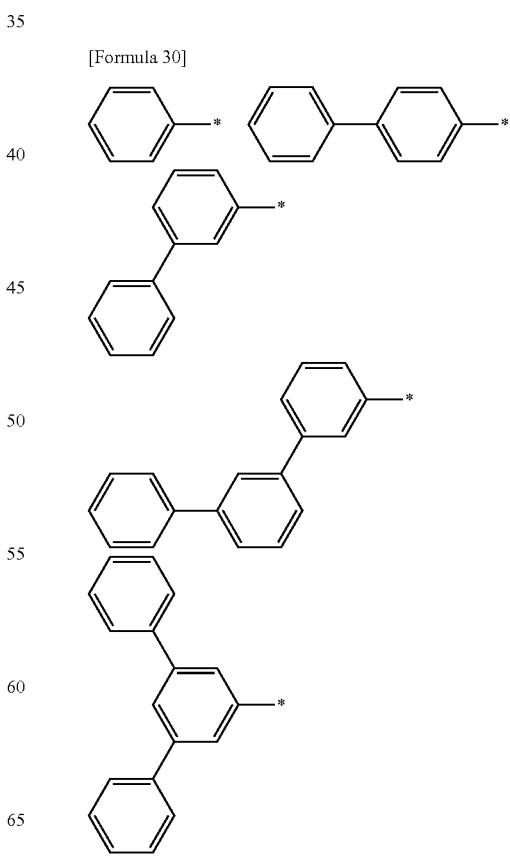

[Formula 31]
[Formula 32]
[Formula 33]
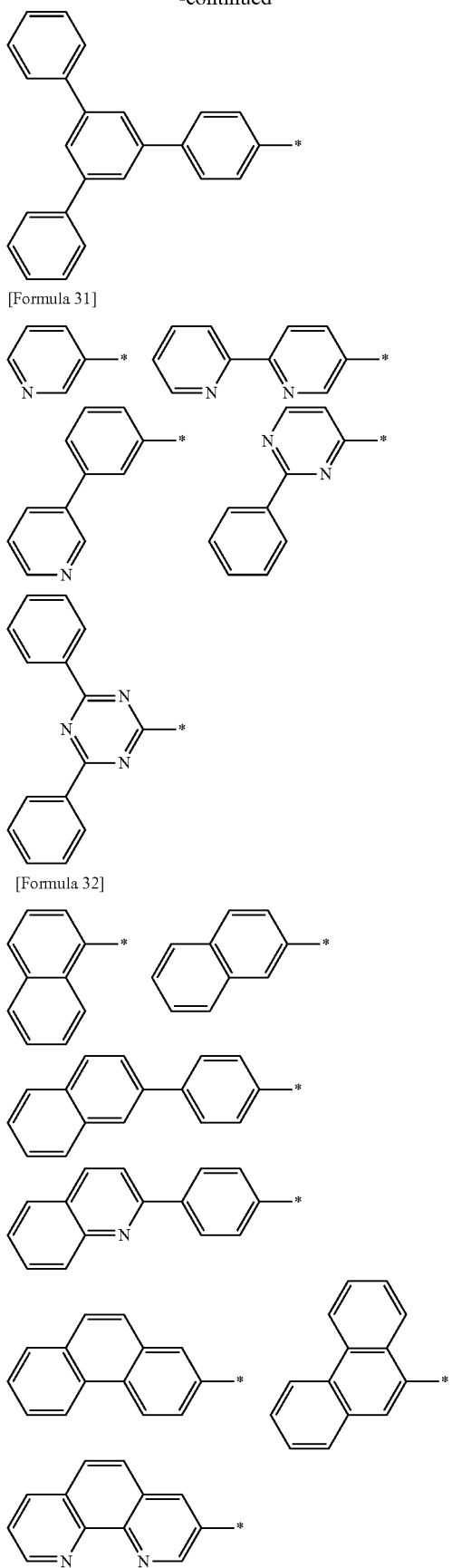
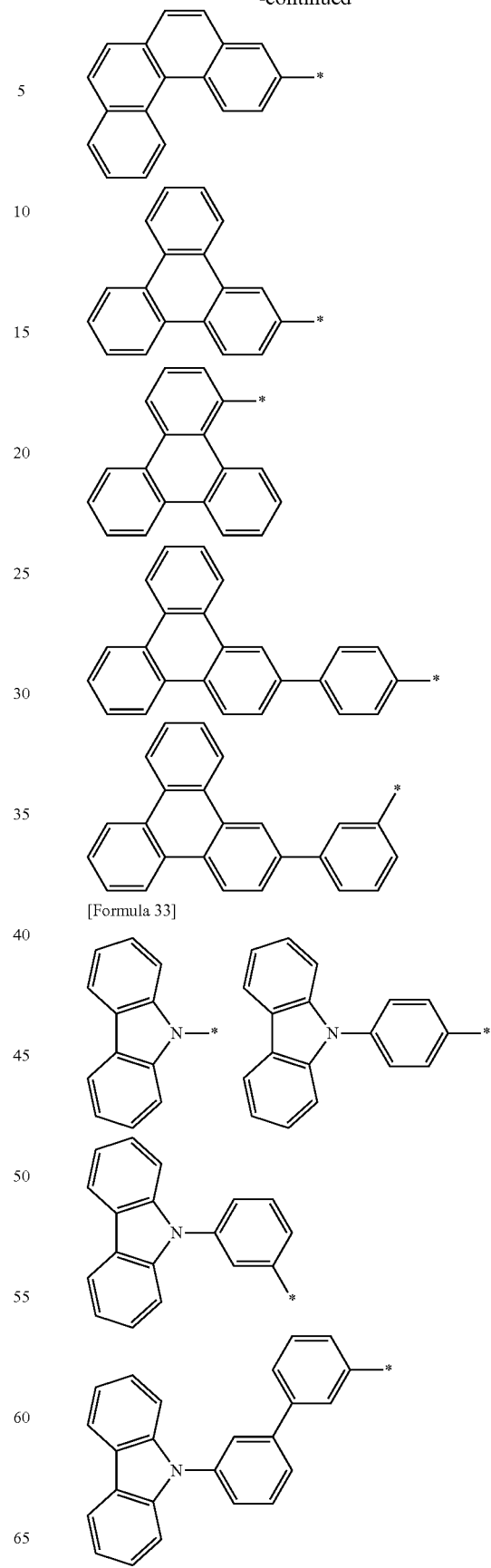

-continued

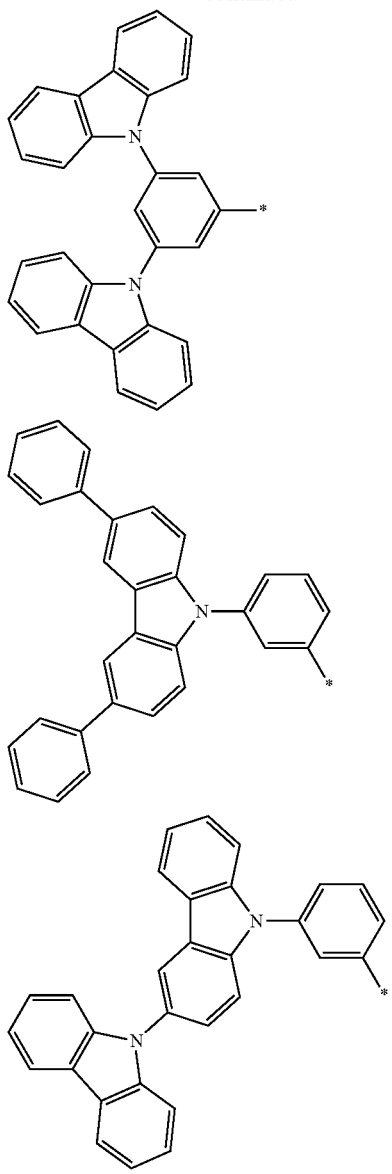

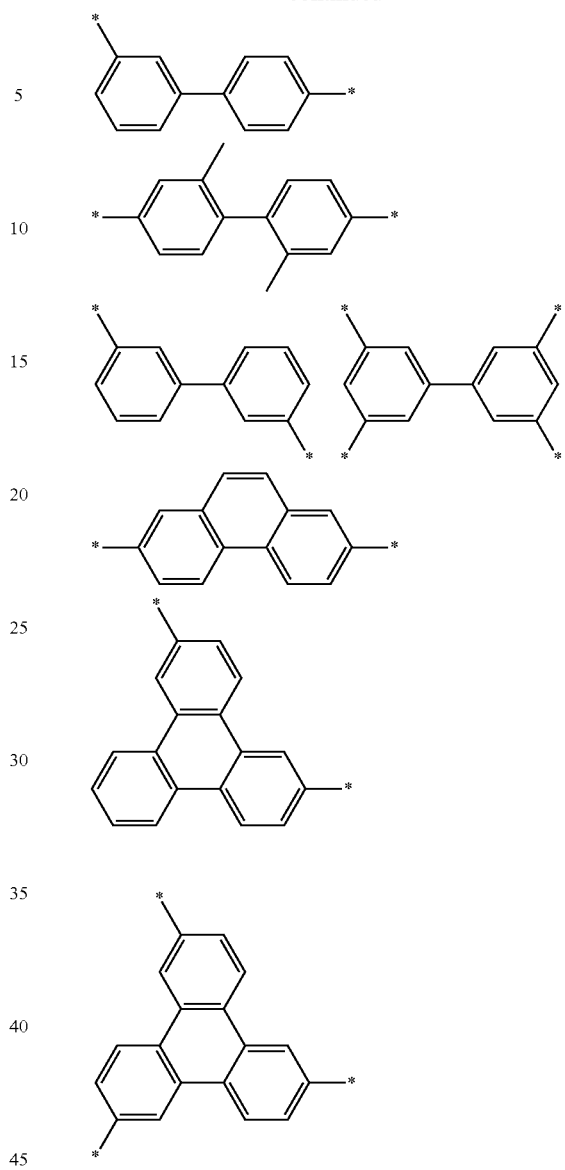

Examples of the structure $H_B$ in the formula (10) and the structure $H_D$ in the formula (11) are shown below. Each of the structures is bonded to the partial structure represented by the formula (1), $R^A$, $H_A$, $H_C$ and the like in the molecule of the first material. In the following examples of the structures, * represents a bonding position to another structure. It should be noted that these specific examples of the structures in the first material in the exemplary embodiment are not exhaustive.

[Formula 34]

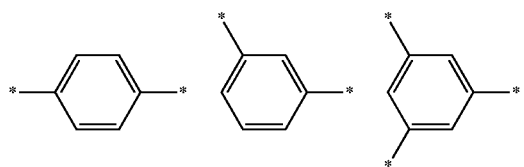

Second Material

The second material in the exemplary embodiment has a partial structure represented by a formula (2) below and a partial structure represented by a formula (3) below in one molecule.

[Formula 35]

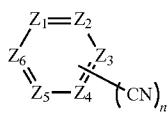
(2)

In the formula (2), CN is a cyano group.
n is an integer of 1 or more, preferably from 1 to 5, more preferably from 2 to 4.
$Z_1$ to $Z_6$ are each independently a nitrogen atom, a carbon atom to be bonded to CN, or a carbon atom to be bonded to another atom in a molecule of the second material. For instance, when $Z_1$ is a carbon atom to be bonded to CN, at least one of the rest five atoms ($Z_2$ to $Z_6$) is a carbon atom to be bonded to another atom in the molecule of the second material. The another atom may be an atom forming the partial structure represented by the formula (3), an atom forming a linking group intervening between the at least one of the rest five atoms ($Z_2$ to $Z_6$) and the partial structure represented by the formula (3), or an atom forming a substituent.

The second material in the exemplary embodiment may have a six-membered ring including $Z_1$ to $Z_6$ as the partial structure, or may have a fused ring including the six-membered ring further fused with a ring as the partial structure.

[Formula 36]

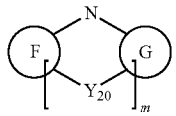
(3)

In the formula (3), F and G each independently represent a cyclic structure. m is 0 or 1. When m is 1, $Y_{20}$ is a single bond, oxygen atom, sulfur atom, selenium atom, carbon atom, silicon atom or germanium atom.

When m is 0 in the formula (3), the formula (3) is represented by a formula (30) below.

[Formula 37]

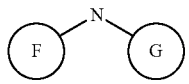
(30)

The cyclic structure F and the cyclic structure G in the formula (30) represent the same as the cyclic structure F and the cyclic structure G in the formula (3).

When m is 1 in the formula (3), the formula (3) is represented by one of formulae (31) to (37) below.

[Formula 38]

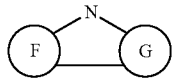
(31)

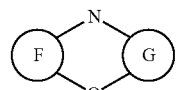
(32)

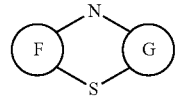
(33)

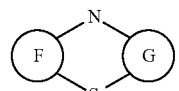
(34)

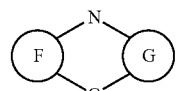
(35)

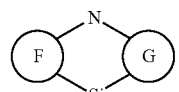
(36)

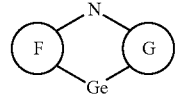
(37)

The cyclic structure F and the cyclic structure G in the formulae (31) to (37) respectively represent the same as the cyclic structure F and the cyclic structure G in the formula (3).

In the exemplary embodiment, the cyclic structure F and the cyclic structure G each are preferably a five-membered ring or a six-membered ring, in which the five-membered ring or the six-membered ring is preferably an unsaturated ring, more preferably an unsaturated six-membered ring.

The second material in the exemplary embodiment is preferably a compound represented by a formula (20) below.

[Formula 39]

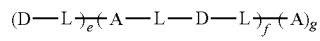
(20)

In the formula (20), A is represented by the formula (2). In the formula (2): CN is a cyano group; n is an integer of 1 or more; and $Z_1$ to $Z_6$ are each independently a nitrogen atom, a carbon atom to be bonded to CN, a carbon atom to be bonded to R, a carbon atom to be bonded to L, or a carbon atom to be bonded to D. At least one of $Z_1$ to $Z_6$ is a carbon atom to be bonded to CN. At least one of $Z_1$ to $Z_6$ is a carbon atom to be bonded to L or D. R is each independently a hydrogen atom, halogen atom, substituted or unsubstituted aryl group having 6 to 30 ring carbon atoms, substituted or unsubstituted heterocyclic group having 5 to 30 ring atoms, substituted or unsubstituted alkyl group having 1 to 30 carbon atoms, substituted or unsubstituted alkylsilyl group having 3 to 30 carbon atoms, substituted or unsubstituted arylsilyl group having 6 to 60 ring carbon atoms, substituted or unsubstituted alkoxy group having 1 to 30 carbon atoms, substituted or unsubstituted aryloxy group having 6 to 30 ring carbon atoms, substituted or unsubstituted alkylamino group having 2 to 30 carbon atoms, substituted or unsubstituted arylamino group having 6 to 60 ring carbon atoms, substituted or unsubstituted alkylthio group having 1 to 30 carbon atoms, or substituted or unsubstituted arylthio group 6 to 30 ring carbon atoms.

In the formula (20), D is represented by the formula (3). The cyclic structure F and the cyclic structure G in the formula (3) may be unsubstituted or substituted. m is 0 or 1. When m is 1, $Y_{20}$ is a single bond, oxygen atom, sulfur atom, selenium atom, carbonyl group, $CR_{21}R_{22}$, $SiR_{23}R_{24}$ or $GeR_{25}R_{26}$, in which $R_{21}$ to $R_{26}$ represent the same as R. When m is 1 in the formula (3), the formula (3) is represented by one of the formulae (31) to (34) and formulae (38) to (41) below.

[Formula 40]

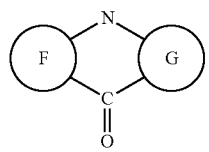
(38)

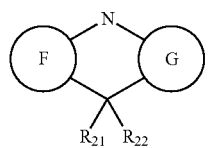
(39)

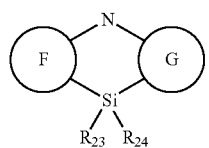
(40)

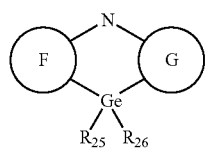
(41)

In the Formula (20):

(i) When L Intervenes Between a and d,

L is a single bond, substituted or unsubstituted aromatic hydrocarbon group having 6 to 14 ring carbon atoms, substituted or unsubstituted heterocyclic group having 5 to 14 ring atoms, $CR_{81}R_{82}$, $NR_{83}$, O, S, $SiR_{84}R_{85}$, $CR_{86}R_{87}$—$CR_{88}R_{89}$, $CR_{90}$=$CR_{91}$, substituted or unsubstituted aliphatic hydrocarbon cyclic group, or substituted or unsubstituted aliphatic heterocyclic group, in which $R_{81}$ to $R_{91}$ each independently represent the same as R.

In the Formula (20), (ii) when L is positioned at a terminal end in the molecule of the second material, L represents the same as R.

In the formula (20), f is an integer of 1 or more, and e and g each independently are an integer of 0 or more. A plurality of A may be mutually the same or different. A plurality of D may be mutually the same or different. A plurality of L may be mutually the same or different.

The formula (20) is represented by, for instance, formulae (201) to (220) below.

TABLE 1

| Formula No. | e, f, g in Formula (20) | Formula |
|---|---|---|
| (201) | e = 0, f = 1, g = 0 | A-L-D |
| (202) | e = 0, f = 1, g = 0 | A-D |
| (203) | e = 0, f = 1, g = 1 | A-L-D-L-A |
| (204) | e = 0, f = 1, g = 1 | A-D-A |
| (205) | e = 1, f = 1, g = 0 | D-L-A-L-D |
| (206) | e = 1, f = 1, g = 0 | D-A-D |

TABLE 2

| Formula No. | e, f, g in Formula (20) | Formula |
|---|---|---|
| (207) | e = 1, f = 1, g = 1 | D-L-A-L-D-L-A |
| (208) | e = 1, f = 1, g = 1 | D-A-D-A |
| (209) | e = 1, f = 2, g = 0 | D-L-A-L-D-L-A-L-D |
| (210) | e = 1, f = 2, g = 0 | D-A-D-A-D |
| (211) | e = 0, f = 2, g = 1 | A-L-D-L-A-L-D-L-A |
| (212) | e = 0, f = 2, g = 1 | A-D-A-D-A |

Table 3

| Formula No. | e, f, g in Formula (20) | Formula |
|---|---|---|
| (213) | e = 2, f = 1, g = 0 | D—L—A—L—D<br>\|<br>L<br>\|<br>D |
| (214) | e = 2, f = 1, g = 0 | D—A—D<br>\|<br>D |
| (215) | e = 3, f = 1, g = 0 | D<br>\|<br>L<br>\|<br>D—L—A—L—D<br>\|<br>L<br>\|<br>D |
| (216) | e = 3, f = 1, g = 0 | D<br>\|<br>D—A—D<br>\|<br>D |

Table 4

| Formula No. | e, f, g in Formula (20) | Formula |
|---|---|---|
| (217) | e = 0, f = 1, g = 2 | A—L—D—L—A<br>\|<br>L<br>\|<br>A |
| (218) | e = 0, f = 1, g = 2 | A—D—A<br>\|<br>A |

Table 4-continued

| Formula No. | e, f, g in Formula (20) | Formula |
|---|---|---|
| (219) | e = 0, f = 1, g = 3 | 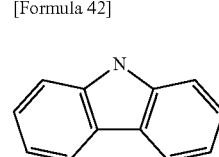 |
| (220) | e = 0, f = 1, g = 3 | 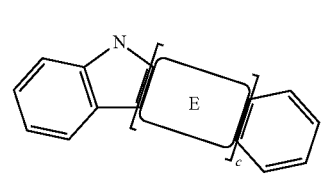 |

In a repeating unit put in parentheses with a repeating number f in the formula (20), D may be bonded to A via L or A may be bonded D via L. For instance, the second material may have a branched structure as represented by formulae (221) to (228) below

[Formula 41]

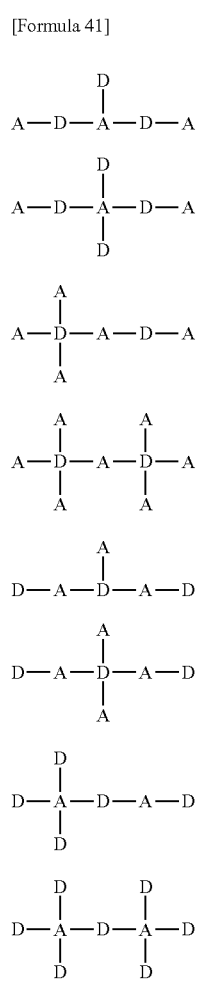

(221)
(222)
(223)
(224)
(225)
(226)
(227)
(228)

The second material in the exemplary embodiment is not limited to the compounds represented by the formulae (221) to (228). It should be noted that omission of L in the formulae (221) to (228) indicates that L is a single bond intervening between A and D, or L is a hydrogen atom present at the terminal end of the molecule of the second material.

In order to keep a small ΔST in the molecule, L is preferably not a fused aromatic ring in terms of a molecular design. However, L may be the fused aromatic ring as long as thermally activated delayed fluorescence can be obtained. Moreover, the second material in the exemplary embodiment is preferably a low-molecular material due to the necessity of a molecular design for accurately positioning A and D in one molecule. Accordingly, the second material in the exemplary embodiment preferably has a molecular weight of 5000 or less, more preferably 3000 or less. The second material in the exemplary embodiment has the partial structures represented by the formulae (2) and (3), so that the organic EL device containing the second material can emit thermally activated delayed fluorescence.

In the exemplary embodiment, the formula (3) is preferably represented by at least one of formulae (3a) and (3b) below.

[Formula 42]

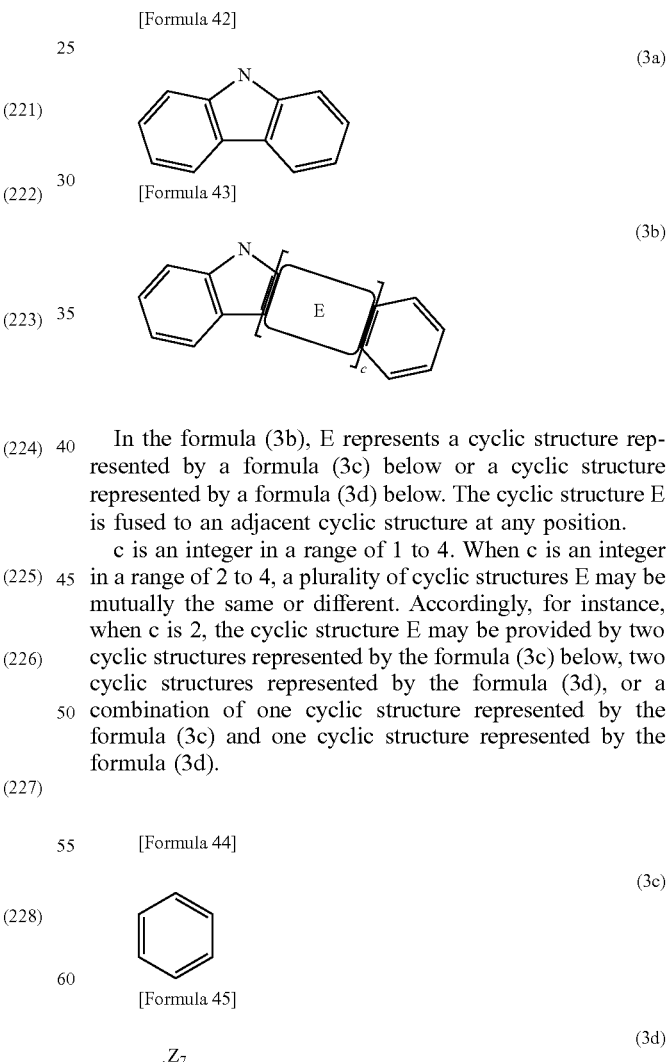

(3a)

[Formula 43]

(3b)

In the formula (3b), E represents a cyclic structure represented by a formula (3c) below or a cyclic structure represented by a formula (3d) below. The cyclic structure E is fused to an adjacent cyclic structure at any position.

c is an integer in a range of 1 to 4. When c is an integer in a range of 2 to 4, a plurality of cyclic structures E may be mutually the same or different. Accordingly, for instance, when c is 2, the cyclic structure E may be provided by two cyclic structures represented by the formula (3c) below, two cyclic structures represented by the formula (3d), or a combination of one cyclic structure represented by the formula (3c) and one cyclic structure represented by the formula (3d).

[Formula 44]

(3c)

[Formula 45]

(3d)

In the formula (3d), $Z_7$ is a carbon atom, nitrogen atom, sulfur atom or oxygen atom.

A molecular design in which the partial structures represented by the formulae (2) and (3) are simultaneously held in one molecule can effectively decrease ΔST.

The second material in the exemplary embodiment preferably has a structure represented by a formula (3e) below in the molecule.

[Formula 46]

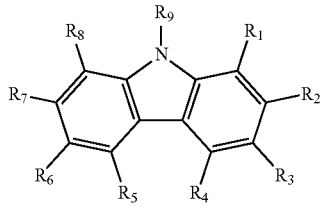

(3e)

In the formula (3e), $R_1$ to $R_9$ are each independently a hydrogen atom, halogen atom, substituted or unsubstituted aryl group having 6 to 30 ring carbon atoms, substituted or unsubstituted heterocyclic group having 5 to 30 ring atoms, substituted or unsubstituted alkyl group having 1 to 30 carbon atoms, substituted or unsubstituted alkylsilyl group having 3 to 30 carbon atoms, substituted or unsubstituted arylsilyl group having 6 to 60 ring carbon atoms, substituted or unsubstituted alkoxy group 1 to 30 carbon atoms, substituted or unsubstituted aryloxy group having 6 to 30 ring carbon atoms, substituted or unsubstituted alkylamino group having 2 to 30 carbon atoms, substituted or unsubstituted arylamino group having 6 to 60 ring carbon atoms, substituted or unsubstituted alkylthio group having 1 to 30 carbon atoms, substituted or unsubstituted arylthio group having 6 to 30 ring carbon atoms, or a single bond to be bonded to another atom in the molecule of the second material. At least one of $R_1$ to $R_9$ is a single bond to be bonded to another atom in the molecule of the second material.

In the formula (3e), at least one of combinations of substituents selected from $R_1$ to $R_9$ may be bonded to each other to form a cyclic structure. In other words, in the formula (3e) where $R_1$ to $R_8$ are respectively bonded to carbon atoms of the six-membered ring and $R_9$ is bonded to a nitrogen atom of the five-membered ring, the cyclic structure may be formed by adjacent substituents selected from $R_1$ to $R_8$ bonded to adjacent carbon atoms and $R_9$ bonded to the nitrogen atom of the five-membered ring. Specifically, at least one of combinations of substituents selected from a combination of $R_1$ and $R_2$, a combination of $R_2$ and $R_3$, a combination of $R_3$ and $R_4$, a combination of $R_4$ and $R_5$, a combination of $R_5$ and $R_6$, a combination of $R_6$ and $R_7$, a combination of $R_7$ and $R_8$, a combination of $R_8$ and $R_9$, and a combination of $R_1$ and $R_9$ may be bonded to form a cyclic structure.

In the exemplary embodiment, the cyclic structure formed by bonding of the substituents is preferably a fused ring. For instance, when the cyclic structure is formed in the formula (3e), the thus-formed cyclic structure is preferably a fused six-membered ring.

The second material in the exemplary embodiment preferably has a structure represented by a formula (3f) below in the molecule.

[Formula 47]

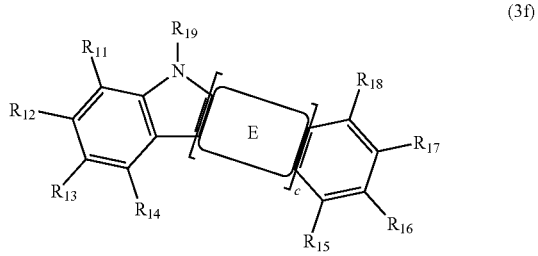

(3f)

In the formula (3f), $R_{11}$ to $R_{19}$ are each independently the same as $R_1$ to $R_9$ in the formula (3e).

At least one of $R_{11}$ to $R_{19}$ is a single bond to be bonded to another atom in the molecule of the second material.

In the formula (3f), at least one of combinations of substituents selected from $R_{11}$ to $R_{19}$ may be bonded to each other to form a cyclic structure.

In the formula (3f), E represents a cyclic structure represented by a formula (3g) below or a cyclic structure represented by a formula (3h) below. The cyclic structure E is fused to an adjacent cyclic structure at any position.

c indicates the number of the cyclic structure E and is an integer in a range of 1 to 4. When c is an integer in a range of 2 to 4, a plurality of cyclic structures E may be mutually the same or different. Accordingly, for instance, when c is 2, the cyclic structure E may be provided by two cyclic structures represented by the formula (3g) below, two cyclic structures represented by the formula (3h), or a combination of one cyclic structure represented by the formula (3g) and one cyclic structure represented by the formula (3h).

[Formula 48]

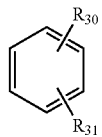

(3g)

(3h)

In the formula (3g), $R_{30}$ and $R_{31}$ each independently represent the same as $R_1$ to $R_9$. $R_{30}$ and $R_{31}$ may be bonded to each other to form a cyclic structure. $R_{30}$ and $R_{31}$ are respectively bonded to carbon atoms forming the six-membered ring of the formula (3g).

In the formula (3h), $Z_8$ is $CR_{32}R_{33}$, $NR_{34}$, sulfur atom or oxygen atom. $R_{32}$ to $R_{34}$ each independently represent the same as $R_1$ to $R_9$.

In the formula (3f), at least one of combinations of substituents selected from $R_{11}$ to $R_{19}$ and $R_{30}$ to $R_{34}$ may be bonded to each other to form a cyclic structure.

The second material in the exemplary embodiment is preferably represented by a formula (2A) below.

[Formula 49]

(2A)

In the formula (2A), n is an integer of 1 or more, t is an integer of 1 or more, and u is an integer of 0 or more. $L_A$ is a substituted or unsubstituted aromatic hydrocarbon ring having 6 to 30 ring carbon atoms or heterocyclic group having 6 to 30 ring atoms. CN is a cyano group.

$D_1$ and $D_2$ are each independently represented by the formula (3). The cyclic structure F and the cyclic structure G in the formula (3) may be unsubstituted or substituted. m is 0 or 1. When m is 1, $Y_{20}$ is a single bond, oxygen atom, sulfur atom, selenium atom, carbonyl group, $CR_{21}R_{22}$, $SiR_{23}R_{24}$ or $GeR_{25}R_{26}$, in which $R_{21}$ to $R_{26}$ represent the same as R. When m is 1, the formula (3) is represented by one of the formulae (31) to (34) and the formulae (38) to (41).

$D_1$ and $D_2$ may be the same or different. When t is 2 or more, a plurality of $D_1$ may be the same or different. When u is 2 or more, a plurality of $D_2$ may be the same or different.

In the exemplary embodiment, $L_A$ is preferably a substituted or unsubstituted aromatic hydrocarbon ring having 6 to 14 ring carbon atoms. Examples of the aromatic hydrocarbon ring having 6 to 14 ring carbon atoms include benzene, naphthalene, fluorene, and phenanthrene. An aromatic hydrocarbon ring having 6 to 10 ring carbon atoms is further preferable.

Examples of the heterocyclic ring having 6 to 30 ring atoms in $L_A$ include pyridine, pyrimidine, pyrazine, quinoline, quinazoline, phenanthroline, benzofuran, and dibenzofuran.

In the exemplary embodiment, in the formula (2A), $D_1$ or $D_2$ may be bonded to a first carbon atom forming the aromatic hydrocarbon ring represented by $L_A$ and CN may be bonded to a second carbon atom adjacent to the first carbon atom. In the compound of the exemplary embodiment, for instance, as shown by a partial structure represented by a formula (2B) below, D may be bonded to the first carbon atom $C_1$ and a cyano group may be bonded to the second carbon atom $C_2$ adjacent to the first carbon atom $C_1$. D in the formula (2B) below represents the same as $D_1$ or $D_2$. In the formula (2B) below, a wavy part represents a bonding position to another structure or another atom.

[Formula 50]

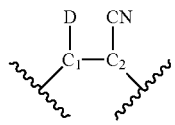

(2B)

Since $D_1$ or $D_2$ each having a skeleton represented by the formula (3a) or the formula (3b) and the cyano group adjacent to $D_1$ or $D_2$ are bonded to the aromatic hydrocarbon ring represented by $L_A$, a value of ΔST of the compound is reducible.

In the exemplary embodiment, t is preferably an integer of 2 or more. When two or more $D_1$ are bonded to the aromatic hydrocarbon ring represented by $L_A$, a plurality of $D_1$ may have the same structure or different structures.

The second material in the exemplary embodiment is preferably represented by a formula (21) below.

[Formula 51]

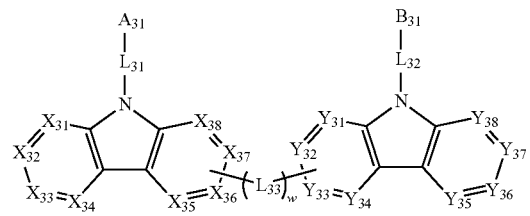

(21)

In the formula (21), $A_{31}$ and $B_{31}$ each independently represent a substituted or unsubstituted aromatic hydrocarbon group having 6 to 30 ring carbon atoms or a substituted or unsubstituted heterocyclic group having 5 to 30 ring atoms.

$X_{31}$ to $X_{38}$ and $Y_{31}$ to $Y_{38}$ are each independently a nitrogen atom, a carbon atom to be bonded to $R^D$, or a carbon atom to be bonded to $L_{33}$. At least one of $X_{35}$ to $X_{38}$ is a carbon atom to be bonded to $L_{33}$. At least one of $Y_{31}$ to $Y_{34}$ is a carbon atom to be bonded to $L_{33}$.

$R^D$ is each independently a hydrogen atom, halogen atom, substituted or unsubstituted aromatic hydrocarbon group having 6 to 30 ring carbon atoms, substituted or unsubstituted heterocyclic group having 5 to 30 ring atoms, substituted or unsubstituted alkyl group having 1 to 30 carbon atoms, or substituted or unsubstituted silyl group.

$L_{31}$ and $L_{32}$ are each independently a single bond or a linking group. Examples of the linking group in $L_{31}$ and $L_{32}$ includes a substituted or unsubstituted aromatic hydrocarbon group having 6 to 30 ring carbon atoms, substituted or unsubstituted heterocyclic group having 5 to 30 ring atoms, a multi-linking group formed by bonding of two to four groups selected from the aromatic hydrocarbon group, a multi-linking group formed by bonding of two to four groups selected from the heterocyclic group, or a multi-linking group formed by bonding of two to four groups selected from the aromatic hydrocarbon group and heterocyclic group.

$L_{33}$ represents a substituted or unsubstituted monocyclic aromatic hydrocarbon group having 6 or less ring carbon atoms or a substituted or unsubstituted monocyclic heterocyclic group having 6 or less ring atoms.

w is an integer of 0 to 3. When w is 0, at least one of $X_{35}$ to $X_{38}$ is directly bonded to at least one of $Y_{31}$ to $Y_{34}$.

The monocyclic hydrocarbon group is not a fused ring but is a group derived from a single hydrocarbon ring (aliphatic cyclic hydrocarbon or aromatic hydrocarbon). The monocyclic heterocyclic group is a group derived from a single heterocyclic ring.

The formula (21) may satisfy at least one of the following conditions (i) and (ii).
  (i) At least one of $A_{31}$ and $B_{31}$ is a cyano-substituted aromatic hydrocarbon group having 6 to 30 ring carbon atoms or a cyano-substituted heterocyclic group having 6 to 30 ring atoms.

(ii) At least one of $X_{31}$ to $X_{34}$ and $Y_{35}$ to $Y_{38}$ is a carbon atom bonded to $R^D$, in which at least one of $R^D$ is a cyano-substituted aromatic hydrocarbon group having 6 to 30 ring carbon atoms or a cyano-substituted heterocyclic group having 6 to 30 ring atoms.

When a plurality of $R^D$ are present, the plurality of $R^D$ may be the same or different.

In the formula (21), when the aromatic hydrocarbon group having 6 to 30 ring carbon atoms or the heterocyclic group having 6 to 30 ring atoms, both of which are represented by $A_{31}$ and $B_{31}$, has a substituent, the substituent is preferably at least one selected from the group consisting of a cyano group, halogen atom, alkyl group having 1 to 20 carbon atoms, cycloalkyl group having 3 to 20 carbon atoms, alkoxy group having 1 to 20 carbon atoms, haloalkyl group having 1 to 20 carbon atoms, haloalkoxy group having 1 to 20 carbon atoms, alkylsilyl group having 1 to 10 carbon atoms, aryl group having 6 to 30 ring carbon atoms, aryloxy group having 6 to 30 ring carbon atoms, aralkyl group having 6 to 30 carbon atoms, and heterocyclic group having 5 to 30 ring atoms. When a plurality of substituents are present, the substituents may be mutually the same or different.

In the formula (21), it is preferable that the condition (i) is satisfied and the condition (ii) is not satisfied.

Alternatively, in the formula (21), it is preferable that the condition (ii) is satisfied and the condition (i) is not satisfied.

Alternatively, it is preferable that the condition (i) and the condition (ii) are satisfied.

In the formula (21), at least one of $A_{31}$ and $B_{31}$ is preferably a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, or a cyano-substituted triphenylenyl group.

In the formula (21), at least one of $X_{31}$ to $X_{34}$ and $Y_{35}$ to $Y_{38}$ is preferably $CR^D$, in which at least one of $R^D$ in $X_{31}$ to $X_{34}$ and $Y_{35}$ to $Y_{38}$ is preferably a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, or a cyano-substituted triphenylenyl group.

In the formula (21), it is preferable that $X_{36}$ is bonded to $Y_{33}$ via $L_{33}$ or directly bonded to $Y_{33}$.

In the formula (21), it is preferable that $X_{36}$ is bonded to $Y_{32}$ via $L_{33}$ or directly bonded to $Y_{32}$.

In the formula (21), it is preferable that $X_{37}$ is bonded to $Y_{33}$ via $L_{33}$ or directly bonded to $Y_{33}$.

In the formula (21), w is preferably 0.

Alternatively, in the formula (21), w is preferably 1.

In the formula (21), $L_{31}$ and $L_{32}$ are preferably a single bond or a substituted or unsubstituted aromatic hydrocarbon group having 6 to 30 ring carbon atoms.

Specific examples of the second material in the exemplary embodiment are shown below. It should be noted that these specific examples of the second material in the exemplary embodiment are not exhaustive.

[Formula 52]

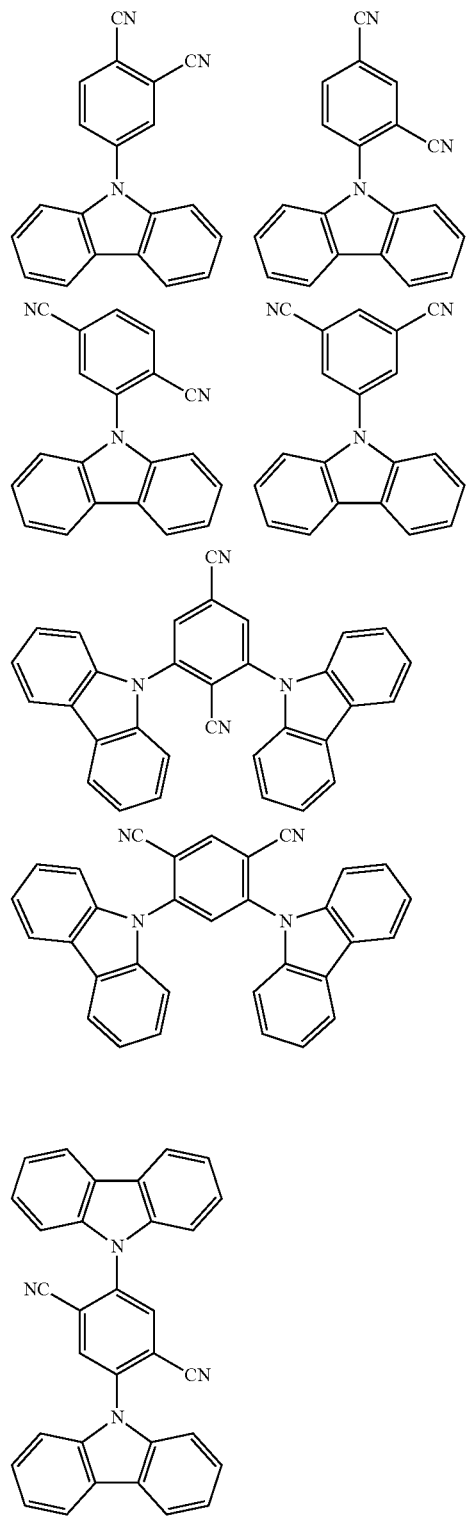

[Formula 53]
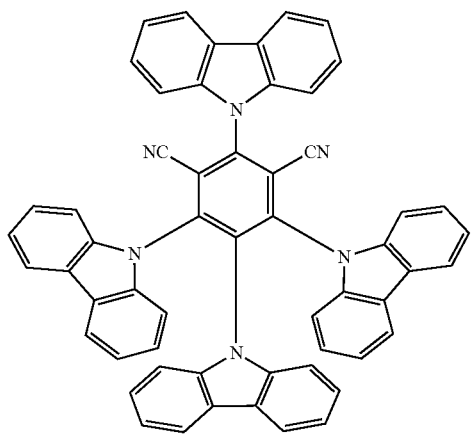
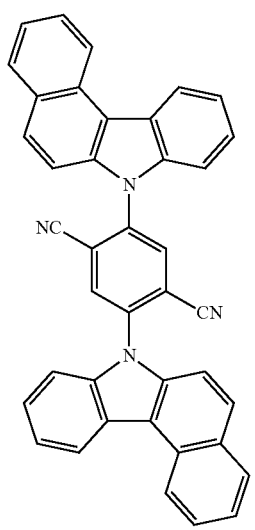
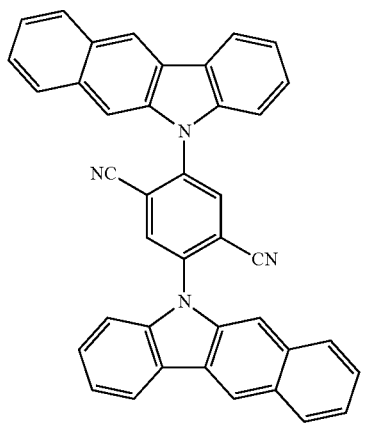
[Formula 54]
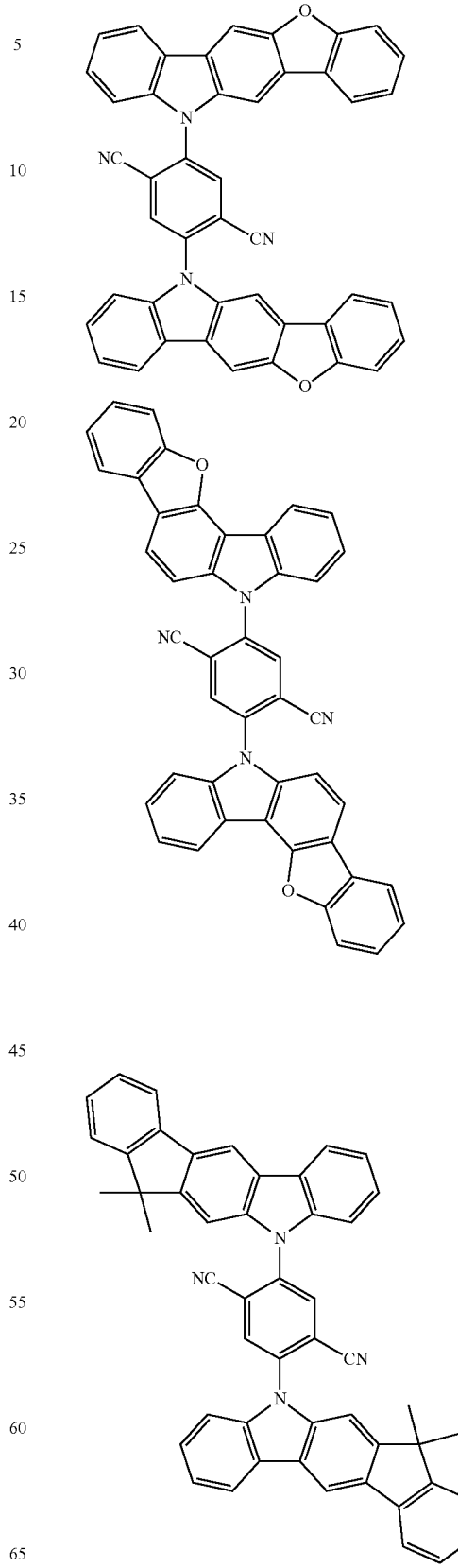

-continued
[Formula 55]
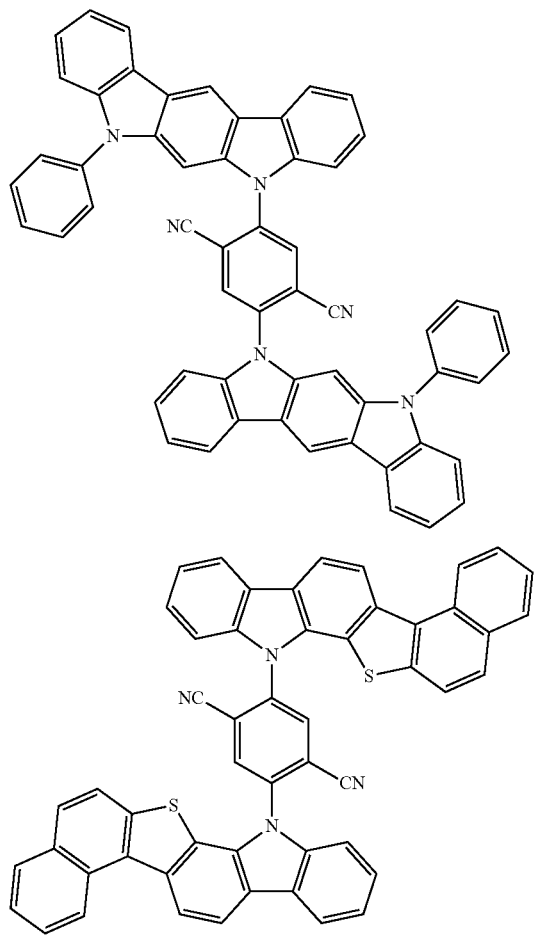
[Formula 56]
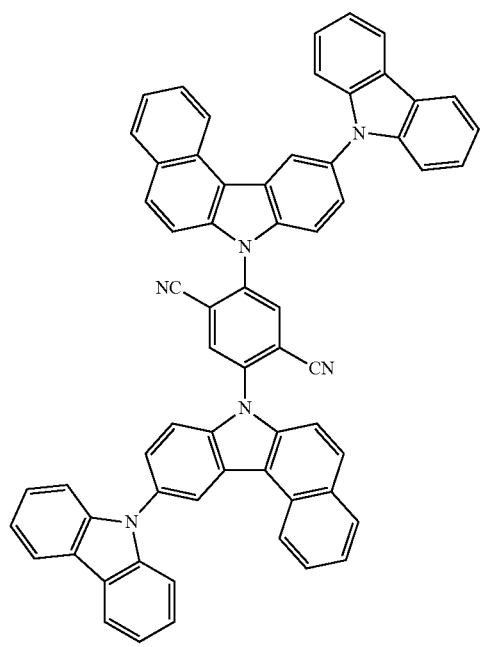
-continued
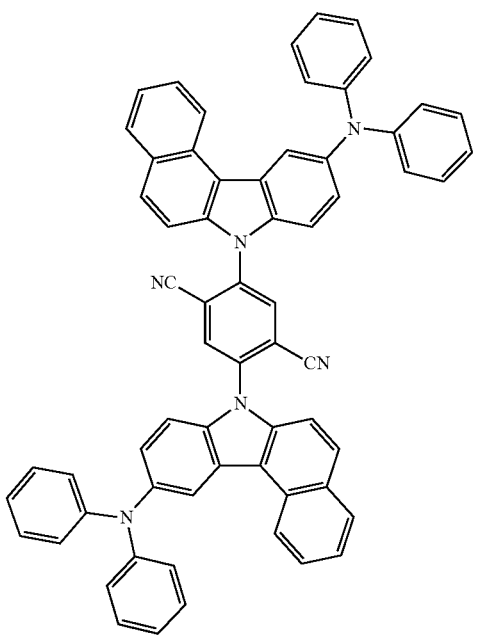
[Formula 57]
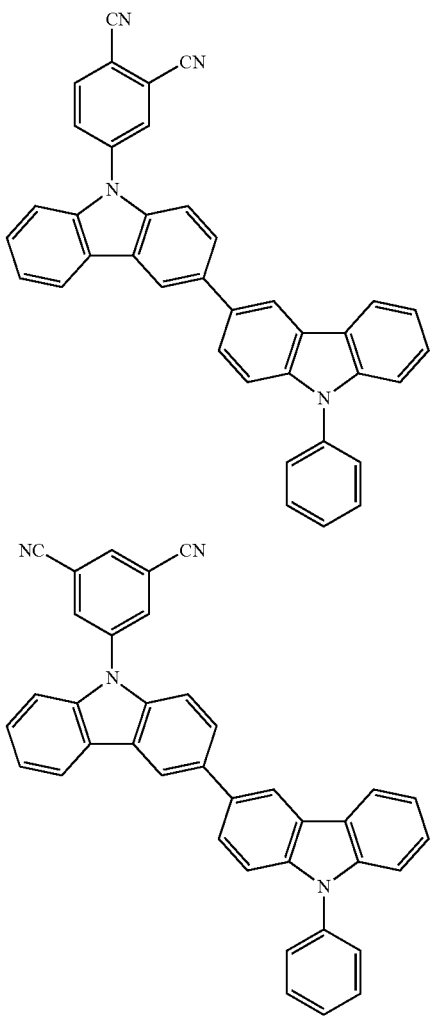

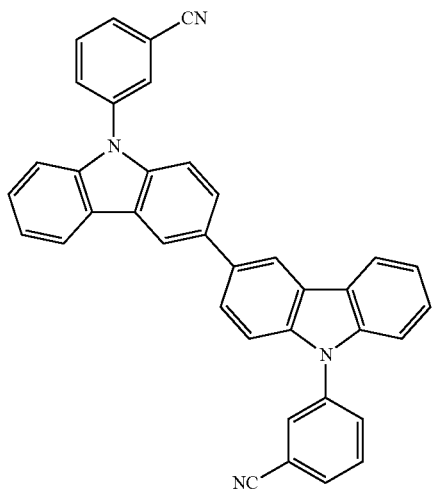

[Formula 58]

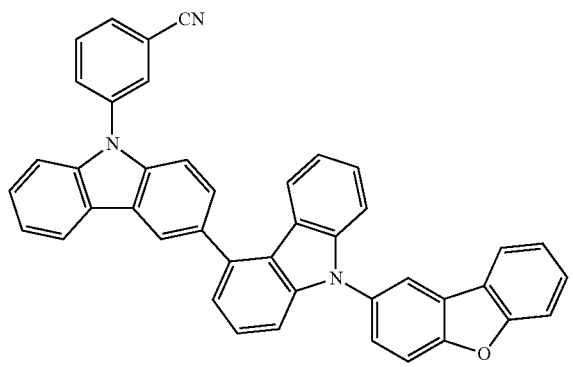

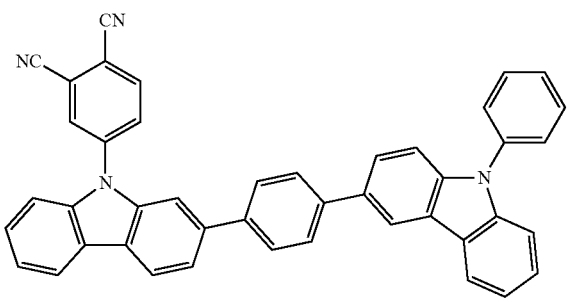

[Formula 59]

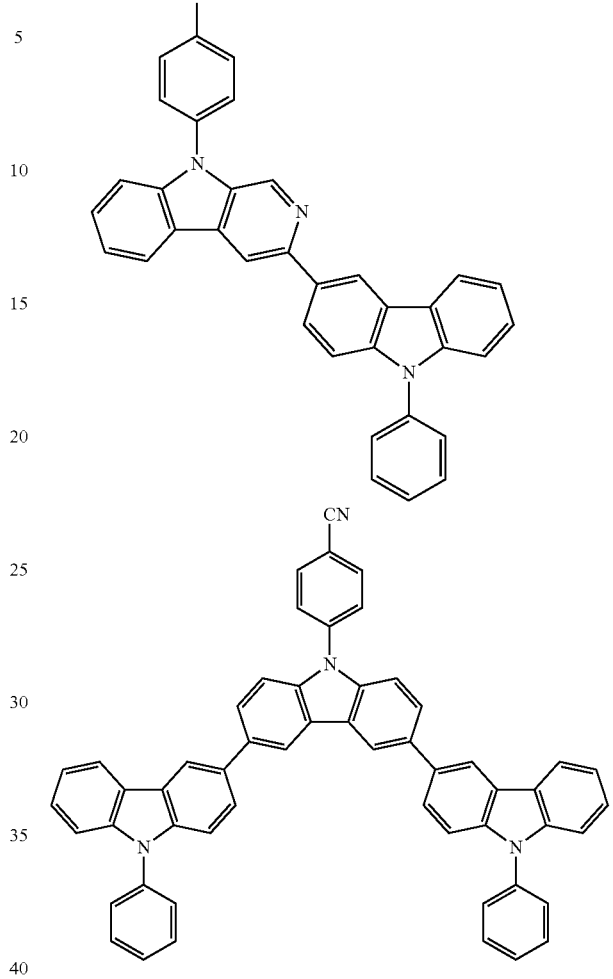

In the exemplary embodiment, a film thickness of the emitting layer of the organic EL device is preferably in a range of 5 nm to 50 nm, more preferably in a range of 7 nm to 50 nm and most preferably in a range of 10 nm to 50 nm. The thickness of less than 5 nm may cause difficulty in forming the emitting layer and in controlling chromaticity, while the thickness of more than 50 nm may raise drive voltage.

In the emitting layer of the organic EL device in the exemplary embodiment, a ratio of the first material and the second material in the emitting layer is preferably in a range of 99:1 to 1:99 by a mass ratio. A content ratio of the second material in the emitting layer is preferably in a range from 5 mass % to 80 mass %, more preferably in a range from 20 mass % to 80 mass %.

Manufacturing Method of First Material and Second Material

The first material can be manufactured, for instance, in the following manner.

For instance, when a compound having the partial structure represented by the formula (1) is manufactured, firstly, a starting material is a commercially available compound in which $X_1$, $X_2$, $X_5$, $X_6$ and $X_{11}$ to $X_{14}$ of the formula (1) are a nitrogen atom or a carbon atom bonded to a hydrogen atom. A hydrogen atom in the starting material is substituted by a halogen atom, an alkyl group or the like by a known method to provide the first material. The halogen atom can be further substituted by an aryl group or the like by a Suzuki coupling method or the like.

For instance, in the partial structure represented by the formula (1) in which $X_1$ and $X_2$ are carbon atoms to be bonded to the structure represented by the formula (1a) and the carbon atoms at $X_1$ and $X_2$ are bonded to halogen atoms, the halogen atom bonded to $X_1$ is substituted by an ortho-hydroxyphenyl group or the like by the Suzuki coupling method or the like. Subsequently, the halogen atom bonded to $X_2$ is substituted by the hydroxyl group or the like in the presence of a base through an intramolecular substitution reaction, so that the first material is obtained.

Moreover, for instance, when a material in which $H_C$ of the formula (11) is represented by the formula (110) is used, a synthetic intermediate (A) formed by bonding a leaving group (e.g., bromine group) to a carbon atom to be bonded to $H_D$ among $X_1, X_2, X_5, X_6, X_{11}$ to $X_{14}$ in the formula (110) is cross-coupled to a synthetic intermediate (B) formed by bonding a leaving group (e.g., bromine group) to a carbon atom to be bonded to the partial structure $H_D$ represented by the formula (11), so that the first material is obtained. Herein, as the cross-coupling, for instance, the leaving group (e.g., bromine group) in the synthetic intermediate (A) is reacted with bis(pinacolato)diboron and the like in the presence of a catalyst (e.g., tetrakis(triphenylphosphine) palladium) to be changed to a boronic acid ester group. Subsequently, the boronic acid ester group is coupled to the synthetic intermediate (B) by the Suzuki coupling or the like in the presence of a basic aqueous solution.

The second material can be manufactured, for instance, by reacting a commercially available compound having the partial structure represented by the formula (2), in which at least one of $Z_1$ to $Z_6$ is a carbon atom bonded to a halogen atom, with a compound having the partial structure represented by the formula (3) in which a hydrogen atom is bonded to a nitrogen atom bonded to each of the cyclic structure F and the cyclic structure G, in the presence of a catalyst (e.g., tetrakis(triphenylphosphine)palladium).

Combination of First Material and Second Material

In the exemplary embodiment, a combination of the first and second materials respectively having specific structures is used in the emitting layer. Such a combination can be found by measuring transient PL.

Correlation between the first material and the second material will be described based on the transient PL.

Figure 2:
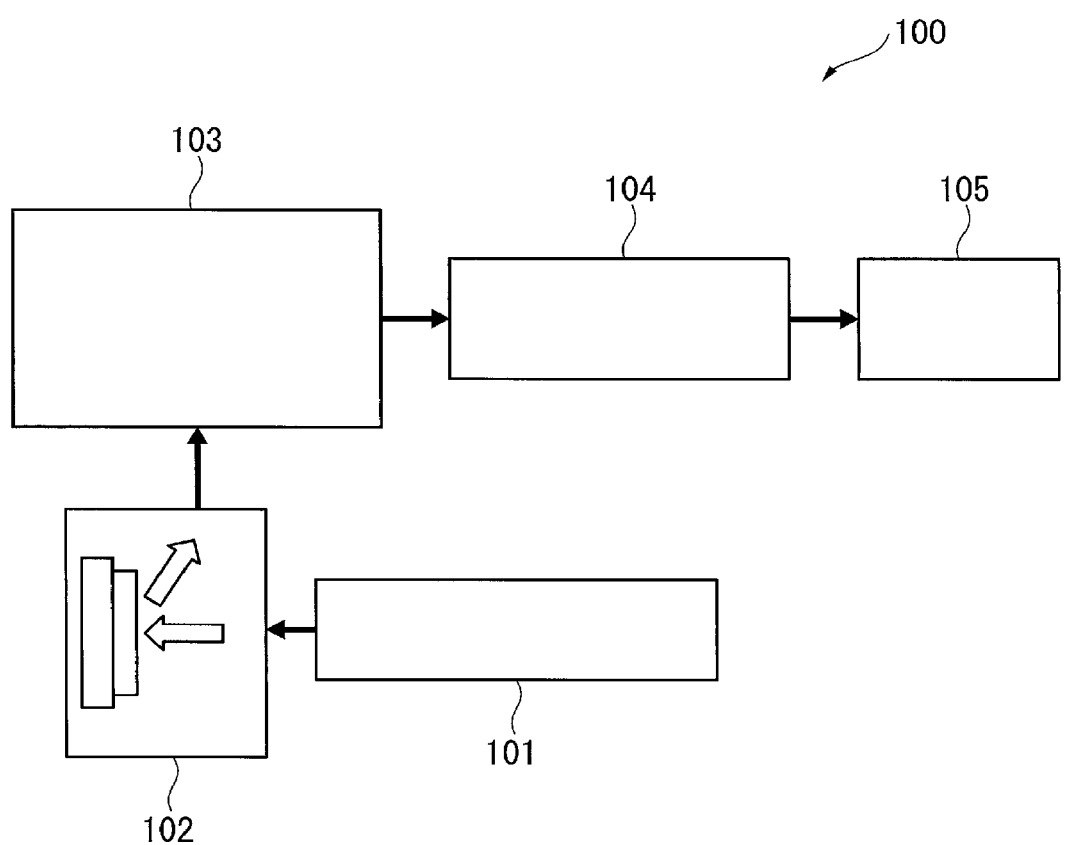
FIG. 2 is a schematic illustration of a device for measuring a transient PL.

FIG. 2 is a schematic illustration of a device for measuring the transient PL.

In the exemplary embodiment, a transient PL measuring device 100 includes a pulse laser 101 configured to irradiate light having a predetermined wavelength, a sample chamber 102 configured to house a measurement sample, a spectrometer 103 configured to disperse the light irradiated from the measurement sample, a streak camera 104 configured to produce a two-dimensional image, and a personal computer 105 configured to import and analyze the two-dimensional image. It should be noted that the transient PL is measured not only by the device described in the exemplary embodiment but also by any device.

The sample to be housed in the sample chamber 102 is obtainable by forming on a quartz substrate a thin film that is made of a matrix material doped with a doping material at a concentration of 12 mass %.

The thin film sample housed in the sample chamber 102 is irradiated with pulse laser from the pulse laser 101 to be excited. Light is emitted from a 90-degree direction of the excited light, dispersed by the spectrometer 103, and formed into a two-dimensional image through the streak camera 104. In the thus-obtained two-dimensional image, an ordinate axis corresponds to time, an abscissa axis corresponds to a wavelength, and a bright spot corresponds to a luminous intensity. The two-dimensional image is taken at a predetermined time axis, thereby obtaining an emission spectrum with an ordinate axis representing luminous intensity and an abscissa axis representing wavelength. Further, the two-dimensional image is taken at a wavelength axis, thereby obtaining a decay curve with an ordinate axis representing the logarithm of luminous intensity and an abscissa axis representing time.

For instance, a thin film sample A was prepared using a reference compound H1 below as a matrix material and a compound D1 below as a doping material, and transient PL was measured.

[Formula 60]

(Reference Compound H1)

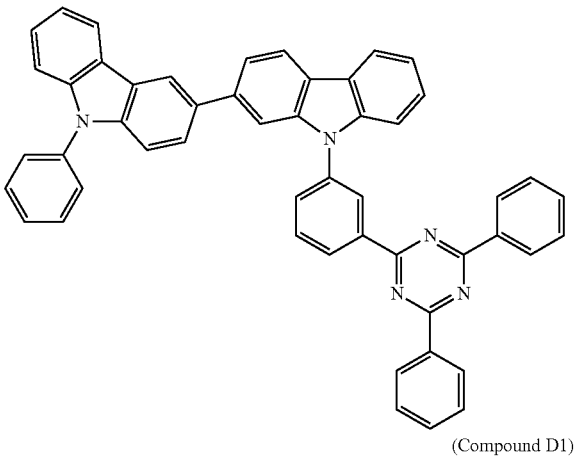

(Compound D1)

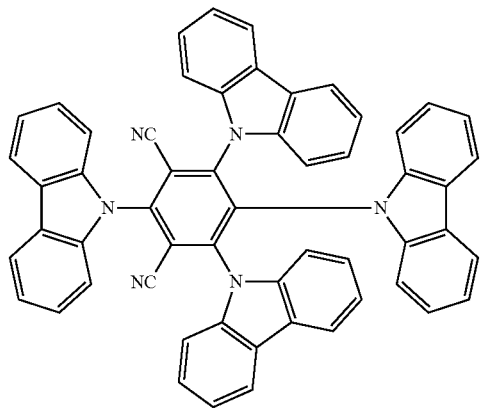

A luminescence spectrum of a co-deposition film of the thin film sample A containing the reference compound H1 and the compound D1 exhibited a larger luminous intensity at a long-wavelength side than a peak wavelength of a luminescence spectrum of the original organic molecule (the compound D1). It is presumed that such an increase in the luminous intensity at the long-wavelength side is caused by formation of exciplexes due to physical bonding between the organic molecules of the matrix material and the doping material. In general, the exciplexes are formed by physically bonding different types of organic molecules. This is because an emission level in the exciplexes is formed closer to the long-wavelength side than an emission level in the organic molecule of the doping material.

Moreover, a triplet energy of the reference compound H1 is higher than a triplet energy of the compound D1. Based on this, it is considered that the luminescence spectrum observed in the transient PL is derived from the compound D1 having a triplet energy lower than that of the reference compound H1 or derived from newly formed exciplexes. It is also found that such a highly accepting compound having a CN group (e.g., the compound D1) cannot hold excitons even when the matrix material is selected only because of a high triplet energy.

The behavior of delayed fluorescence can be analyzed based on the decay curve obtained by the transient PL measurement. The transient PL is a process where a sample is irradiated with a pulse laser to be excited, and a decay behavior (transient characteristics) of PL emission after the irradiation is measured. PL emission using a TADF material is divided into an emission component from singlet excitons generated by the first PL excitation and an emission component from singlet excitons generated via triplet excitons. The lifetime of the singlet excitons generated by the first PL excitation is in a nano-second order and considerably short. Emission from these singlet excitons thus decays immediately after the irradiation with the pulse laser.

In contrast, delayed fluorescence, which is emission from the singlet excitons generated via long-life triplet excitons, decays slowly. There is thus a large difference in time between emission from the singlet excitons generated by the first PL excitation and emission from the singlet excitons generated via triplet excitons. Therefore, a luminous intensity resulting from the delayed fluorescence can be obtained.

Respective decay curves of the thin film sample A and a thin film sample B were analyzed. The thin film sample B was prepared in the same manner as described above using a reference compound H2 below as the matrix material and the compound D1 as the doping material.

[Formula 61]

Reference Compound H2)

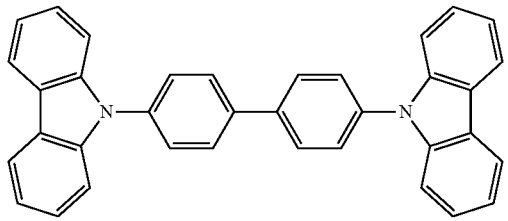

Figure 3:
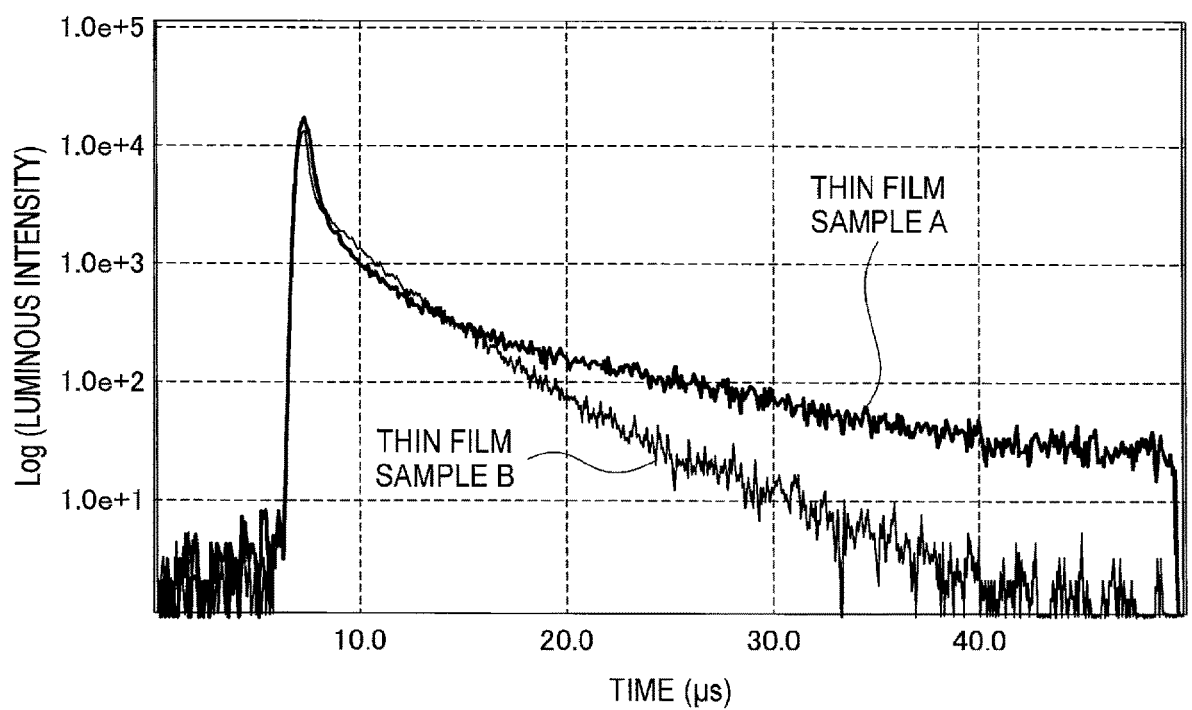
FIG. 3 shows an example of a decay curve of the transient PL.

FIG. 3 shows a decay curve obtained from transient PL measured using each of the thin film samples A and B.

In both of the thin film samples A and B, the compound D1 (i.e., a delayed fluorescent compound) is used as the doping material and is dispersed in the matrix material. Accordingly, it is presumed that the transient PL of the co-deposition film of each of the thin film samples is to be observed as a monoexponential function. However, in the transient PL of the co-deposition film of the thin film sample A, a curved part derived from the delayed fluorescence in the decay curve is observed as a luminescence component expressed by a non-monoexponential function as shown in FIG. 3. It is considered that the above observation as the monoexponential function is caused by energy transfer between the emission level of the exciplexes and the emission level of the compound D1. On the other hand, in the transient PL of the co-deposition film of the thin film sample B, a curved part derived from the delayed fluorescence in the decay curve is observed as a luminescence component expressed by the monoexponential function as shown in FIG. 3. Accordingly, it is presumed that a combination of the reference compound H2 and the compound D1 is unlikely to form exciplexes.

Based on the above study, it is confirmed that selection of a suitable combination of the matrix material and the doping material through an observation of the transient PL luminescence spectrum of the co-deposition films allows the matrix material to trap the triplet energy of the doping material. When an unsuitable combination of the matrix material and the doping material is selected, it is confirmed that triplet energy of the excitons cannot be effectively trapped due to formation of the exciplexes of the matrix material and the doping material even when the triplet energy of the matrix material is large. It is considered that, when the trapping of the triplet energy is weak, a part of the decay curve is observed as the non-monoexponential function and a thermal deactivation mode caused by the formation of the exciplexes increasingly appears to decrease the luminous efficiency. Since the exciplexes are formed at the long-wavelength side of the transient PL luminescence spectrum as described above, the exciplexes are considered to have a triplet energy lower than that of the original molecule. In other words, it is expected that the energy is transferred to a lower triplet energy state of the exciplexes to decrease the luminous efficiency in a non-emission mode.

Based on the above study of the transient PL, it is found crucial to combine the first material with the second material so that the exciplexes are unlikely to be formed even when the first material and the second material are adjacent to each other in the emitting layer.

It is preferable that the compounds for the first material and the second material according to the exemplary embodiment are selectively combined so that the exciplexes are unlikely to be formed. The formation of the exciplexes can be confirmed by the above-described transient PL measurement of the co-deposition films.

In the exemplary embodiment, it is preferable that the first material and the second material are selected from a compound satisfying a relationship represented by a numerical formula (Numerical Formula 1) below between an energy gap $T_{77K}(M1)$ at 77K of the first material and an energy gap $T_{77K}(M2)$ at 77K of the second material. The energy gap at 77K will be described later.

$$T_{77K}(M1) > T_{77K}(M2) \qquad \text{(Numerical Formula 1)}$$

Delayed Fluorescence

An emission decay curve with an ordinate axis representing luminous intensity and an abscissa axis representing time can be obtained by the transient PL measurement. Based on the emission decay curve, a fluorescence intensity ratio between fluorescence emitted from a singlet state generated by photo-excitation and delayed fluorescence emitted from a singlet state generated via a triplet state can be estimated. In a delayed fluorescent material, a ratio of the intensity of the slowly decaying delayed fluorescence to the intensity of the promptly decaying fluorescence is relatively large. Herein, the delayed fluorescent material refers to a material having an integrated value of a time-dependent luminous intensity at and after the elapse of 1 micro second after photo-excitation, the integrated value being 5% or more of an integrated value of a time-dependent luminous intensity within 1 micro second after photo-excitation, in the emission decay curve measured at the room temperature.

However, some delayed fluorescent materials have an extremely small ratio of the triplet state in the excited states generated by the photo-excitation, so that only a slight delayed fluorescence is observed despite the inherently delayed-fluorescent materials. Such materials are defined as the delayed fluorescent material with a proviso that a ratio of an emission via the singlet state is larger than a ratio of non-radiational deactivation in a course where the triplet state is relaxed to the ground state at the room temperature. The measurement of the transient PL herein needs to be conducted under conditions that exciplexes are not formed and a quencher and the like in the triplet state are absent.

Relationship with Respect to Ionization Potential

In general, a material having a large ionization potential is referred to as an acceptor molecule and a material having a small ionization potential is referred to as a donor molecule. When the acceptor molecule is adjacent to the donor molecule, it is presumed that exciplexes are easily formed. The second material of the exemplary embodiment has a CN group exhibiting a strong acceptor property. For this reason, it is considered that the second material and an aminic material (i.e., a general hole transporting material of the organic EL device) easily form the exciplexes.

In a combination of the reference compound H1 and the compound D1 (the second material), the ionization potential of the doping material in a form of the compound D1 is larger than the ionization potential of the matrix material in a form of the reference compound H1. In this combination, the exciplexes are formed at a high probability. On the other hand, in a combination of the reference compound H2 and the compound D1, since the ionization potential of the reference compound H2 is larger than the ionization potential of the compound D1, the formation of the exciplexes can be efficiently inhibited. Each of the reference compound H1 and the reference compound H2 is a compound having a dicarbazole skeleton. It is generally known that the donor property differs depending on a bonding pattern of carbazole skeletons. In the reference example, it is known that the reference compound H1 has a smaller ionization potential and a stronger donor property.

Further, an ionization potential of a reference compound H3 below is larger than the ionization potential of the compound D1. Accordingly, a combination of the reference compound H3 and the compound D1 can efficiently inhibit the formation of the exciplexes.

[Formula 62]

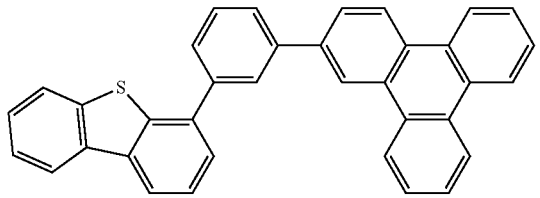

(Reference Compound H3)

Since a compound (e.g., the reference compound H3) having a partial structure in which two or more six-membered rings are fused to a cyclic structure including a sulfur atom and an oxygen atom has a larger ionization potential than an ionization potential of the carbazole compound (e.g., the reference compound H2), the exciplexes are unlikely to be formed. Moreover, since this compound has a large triplet energy, the compound can efficiently trap the triplet energy of the doping material and is strong in structure, so that a lifetime of the organic EL device can be prolonged.

Accordingly, in the organic EL device 1 in the exemplary embodiment, the luminous efficiency of the organic EL device can be improved and the lifetime thereof can be prolonged by containing the compound with the partial structure represented by the formula (1) (i.e., the first material) and the compound (i.e., the second material) in the emitting layer in a manner to satisfy the relationship represented by the numerical formula (Numerical Formula 1).

In the organic EL device 1 in the exemplary embodiment, it is preferable to combine the first material with the second material so that the ionization potential IP(M2) of the second material is smaller than the ionization potential IP(M1) of the first material. Specifically, the ionization potential Ip(M1) of the first material and the ionization potential IP(M2) of the second material preferably satisfy a relationship of a numerical formula (Numerical Formula 3) below.

$$Ip(M1)>Ip(M2) \quad \text{(Numerical Formula 3)}$$

In the exemplary embodiment, the ionization potential Ip(M1) of the first material is preferably 5.9 eV or more.

The formation of the exciplexes can be inhibited by satisfying the above relationship.

In the exemplary embodiment, when the second material having a cyano group is used, the exciplexes are easily formed in combination with the first material in a form of the aminic compound. It is considered that the exciplexes are easily formed in the emitting layer since the second material having a cyano group has a large ionization potential and the aminic compound has a small ionization potential.

Accordingly, for instance, when the second material having the partial structure represented by the formula (2) and the partial structure represented by the formula (3) in one molecule is used, the first material to be used is preferably a non-aminic compound.

It should be noted that the ionization potential can be measured using a photoelectron spectroscopy device under the atmosphere. Specifically, a material was irradiated with light and the amount of electrons generated by charge separation was measured. The measuring device may be, for instance, a photoelectron spectroscopy device manufactured by RIKEN KEIKI Co., Ltd. (device name: AC-3).

Since the first material in the exemplary embodiment has a large triplet energy, the triplet energy can be efficiently trapped within the emitting layer. Moreover, the first material in the exemplary embodiment has a large ionization potential to be unlikely to form the exciplexes in combination with the second material and unlikely to form an aggregate and the like having a small triplet energy. Accordingly, the first material in the exemplary embodiment can improve the luminous efficiency of the organic EL device.

Moreover, the second material having a CN group has a high acceptor property, so that the second material tends to trap electrons to inhibit electron transfer within the emitting layer. Accordingly, when the hole transporting property of the first material is too high relative to the electron transporting property thereof, the holes and the excited energy are transferred to the cathode and the organic layer formed near the cathode, thereby decreasing the luminous efficiency. Since the first material in the exemplary embodiment has adequate hole transporting property and electron transporting property, the luminous efficiency can be further improved. Further, since the first material has a rigid structure with the fused rings, a chemical change due to heat and a physical change of the thin film are small, so that the lifetime of the organic EL device can be prolonged.

ΔST

In the exemplary embodiment, a difference ΔST(M2) between a singlet energy S(M2) of the second material and the energy gap $T_{77K}$(M2) at 77K of the second material preferably satisfies a relationship of a numerical formula (Numerical Formula 2) below.

$$\Delta ST(M2) = S(M2) - T_{77K}(M2) < 0.3 \text{ eV} \quad \text{(Numerical Formula 2)}$$

ΔST(M2) is preferably less than 0.2 [eV].

From quantum chemical viewpoint, a decrease in the energy difference (ΔST) between the singlet energy S and the triplet energy T can be achieved by a small exchange interaction therebetween. Physical details of the relationship between ΔST and the exchange interaction are exemplarily described in Reference Documents 1 and 2 below:

Reference Document 1: Organic EL Symposium, proceeding for the tenth meeting edited by Chihaya Adachi et al., S2-5, p 11-12; and Reference Document 2: Organic Photochemical Reaction Theory edited by Katsumi Tokumaru, Tokyo Kagaku Dojin Co., Ltd. (1973).

Such a material can be synthesized according to molecular design based on quantum calculation. Specifically, the material is a compound in which a LUMO electron orbit and a HOMO electron orbit are localized to avoid overlapping.

Examples of the compound having a small ΔST used as the second material of the exemplary embodiment include compounds in which a donor element is bonded to an acceptor element in a molecule and ΔST is in a range of 0 eV or more and less than 0.3 eV in view of electrochemical stability (oxidation-reduction stability).

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that ΔST can be further reduced by the interaction of the molecules. In such a case, ΔST can be extremely small in a range from 0 eV to 0.2 eV.

TADF Mechanism

As described above, when ΔST(M2) of the second material is small, inverse intersystem crossing from the triplet level of the second material to the singlet level thereof is easily caused by heat energy given from the outside. An energy state conversion mechanism to perform spin exchange from the triplet state of electrically excited excitons within the organic EL device to the singlet state by inverse intersystem crossing is referred to as TADF Mechanism.

In the organic EL device of the exemplary embodiment, the second material is preferably a compound having a small ΔST(M2) so that inverse intersystem crossing from the triplet energy level of the second material to the singlet energy level thereof is easily caused by a heat energy given from the outside.

FIG. 4 shows an example of a relationship in energy levels of the first and second materials in the emitting layer. In FIG. 4, S0 represents a ground state, $S1_H$ represents a lowest singlet state of the first material, $T1_H$ represents a lowest triplet state of the first material, $S1_D$ represents a lowest singlet state of the second material, and $T1_D$ represents a lowest triplet state of the second material. A dashed arrow represents energy transfer between the excited states. As shown in FIG. 4, when a material having a small ΔST(M2) is used as the second material, energy is transferred to the lowest singlet state $S1_D$ of the second material or the lowest triplet state $T1_D$ of the second material by Dexter energy transfer from the lowest triplet state $T1_H$ of the first material. Further, inverse intersystem crossing from the lowest triplet state $T1_D$ of the second material to the lowest singlet state $S1_D$ can be caused by heat energy. As a result, fluorescence from the lowest singlet state $S1_D$ of the second material can be observed. It is inferred that the internal quantum efficiency can be theoretically raised up to 100% also by using delayed fluorescence by the TADF mechanism.

It should be noted that the relationship in the energy level between the first material and the second material as shown in FIG. 4 is not exhaustive. For instance, the emitting layer may be formed using the second material having a small ΔST(M2) so that the inverse intersystem crossing easily occurs from the lowest triplet state $T1_D$ to the lowest singlet state $S1_D$ by heat energy and energy is transferred from the lowest singlet state $S1_D$ of the second material to the lowest singlet state $S1_H$ of the first material.

Relationship Between Triplet Energy and Energy Gap at 77K

Description will be made on a relationship between a triplet energy and an energy gap at 77K. In the exemplary embodiment, the energy gap at 77 [K] is different from a typical triplet energy in some aspects.

Triplet energy is measured as follows. Firstly, a compound (measurement target) is deposited on a quartz substrate to prepare a sample, or alternatively, a solution in which a compound (measurement target) is dissolved in an adequate solvent is encapsulated in a quartz glass tube to prepare a sample. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. The triplet energy is calculated by a predetermined conversion equation based on a wavelength value at an intersection of the tangent and the abscissa axis.

The compound used in the exemplary embodiment is preferably a compound having a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. When the measurement is conducted using a thin film, a compound (measurement target) is deposited at a film thickness of 100 nm on a quartz substrate to prepare a sample. A phosphorescent spectrum (ordinate axis: phosphorescent luminous intensity, abscissa axis: wavelength) of the sample was measured at a low temperature (77K). A tangent was drawn to the rise of the phosphorescent spectrum on the short-wavelength side. An energy amount was calculated as the energy gap $T_{77K}$ at 77K according to a conversion equation 1 below based on a wavelength value $\lambda_{edge}$ (nm) at an intersection of the tangent and the abscissa axis.

$$T_{77K} [\text{eV}] = 1239.85/\lambda_{edge} \quad \text{Conversion Equation 1:}$$

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent was increased as the curve rose (i.e., a value of the ordinate axis was increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being the closest to the short-wavelength side and having the maximum inclination is defined as a tangent to the rise of the phosphorescence spectrum on the short-wavelength side.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

Singlet Energy S

Singlet energy S is measured as follows.

A compound (measurement target) is deposited at a film thickness of 100 nm on a quartz substrate to prepare a sample. A luminescence spectrum (ordinate axis: luminous intensity, abscissa axis: wavelength) of the sample is measured at a normal temperature (300K). A tangent is drawn to the rise of the luminescence spectrum on the short-wavelength side. The singlet energy S is calculated by a predetermined conversion equation 2 below based on a wavelength value $\lambda_{edge}$ (nm) at an intersection of the tangent and the abscissa axis.

$$S(eV)=1239.85/\lambda_{edge} \quad \text{Conversion Equation 2:}$$

An absorption spectrum is measured with a spectrophotometer. For instance, a spectrophotometer (U3310 manufactured by Hitachi, Ltd.) is usable.

The tangent to the rise of the emission spectrum on the short-wavelength side is drawn as follows. While moving on a curve of the emission spectrum from the short-wavelength side to the maximum spectral value closest to the short-wavelength side among the maximum spectral values, a tangent is checked at each point on the curve toward the long-wavelength of the emission spectrum. An inclination of the tangent was increased as the curve rose (i.e., a value of the ordinate axis was increased). A tangent drawn at a point of the maximum inclination (i.e., a tangent at an inflection point) is defined as the tangent to the rise of the luminescence spectrum on the short-wavelength side.

When the measurement result of the sample deposited on the quartz substrate is significantly different from the measurement result of the solution, formation of molecule aggregate, a strong interaction with the solvent and the like are conceivable as the cause. Accordingly, the above measurement may be conducted using the sample prepared by co-depositing on the quartz substrate a compound (measurement target) and an appropriate material having a large energy gap not to form exciplexes.

In the exemplary embodiment, a difference between the singlet energy S and the energy gap $T_{77K}$ is defined as $\Delta ST$.

In the organic EL device of the exemplary embodiment, the second material contained in the emitting layer preferably emits light.

In the organic EL device of the exemplary embodiment, the emitting layer preferably contains no metal complex.

Substrate

A substrate is used as a support for the organic EL device. For instance, glass, quartz, plastics and the like are usable as the substrate. A flexible substrate is also usable. The flexible substrate is a bendable substrate, which is exemplified by a plastic substrate formed of polycarbonate, polyarylate, polyethersulfone, polypropylene, polyester, polyvinyl fluoride, and polyvinyl chloride. Moreover, an inorganic vapor deposition film is also usable.

Anode Metal, alloy, an electrically conductive compound and a mixture thereof, which have a large work function, specifically, of 4.0 eV or more, is preferably usable as the anode formed on the substrate. Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), or nitrides of a metal material (e.g., titanium nitride) are usable.

The above materials are typically deposited as a film by sputtering. For instance, indium zinc oxide can be deposited as a film by sputtering using a target that is obtained by adding zinc oxide in a range from 1 mass % to 10 mass % to indium oxide. Moreover, for instance, indium oxide containing tungsten oxide and zinc oxide can be deposited as a film by sputtering using a target that is obtained by adding tungsten oxide in a range from 0.5 mass % to 5 mass % and zinc oxide in a range from 0.1 mass % to 1 mass % to indium oxide. In addition, vapor deposition, coating, ink jet printing, spin coating and the like may be used for forming a film.

Among EL layers formed on the anode, a hole injecting layer formed adjacent to the anode is formed of a composite material that facilitates injection of holes irrespective of the work function of the anode. Accordingly, a material usable as an electrode material (e.g., metal, alloy, an electrically conductive compound, a mixture thereof, and elements belonging to Groups 1 and 2 of the periodic table of the elements) is usable as the material for the anode.

The elements belonging to Groups 1 and 2 of the periodic table of the elements, which are materials having a small work function, namely, an alkali metal such as lithium (Li) and cesium (Cs) and an alkaline earth metal such as magnesium (Mg), calcium (Ca) and strontium (Sr), alloy thereof (e.g., MgAg, AlLi), a rare earth metal such as europium (Eu) and ytterbium (Yb), and alloy thereof are also usable as the material for the anode. When the anode is formed of the alkali metal, alkaline earth metal and alloy thereof, vapor deposition and sputtering are usable. Further, when the anode is formed of silver paste and the like, coating, ink jet printing and the like are usable.

Cathode

Metal, alloy, an electrically conductive compound, a mixture thereof and the like, which have a small work function, specifically, of 3.8 eV or less, is preferably usable as a material for the cathode. Specific examples of the material for the cathode include: the elements belonging to Groups 1 and 2 of the periodic table of the elements, namely, an alkali metal such as lithium (Li) and cesium (Cs) and an alkaline earth metal such as magnesium (Mg), calcium (Ca) and strontium (Sr); alloy thereof (e.g., MgAg, AlLi); a rare earth metal such as europium (Eu) and ytterbium (Yb); and alloy thereof.

When the cathode is formed of the alkali metal, alkaline earth metal and alloy thereof, vapor deposition and sputtering are usable. Moreover, when the anode is formed of silver paste and the like, coating, ink jet printing and the like are usable.

By providing an electron injecting layer, various conductive materials such as Al, Ag, ITO, graphene and indium tin oxide containing silicon or silicon oxide are usable for forming the cathode irrespective of the magnitude of the work function. The conductive materials can be deposited as a film by sputtering, ink jet printing, spin coating and the like.

Hole Injecting Layer

A hole injecting layer is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule compound, such that 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenyl carbazole-3-yl)-N-phenylamino]-9-phenyl carbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

Moreover, a high-molecule compound (e.g., an oligomer, dendrimer and polymer) is also usable as the highly hole-injectable substance. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido] (abbreviation: PTPDMA), and poly[N,N'-bis(4-butylphenyl)-N,N'-bis(phenyl)benzidine] (abbreviation: Poly-TPD). Furthermore, the examples of the high-molecule compound include a high-molecule compound added with an acid such as poly(3,4-ethylene dioxythiophene)/poly(styrene sulfonic acid) (PEDOT/PSS), and polyaniline/poly(styrene sulfonic acid) (PAni/PSS).

Hole Transporting Layer

A hole transporting layer is a layer containing a highly hole-transportable substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/VS or more.

A carbazole derivative (e.g., CBP, CzPA, and PCzPA) and an anthracene derivative (e.g., t-BuDNA, DNA, and DPAnth) may be used for the hole transporting layer. A high polymer compound such as poly(N-vinylcarbazole) (abbreviation: PVK) and poly(4-vinyltriphenylamine) (abbreviation: PVTPA) is also usable.

However, any substance having a hole transporting property higher than an electron transporting property may be used in addition to the above substances. A highly hole-transportable substance may be provided in the form of a single layer or a laminated layer of two or more layers of the above substance.

Electron Transporting Layer

An electron transporting layer is a layer containing a highly electron-transportable substance. As the electron transporting layer, 1) a metal complex such as an aluminum complex, beryllium complex and zinc complex, 2) heteroaromatic compound such as an imidazole derivative, benzimidazole derivative, azine derivative, carbazole derivative, and phenanthroline derivative, and 3) a high-molecule compound are usable. Specifically, as a low-molecule organic compound, a metal complex such as Alq, tris(4-methyl-8-quinolinato)aluminum (abbreviation: Almq3), bis(10-hydroxybenzo[h]quinolinato)beryllium (abbreviation: BeBq2), BAlq, Znq, ZnPBO and ZnBTZ are usable. In addition to the metal complex, a heteroaromatic compound such as 2-(4-biphenyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenyl)-1,2,4-triazole (abbreviation: TAZ), 3-(4-tert-butylphenyl)-4-(4-ethylphenyl)-5-(4-biphenyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) are usable. The above-described substances mostly have an electron mobility of $10^{-6}$ cm$^2$/Vs or more. However, any substance having an electron transporting property higher than a hole transporting property may be used for the electron transporting layer in addition to the above substances. The electron transporting layer may be provided in the form of a single layer or a laminated layer of two or more layers of the above substance(s).

Moreover, a high-molecule compound is also usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

An electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, a compound containing an alkali metal, alkaline earth metal and a compound thereof in the electron transportable substance, specifically, a compound containing magnesium (Mg) in Alq and the like may be used. With this compound, electrons can be more efficiently injected from the cathode.

Alternatively, a composite material provided by mixing an organic compound with an electron donor may be used for the electron injecting layer. The composite material exhibits excellent electron injecting property and electron transporting property since the electron donor generates electron in the organic compound. In this arrangement, the organic compound is preferably a material exhibiting an excellent transforming property of the generated electrons. Specifically, for instance, the above-described substance for the electron transporting layer (e.g., the metal complex and heteroaromatic compound) is usable. The electron donor may be any substance exhibiting an electron donating property to the organic compound. Specifically, an alkali metal, alkaline earth metal and a rare earth metal are preferable, examples of which include lithium, cesium, magnesium, calcium, erbium and ytterbium. Moreover, an alkali metal oxide and alkaline earth metal oxide are preferable, examples of which include lithium oxide, calcium oxide, and barium oxide. Further, Lewis base such as magnesium oxide is also usable. Furthermore, tetrathiafulvalene (abbreviation: TTF) is also usable.

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Film Thickness

The thickness of each organic layer of the organic EL device in the exemplary embodiment is subject to no limitation except for the thickness particularly described above. However, the thickness is typically preferably in a range of several nanometers to 1 µm because an excessively thin film is likely to entail defects such as a pin hole while an excessively thick film requires high applied voltage and deteriorates efficiency.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, carbon atom(s) included in the substituent is not counted as the ring carbon atoms. The same applies to the "ring carbon atoms" described below, unless particularly noted. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring or a naphthalene ring is substituted, for instance, by an alkyl group, the carbon atoms of the alkyl group are not counted as the ring carbon atoms. For instance, when a fluorene ring (inclusive of a spirofluorene ring) is bonded as a substituent to a fluorene ring, the carbon atoms of the fluorene ring as a substituent are not counted as the ring carbon atoms.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., hydrogen atom(s) for saturating the valence of the atom which forms the ring) and atom(s) in a substituent by which the ring is substituted are not counted as the ring atoms. The same applies to the "ring atoms" described below, unless particularly noted. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming a substituent are not counted as the ring atoms. For instance, when a fluorene ring (inclusive of a spirofluorene ring) is bonded as a substituent to a fluorene ring, the atoms of the fluorene ring as a substituent are not included in the ring atoms.

Next, each of substituents described in the above formulae herein will be described.

Examples of the aryl group having 6 to 30 ring carbon atoms (occasionally referred to as an aromatic hydrocarbon group) in the exemplary embodiment are a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, more preferably 6 to 14 ring carbon atoms, further preferably 6 to 12 ring carbon atoms. Among the aryl group, a phenyl group, biphenyl group, naphthyl group, phenanthryl group, terphenyl group and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms later described in the exemplary embodiment.

The heterocyclic group (occasionally referred to as heteroaryl group, heteroaromatic ring group or aromatic heterocyclic group) having 5 to 30 ring atoms preferably contains at least one atom selected from the group consisting of nitrogen, sulfur, oxygen, silicon, selenium atom and germanium atom, and more preferably contains at least one atom selected from the group consisting of nitrogen, sulfur and oxygen.

Examples of the heterocyclic group having 5 to 30 ring atoms in the exemplary embodiment are a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazol yl group is preferably substituted by a substituted or unsubstituted aryl group having 6 to 30 ring carbon atoms or a substituted or unsubstituted heterocyclic group having 5 to 30 ring atoms in the exemplary embodiment.

Moreover, the heterocyclic group may be a group derived from any one of moieties represented by formulae (XY-1) to (XY-18).

[Formula 63]

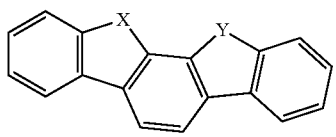
(XY-1)

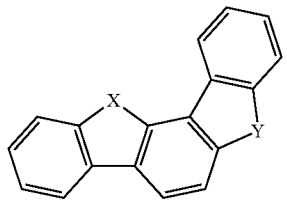
(XY-2)

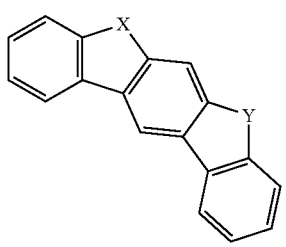
(XY-3)

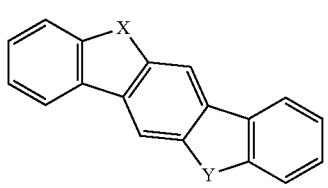
(XY-4)

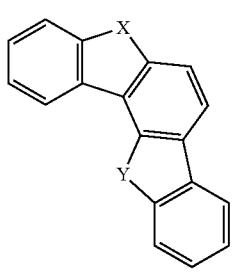
(XY-5)

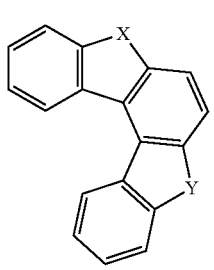
(XY-6)

[Formula 64]

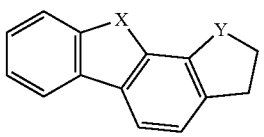
(XY-7)

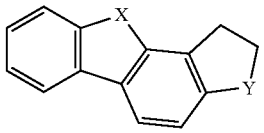
(XY-8)

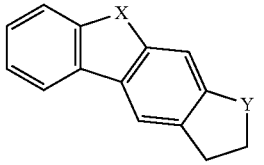
(XY-9)

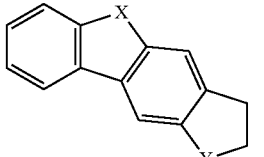
(XY-10)

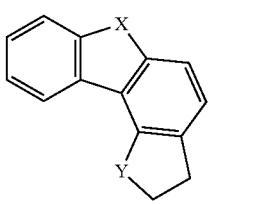
(XY-11)

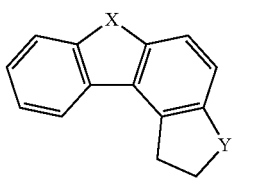
(XY-12)

[Formula 65]

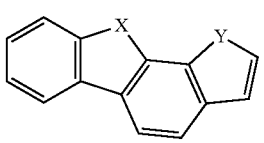
(XY-13)

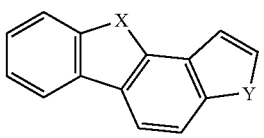
(XY-14)

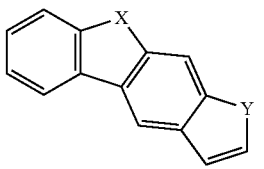
(XY-15)

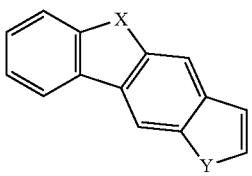

(XY-16)

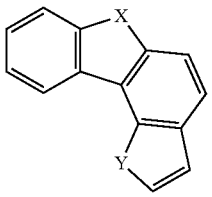

(XY-17)

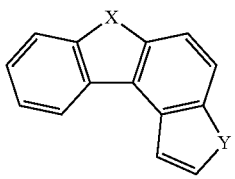

(XY-18)

In the formulae (XY-1) to (XY-18), X and Y are each independently a hetero atom, and are preferably an oxygen atom, sulfur atom, selenium atom, silicon atom or germanium atom. The moieties represented by the formulae (XY-1) to (XY-18) may each be bonded at any position to be a heterocyclic group, which may be substituted.

Examples of the substituted or unsubstituted carbazolyl group may include a group in which a carbazole ring is further fused with a ring(s) as shown in the following formulae. Such a group may be substituted. The group may be bonded at any position as desired.

[Formula 66]

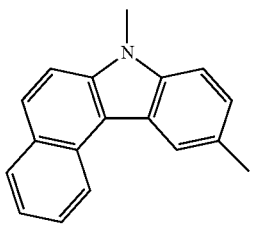

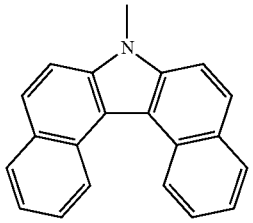

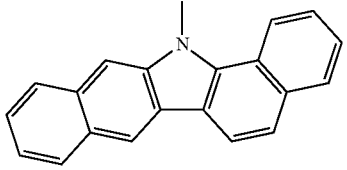

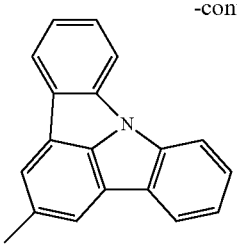

The alkyl group having 1 to 30 carbon atoms in the exemplary embodiment may be linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group in the exemplary embodiment are a cyclopropyl group, cyclobutyl group, cyclopentyl group, cyclohexyl group, 4-methylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group provided by substituting an alkyl group with a halogen atom is exemplified by one provided by substituting an alkyl group having 1 to 30 carbon atoms with one or more halogen groups. Specific examples of the above halogenated alkyl group are a fluoromethyl group, difluoromethyl group, trifluoromethyl group, fluoroethyl group, trifluoromethylethyl group, trifluoroethyl group and pentafluoroethyl group.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, triethylsilyl group, tri-n-butyl silyl group, tri-n-octyl silyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be the same or different.

Examples of the arylsilyl group having 6 to 30 ring carbon atoms in the exemplary embodiment are a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group including three of the aryl group listed as the examples of the aryl group having 6 to 30 ring carbon atoms. The triarylsilyl group preferably has 18 to 30 carbon atoms.

The alkoxy group having 1 to 30 carbon atoms in the exemplary embodiment is represented by —$OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group. The alkoxy group preferably has 1 to 20 carbon atoms.

A halogenated alkoxy group provided by substituting an alkoxy group with a halogen atom is exemplified by one provided by substituting an alkoxy group having 1 to 30 carbon atoms with one or more halogen groups.

The aryloxy group having 6 to 30 ring carbon atoms in the exemplary embodiment is represented by —$OZ_2$. $Z_2$ is exemplified by the above aryl group having 6 to 30 ring carbon atoms. The aryloxy group preferably has 6 to 20 ring carbon atoms. The aryloxy group is exemplified by a phenoxy group.

The alkylamino group having 2 to 30 carbon atoms is represented by —$NHR_V$ or —$N(R_V)_2$. $R_V$ is exemplified by the alkyl group having 1 to 30 carbon atoms.

The arylamino group having 6 to 60 ring carbon atoms is represented by —$NHR_W$ or —$N(R_W)_2$. $R_W$ is exemplified by the above aryl group having 6 to 30 ring carbon atoms.

The alkylthio group having 1 to 30 carbon atoms is represented by —$SR_V$. $R_V$ is exemplified by the alkyl group having 1 to 30 carbon atoms. The alkylthio group preferably has 1 to 20 carbon atoms.

The arylthio group having 6 to 30 ring carbon atoms is represented by —$SR_W$. $R_W$ is exemplified by the above aryl group having 6 to 30 ring carbon atoms. The arylthio group preferably has 6 to 20 ring carbon atoms.

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

Herein, a hydrogen atom includes isotope having different numbers of neutrons, specifically, protium, deuterium and tritium.

Herein, examples of substituents in the exemplary embodiment, such as the substituent meant by "substituted or unsubstituted" and the substituent in the cyclic structures A and B, are an alkenyl group, alkynyl group, aralkyl group, halogen atom, cyano group, hydroxyl group, nitro group and carboxy group, in addition to the above-described aryl group, heterocyclic group, alkyl group (linear or branched alkyl group, cycloalkyl group and haloalkyl group), alkylsilyl group, arylsilyl group, alkoxy group, aryloxy group, alkylamino group, arylamino group, alkylthio group, and arylthio group.

Among the above substituents, an aryl group, heterocyclic group, alkyl group, halogen atom, alkylsilyl group, arylsilyl group and cyano group are preferable. More preferable substituents are one listed as the preferable substituents described for each substituent.

These substituents may be further substituted by the above substituent(s). In addition, plural ones of these substituents may be mutually bonded to form a ring.

The alkenyl group is preferably an alkenyl group having 2 to 30 carbon atoms, which may be linear, branched or cyclic. Examples of the alkenyl group include a vinyl group, propenyl group, butenyl group, oleyl group, eicosapentaenyl group, docosahexaenoyl group, styryl group, 2,2-diphenylvinyl group, 1,2,2-triphenylvinyl group, 2-phenyl-2-propenyl group, cyclopentadienyl group, cyclopentenyl group, cyclohexenyl group, and cyclohexadienyl group.

The alkynyl group is preferably an alkynyl group having 2 to 30 carbon atoms, which may be linear, branched or cyclic. Examples of the alkynyl group include ethynyl, propynyl, and 2-phenylethynyl.

The aralkyl group is preferably an aralkyl group having 6 to 30 ring carbon atoms and is represented by —$Z_3$—$Z_4$. $Z_3$ is exemplified by an alkylene group corresponding to the above alkyl group having 1 to 30 carbon atoms. $Z_4$ is exemplified by the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Examples of the halogen atom include a fluorine atom, chlorine atom, bromine tom and iodine atom, among which a fluorine atom is preferable.

"Unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of a substituted ZZ group. "YY" is larger than "XX" and each of "XX" and "YY" represents an integer of 1 or more.

Herein, "XX to YY atoms" in the description of "substituted or unsubstituted ZZ group having XX to YY atoms" represent atoms of an unsubstituted ZZ group and does not include atoms of a substituent(s) of a substituted ZZ group. "YY" is larger than "XX" and each of "XX" and "YY" represents an integer of 1 or more.

The same description as the above applies to "substituted or unsubstituted" in the following compound or a partial structure thereof.

Herein, when substituents are mutually bonded to form a cyclic structure, the cyclic structure is a saturated ring, unsaturated ring or aromatic ring.

Herein, examples of the aromatic hydrocarbon group and the heterocyclic group for the linking group include a divalent or multivalent group obtained by removing at least one atom from the above-described monovalent groups.

Moreover, herein, examples of the aromatic hydrocarbon group and the heterocyclic group include cyclic structures from which the above-described monovalent groups are derived.

In the exemplary embodiment, examples of the multiple linking group including bonded 2 to 4 groups selected from the above aromatic hydrocarbon groups, the multiple linking group including bonded 2 to 4 groups selected from the above heterocyclic groups, or the multiple linking group including bonded 2 to 4 groups selected from the above aromatic hydrocarbon groups and heterocyclic groups include a divalent group including bonded 2 to 4 groups selected from the above aromatic hydrocarbon groups and heterocyclic groups. Examples of the multiple linking group including 2 to 4 groups selected from the above aromatic hydrocarbon groups and heterocyclic groups include a heterocyclic group-aromatic hydrocarbon group, aromatic hydrocarbon group-heterocyclic group, aromatic hydrocarbon group-heterocyclic group-aromatic hydrocarbon group, heterocyclic group-aromatic hydrocarbon group-heterocyclic group, aromatic hydrocarbon group-heterocyclic group-aromatic hydrocarbon group-heterocyclic group, and heterocyclic group-aromatic hydrocarbon group-heterocyclic group-aromatic hydrocarbon group. Among the above, divalent groups including one of the above aromatic hydrocarbon groups and one of the above heterocyclic groups, i.e., heterocyclic group-aromatic hydrocarbon group and aromatic hydrocarbon group-heterocyclic group, are preferable. It should be noted that specific examples of the aromatic hydrocarbon group and the heterocyclic group in the multiple linking group include the above groups described as the aromatic hydrocarbon group and the heterocyclic group.

The organic EL device of the exemplary embodiment is usable in an electronic device. Examples of the electronic device include a display unit and a light-emitting unit. Examples of the display unit include display components such as an organic EL panel module, TV, mobile phone, tablet, and personal computer. Examples of the light-emitting unit include an illuminator and a vehicle light.

According to the first exemplary embodiment, an organic electroluminescence device configured to emit light and an electronic device including the organic electroluminescence device can be provided. According to the first exemplary embodiment, a luminous efficiency of the organic electroluminescence device can be improved and a lifetime thereof can be prolonged.

Second Exemplary Embodiment

Next, an organic EL device according to a second exemplary embodiment will be described below.

In the second exemplary embodiment, the same materials and compounds as described in the first exemplary embodiment are usable, unless otherwise specified.

The organic EL device according to the second exemplary embodiment includes basically the same structure as that of the organic EL device 1 according to the first exemplary embodiment and a structure of the emitting layer as follows.

Emitting Layer

In the organic EL device in the exemplary embodiment, the emitting layer contains a first material and a second material. The first material is a compound having a different structure from that of the second material.

A singlet energy of the first material is larger than a singlet energy of the second material.

First Material

The first material in the exemplary embodiment is not particularly limited as long as having the singlet energy larger than the singlet energy of the second material. Examples of the first material in the exemplary embodiment are the examples of the first material described in the first exemplary embodiment.

Second Material

The second material in the exemplary embodiment is a compound represented by the formula (21) and satisfying the above condition (i) (i.e., at least one of $A_{31}$ and $B_{31}$ is a cyano-substituted aromatic hydrocarbon group having 6 to 30 ring carbon atoms or a cyano-substituted heterocyclic group having 6 to 30 ring atoms).

In the exemplary embodiment, the second material represented by the formula (21) preferably contains three or less cyano groups in one molecule. In other words, the second material represented by the formula (21) preferably contains one to three cyano groups in one molecule.

In the exemplary embodiment, $A_{31}$ is preferably substituted by two cyano groups.

In the exemplary embodiment, $B_{31}$ is preferably not substituted by a cyano group.

In the exemplary embodiment, preferably, $A_{31}$ and $B_{31}$ are each independently a substituted or unsubstituted aromatic hydrocarbon group having 6 to 10 ring carbon atoms, or substituted or unsubstituted heterocyclic group having 5 to 13 ring atoms.

In the exemplary embodiment, $L_{31}$ and $L_{32}$ are preferably a single bond.

In the exemplary embodiment, preferably, $L_{31}$ and $L_{32}$ are each independently a linking group and the linking group for $L_{31}$ and $L_{32}$ are each independently a substituted or unsubstituted aromatic hydrocarbon group having 6 to 10 ring carbon atoms, or substituted or unsubstituted heterocyclic group having 5 to 10 ring atoms.

When w is 0 in the formula (21), at least one of $X_{35}$ to $X_{38}$ is bonded by a single bond to at least one of $Y_{31}$ to $Y_{34}$. When w is 2 or 3, a plurality of $L_{33}$ may be mutually the same or different. A structure in which at least one of $X_{35}$ to $X_{38}$ is bonded to at least one of $Y_{31}$ to $Y_{34}$ is represented by a formula (21x) below when w is 2 and represented by a formula (21y) below when w is 3.

[Formula 67]

$$-L_{331}-L_{332}- \quad (21x)$$

$$-L_{331}-L_{332}-L_{333}- \quad (21y)$$

in the formulae (21x) and (21y), $L_{331}$ to $L_{333}$ each independently represent the same as $L_{33}$ described above. A substituent of $L_{331}$ and a substituent of $L_{332}$ may be mutually bonded to form a cyclic structure. A substituent of $L_{332}$ and a substituent of $L_{333}$ may be mutually bonded to form a cyclic structure.

In the exemplary embodiment, w is preferably 0.

In the exemplary embodiment, w is preferably 1.

In the exemplary embodiment, $A_{31}$ is preferably bonded to $L_{31}$ at a para position relative to a cyano group substituting $A_{31}$.

For instance, when $A_{31}$ is a cyano-substituted benzene ring and $A_{31}$ is bonded to $L_{31}$ at a para position relative to the cyano group, the formula (21) is represented by a formula (21a), (21b) or (21c).

[Formula 68]

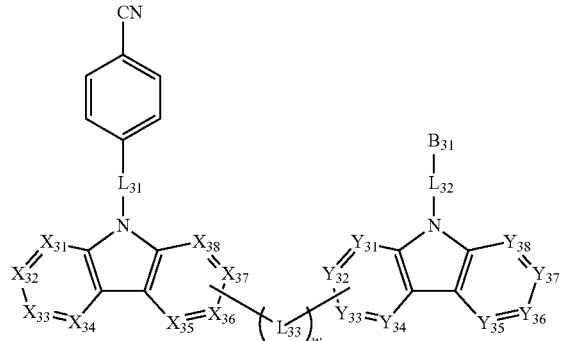

(21a)

[Formula 69]

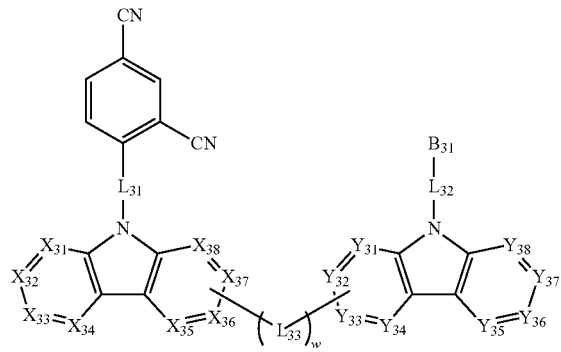

(21b)

[Formula 70]

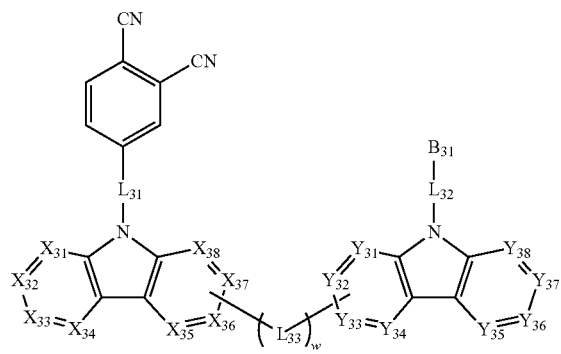

(21c)

In the formulae (21a), (21b) and (21c), $X_{31}$ to $X_{38}$, $Y_{31}$ to $Y_{38}$, $L_{31}$ to $L_{33}$, $B_{31}$ and w respectively represent the same as $X_{31}$ to $X_{38}$, $Y_{31}$ to $Y_{38}$, $L_{31}$ to $L_{33}$, $B_{31}$ and w described above.

In the exemplary embodiment, $A_{31}$ is preferably substituted by a cyano group also at a para position relative to a cyano group substituting $A_{31}$.

For instance, when $A_{31}$ is a benzene ring substituted by two cyano groups and $A_{31}$ is substituted by a cyano group also at a para position relative to the cyano group, the formula (21) is represented by a formula (22) below.

[Formula 71]

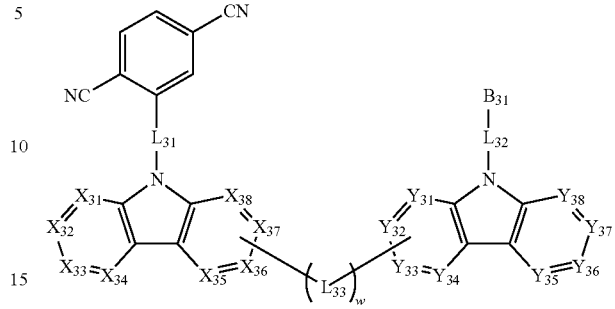

(22)

In the formula (22), $X_{31}$ to $X_{38}$, $Y_{31}$ to $Y_{38}$, $L_{31}$ to $L_{33}$, $B_{31}$ and w respectively represent the same as $X_{31}$ to $X_{38}$, $Y_{31}$ to $Y_{38}$, $L_{31}$ to $L_{33}$, $B_{31}$ and w described above.

Also in the exemplary embodiment, at least one of $A_{31}$ and $B_{31}$ is a group selected from the group consisting of a cyano-substituted phenyl group, a cyano-substituted naphthyl group, a cyano-substituted dibenzofuranyl group, and a cyano-substituted benzothiophenyl group.

In the exemplary embodiment, it is preferable that $X_{36}$ is bonded to $Y_{33}$ via $L_{33}$ or directly bonded to $Y_{33}$.

Moreover, it is preferable that $X_{36}$ is bonded to $Y_{32}$ via $L_{33}$ or directly bonded to $Y_{32}$.

Further, it is preferable that $X_{37}$ is bonded to $Y_{33}$ via $L_{33}$ or directly bonded to $Y_{33}$.

In the exemplary embodiment, the second material is preferably represented by a formula (41) below.

[Formula 72]

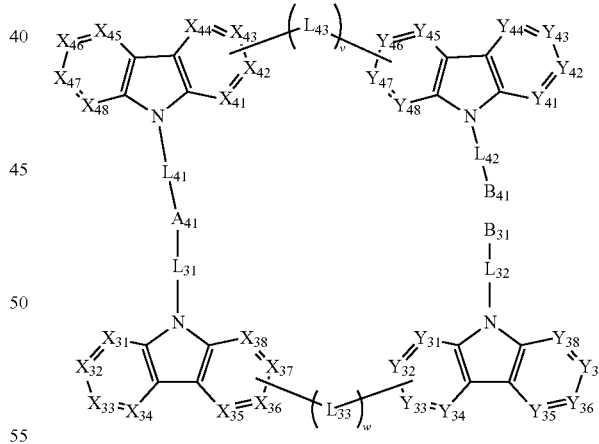

(41)

In the formula (41): $B_{31}$, $X_{31}$ to $X_{38}$, $Y_{31}$ to $Y_{38}$, $L_{31}$, $L_{32}$, $L_{33}$ and w respectively represent the same as $B_{31}$, $X_{31}$ to $X_{38}$, $Y_{31}$ to $Y_{38}$, $L_{31}$, $L_{32}$, $L_{33}$ and w in the formula (21); $A_{41}$ and $B_{41}$ are each independently a substituted or unsubstituted aromatic hydrocarbon group having 6 to 30 ring carbon atoms, or a substituted or unsubstituted heterocyclic group having 5 to 30 ring atoms; and $X_{41}$ to $X_{48}$ and $Y_{41}$ to $Y_{48}$ are each independently a nitrogen atom, a carbon atom to be bonded $R^F$, or a carbon atom to be bonded to $L_{43}$. At least one of $X_{41}$ to $X_{44}$ is a carbon atom to be bonded to $L_{43}$. At least one of $Y_{45}$ to $Y_{48}$ is a carbon atom to be bonded to $L_{43}$.

$R^F$ is each independently a hydrogen atom, halogen atom, substituted or unsubstituted aromatic hydrocarbon group having 6 to 30 ring carbon atoms, substituted or unsubstituted heterocyclic group having 5 to 30 ring atoms, substituted or unsubstituted alkyl group having 1 to 30 carbon atoms, or substituted or unsubstituted silyl group.

$L_{41}$ and $L_{42}$ are each independently a single bond or a linking group. The linking group for L41 and L42 is any one of a substituted or unsubstituted aromatic hydrocarbon group having 6 to 30 ring carbon atoms, substituted or unsubstituted heterocyclic group having 5 to 30 ring atoms, multiple linking group including 2 to 4 groups selected from the above aromatic hydrocarbon groups, multiple linking group including bonded 2 to 4 groups selected from the above heterocyclic groups, and multiple linking group including bonded 2 to 4 groups selected from the above aromatic hydrocarbon groups and heterocyclic groups.

$L_{43}$ is a substituted or unsubstituted monocyclic hydrocarbon group having 6 or less ring carbon atoms or a substituted or unsubstituted monocyclic heterocyclic group having 6 or less ring atoms.

v is an integer of 0 to 3, When v is 0, at least one of $X_{45}$ to $X_{48}$ is directly bonded to at least one of $Y_{41}$ to $Y_{44}$.

At least one of $B_{31}$, $A_{41}$ and $B_{41}$ is a cyano-substituted aromatic hydrocarbon group having 6 to 30 ring carbon atoms or a cyano-substituted heterocyclic group having 6 to 30 ring atoms.

In the exemplary embodiment, $L_{31}$, $L_{32}$, $L_{41}$ and $L_{42}$ are preferably a single bond.

In the exemplary embodiment, preferably, $L_{31}$, $L_{32}$, $L_{41}$ and $L_{42}$ are each independently a linking group and the linking group for $L_{31}$ and $L_{32}$ are each independently a substituted or unsubstituted aromatic hydrocarbon group having 6 to 10 ring carbon atoms, or substituted or unsubstituted heterocyclic group having 5 to 10 ring atoms.

When v is 2 or 3, a plurality of $L_{43}$ may be mutually the same or different.

In the exemplary embodiment, w and v are preferably 0.

Moreover, in the exemplary embodiment, w and v are preferably 1.

In the exemplary embodiment, $A_{41}$ is preferably substituted by two cyano groups.

In the exemplary embodiment, $B_{31}$ and $B_{41}$ are preferably not substituted by a cyano group.

The second material of the exemplary embodiment is preferably a luminescent material, particularly a luminescent material emitting TADF.

In the exemplary embodiment, an orientation parameter S of the emitting layer is preferably in a range from −0.5 to −0.2, more preferably in a range from −0.5 to −0.3, further preferably in a range from −0.5 to −0.4. The orientation parameter S is −0.5 when all the molecules are oriented in parallel to the substrate. The orientation parameter S is 0.0 when all the molecules are oriented at random. In the exemplary embodiment, use of the second material can inhibit a decrease in the luminous efficiency in a high current density region.

Specific examples of the second material of the exemplary embodiment are shown below. The specific examples of the second material described in the first exemplary embodiment encompass a compound satisfying the requirements of the second material in the second exemplary embodiment. Such a compound is usable for the organic EL device in the second exemplary embodiment. It should be noted that the second material according to the invention is not limited to these specific examples.

[Formula 73]

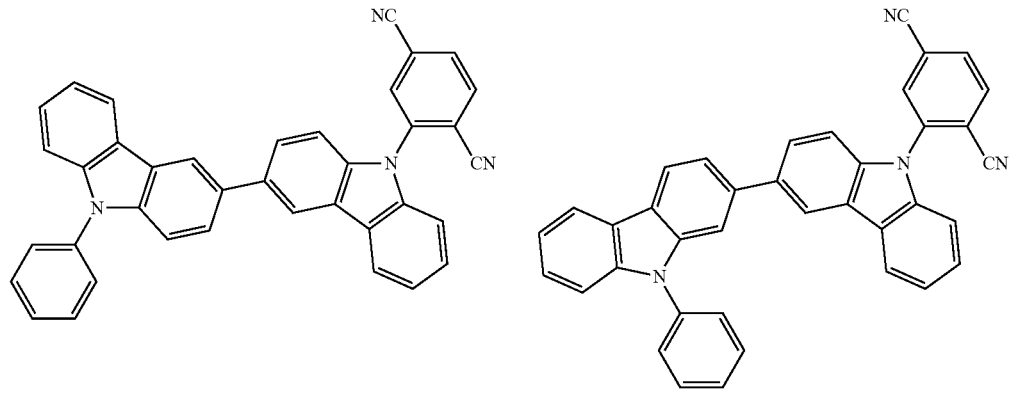

67
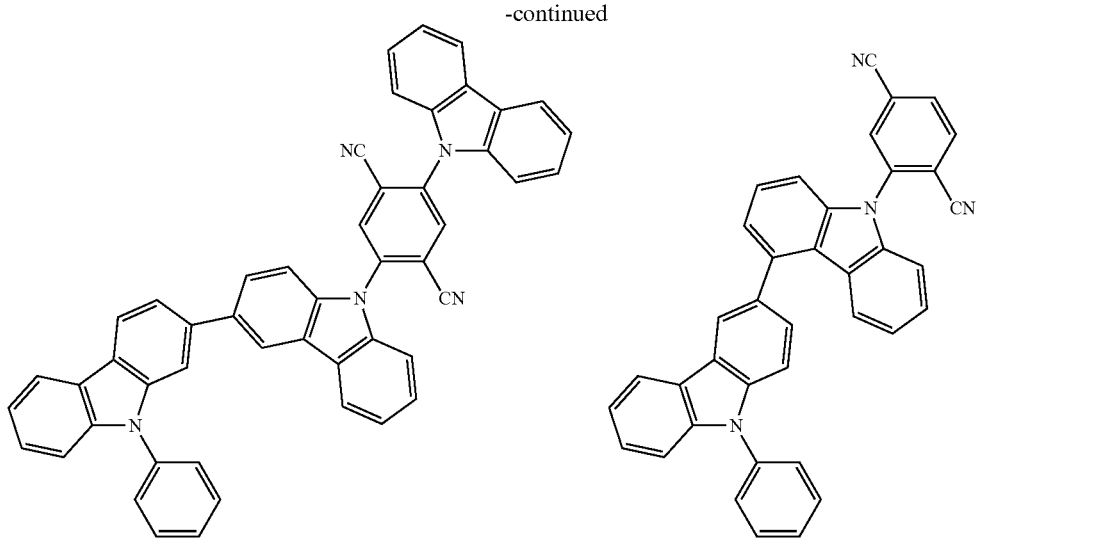
68
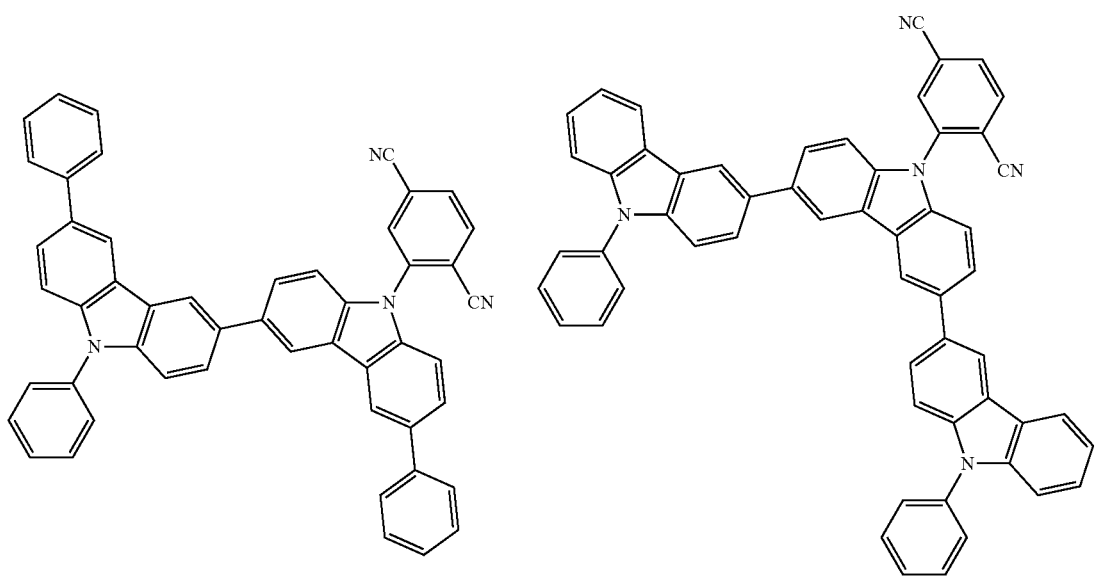
[Formula 74]
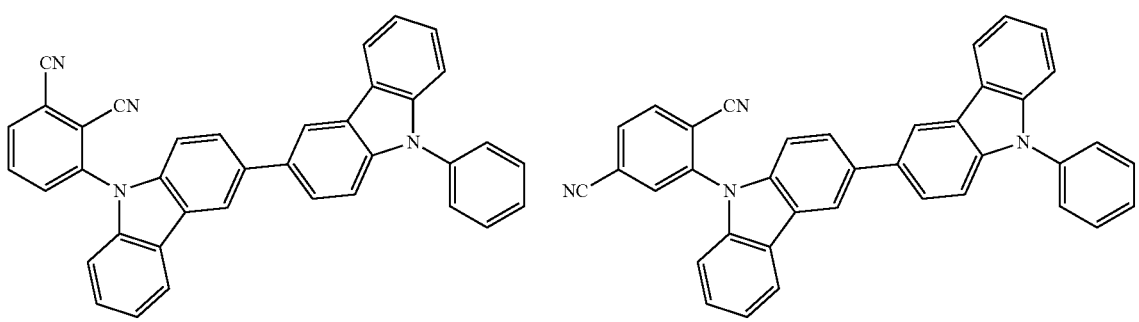

-continued
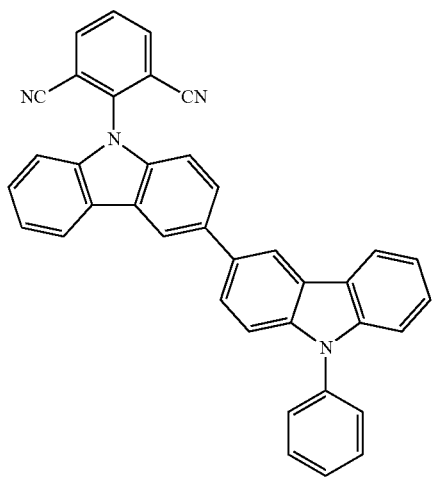
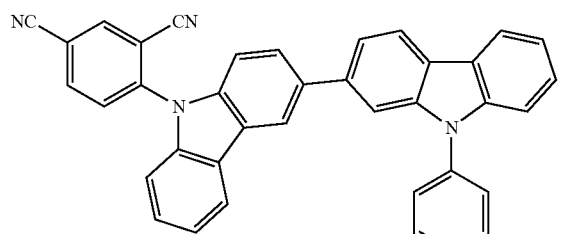
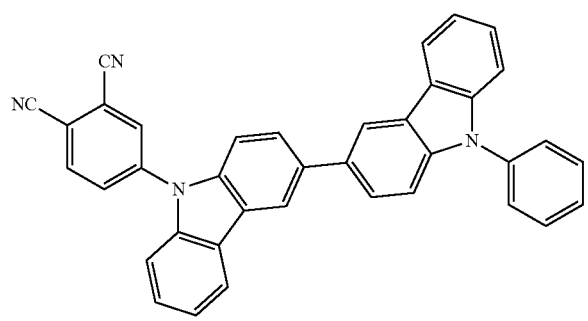
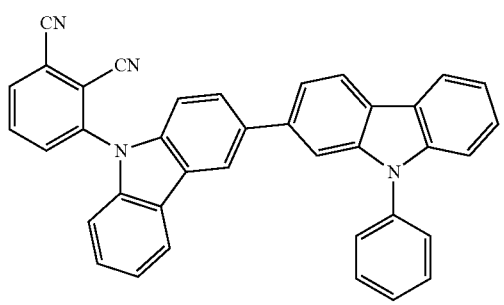
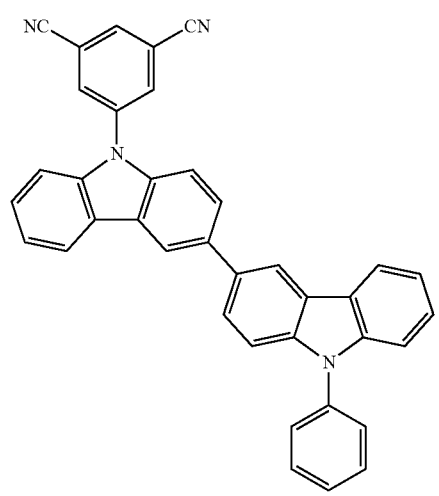
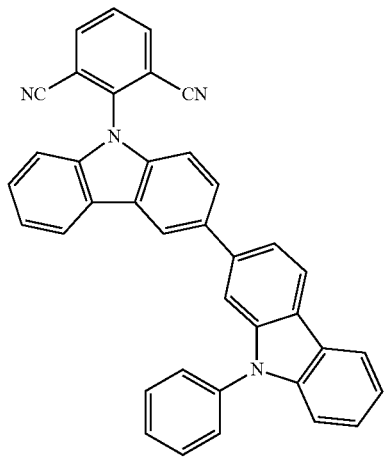
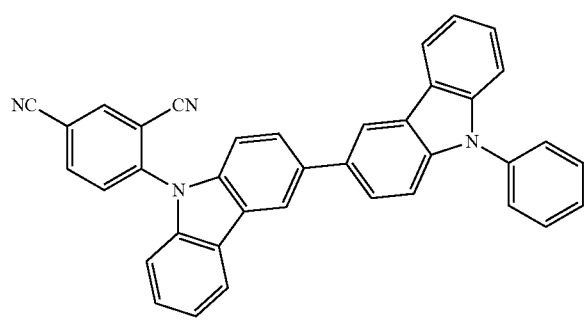
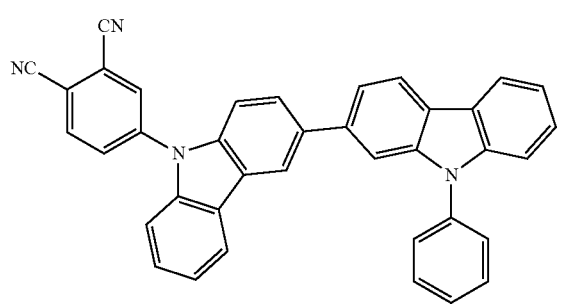

-continued
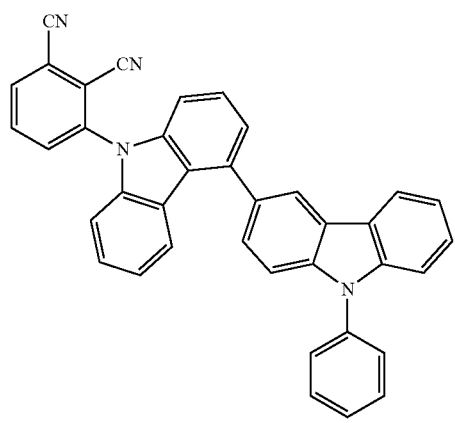
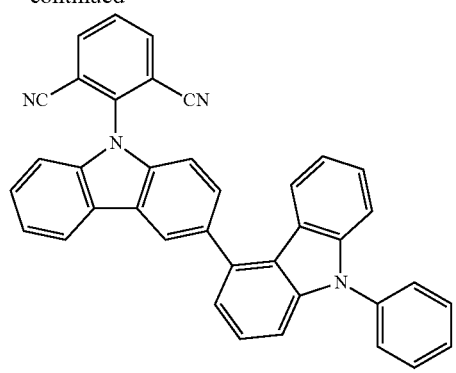
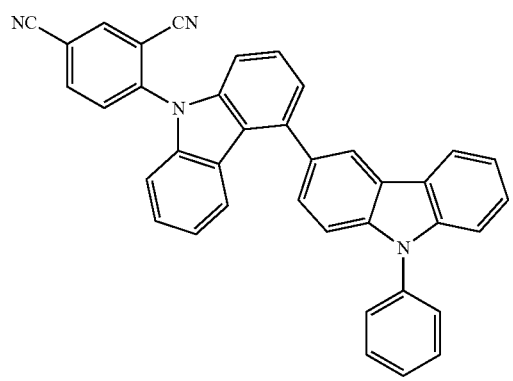
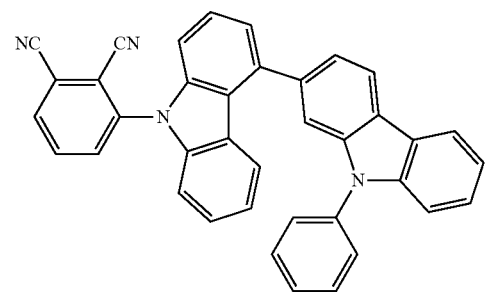
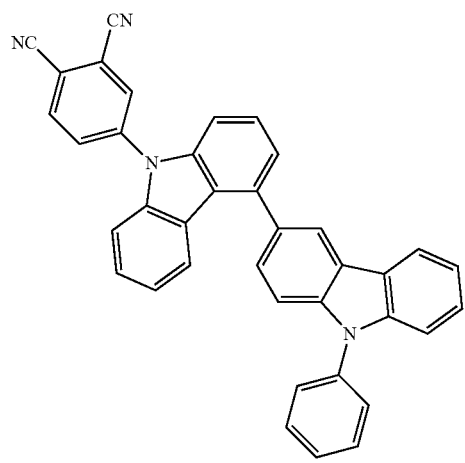
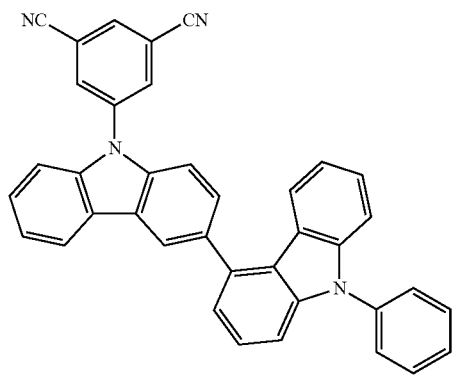

-continued
[Formula 75]
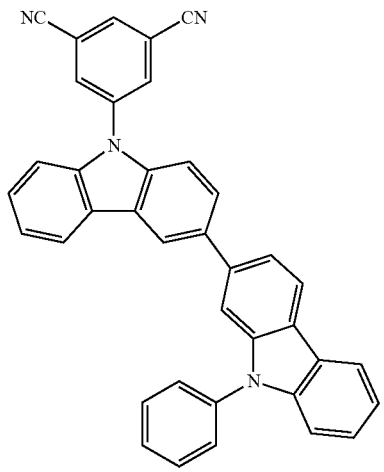
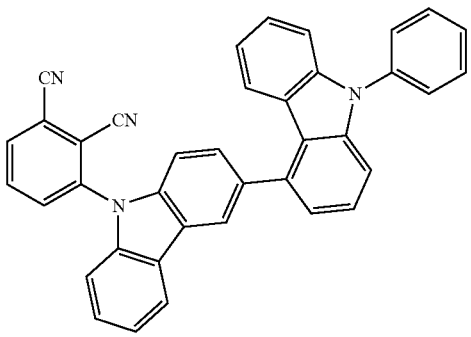
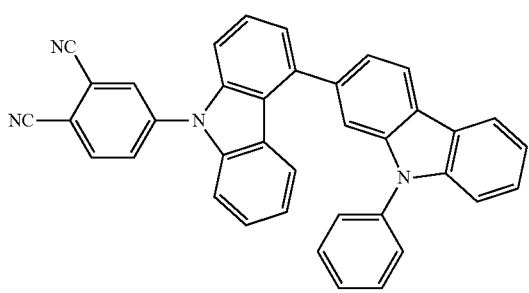
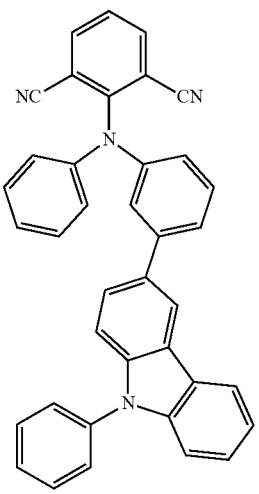
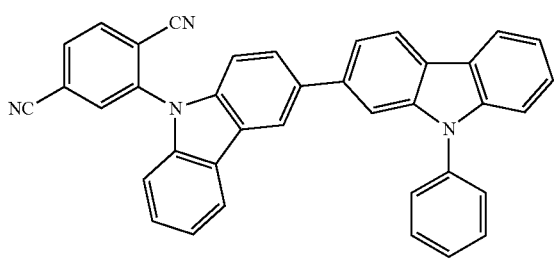
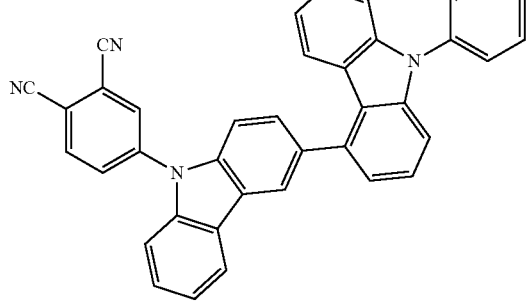
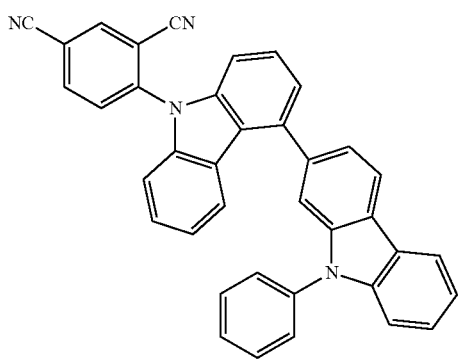
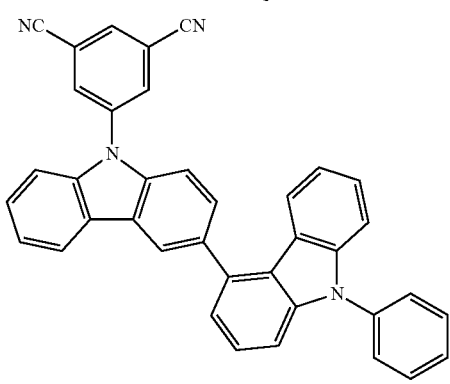

-continued
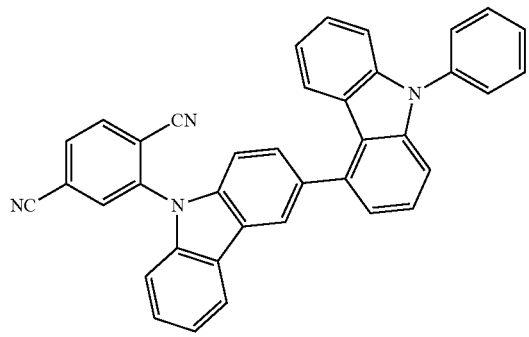
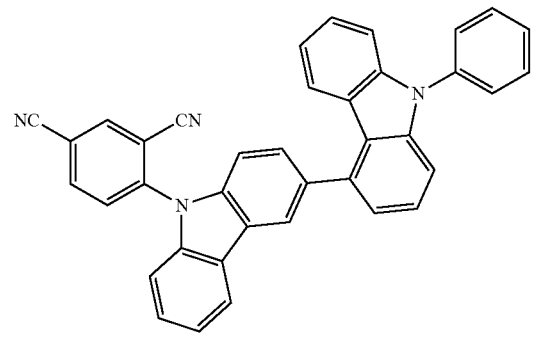
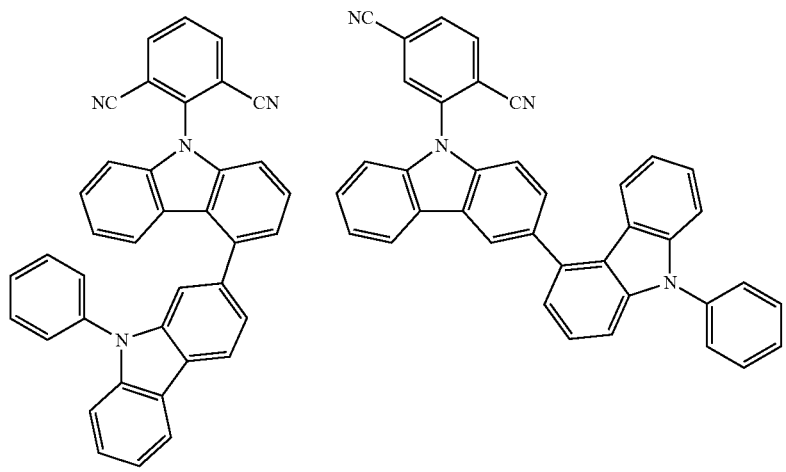
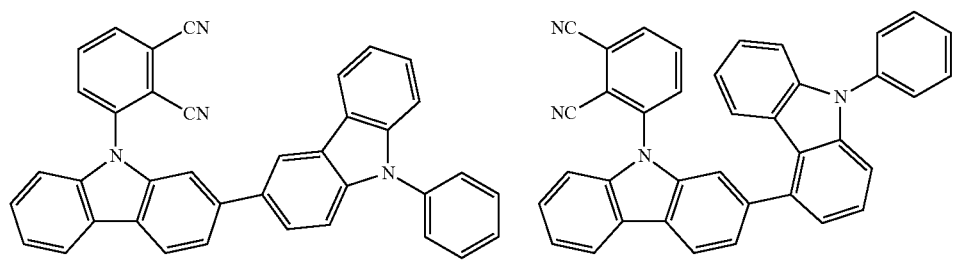
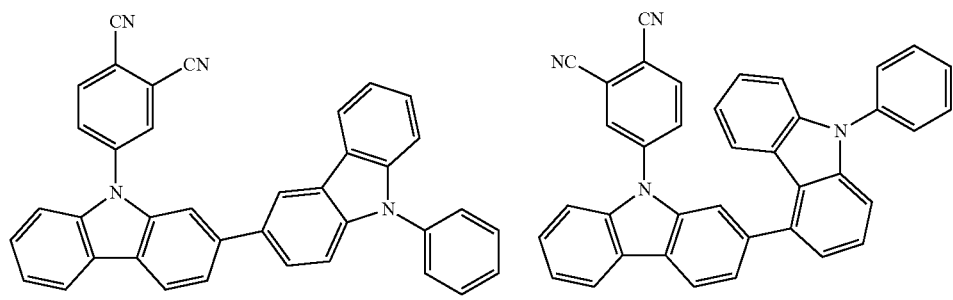

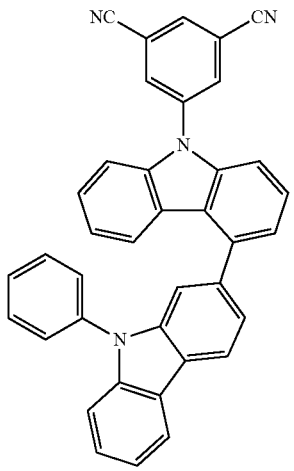
[Formula 76]
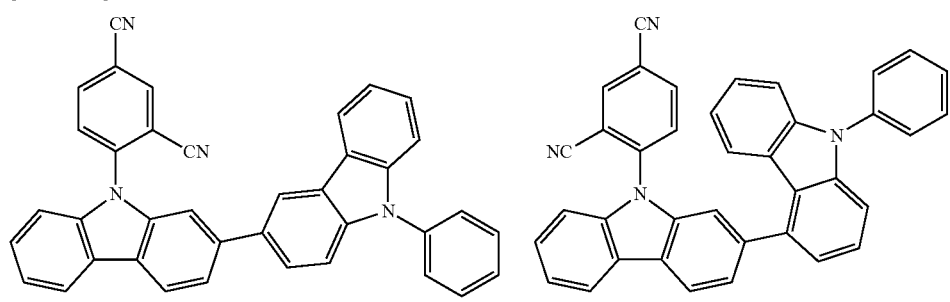
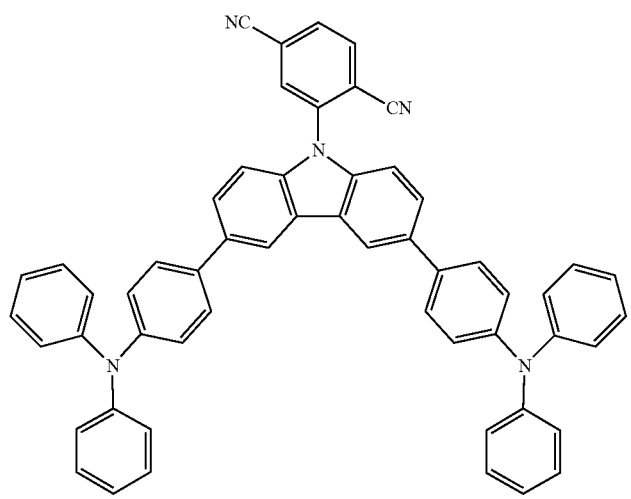

-continued
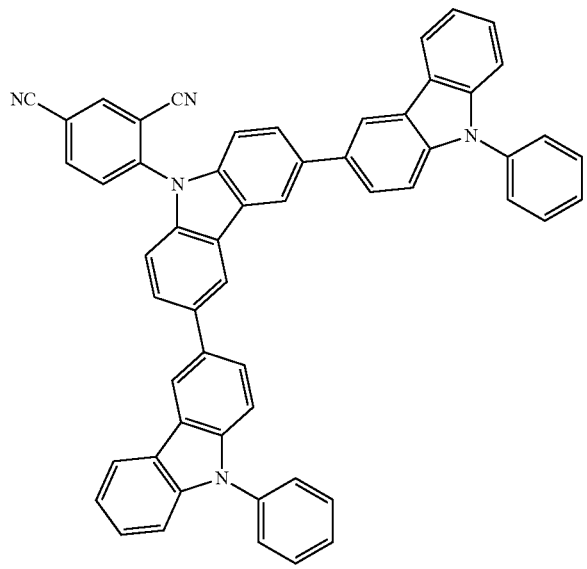
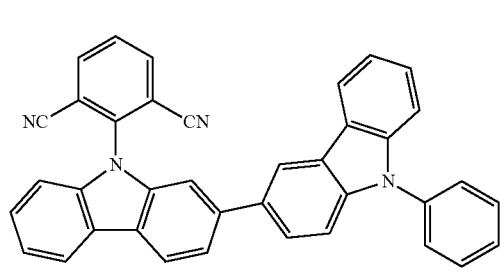 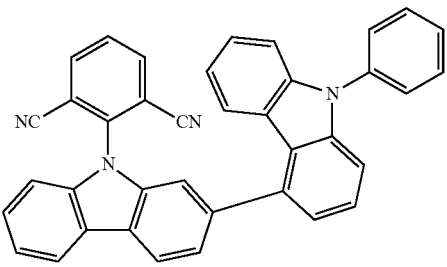
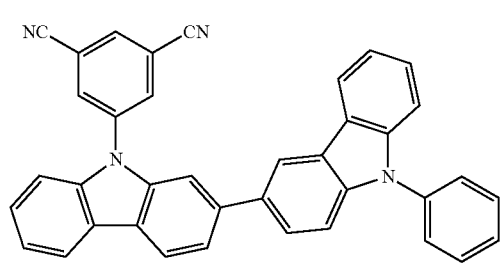 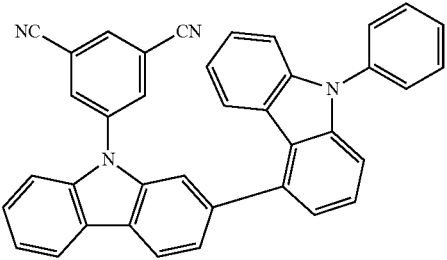
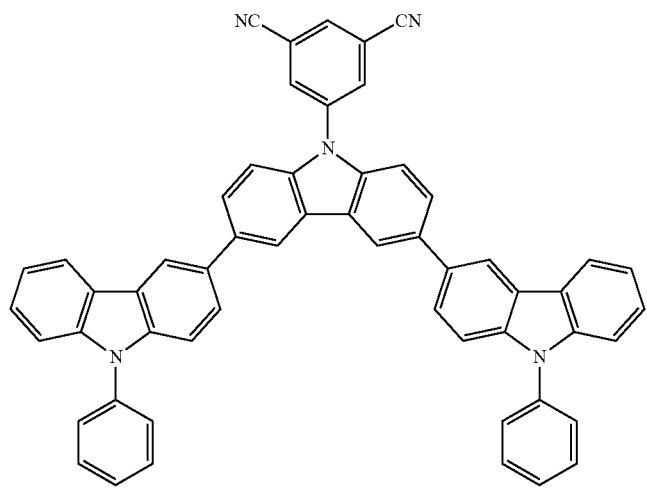

-continued
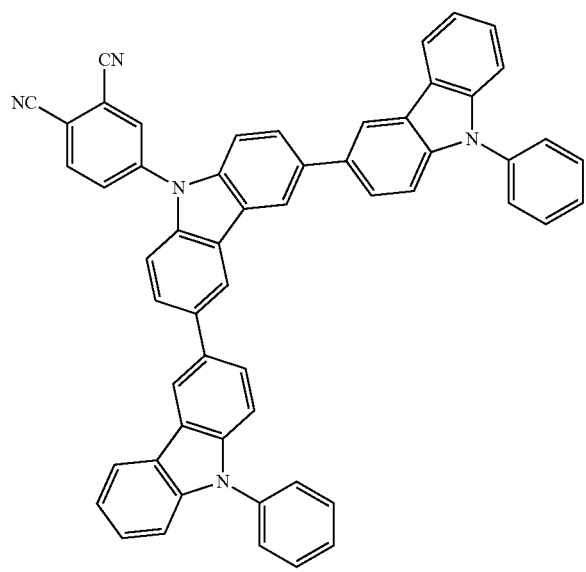
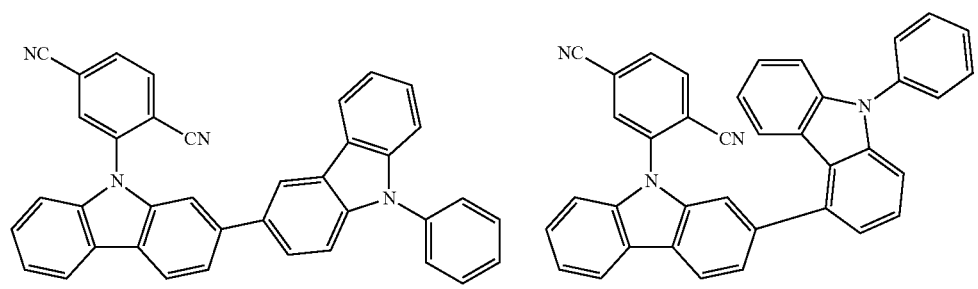
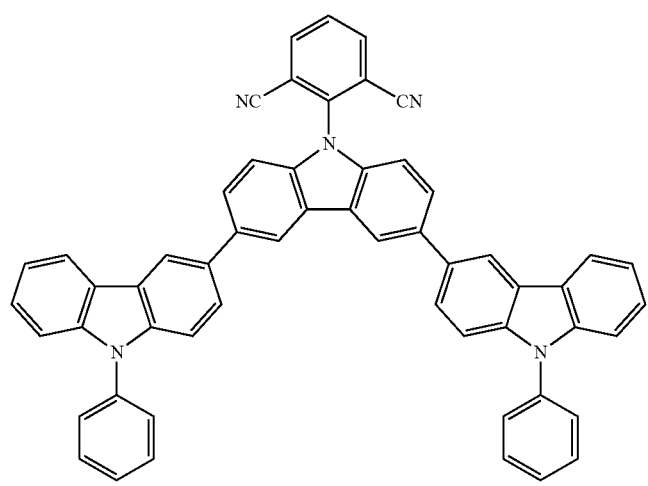

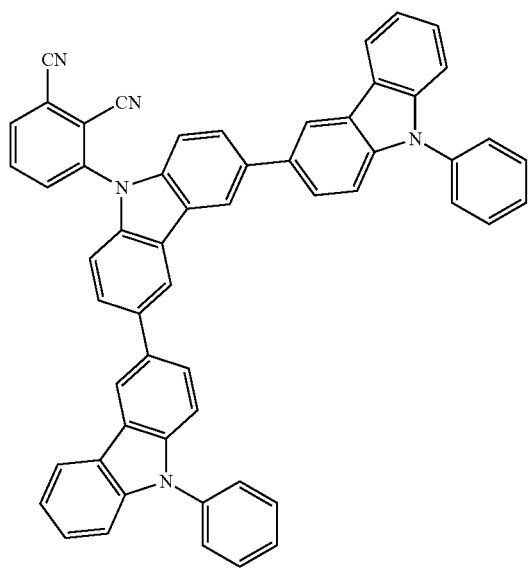
[Formula 77]
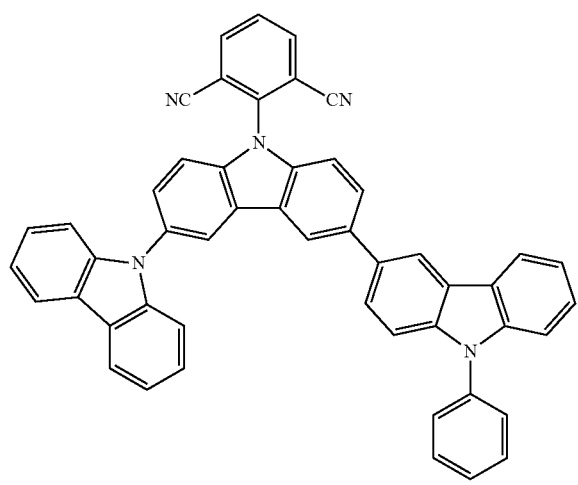
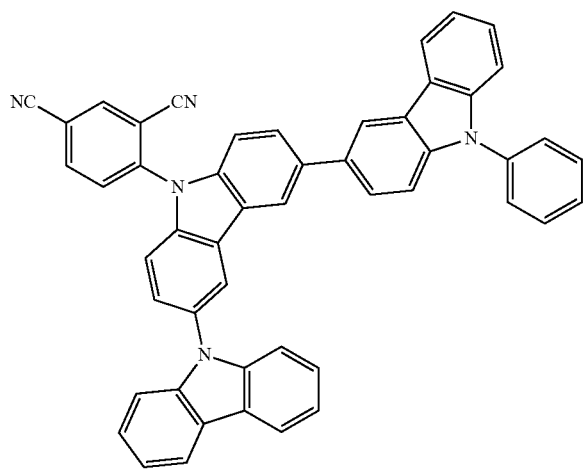

-continued
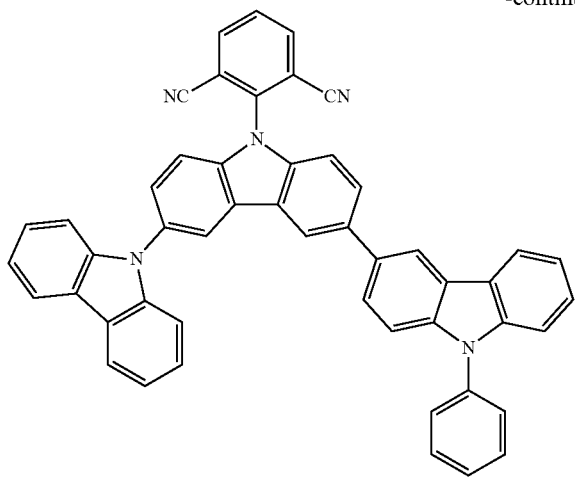
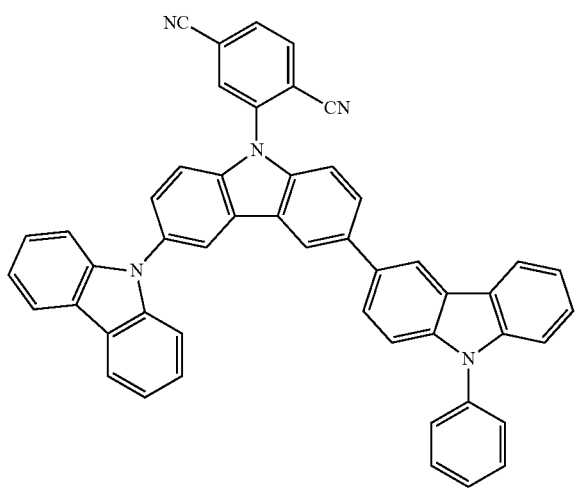
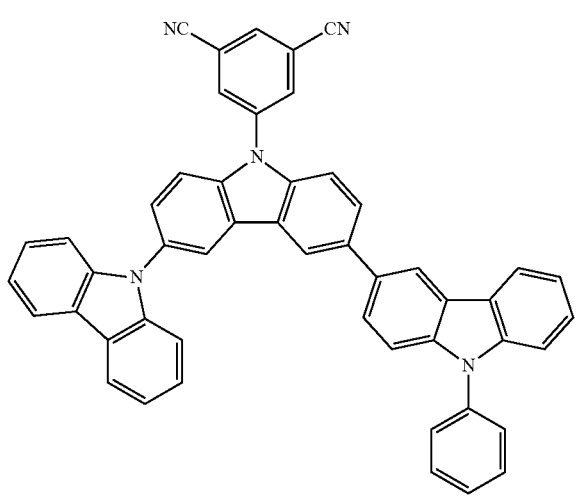

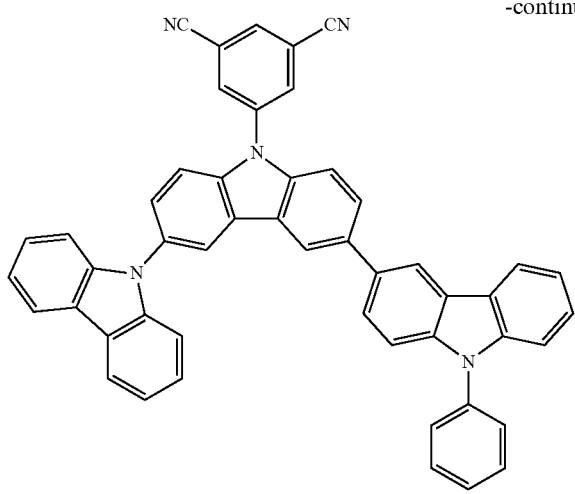
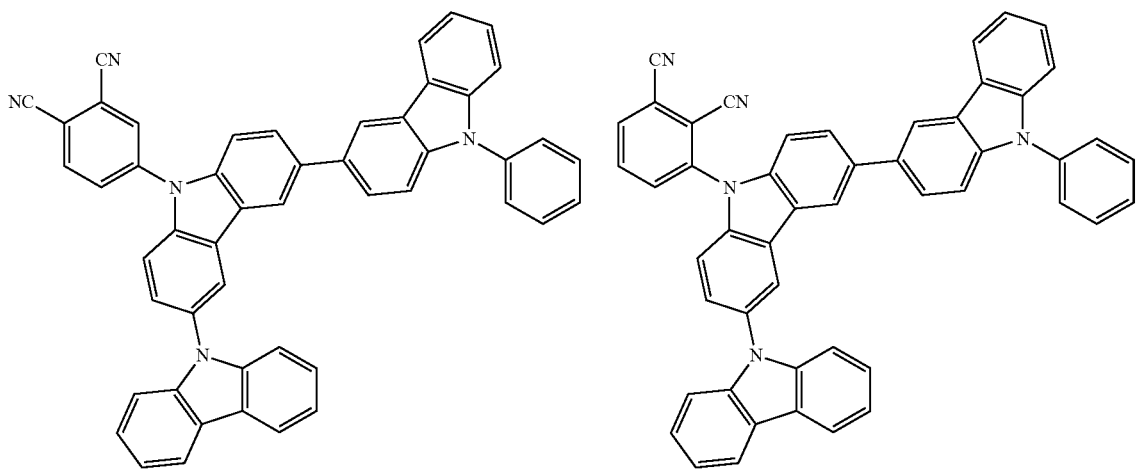
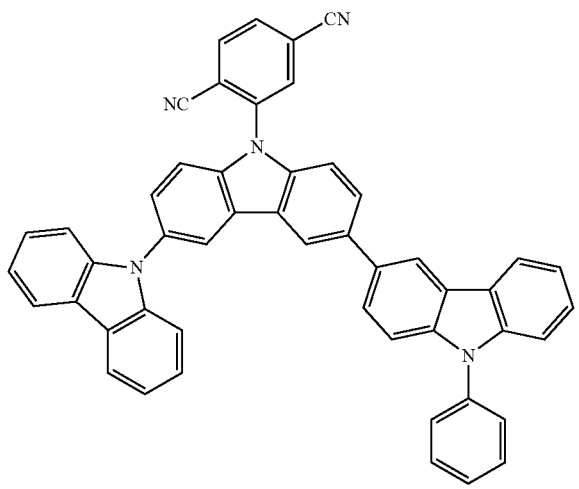 [SMILES: N#Cc1ccc(C#N)c(-n2c3ccc(-c4ccc5c(c4)c4ccccc4n5-c4ccccc4)cc3c3cc(-n4c5ccccc5c5ccccc54)ccc32)c1]

[Formula 78]
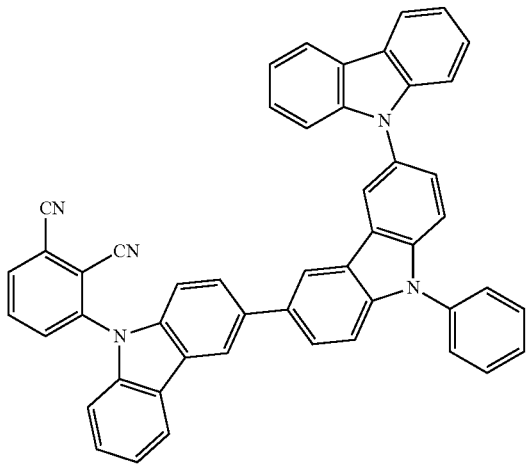
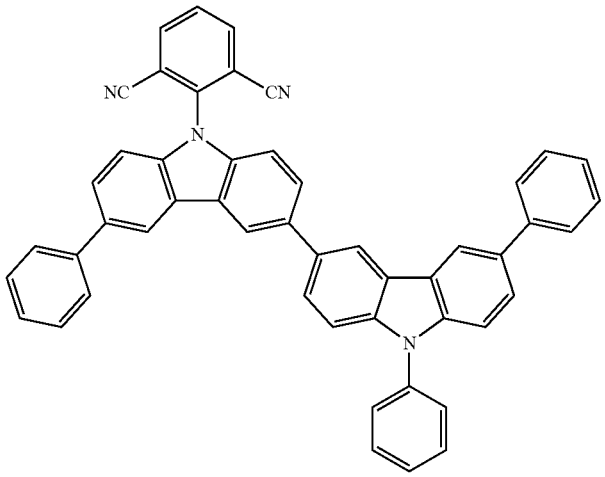
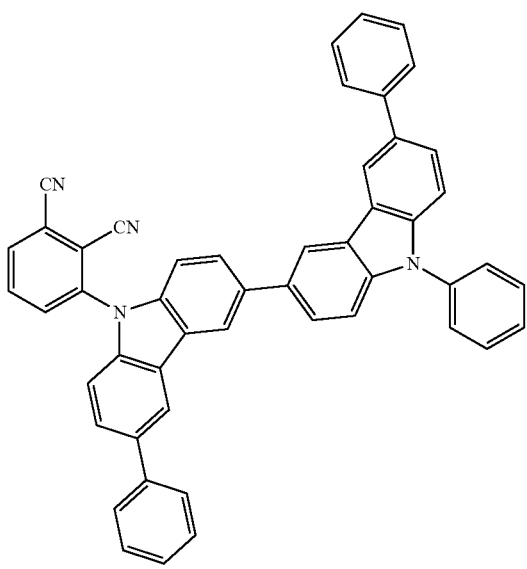
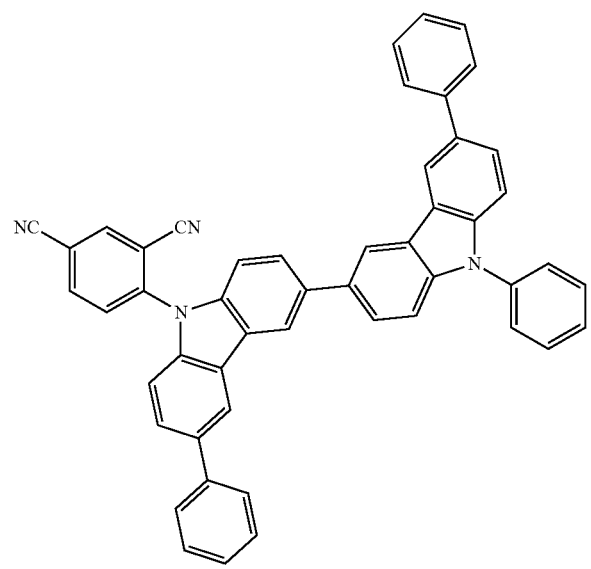
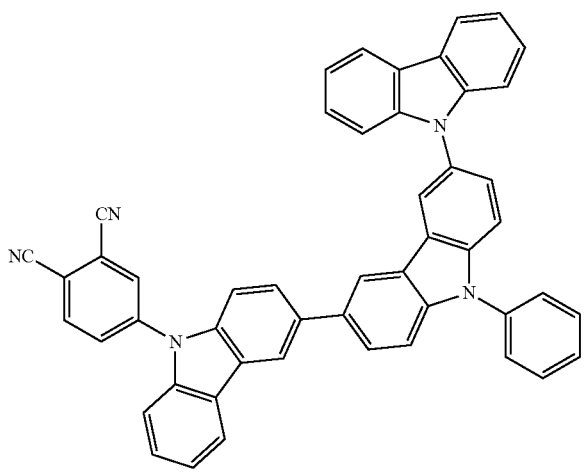

-continued
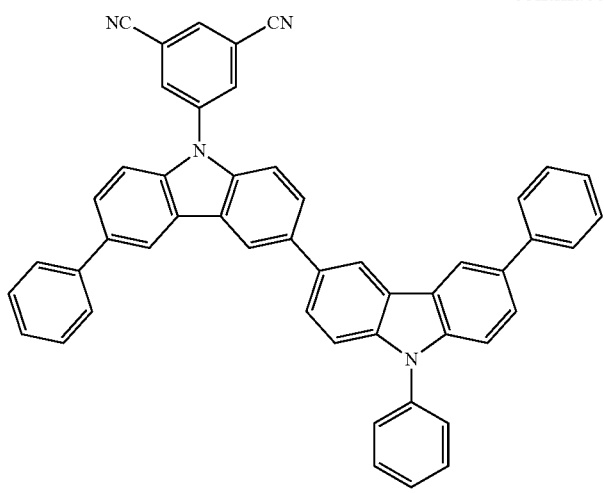
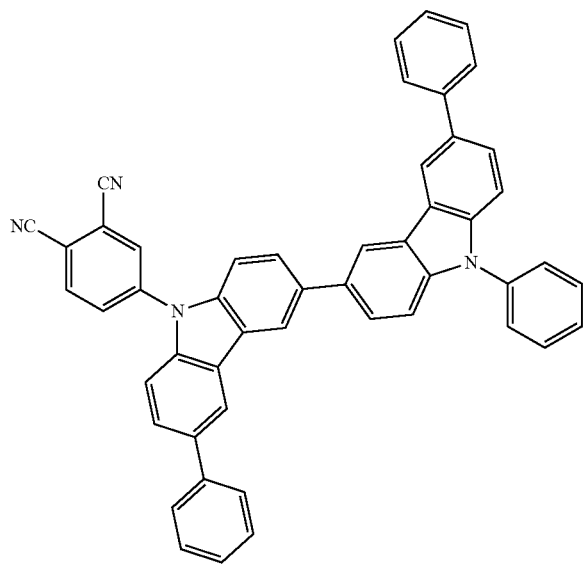
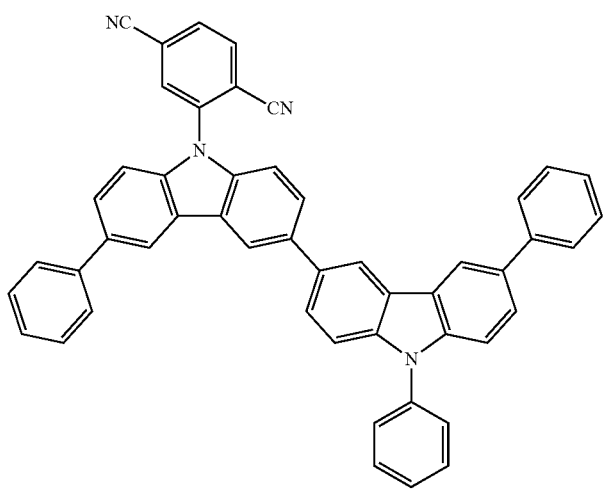

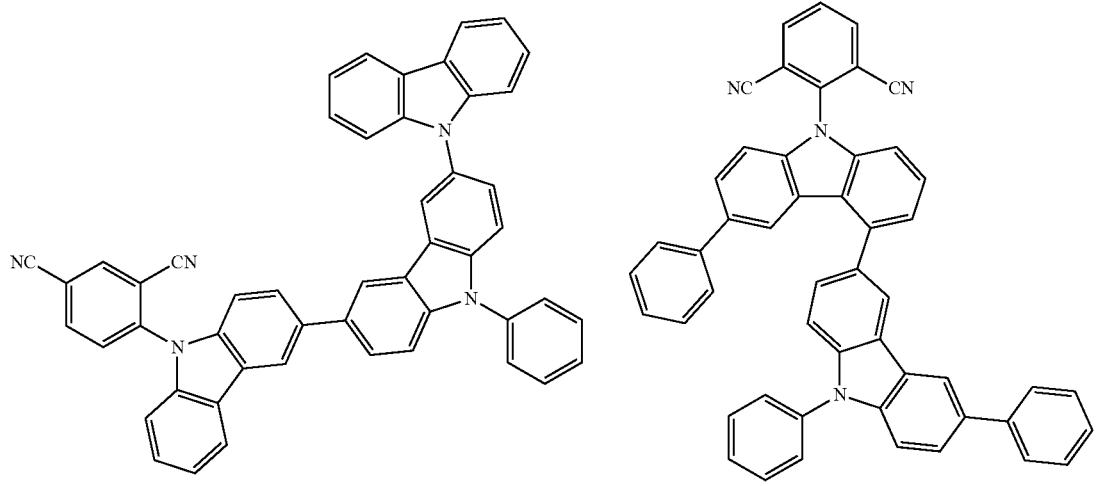
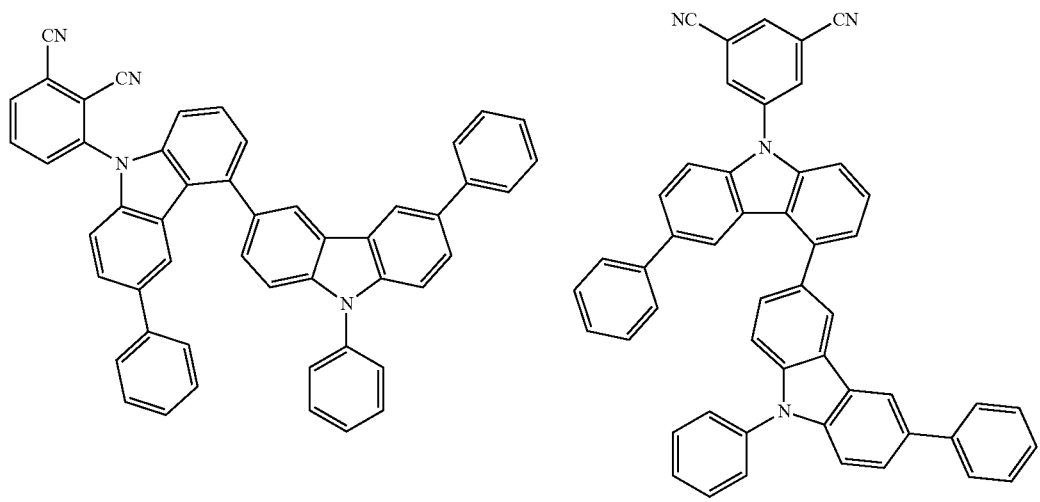
[Formula 79]
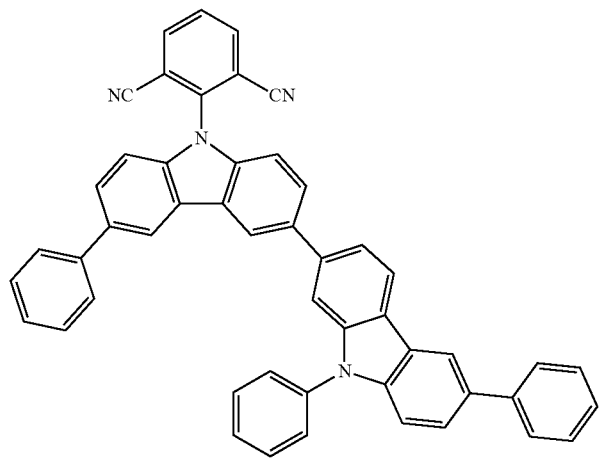

-continued
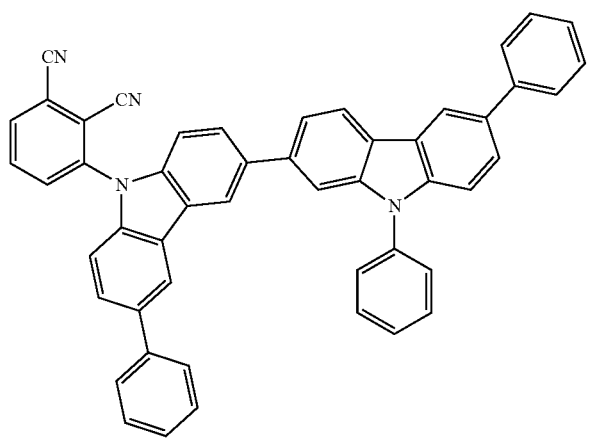
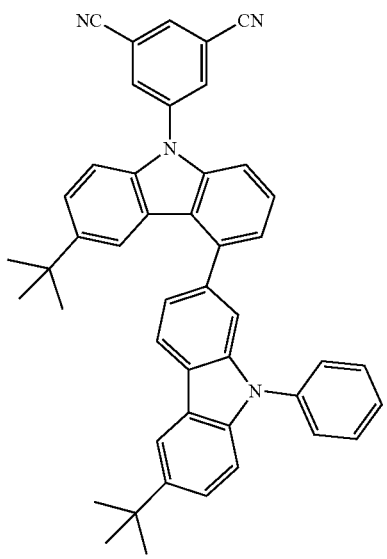
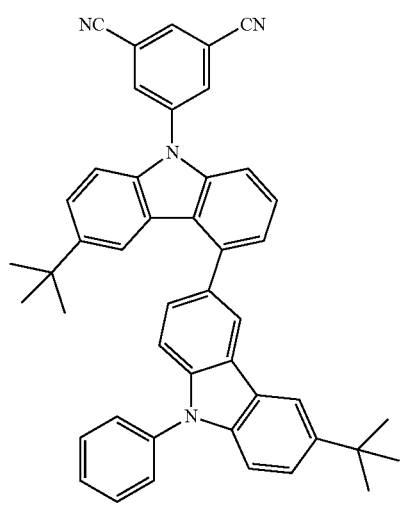
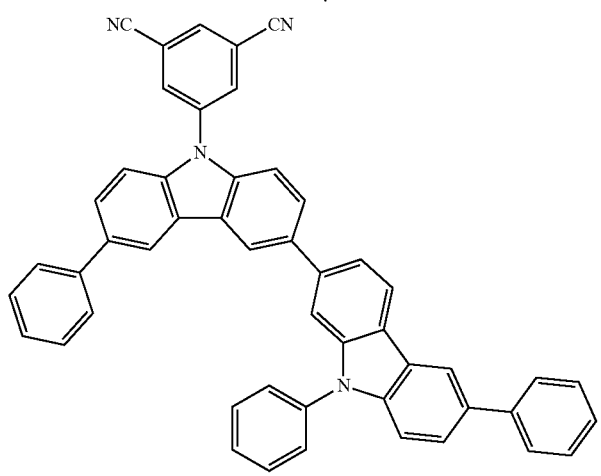
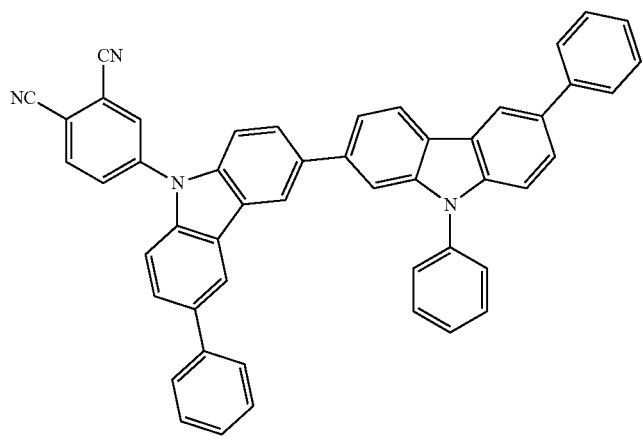
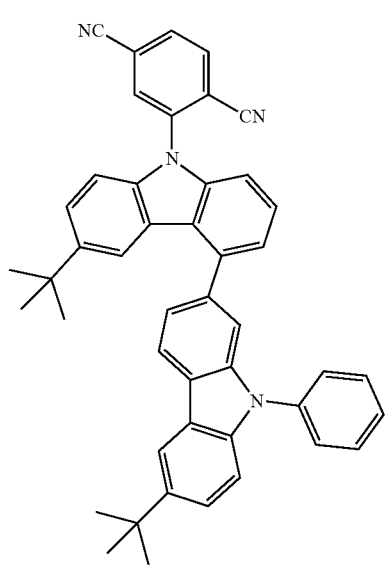

97
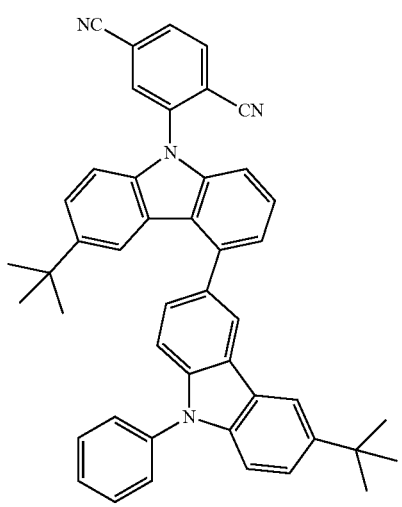
98
-continued
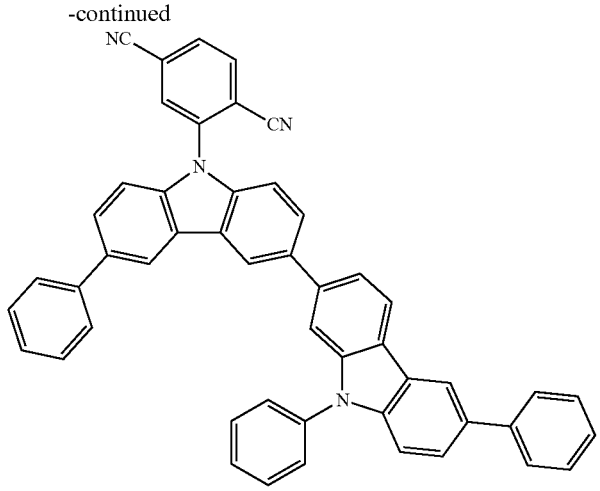
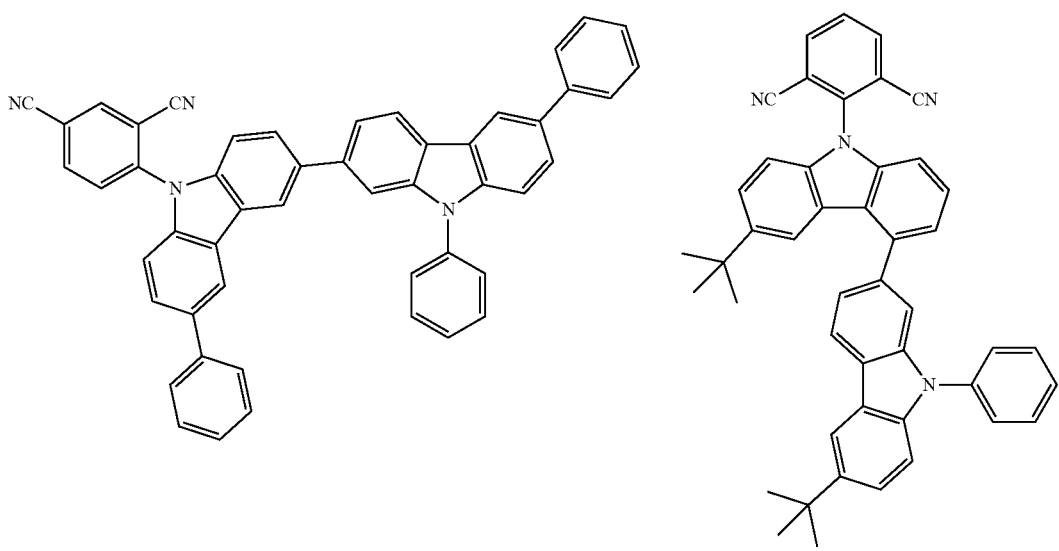
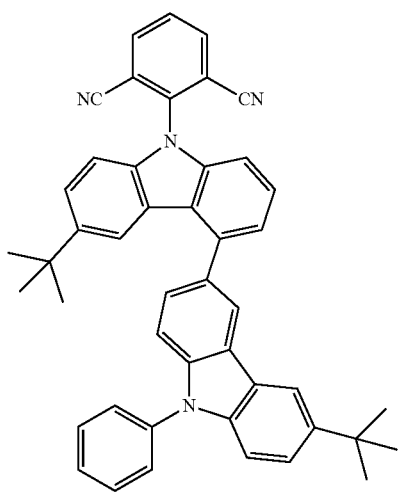

-continued
[Formula 80]
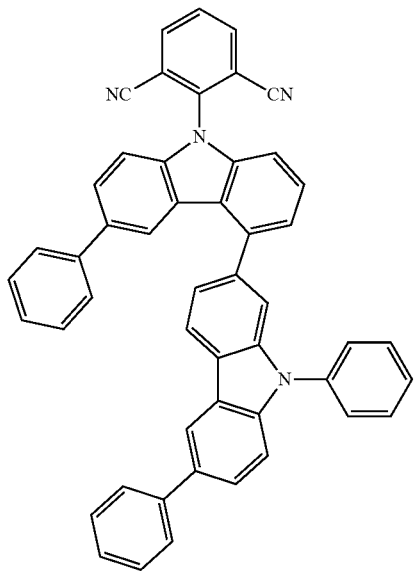
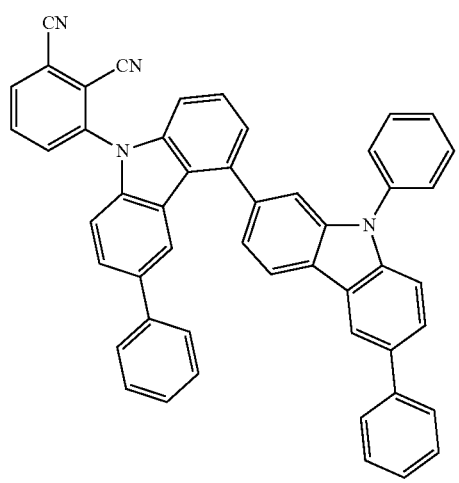
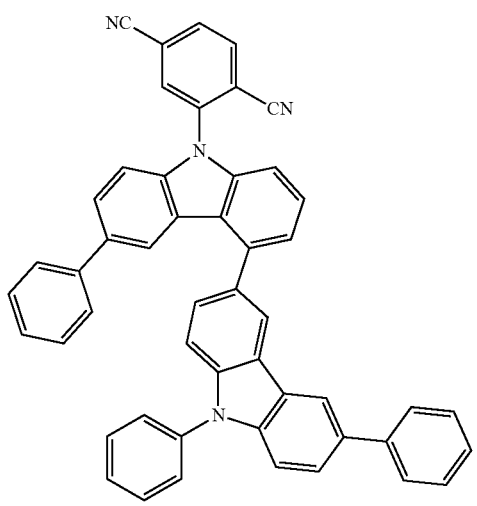
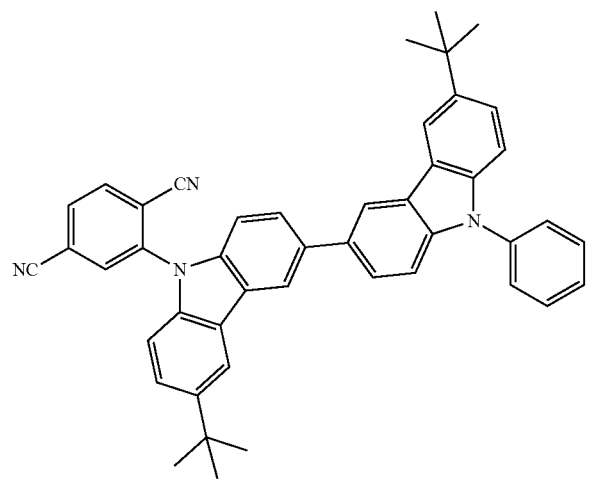
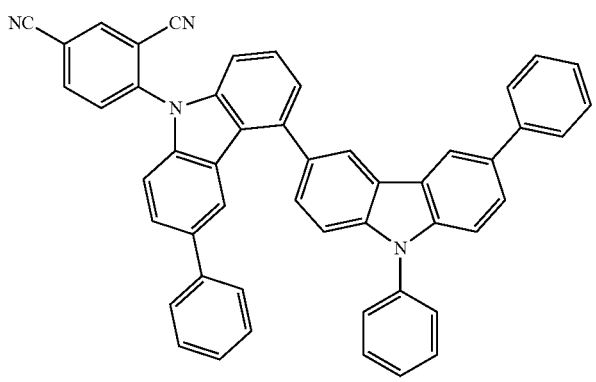

-continued
101
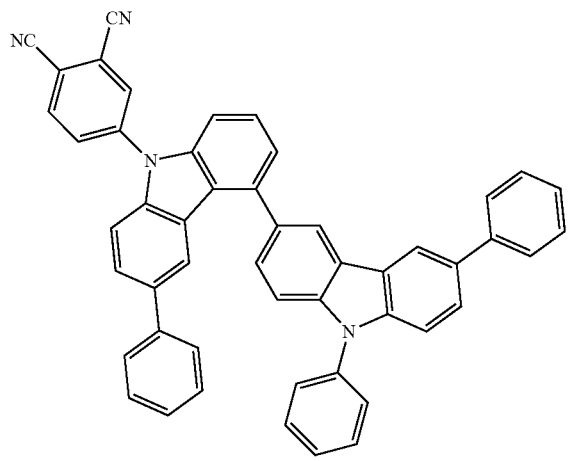
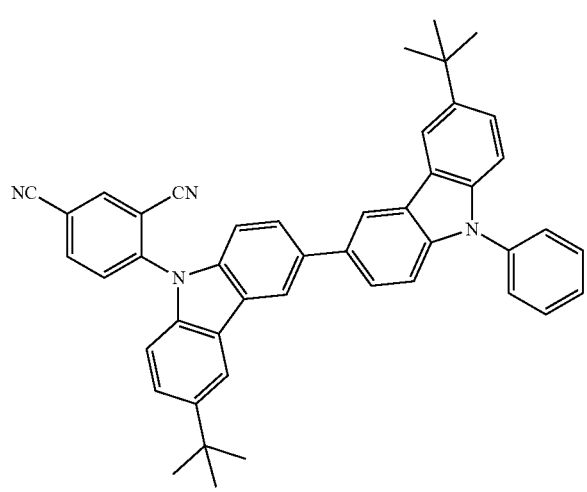
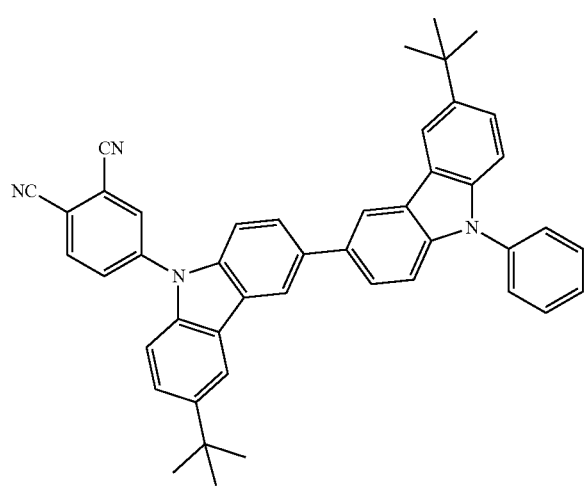
102
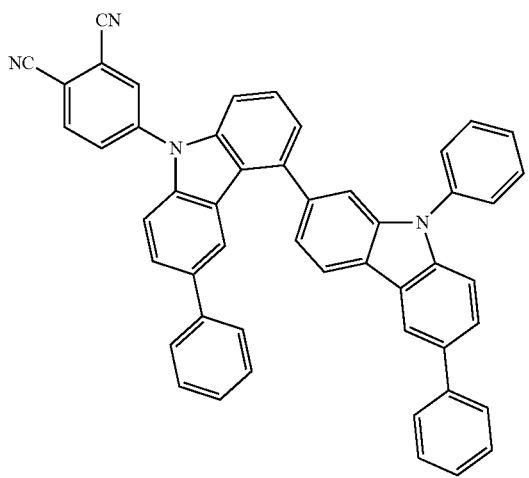

103
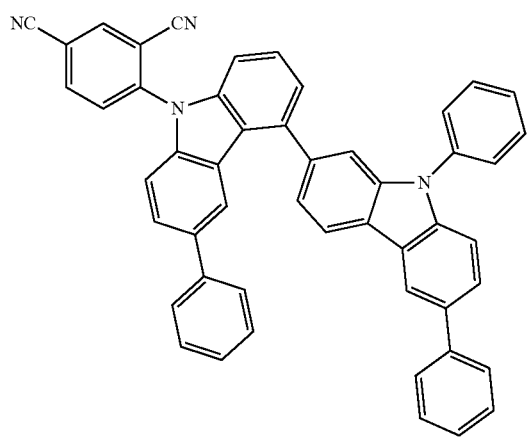
104
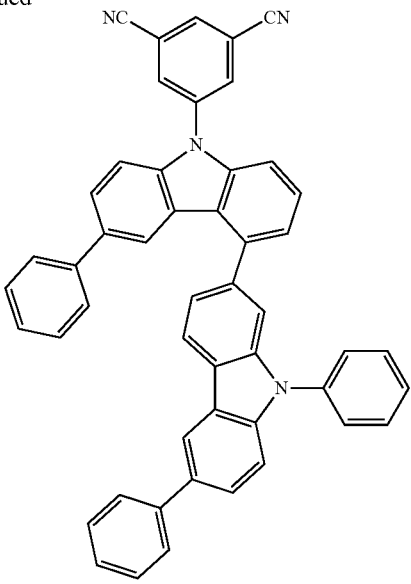
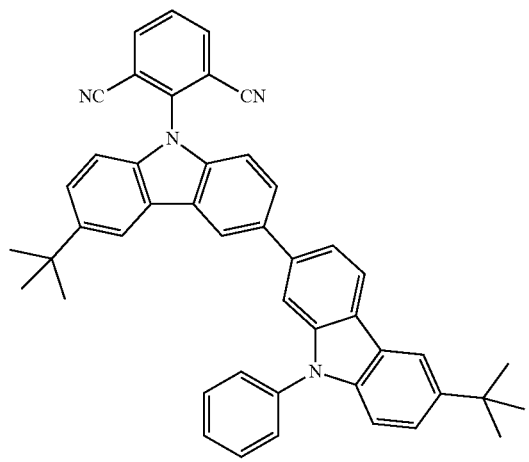
[Formula 81]
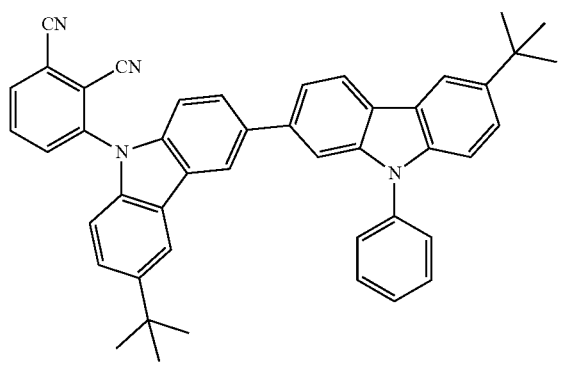
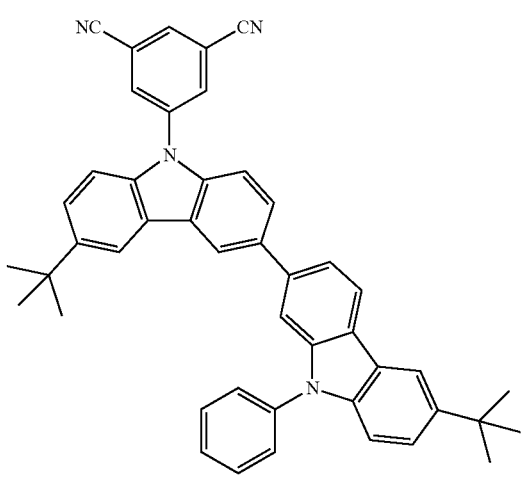

-continued
105
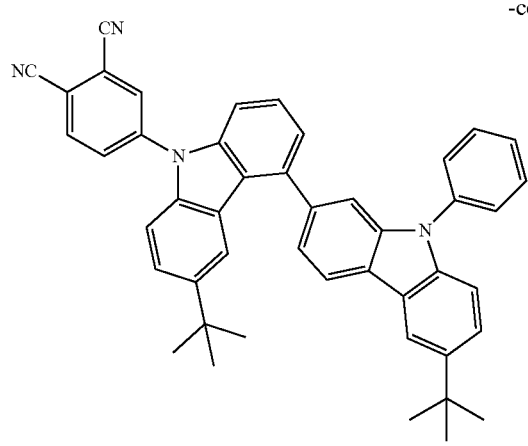
106
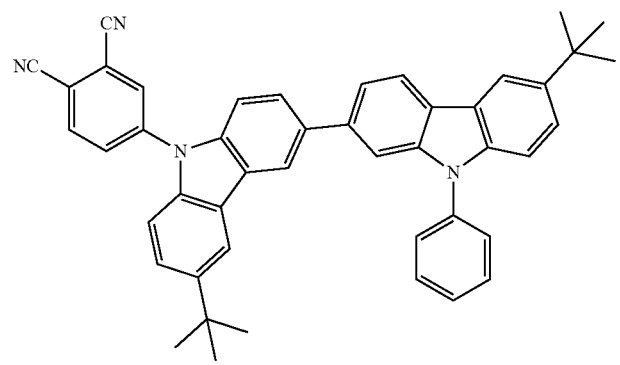
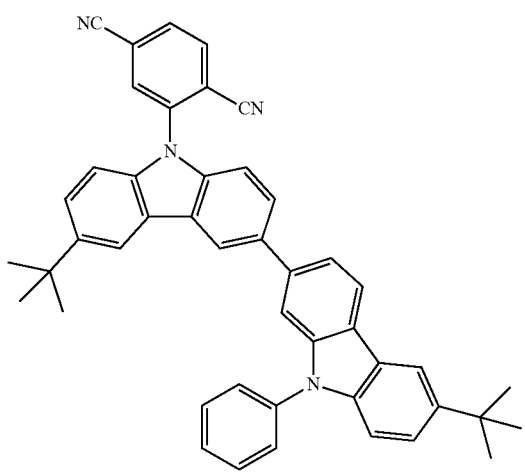
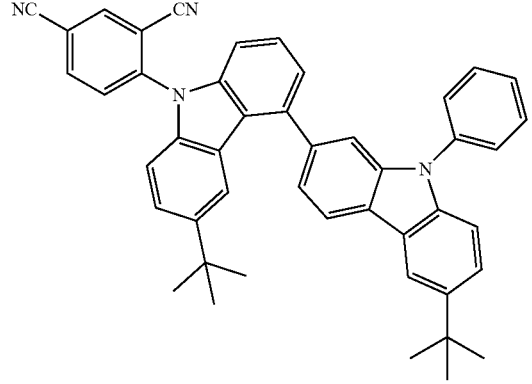
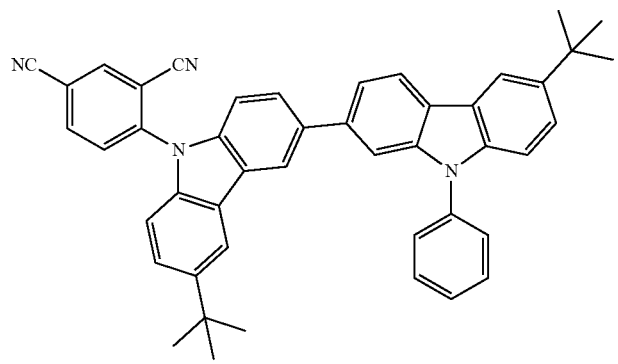

[Formula 82]
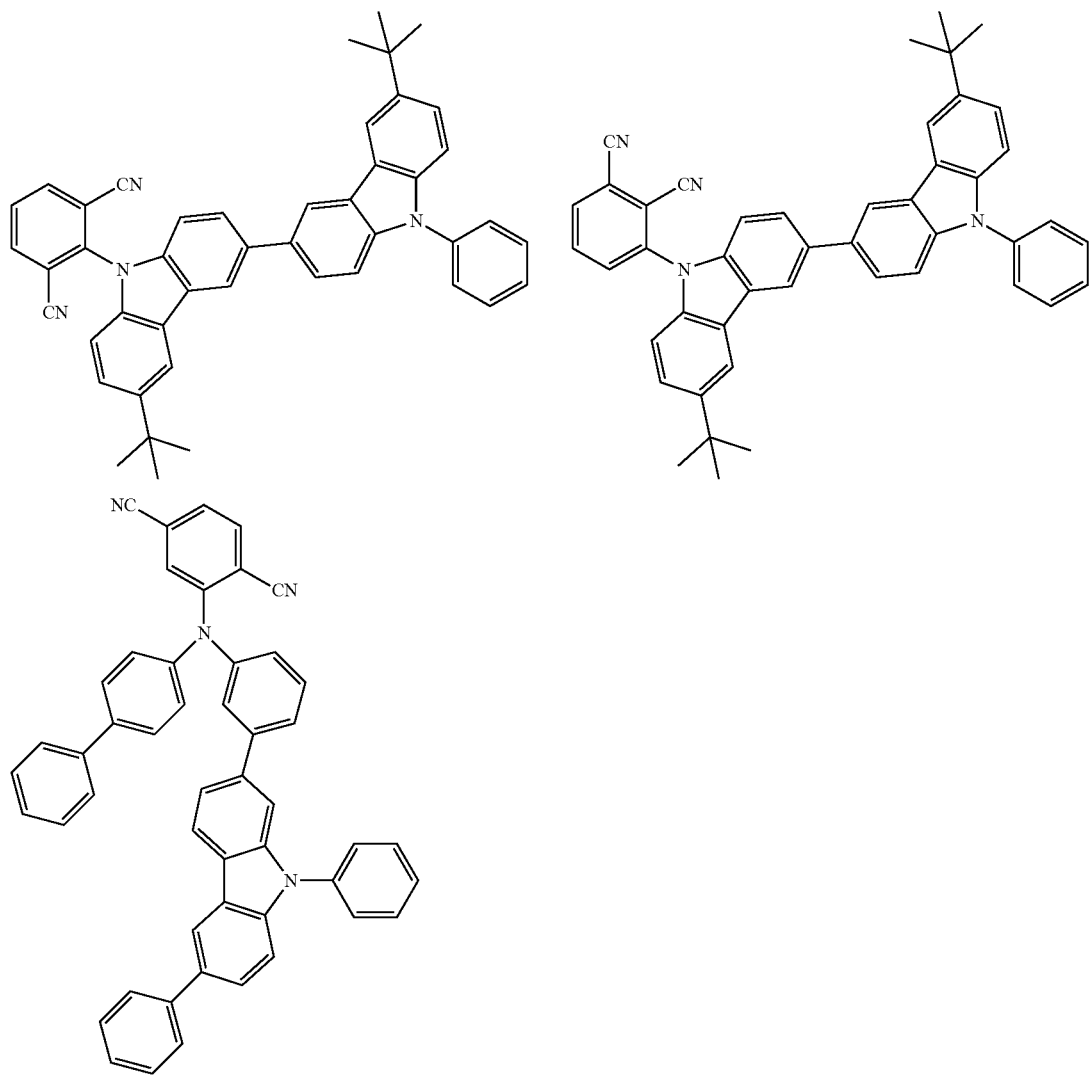
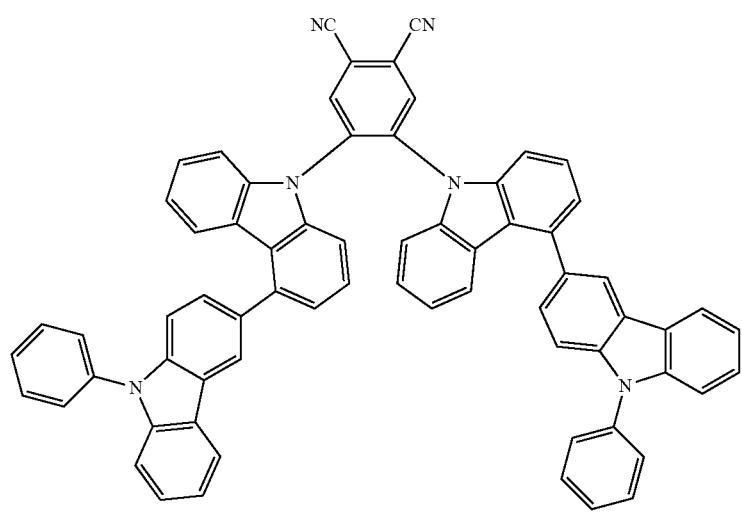

-continued
109
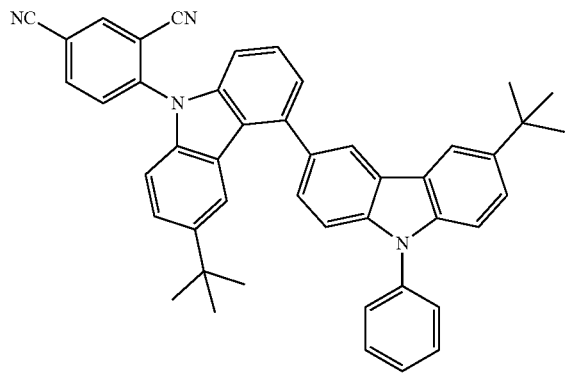
110
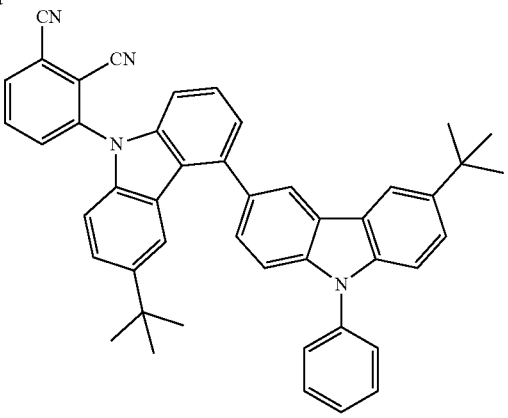
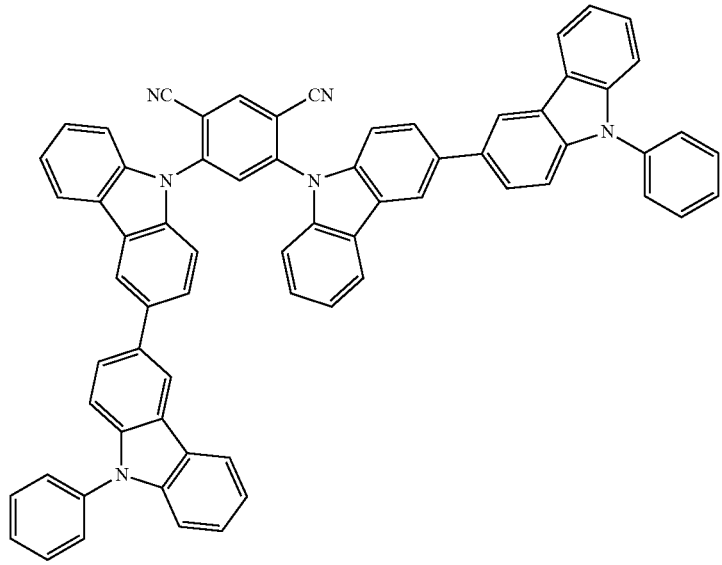
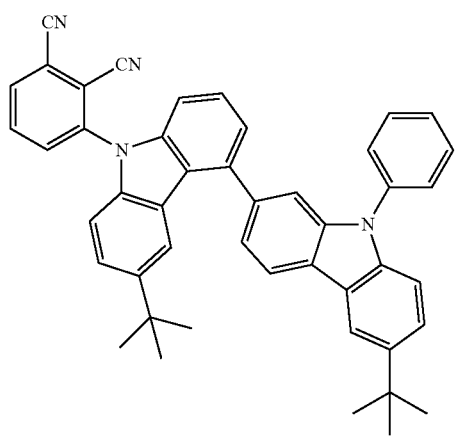
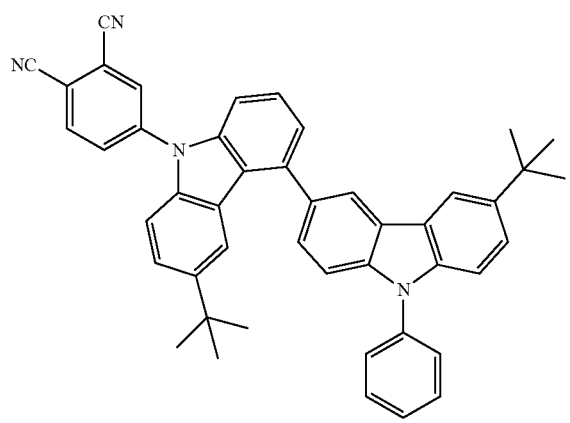

[Formula 83]
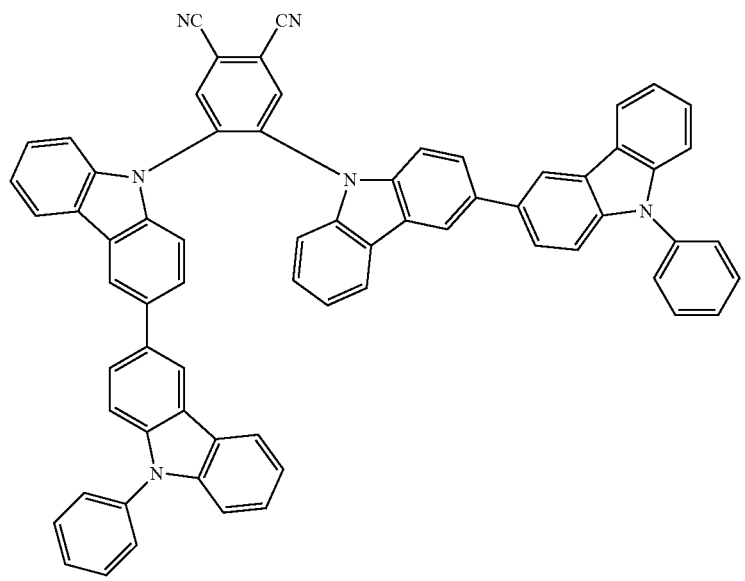
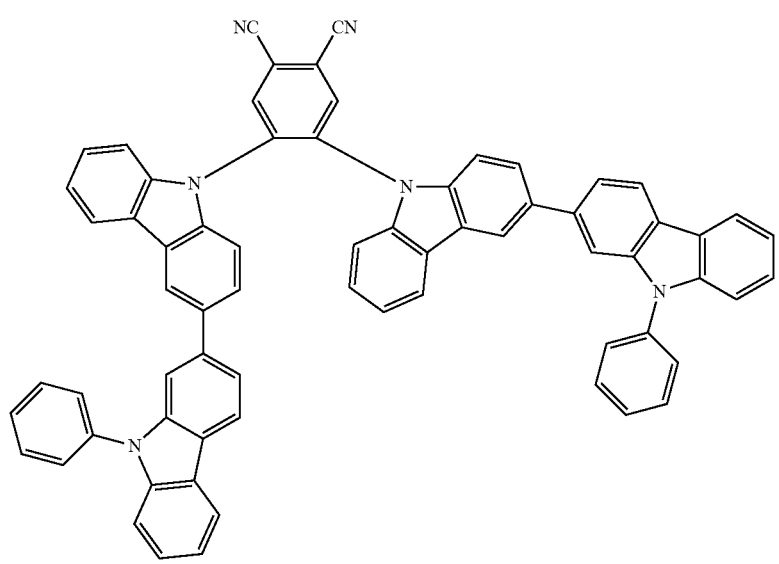
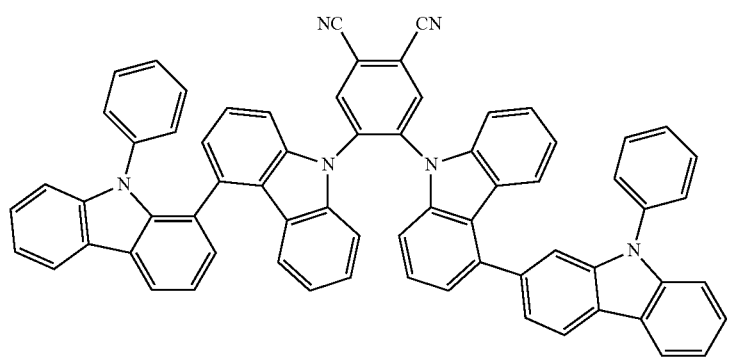

[Formula 84]
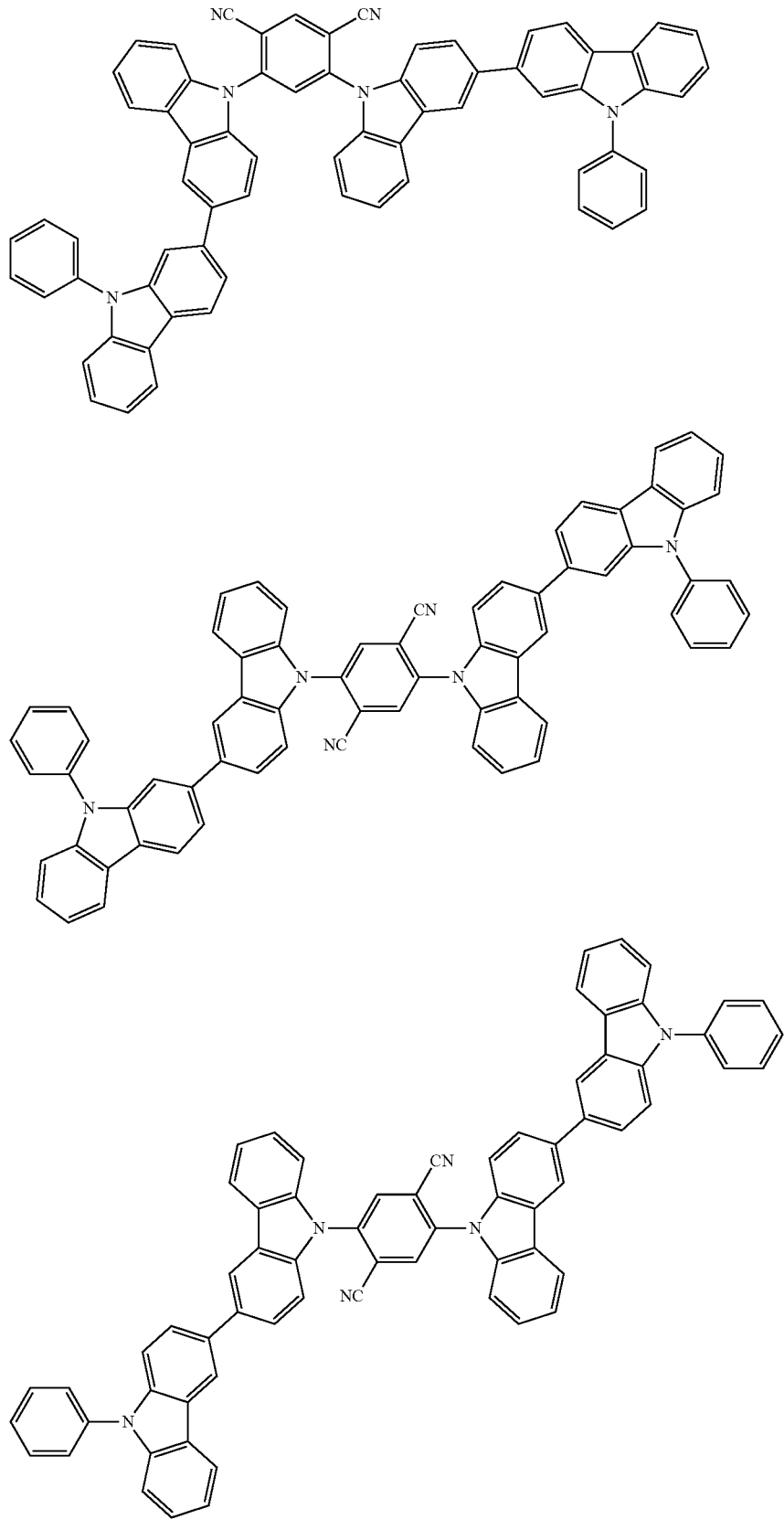

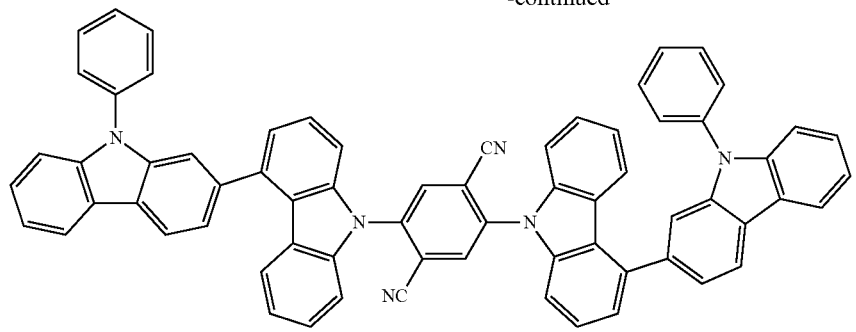
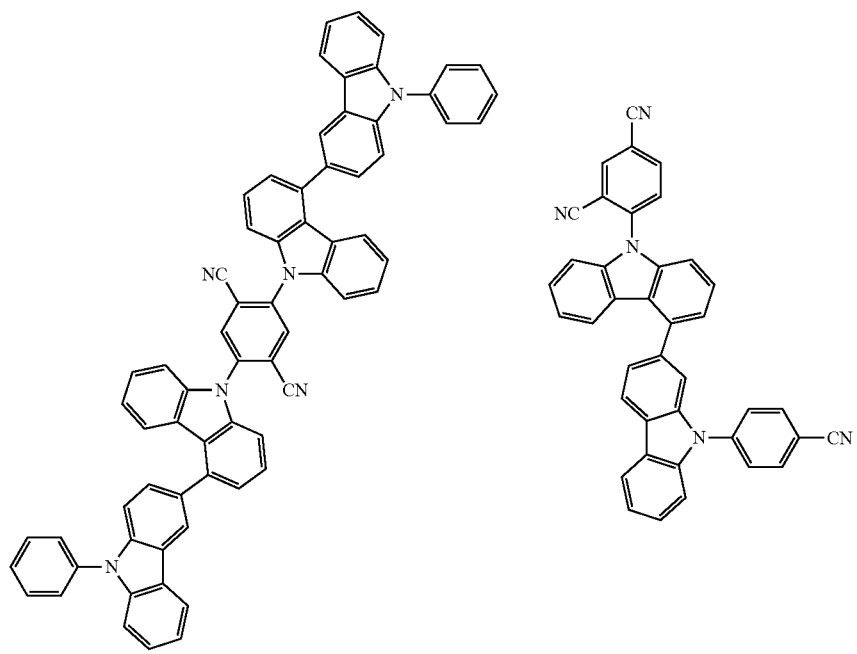
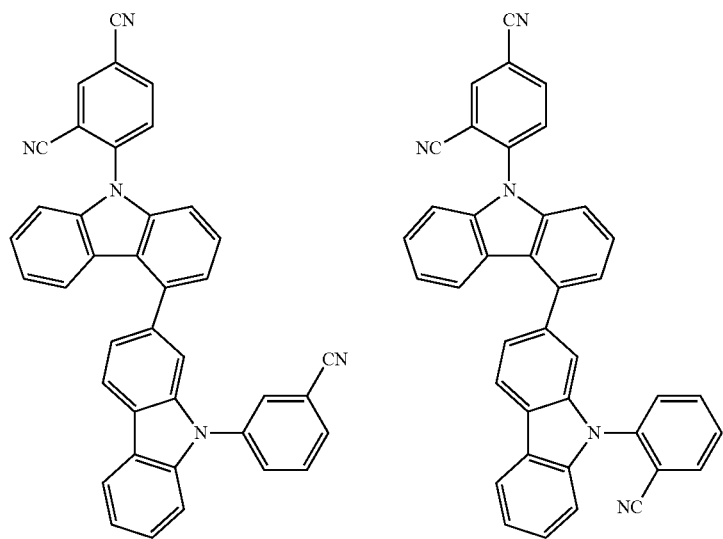

117
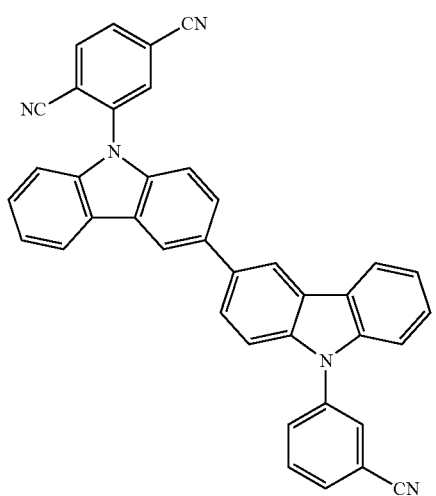
118
-continued
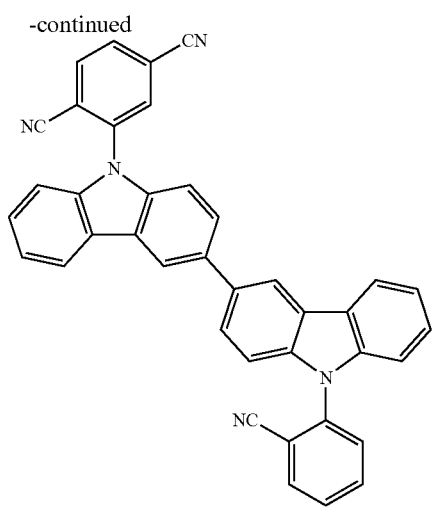
[Formula 85]
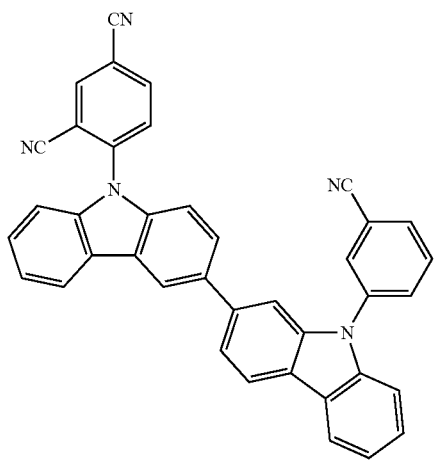
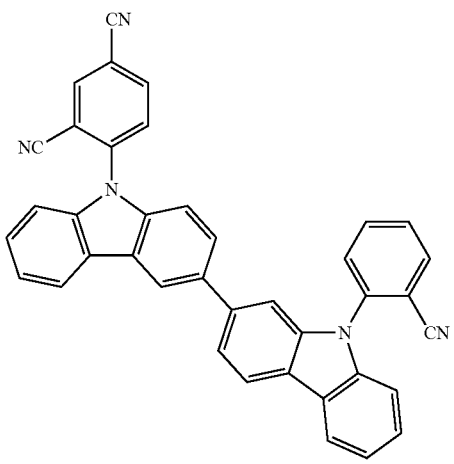
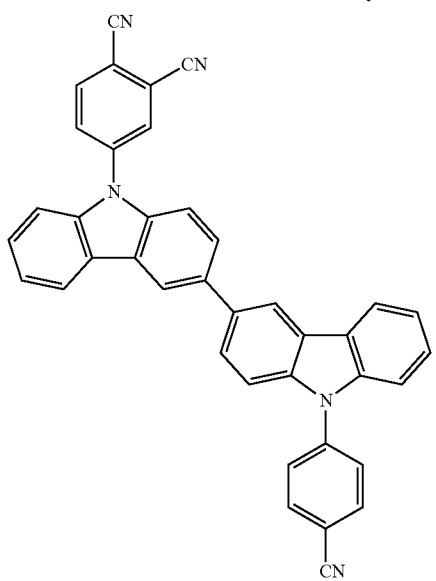
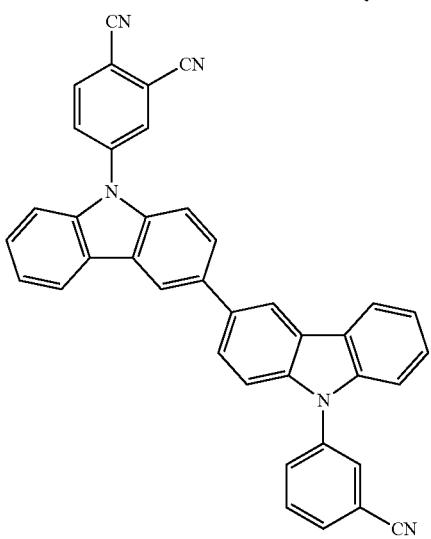

-continued
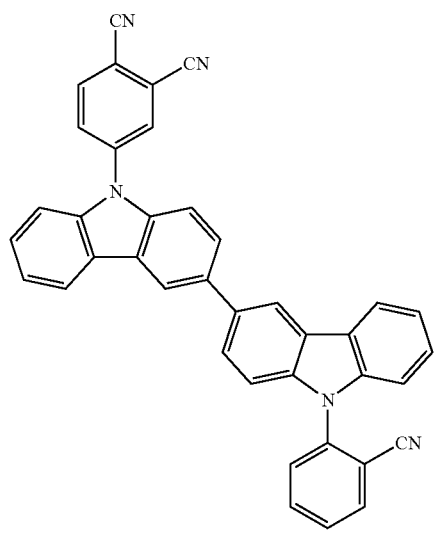
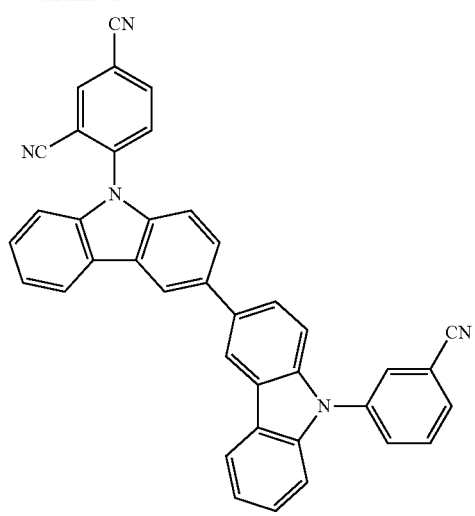
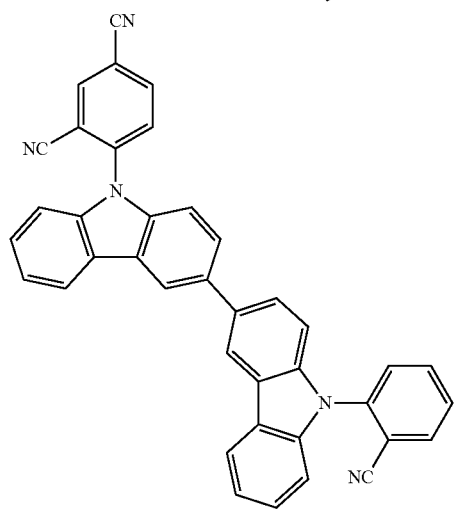
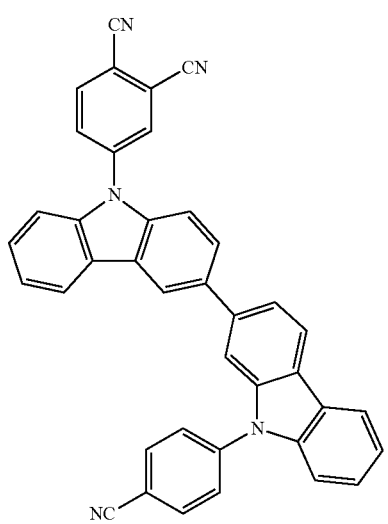
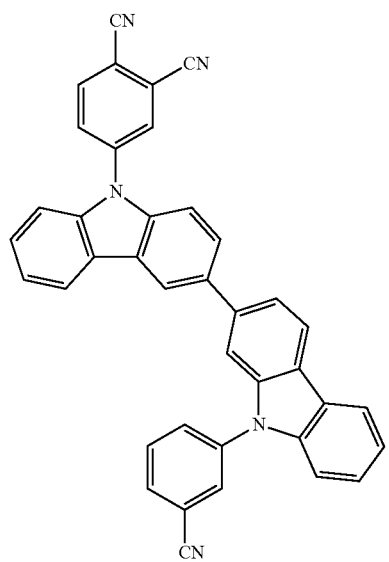
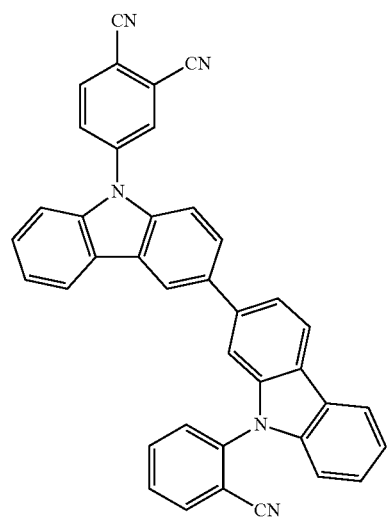

121
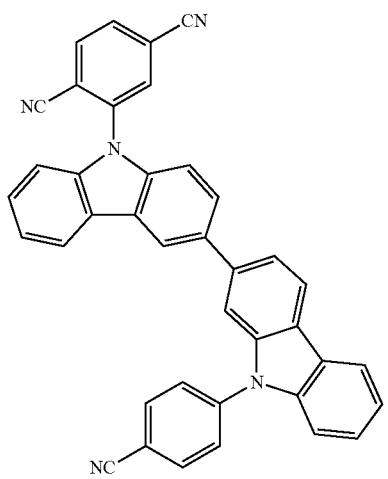
-continued
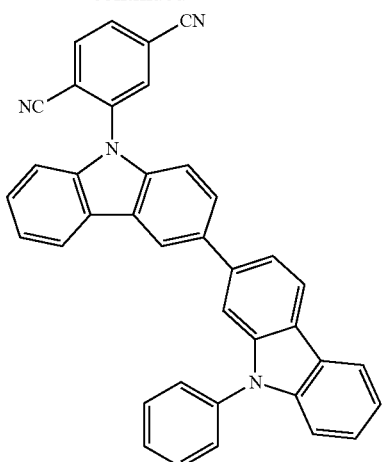
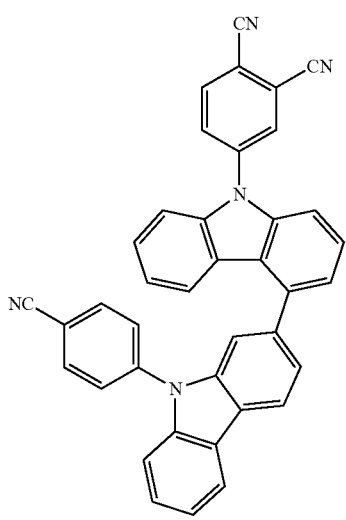
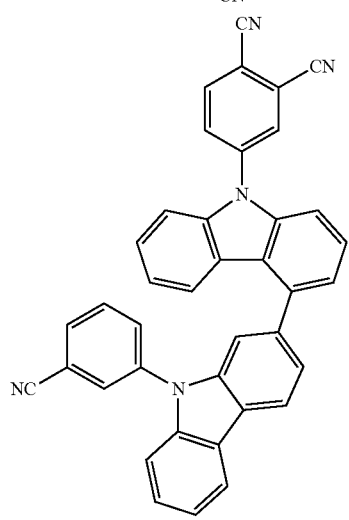
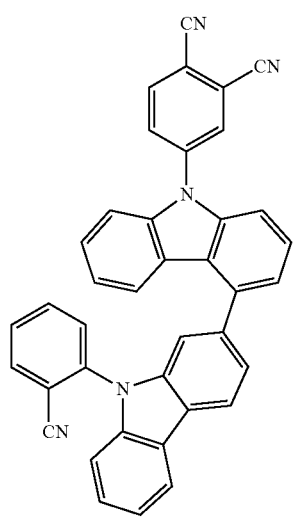
[Formula 86]
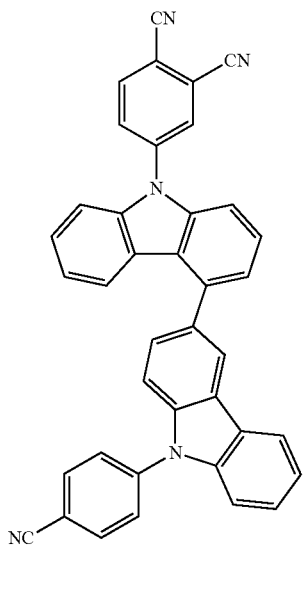
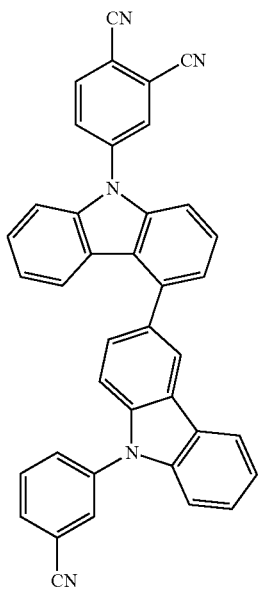
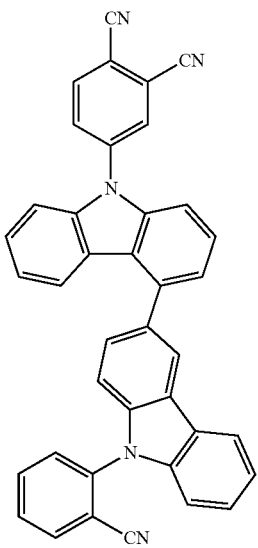

-continued
123
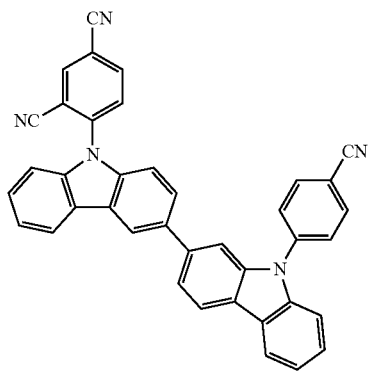
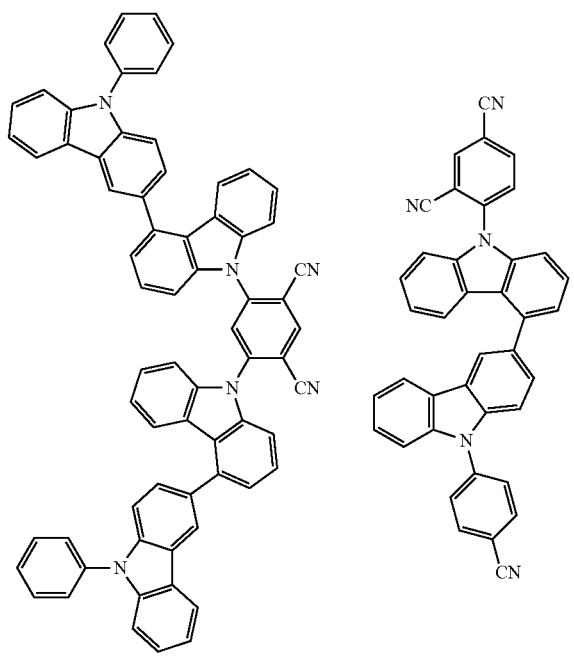
124
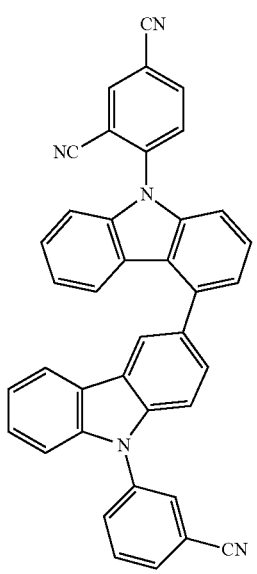
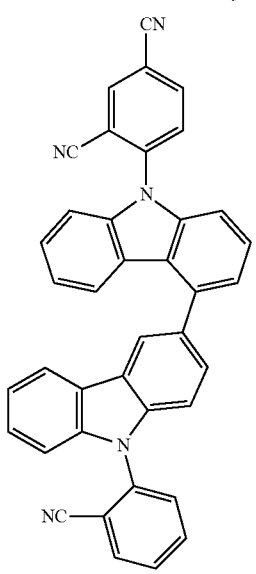
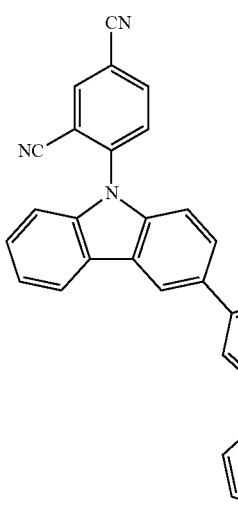
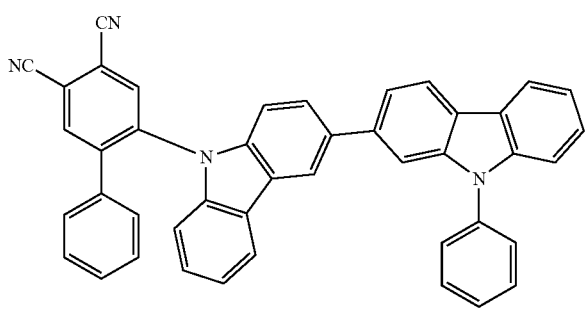

125
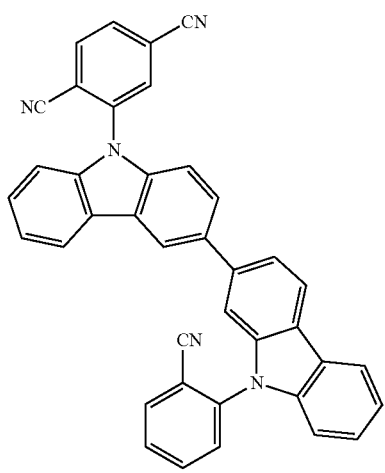
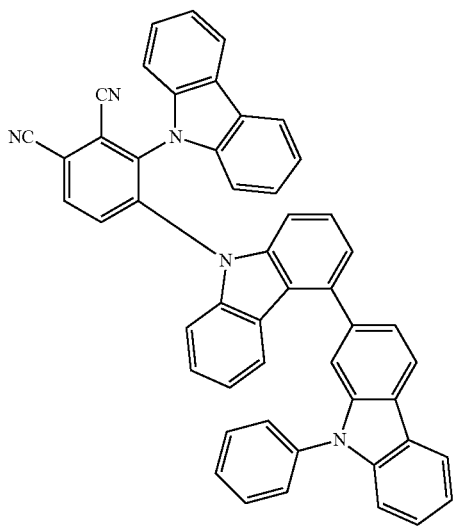
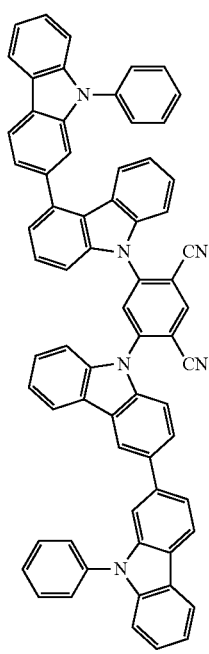
126
-continued
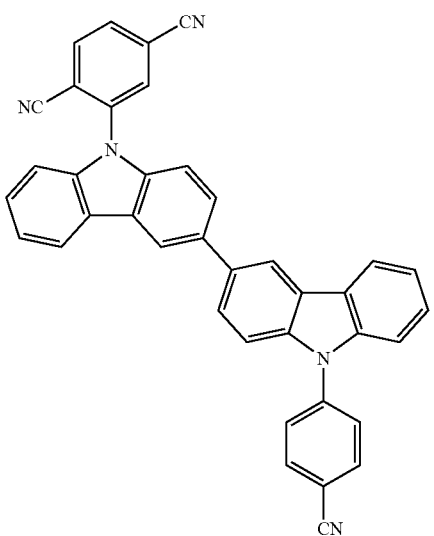
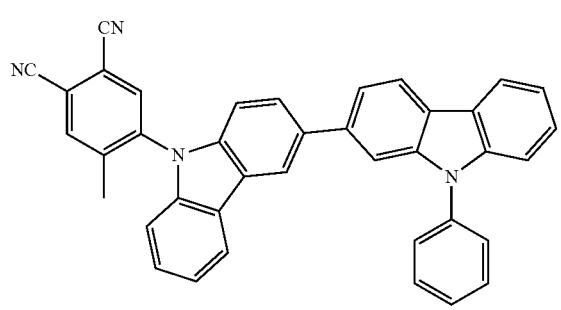

-continued
[Formula 87]
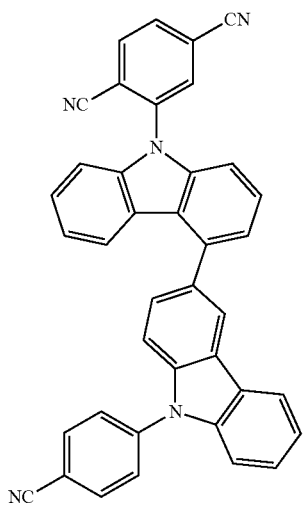 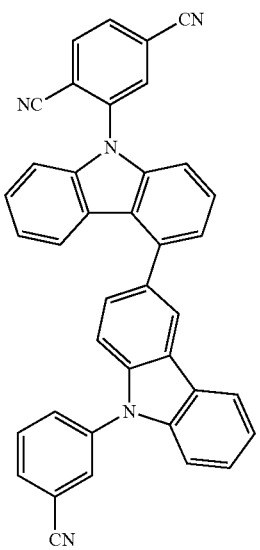 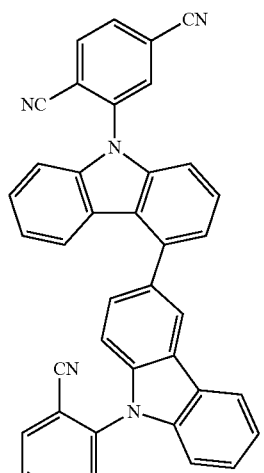
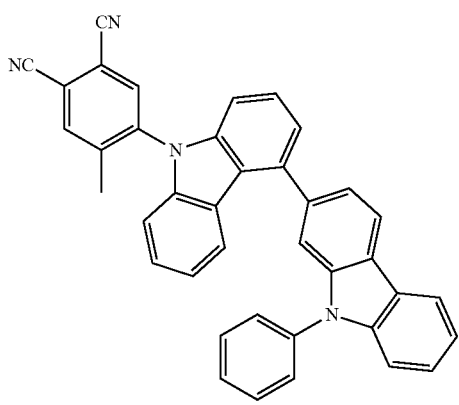 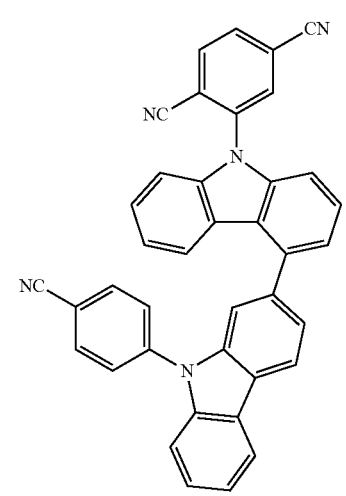
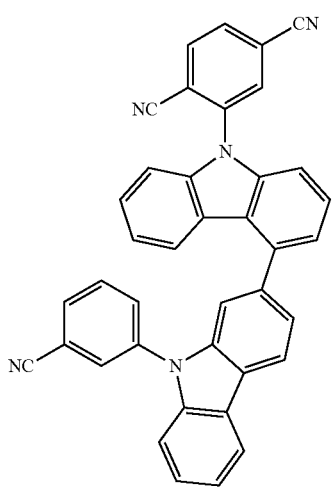 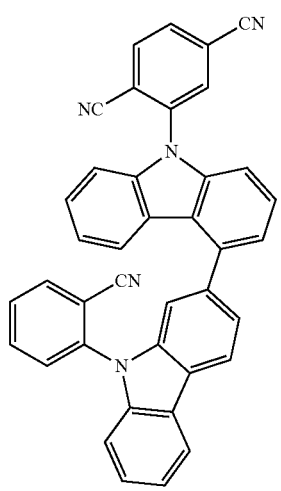 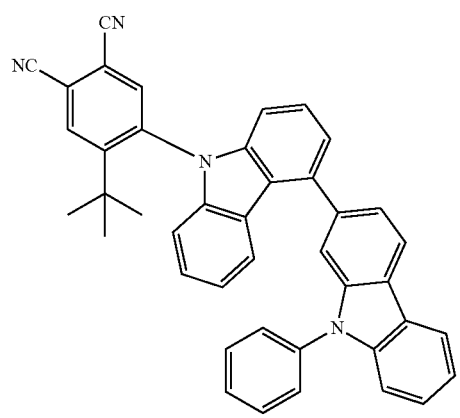

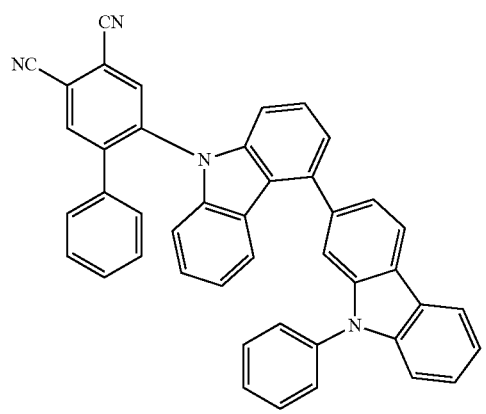
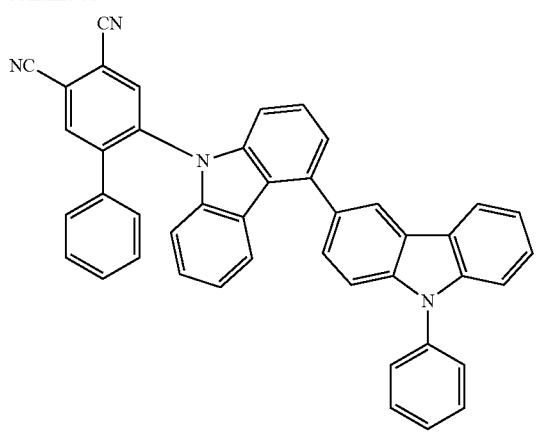
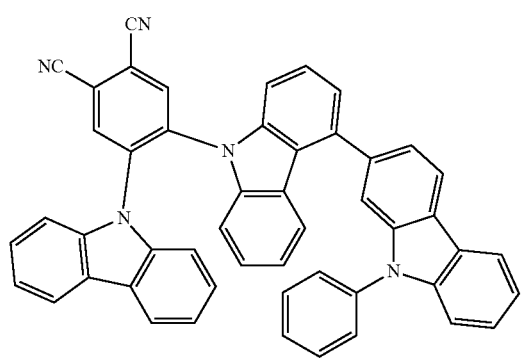
[Formula 88]
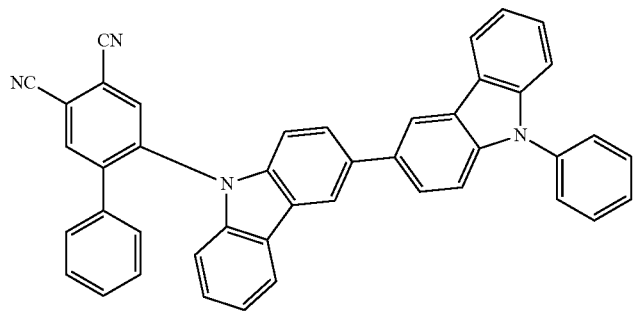
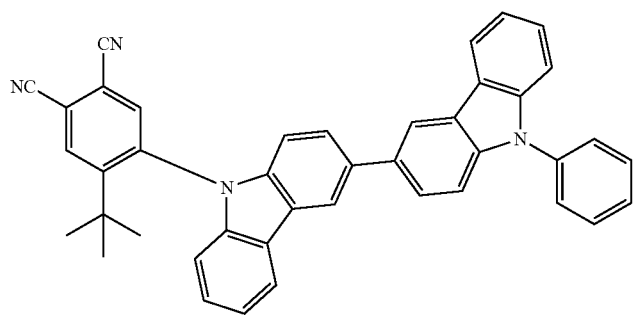

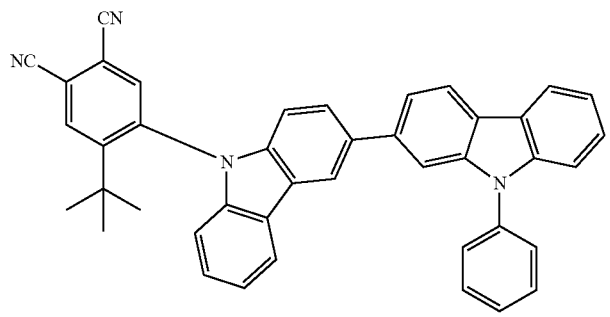
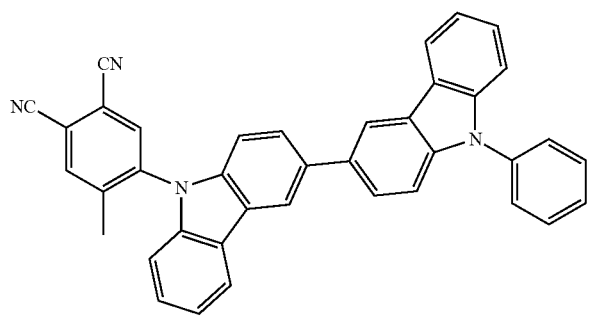
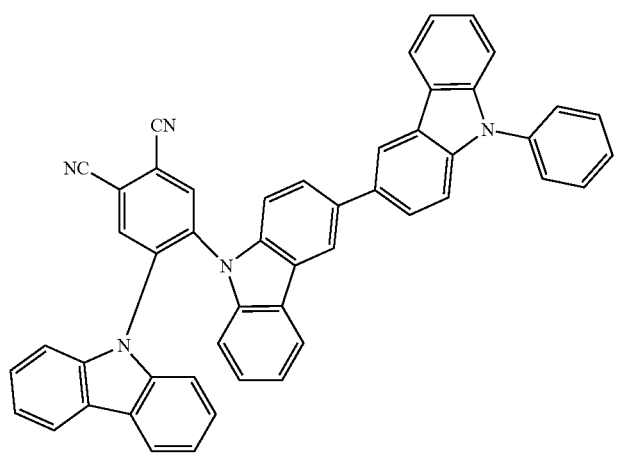
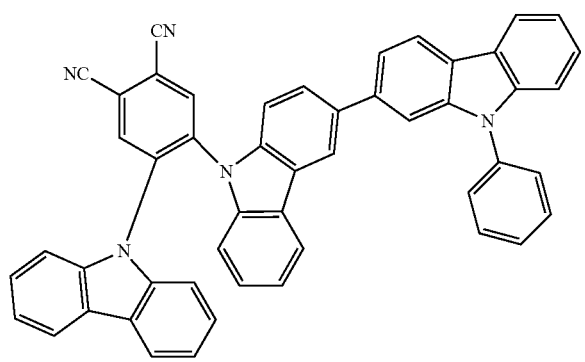

-continued
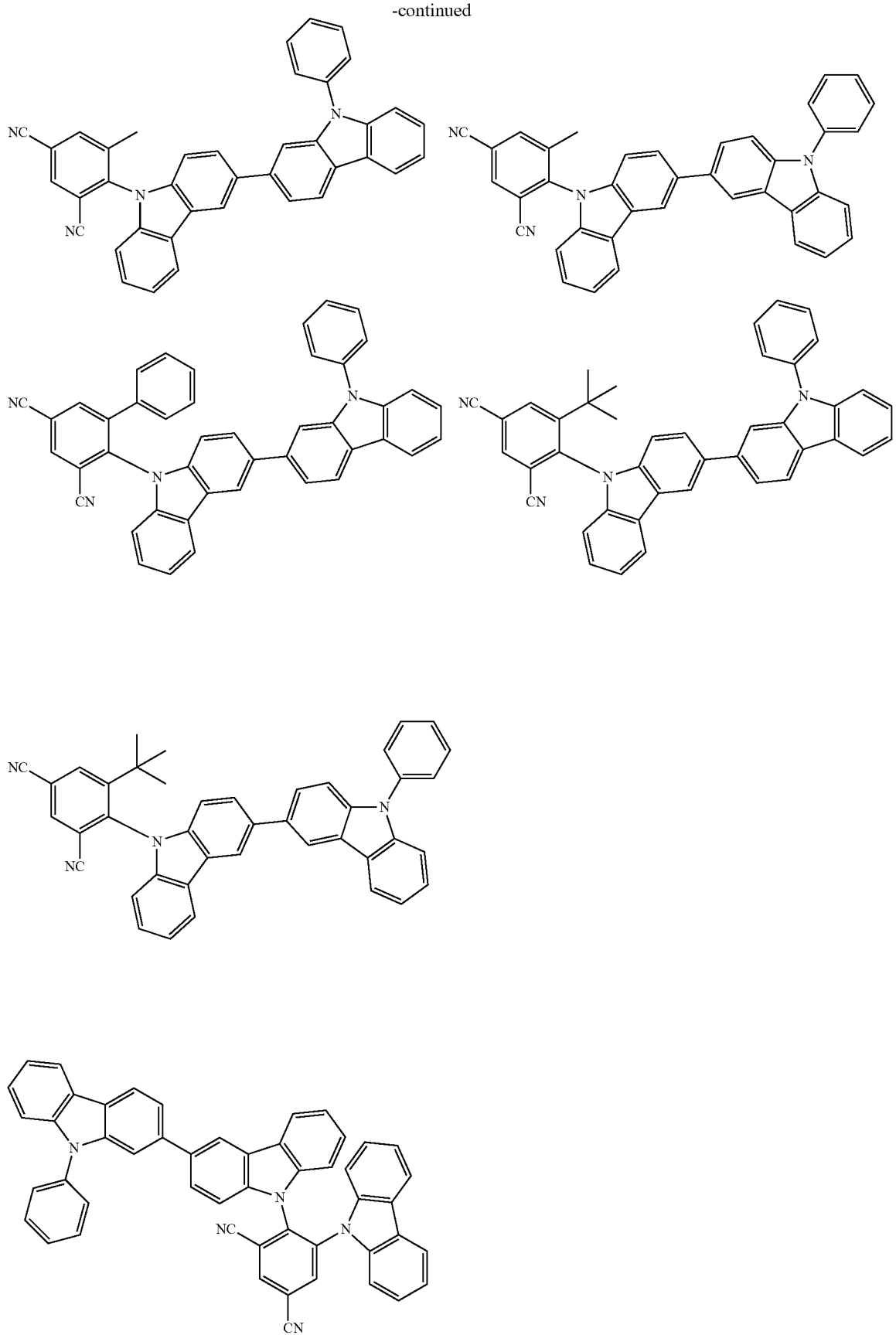

-continued
[Formula 89]
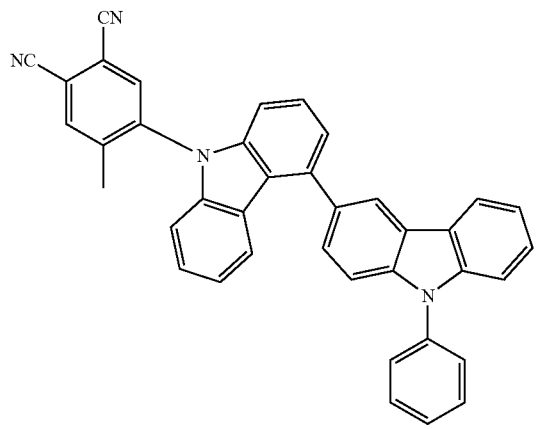
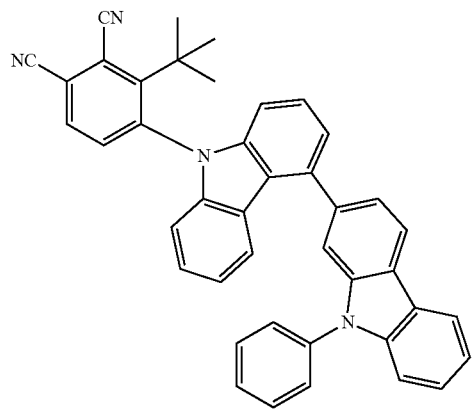
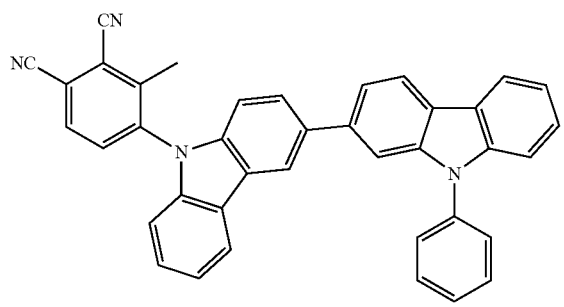
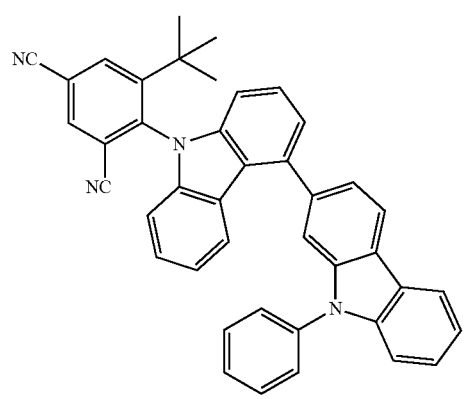
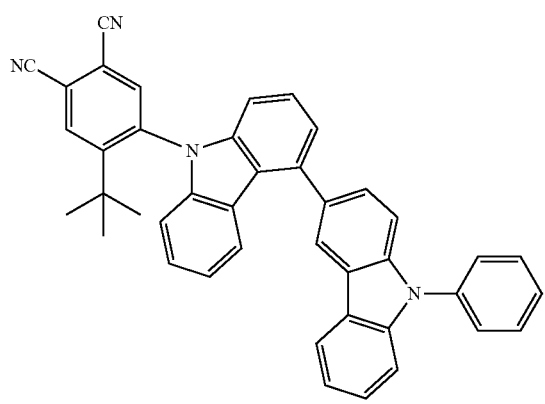
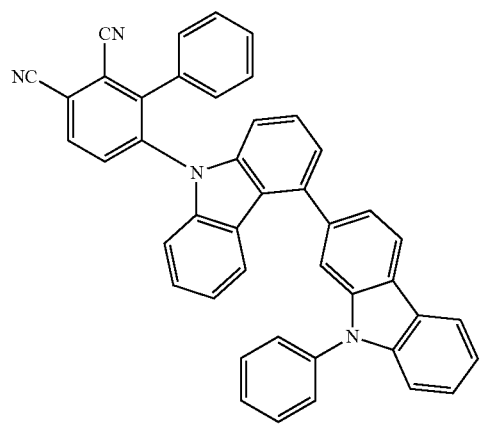
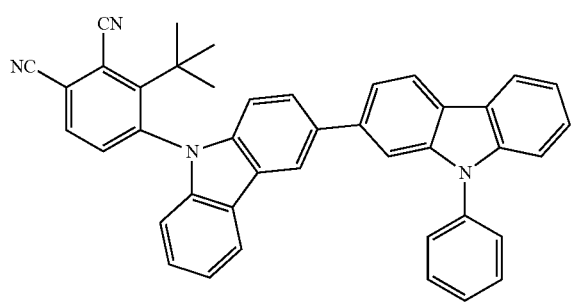
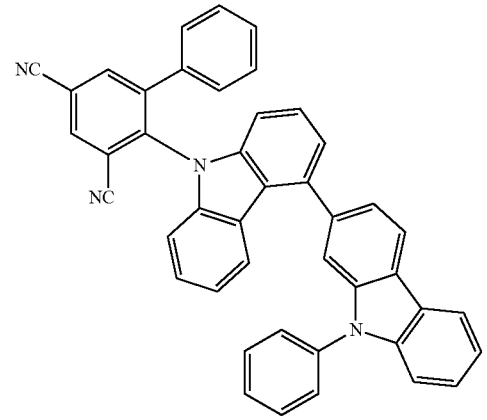

-continued
137
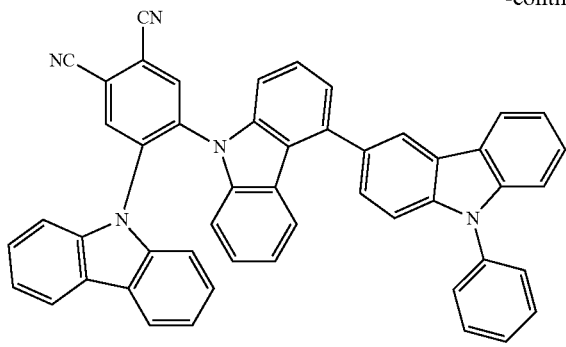
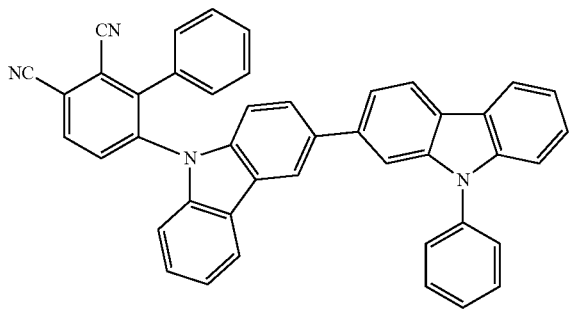
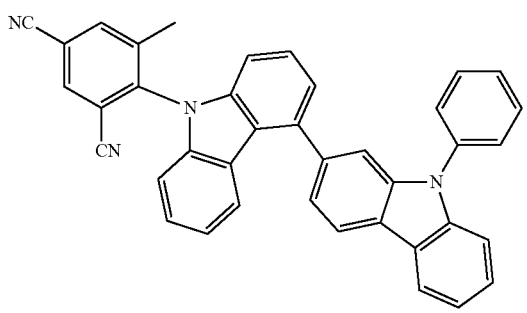
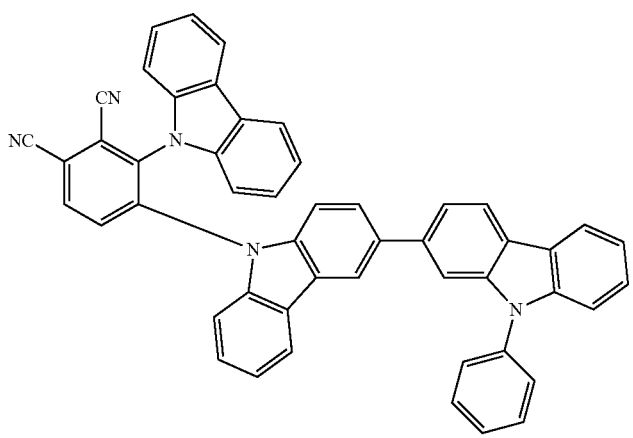
138
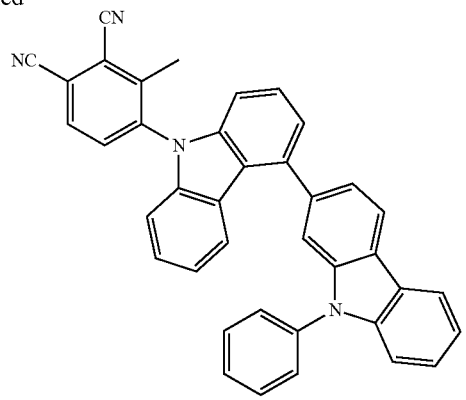
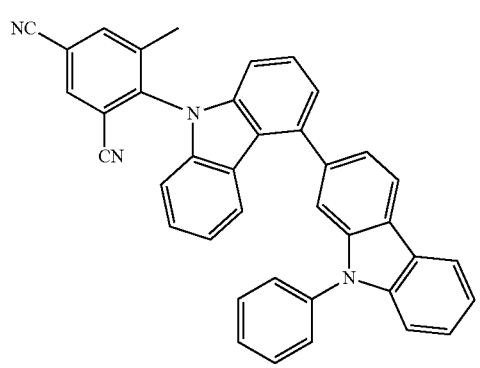
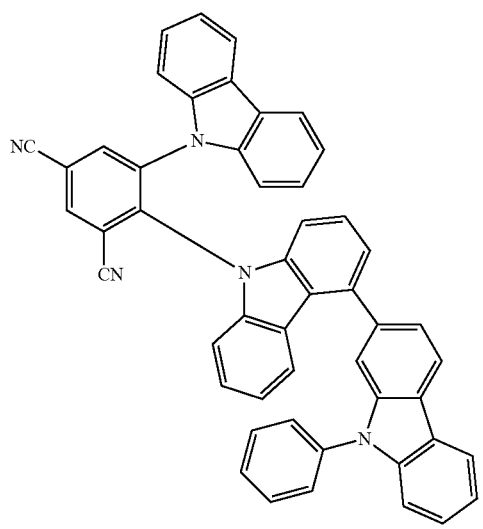

[Formula 90]
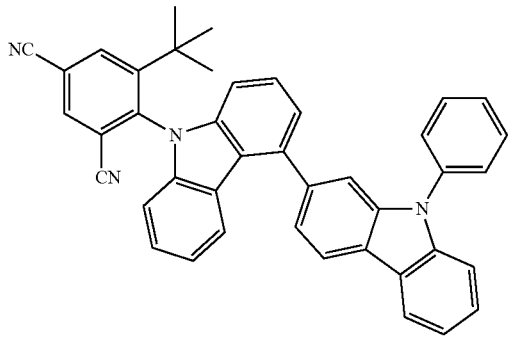
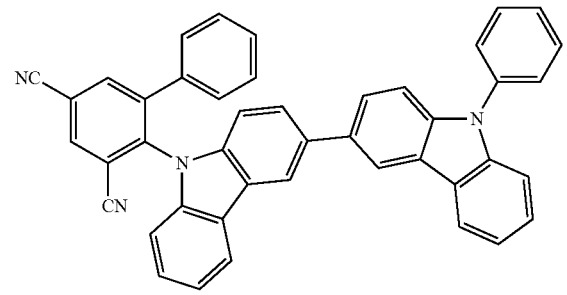
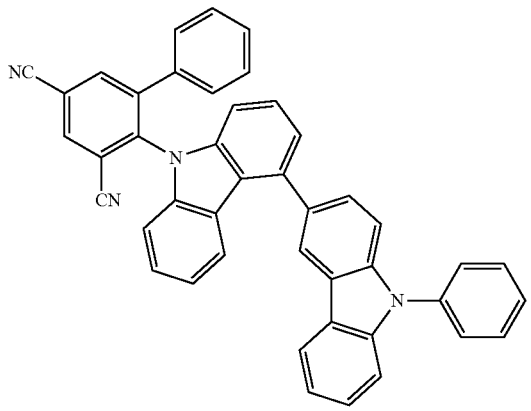
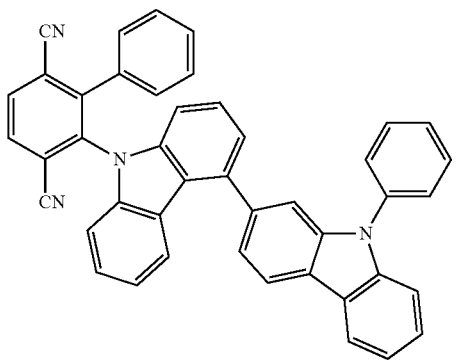
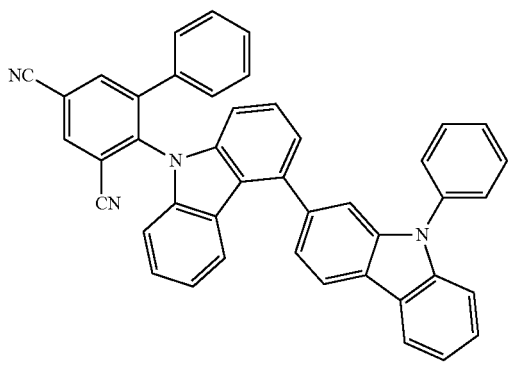
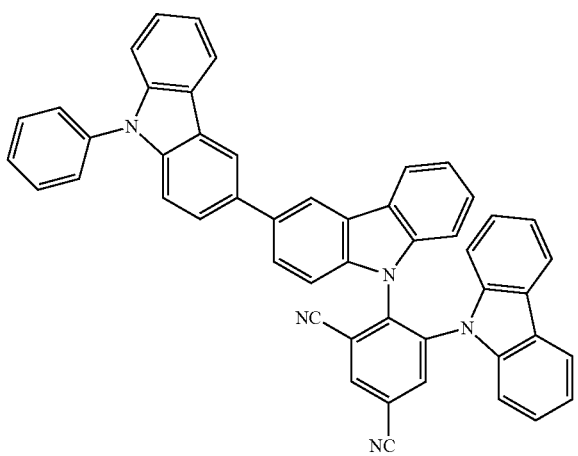

-continued
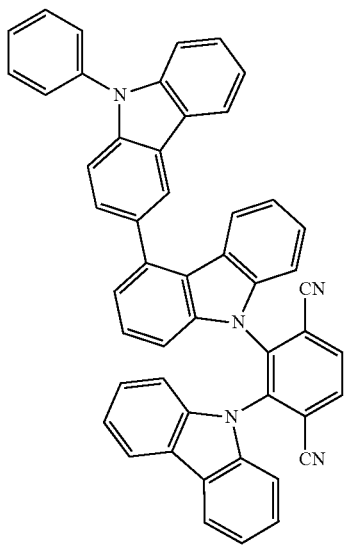 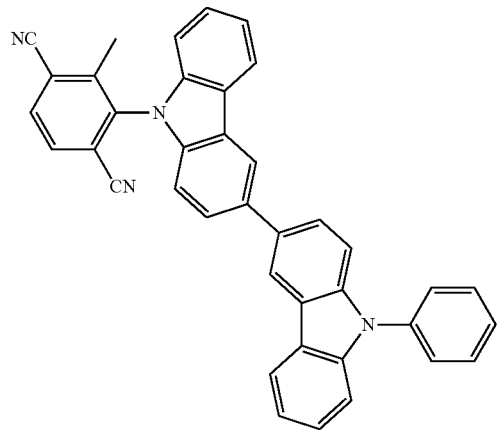
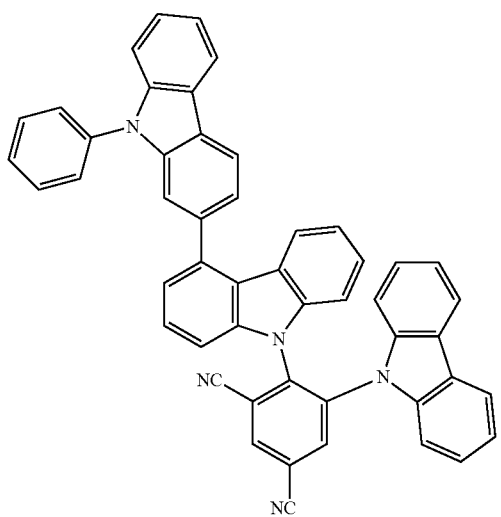 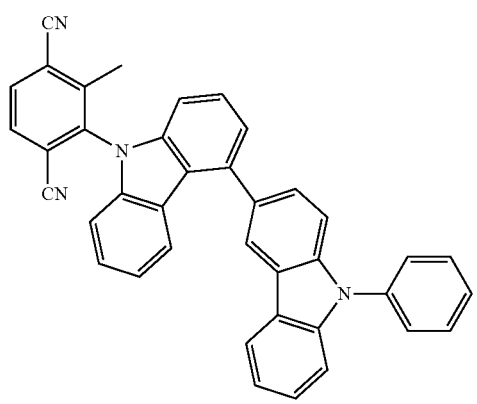
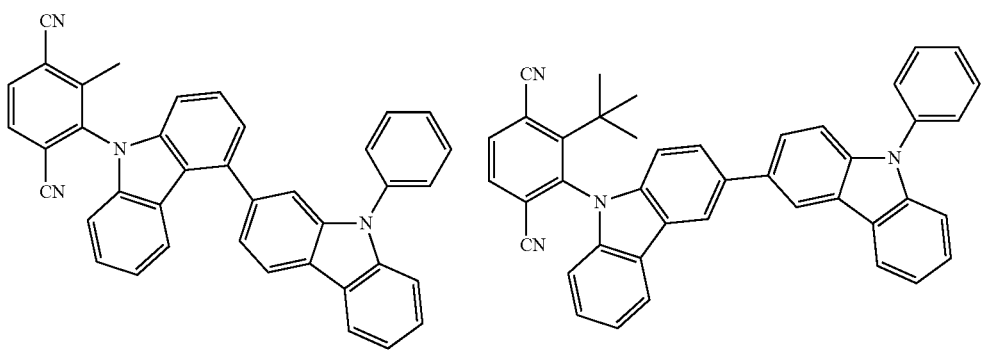

143
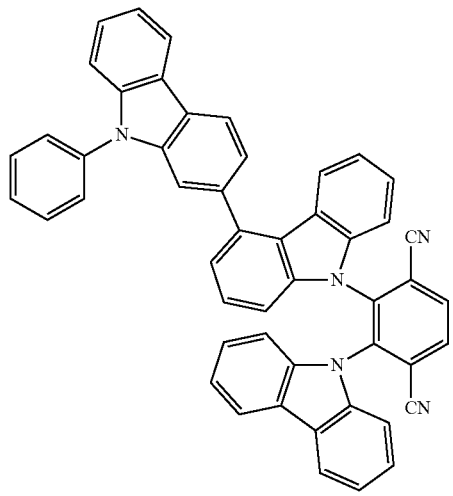
144
-continued
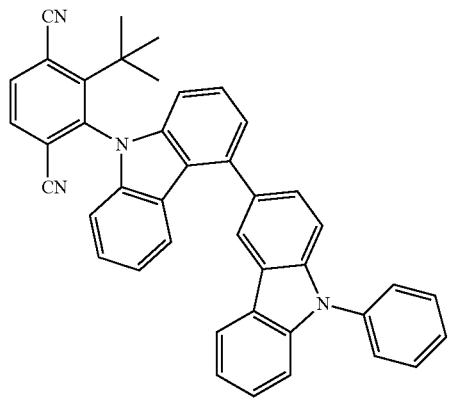
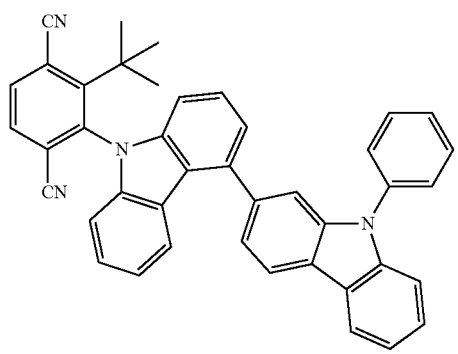
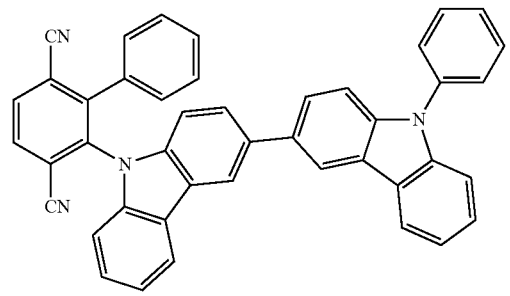
[Formula 91]
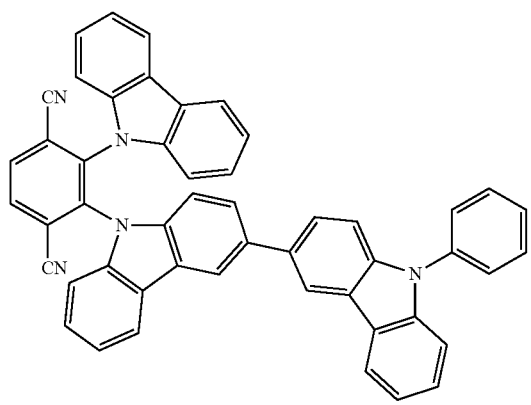
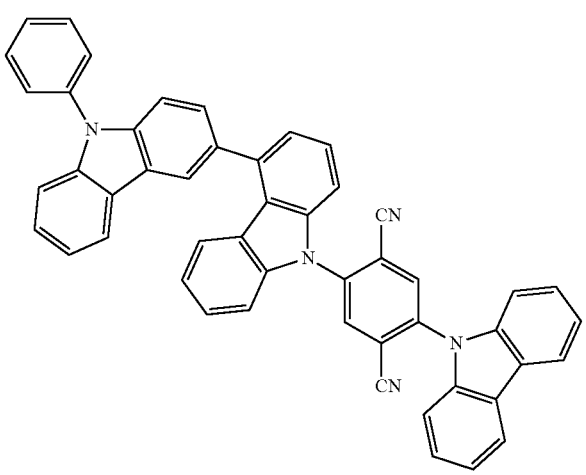

-continued
145
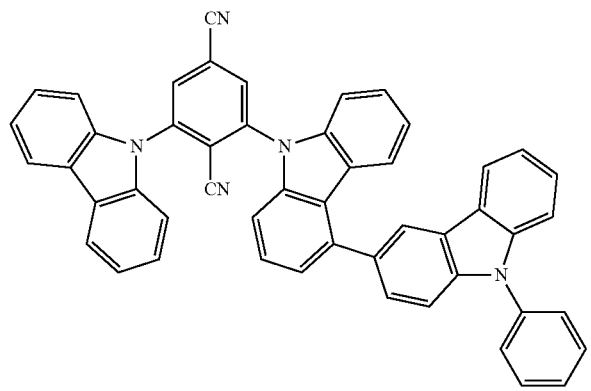
146
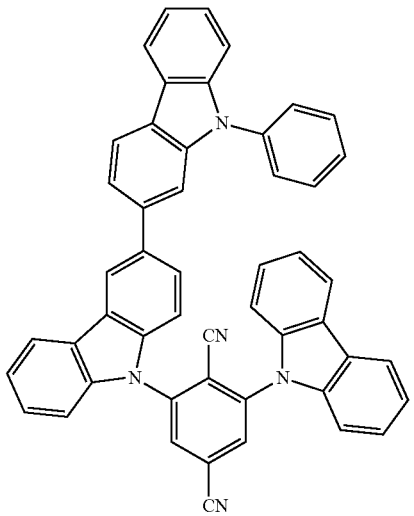
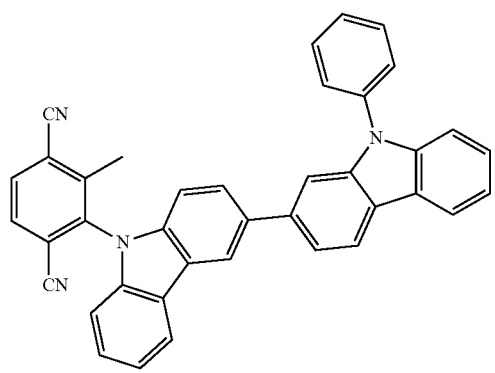
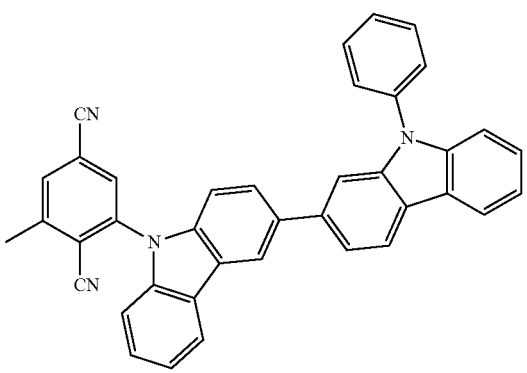
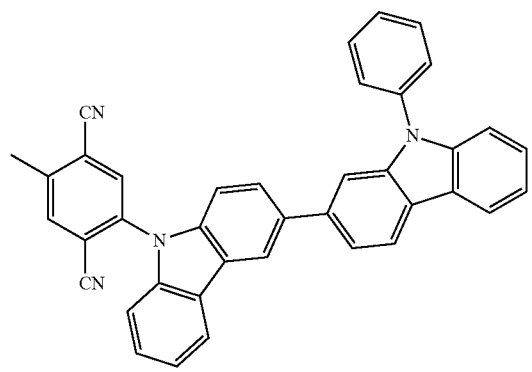

-continued
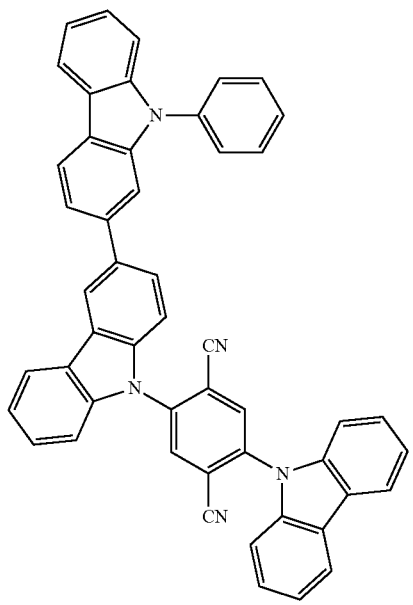
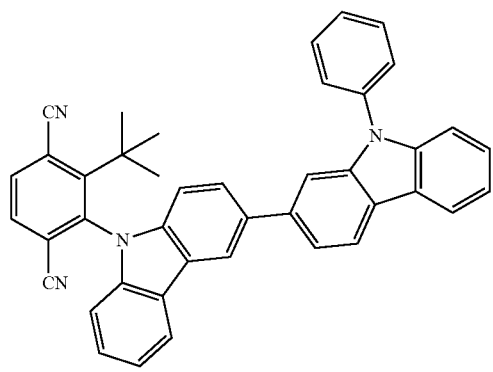
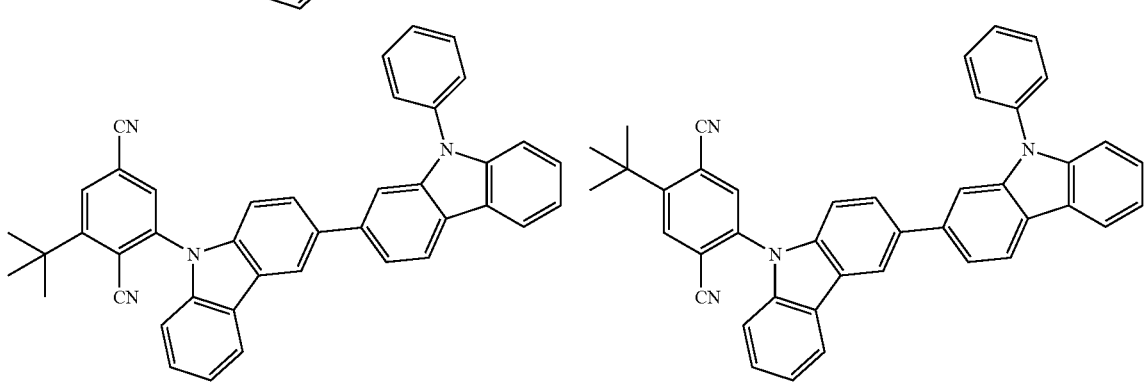
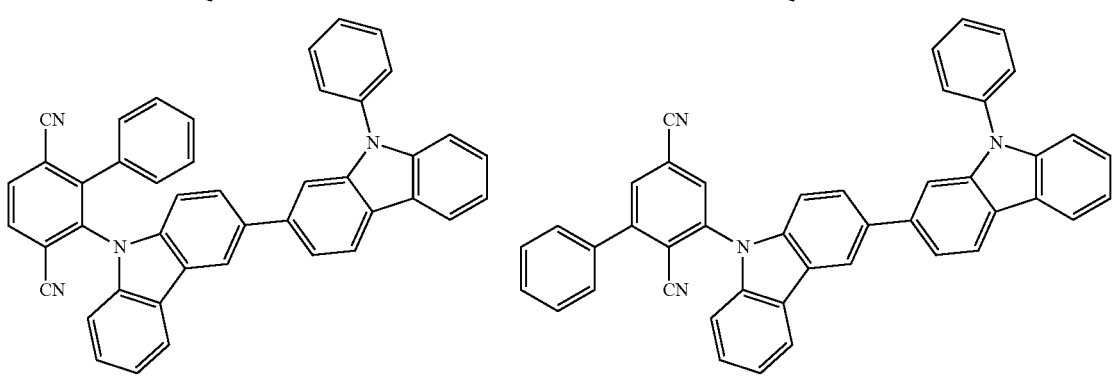
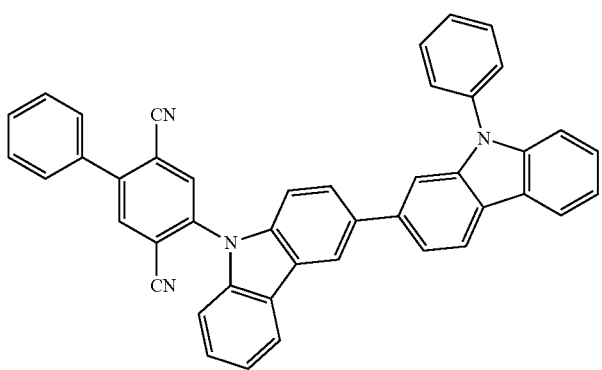

149
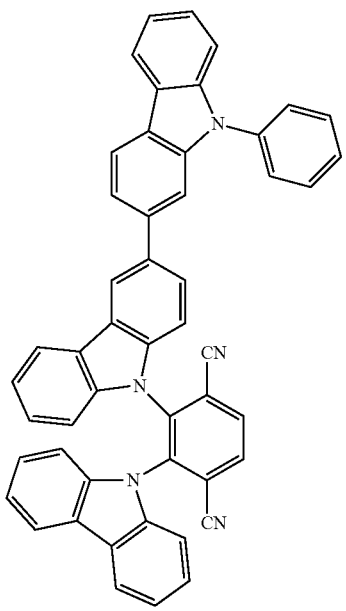
150
-continued
[Formula 92]
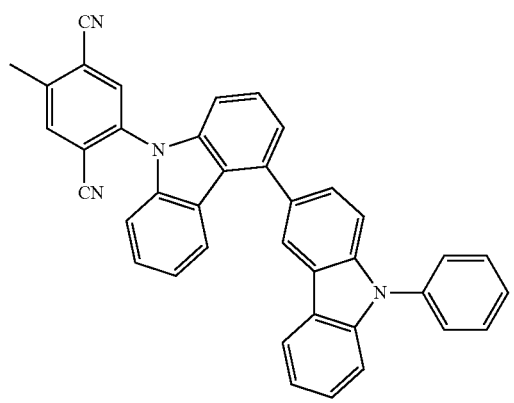 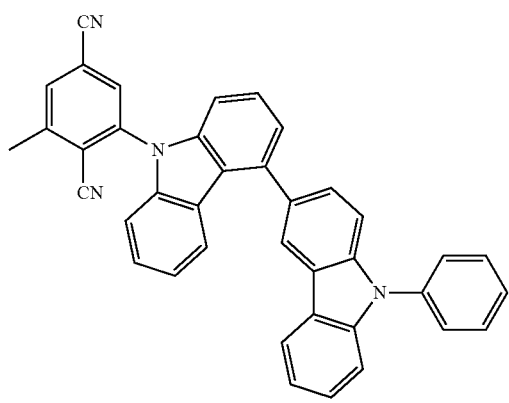
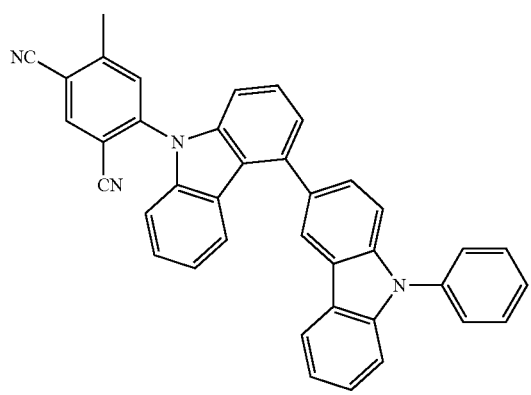 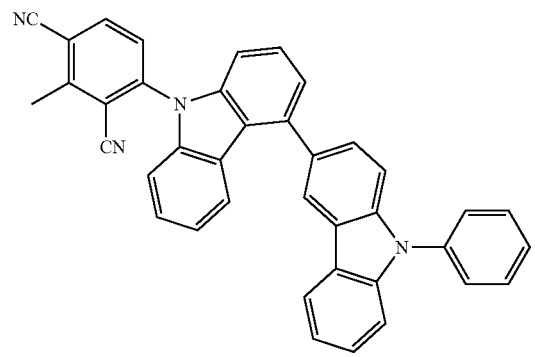

-continued
| 151 | 152 |
|---|---|
| 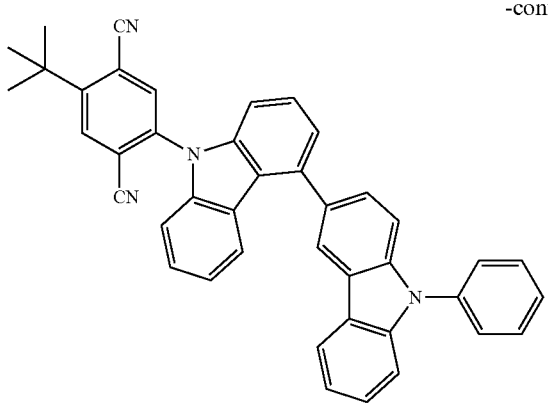 | 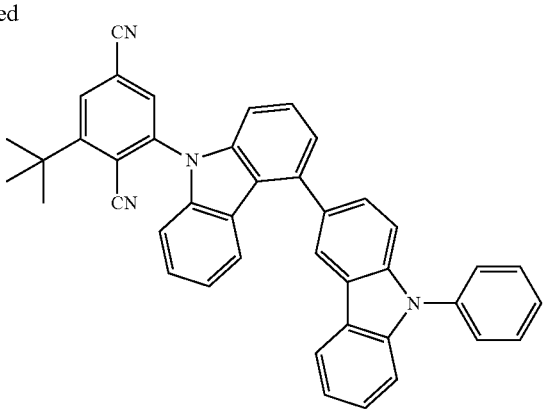 |
| 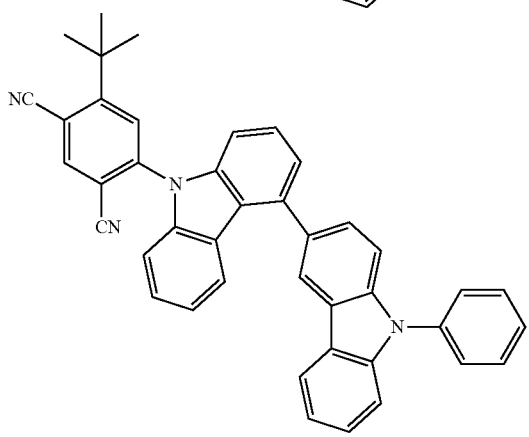 | 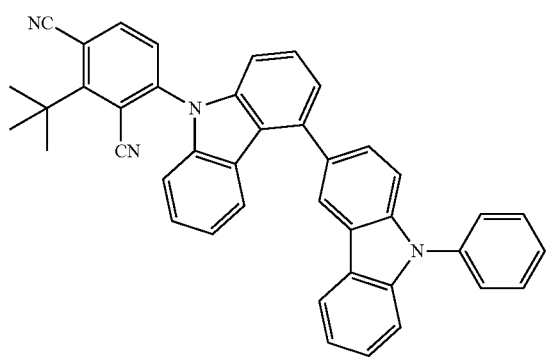 |
| 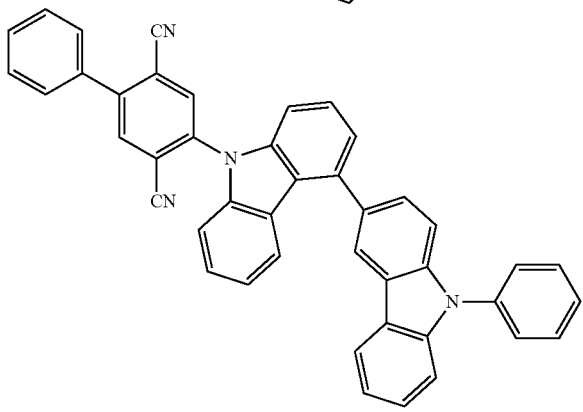 | |
| 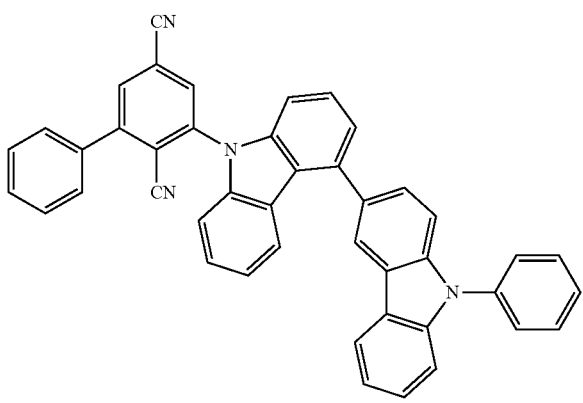 | |

-continued
153
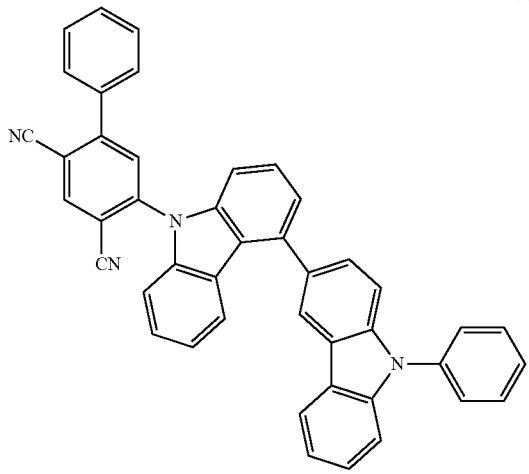
154
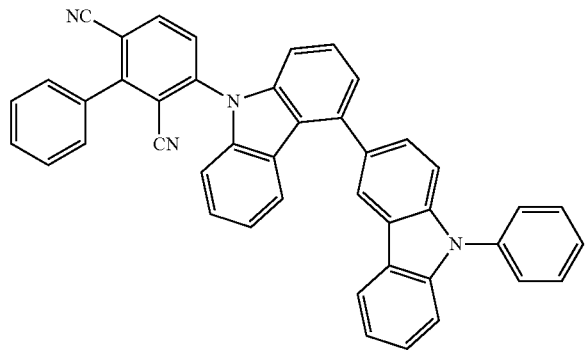
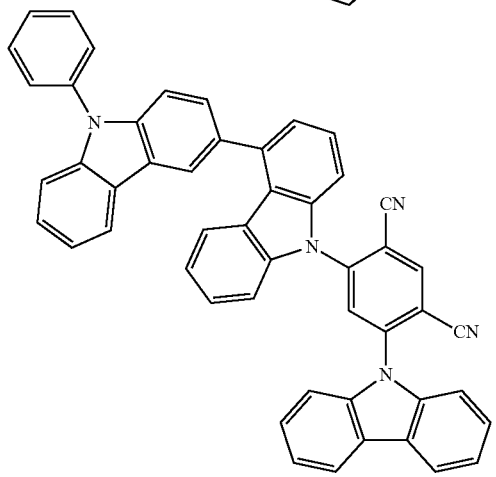
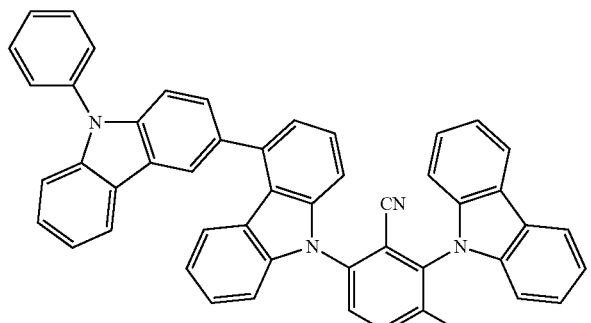
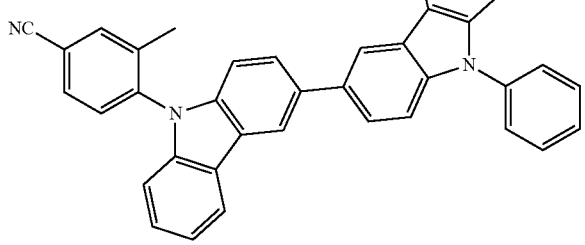
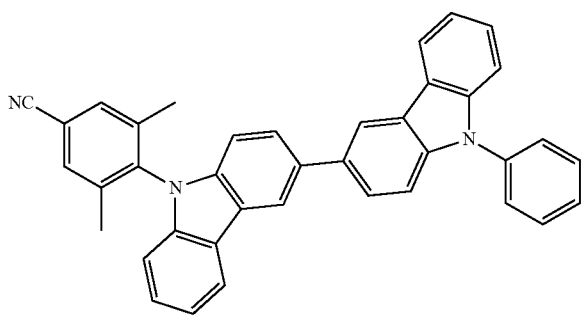

[Formula 93]
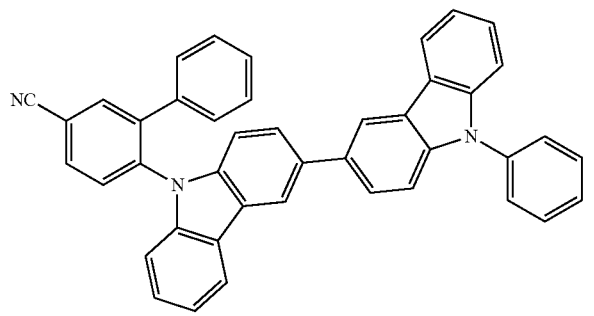
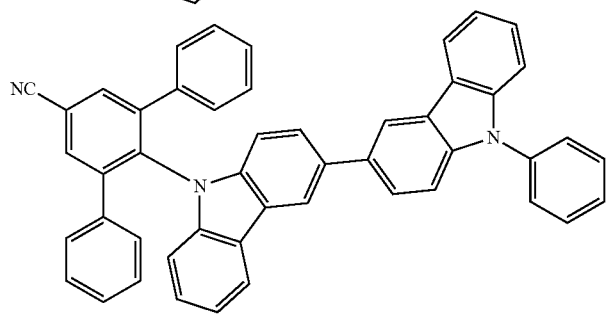
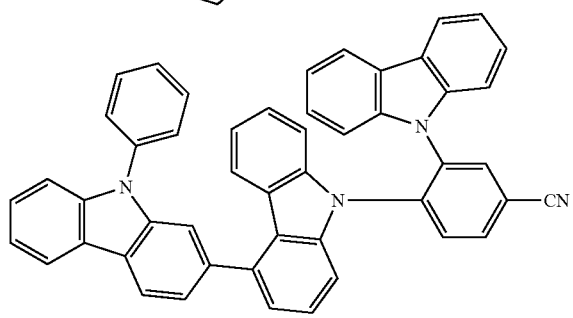
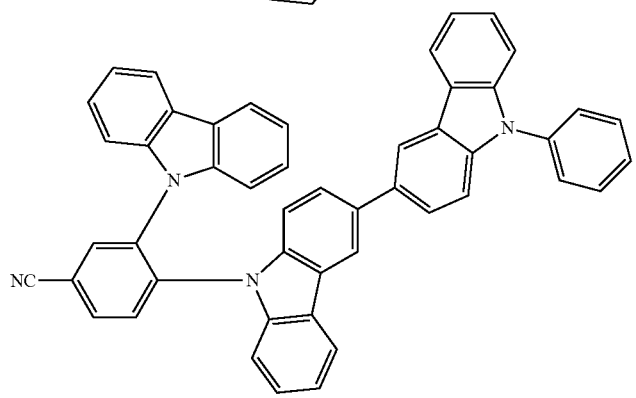
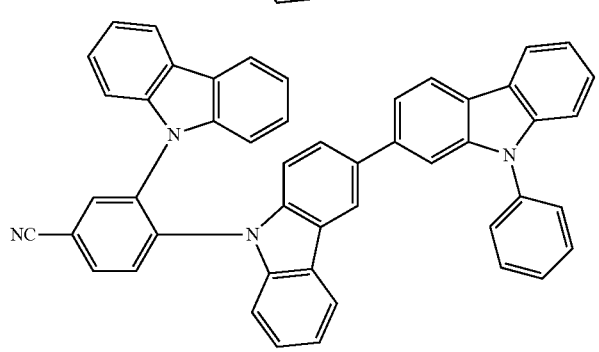
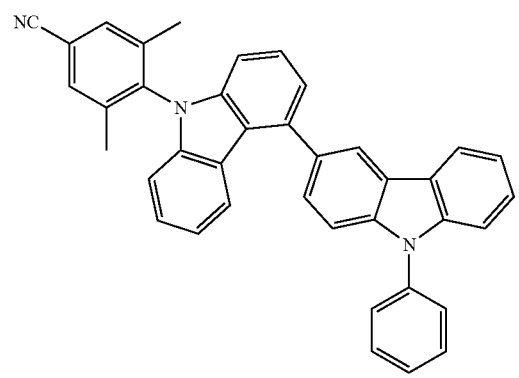

-continued
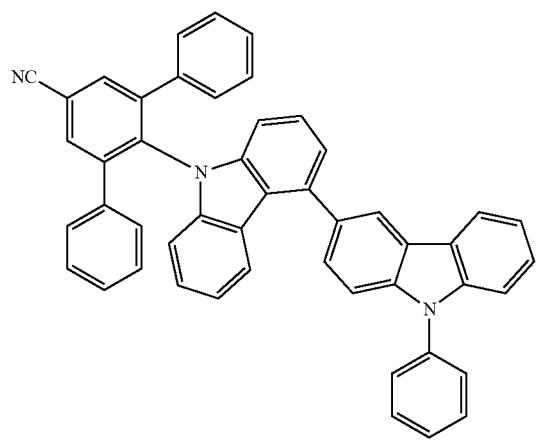
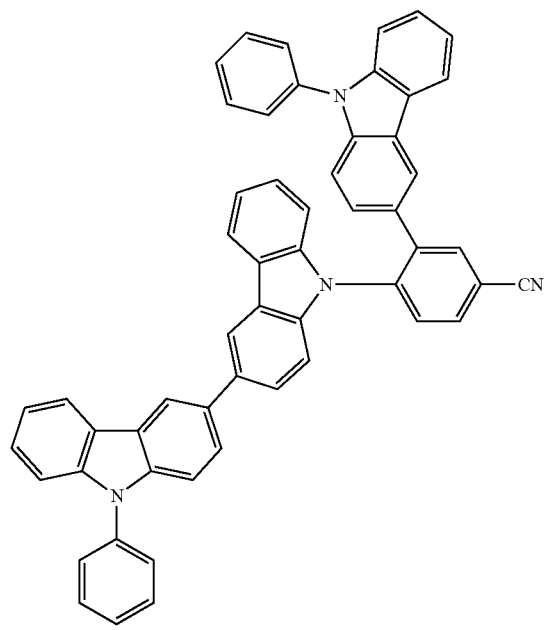
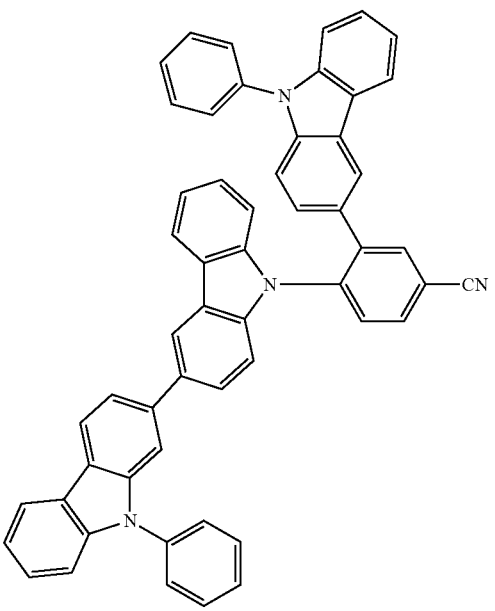
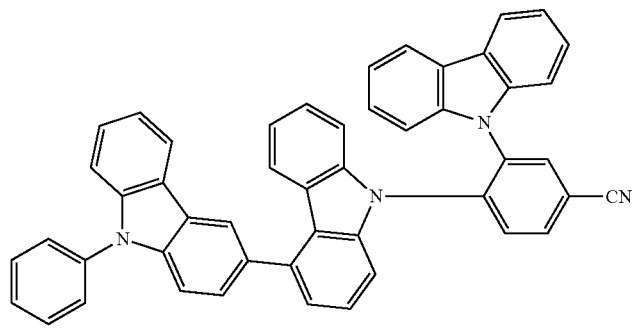
[Formula 94]
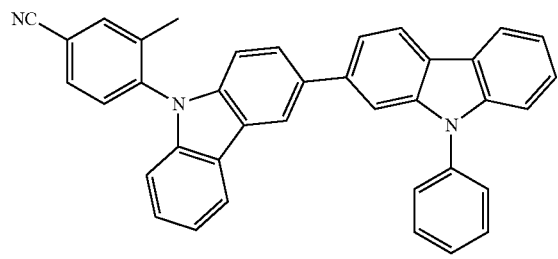
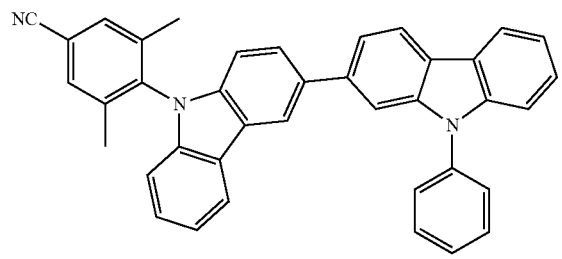

-continued
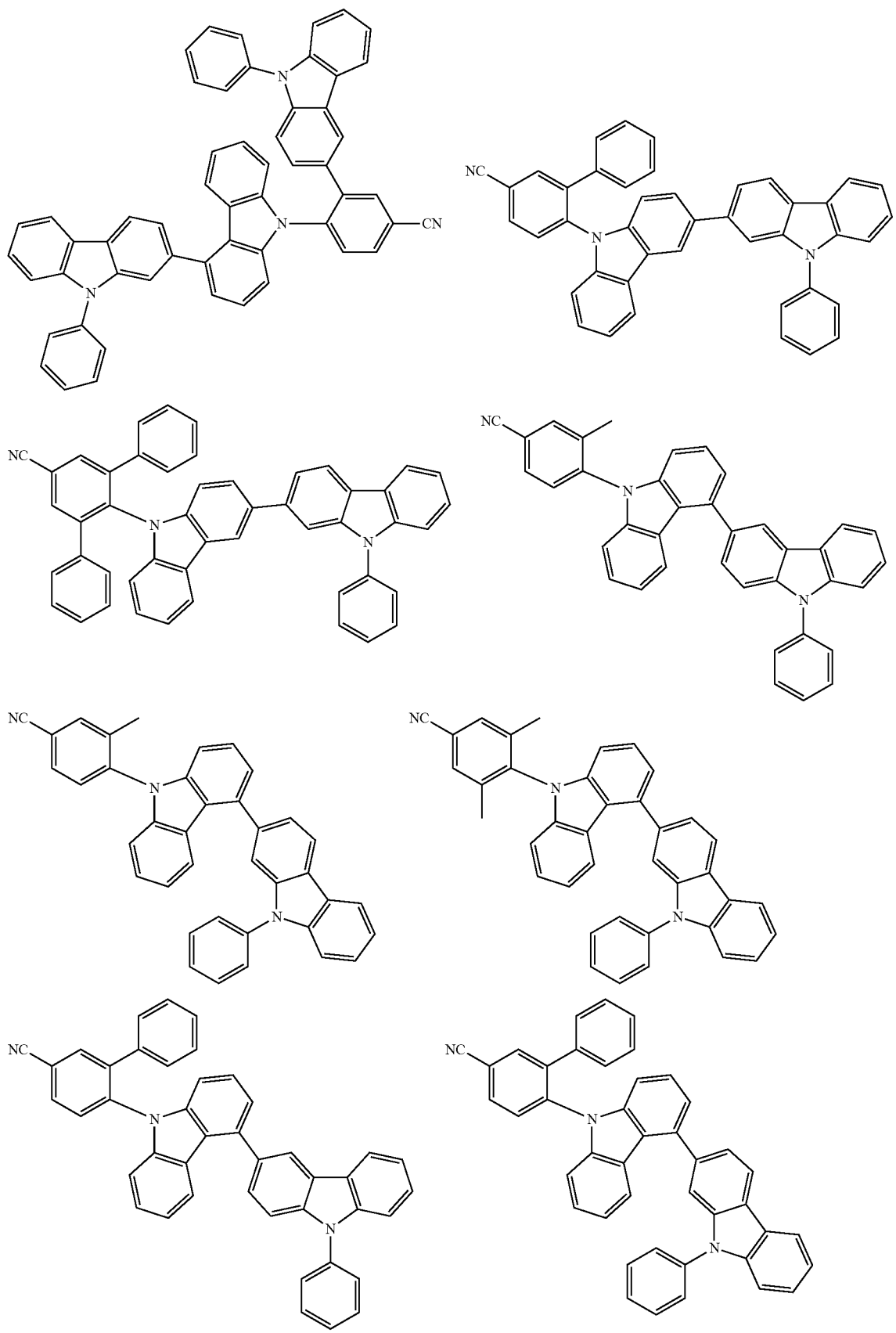

161 162
-continued
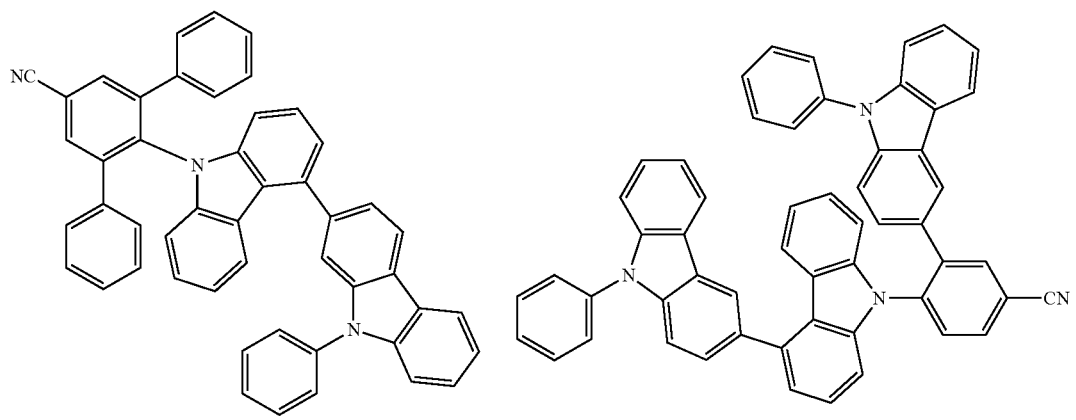
[Formula 95]
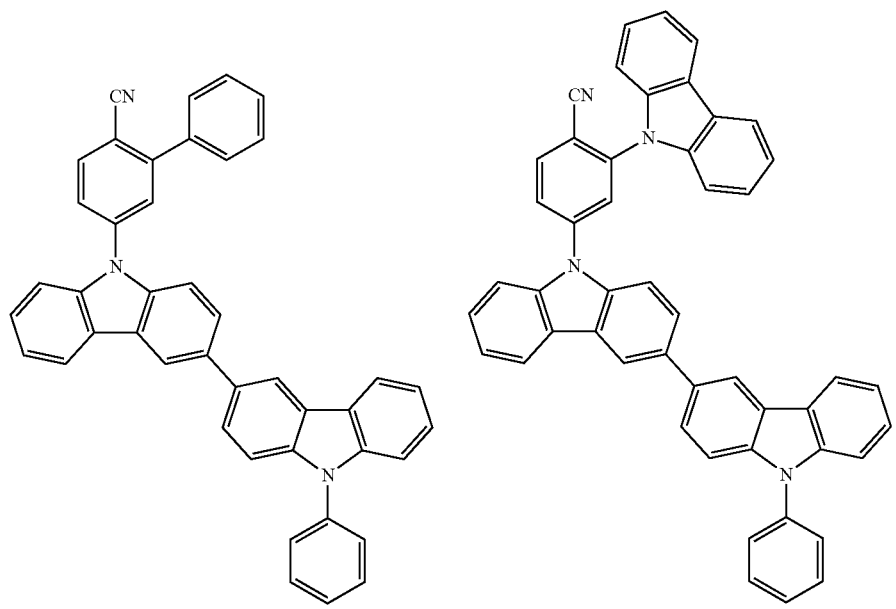

-continued
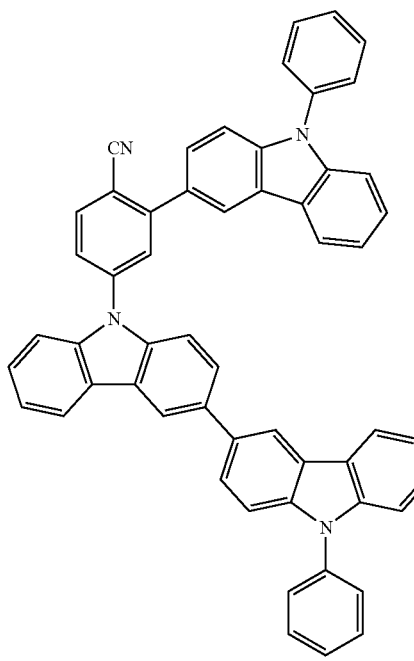 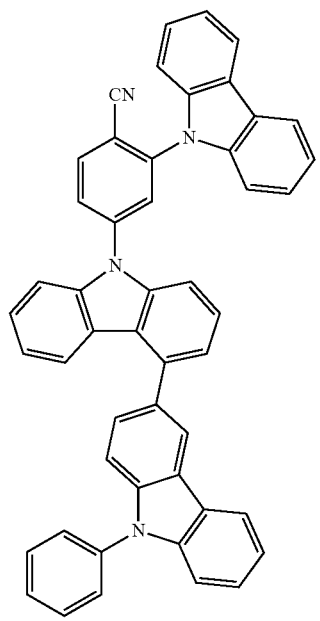
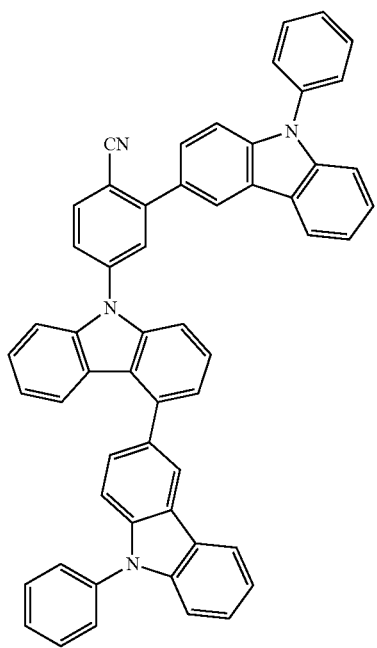 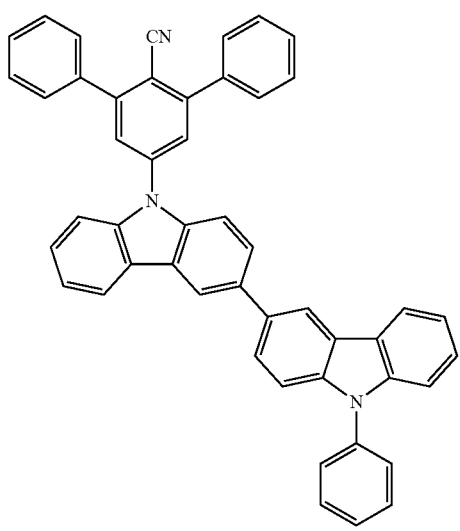

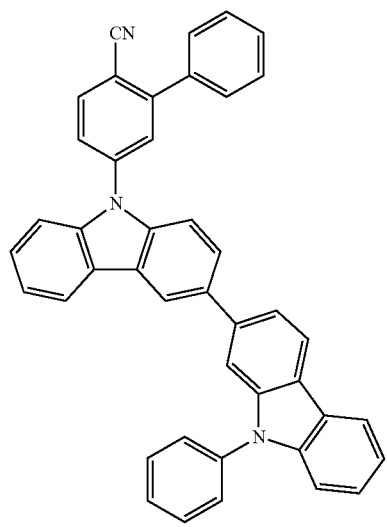
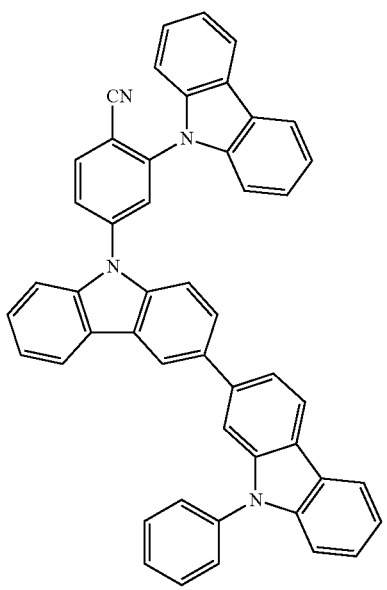
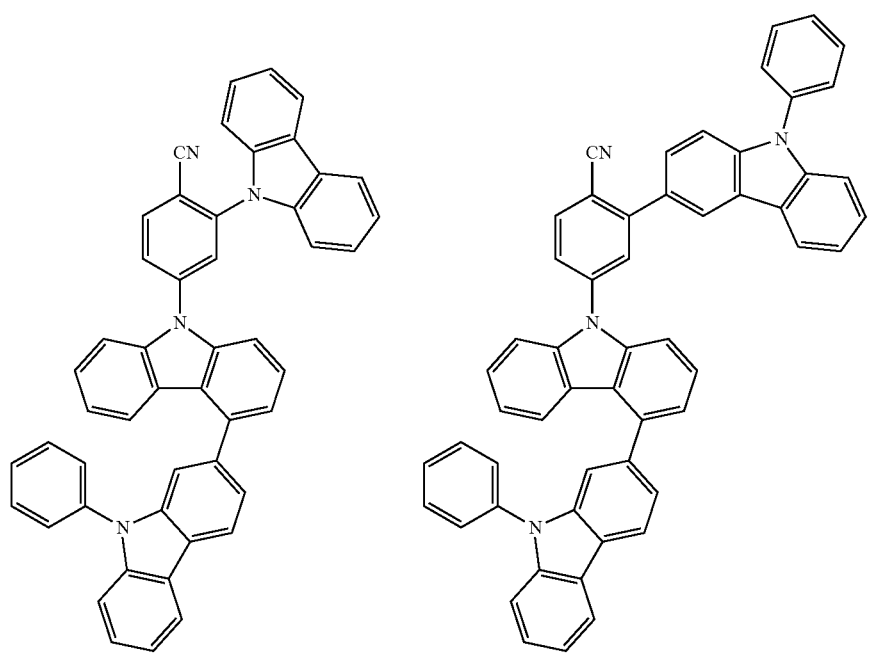

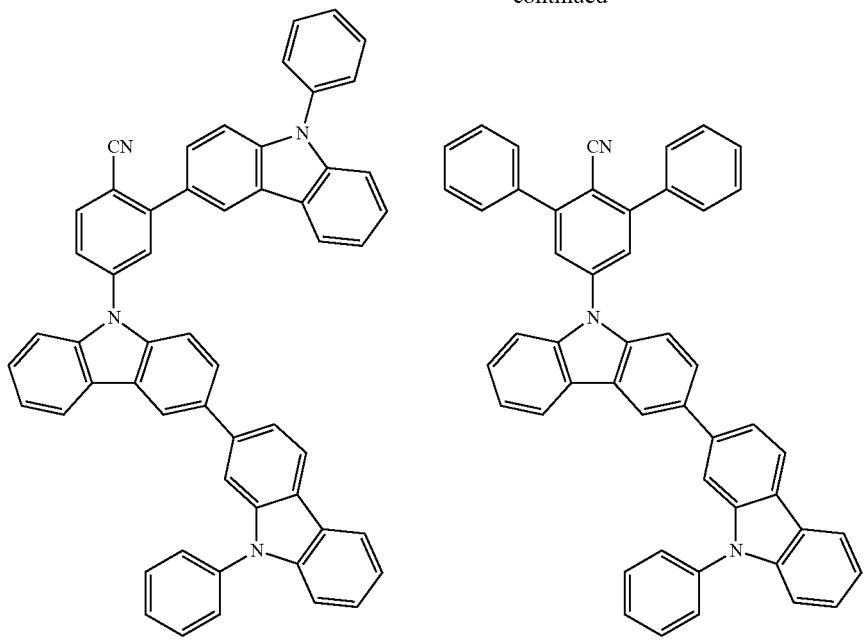
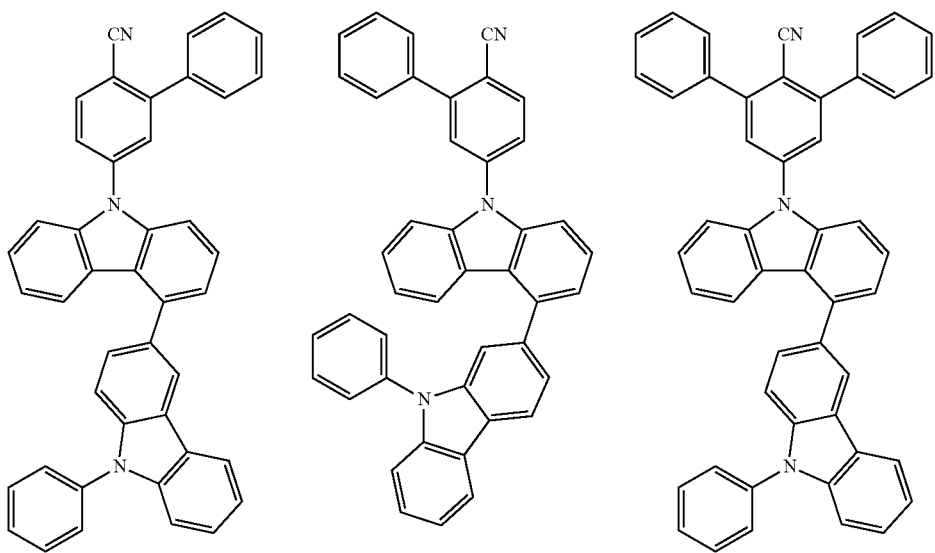

[Formula 96]
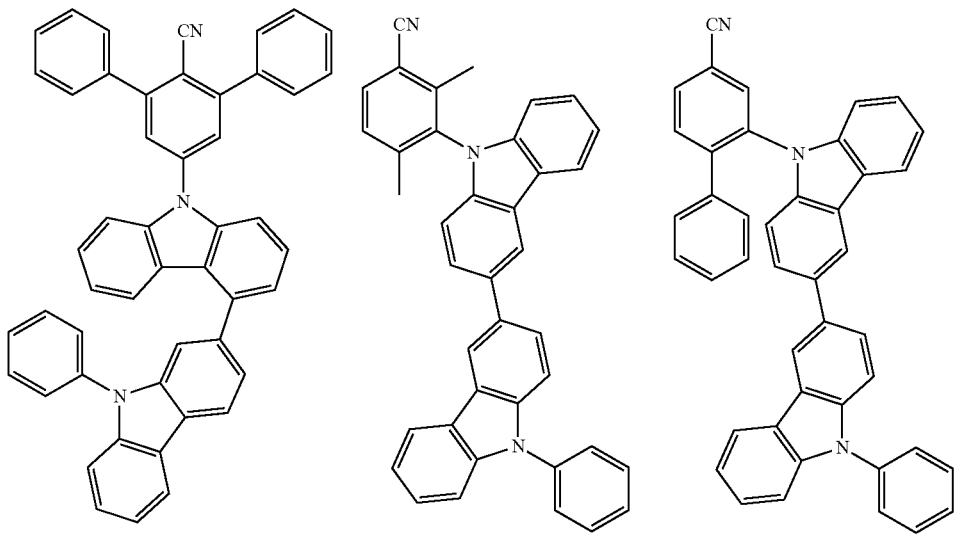
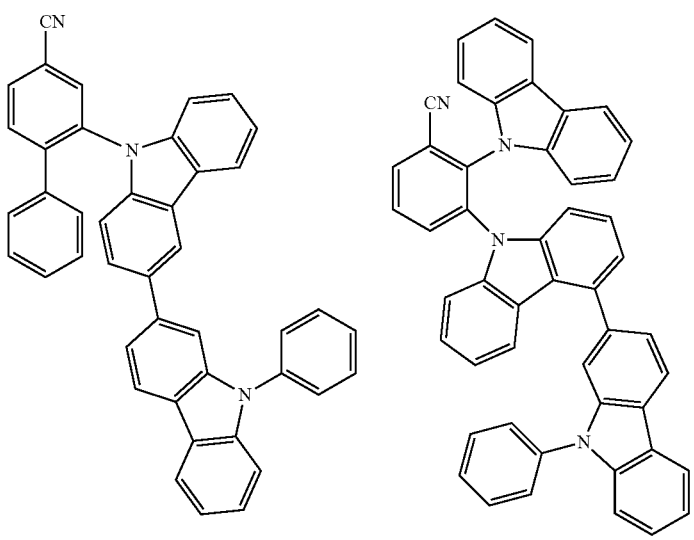
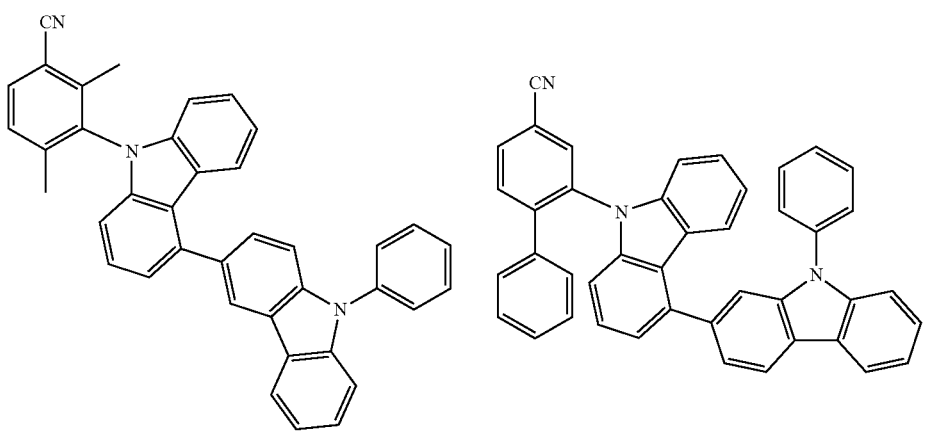

-continued
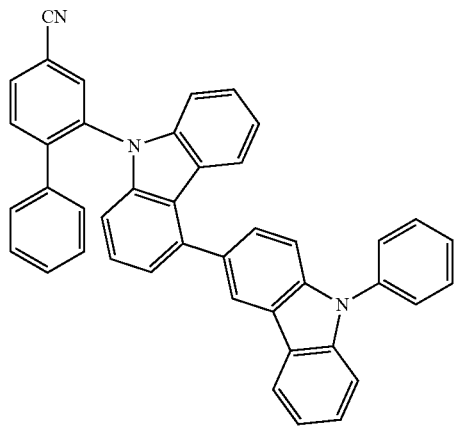
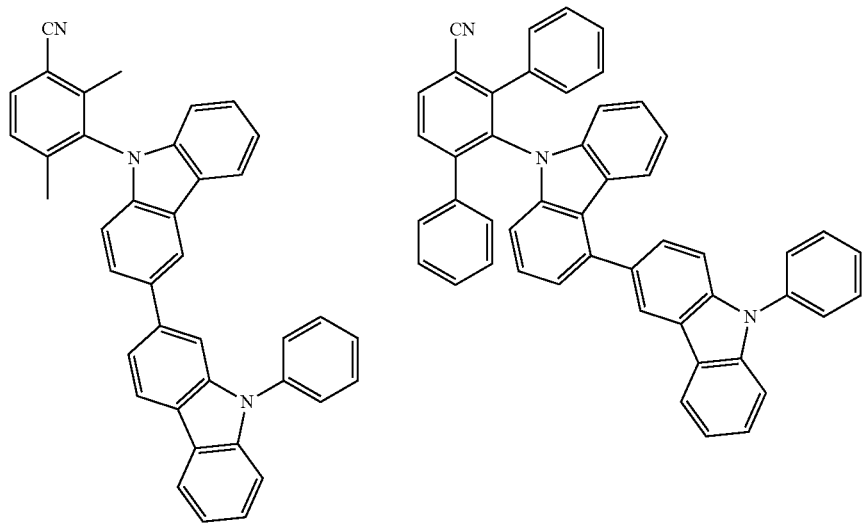
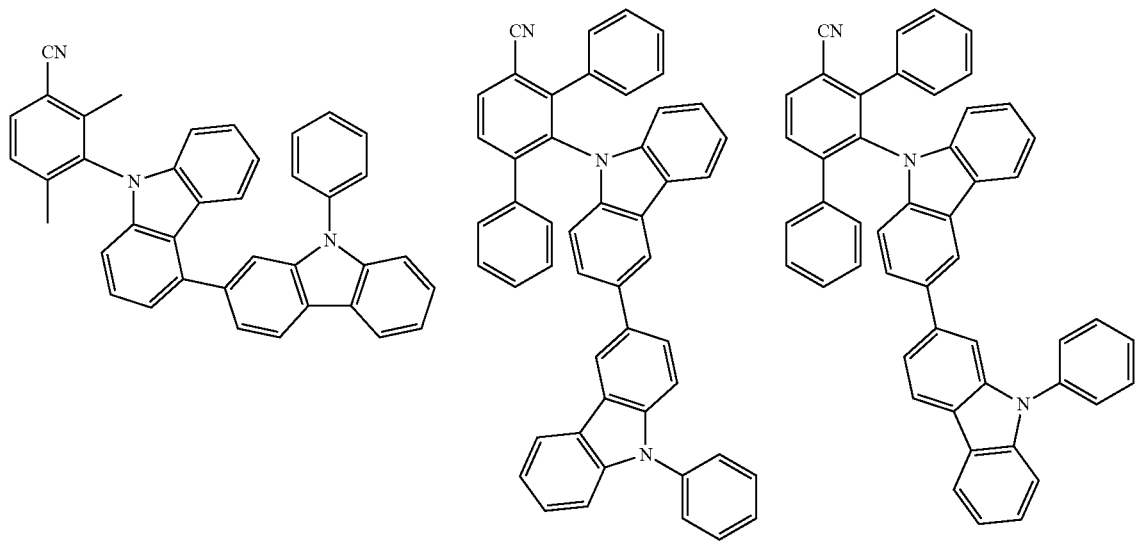

-continued
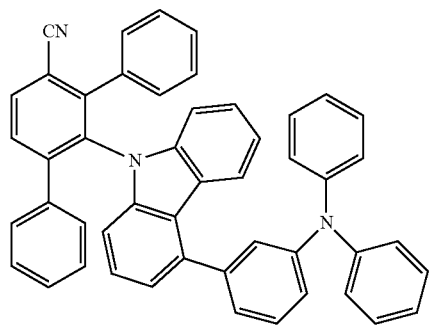
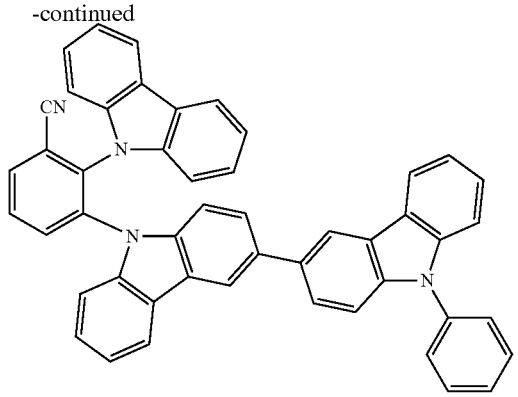
[Formula 97]
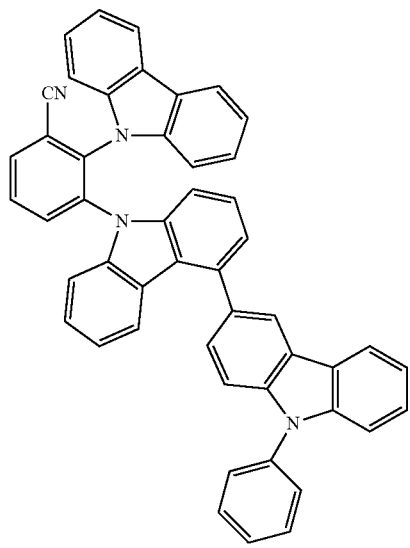
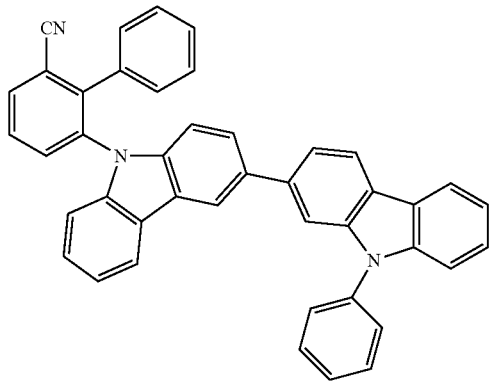
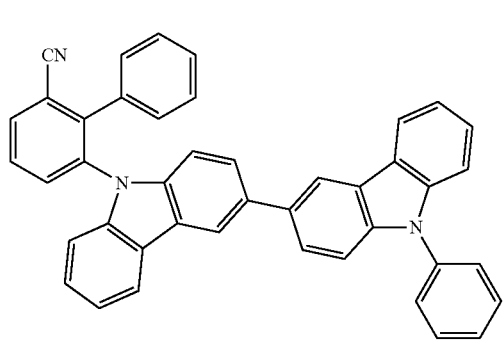
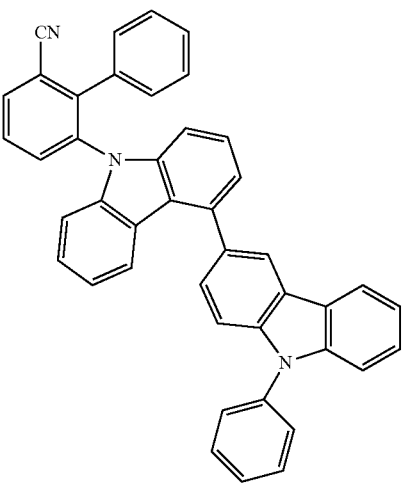

-continued
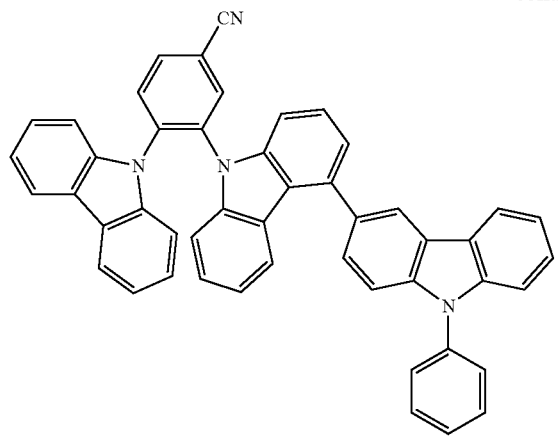
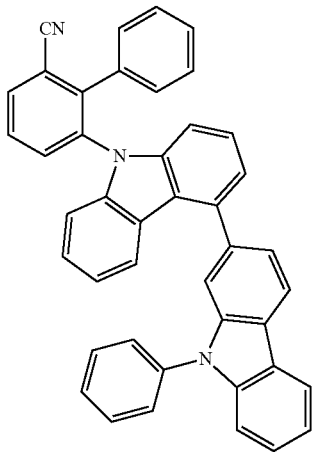
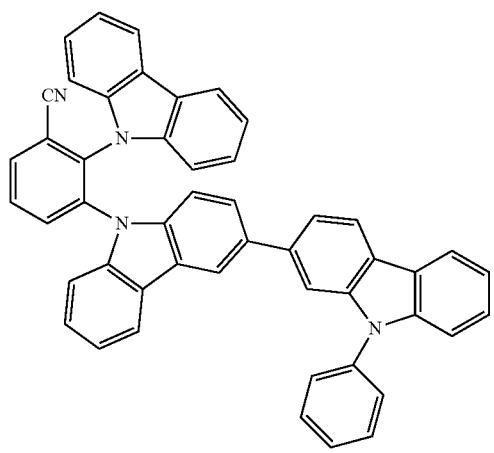
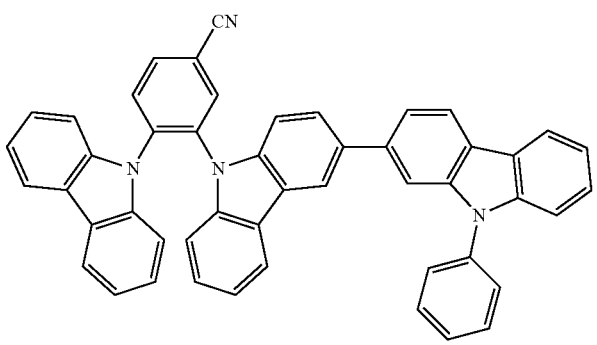
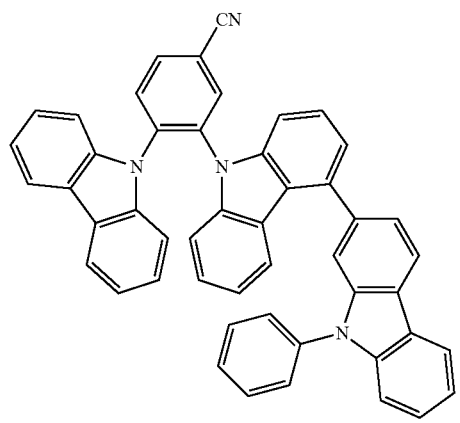
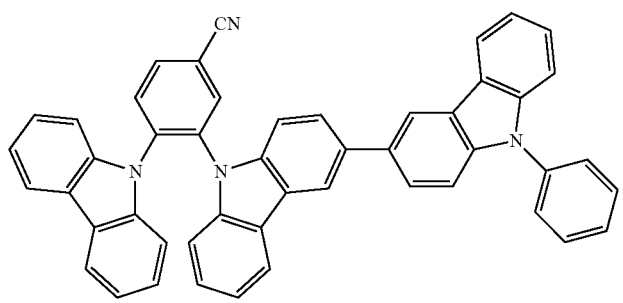
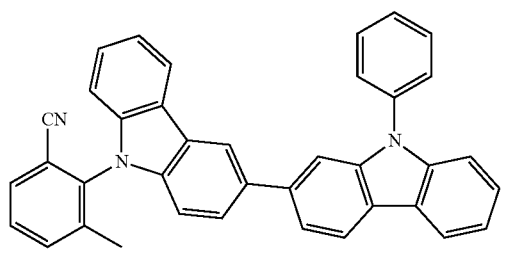
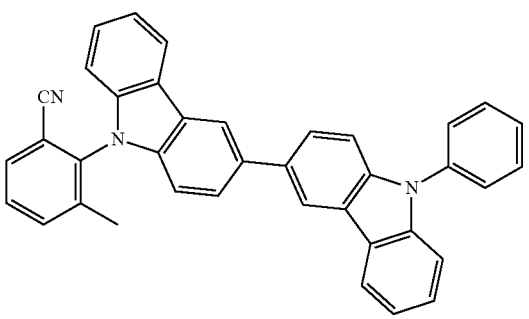

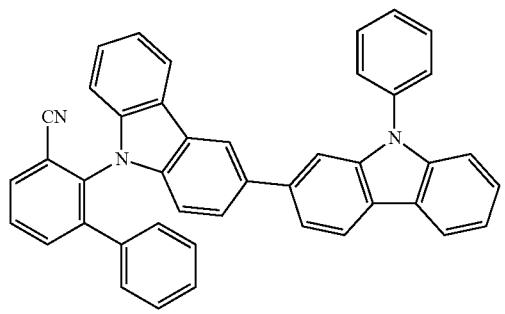
[Formula 98]
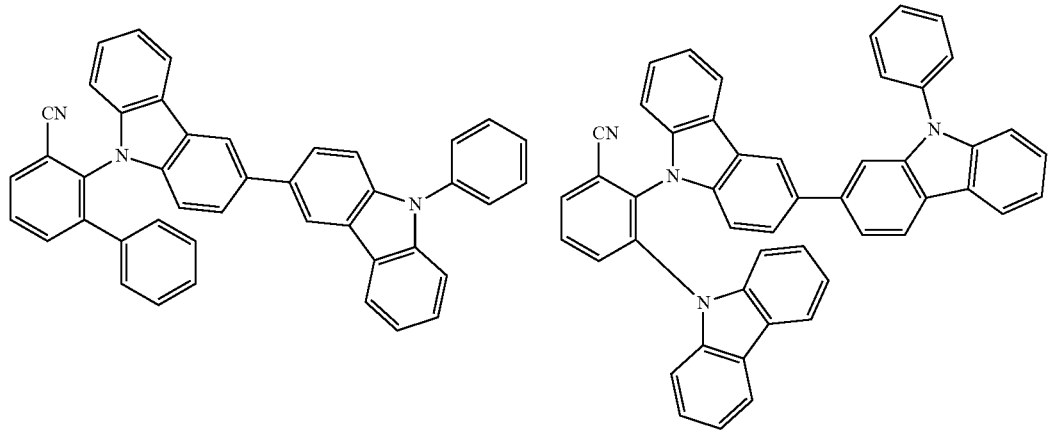
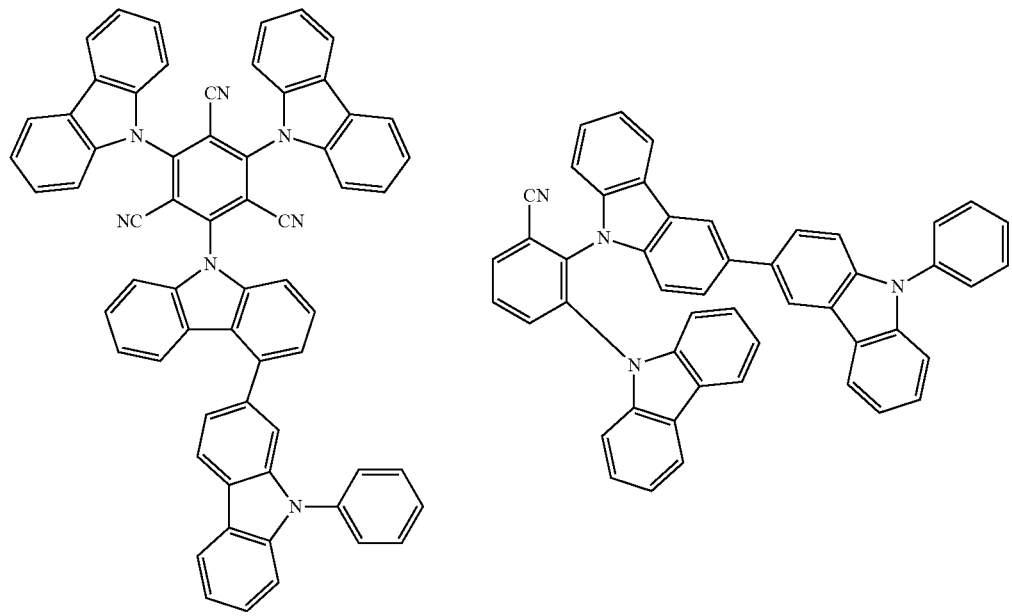

-continued
179
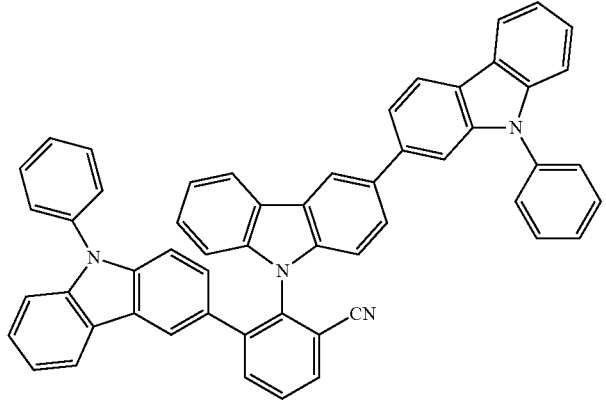
180
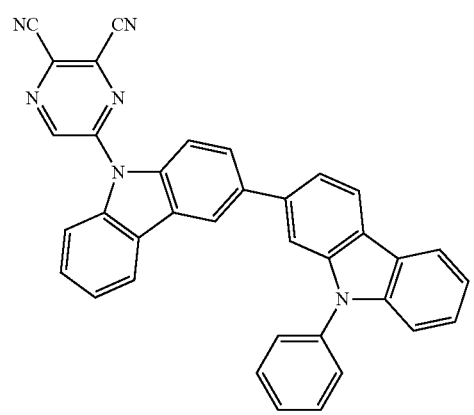
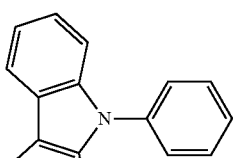
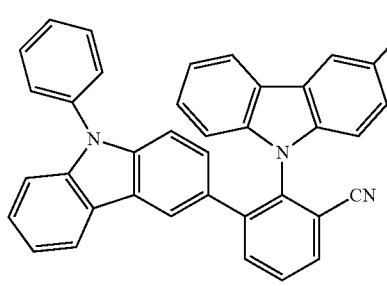
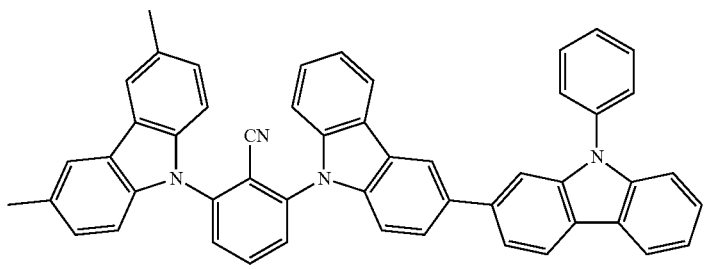
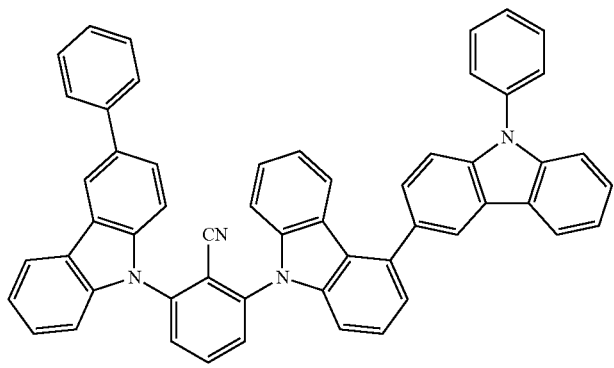

[Formula 99]
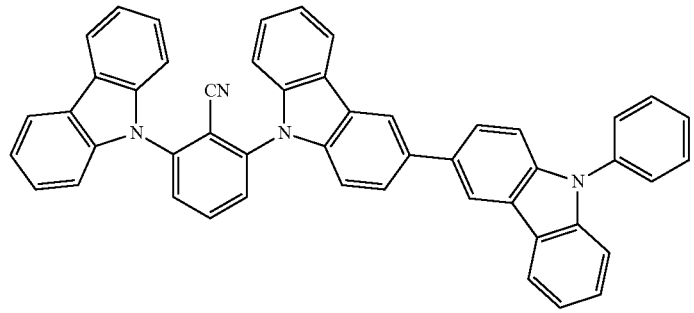
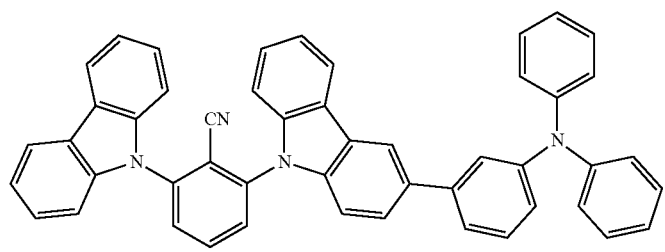
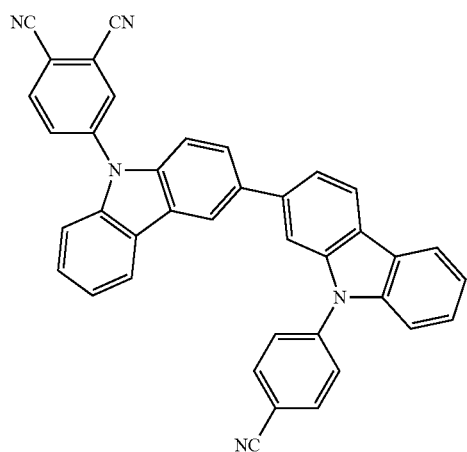
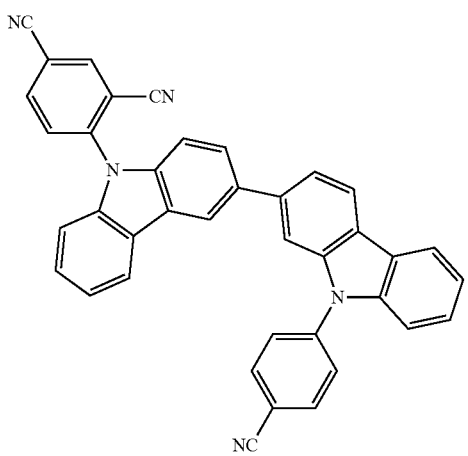
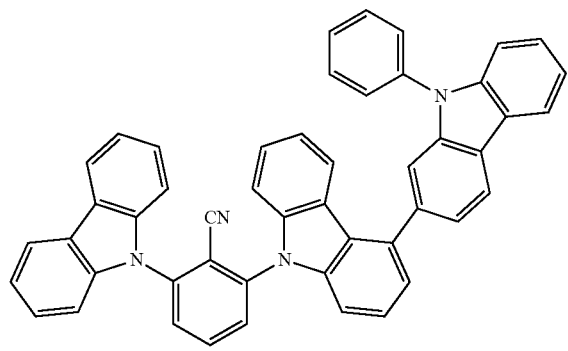

-continued
183
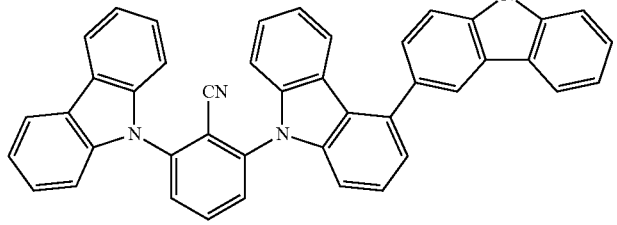
184
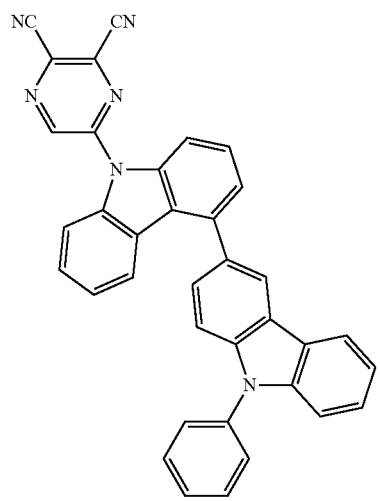
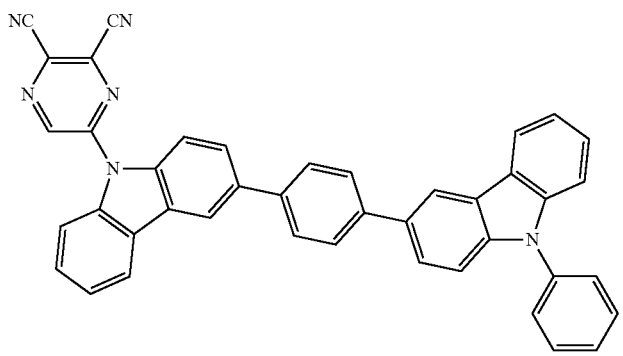
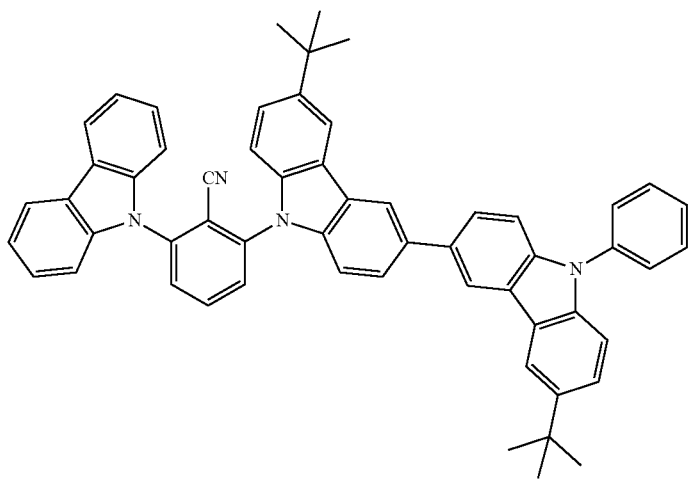

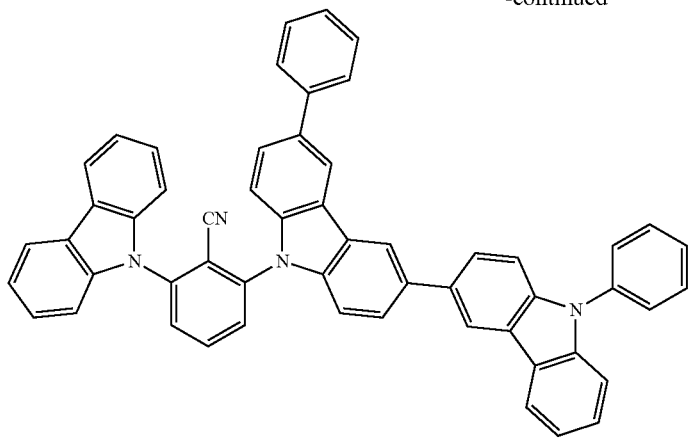

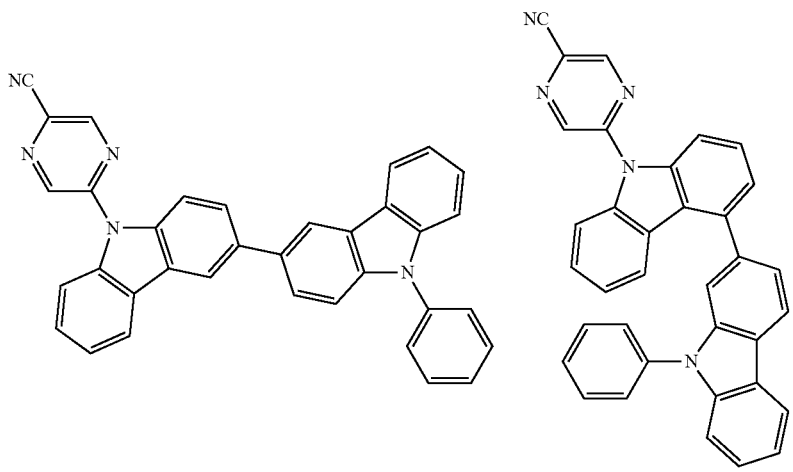

Combination of First Material and Second Material

Also in the second exemplary embodiment, the first material and the second material may be combined in the same viewpoint as in the first exemplary embodiment. Also in the second exemplary embodiment, the first material and the second material preferably satisfy the relationship represented by Numerical Formula 1. Also in the second exemplary embodiment, the first material and the second material preferably satisfy the relationship represented by Numerical Formula 2. Also in the second exemplary embodiment, the first material and the second material preferably satisfy the relationship represented by Numerical Formula 3.

In the organic EL device of the exemplary embodiment, the second material contained in the emitting layer preferably emits light. In the organic EL device of the exemplary embodiment, the emitting layer preferably contains no metal complex.

The organic EL device according to the second exemplary embodiment is also usable in an electronic device in the same manner as the organic EL device according to the first exemplary embodiment.

According to the second exemplary embodiment, an organic electroluminescence device configured to emit TADF and an electronic device including the organic electroluminescence device can be provided.

Third Exemplary Embodiment

Next, an organic EL device according to a third exemplary embodiment will be described below.

In the third exemplary embodiment, the same materials and compounds as described in the first exemplary embodiment are usable, unless otherwise specified.

The organic EL device according to the third exemplary embodiment includes basically the same structure as that of the organic EL device 1 according to the first exemplary embodiment and a structure of the emitting layer as follows.

Specifically, the emitting layer of the organic EL device in the third exemplary embodiment includes the first material and the second material, in which the singlet energy of the first material is larger than the singlet energy of the second material.

First Material

The first material in the exemplary embodiment is not particularly limited as long as having the singlet energy larger than the singlet energy of the second material. Examples of the first material in the exemplary embodiment include the examples of the first material described in the first exemplary embodiment.

Second Material

The second material of the exemplary embodiment is represented by a formula (31) below.

[Formula 100]

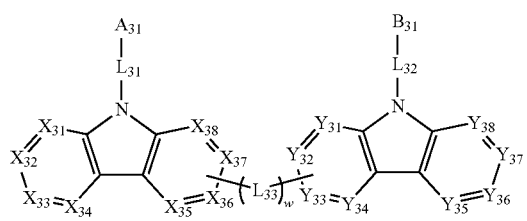

(31)

In the formula (31), $A_{31}$ and $B_{31}$ are each independently a substituted or unsubstituted aromatic hydrocarbon group having 6 to 30 ring carbon atoms, or substituted or unsubstituted heterocyclic group having 5 to 30 ring atoms.

$X_{31}$ to $X_{38}$ and $Y_{31}$ to $Y_{38}$ are each independently a nitrogen atom, a carbon atom to be bonded to $R^E$, or a carbon atom to be bonded to $L_{33}$. At least one of $X_{35}$ to $X_{38}$ is a carbon atom to be bonded to $L_{33}$. At least one of $Y_{31}$ to $Y_{34}$ is a carbon atom to be bonded to $L_{33}$.

$R^E$ is each independently selected from the group consisting of a hydrogen atom, cyano group, substituted or unsubstituted amino group, and substituted or unsubstituted alkoxy group. When a plurality of $R^E$ are present, at least one of the plurality of $R^E$ is selected from the group consisting of a cyano group, substituted or unsubstituted amino group, and substituted or unsubstituted alkoxy group.

$L_{31}$ and $L_{32}$ are each independently a single bond or a linking group. The linking group for $L_{31}$ and $L_{32}$ is any one of a substituted or unsubstituted aromatic hydrocarbon group having 6 to 30 ring carbon atoms, substituted or unsubstituted heterocyclic group having 5 to 30 ring atoms, multiple linking group including 2 to 4 groups selected from the above aromatic hydrocarbon groups, multiple linking group including bonded 2 to 4 groups selected from the above heterocyclic groups, and multiple linking group including bonded 2 to 4 groups selected from the above aromatic hydrocarbon groups and heterocyclic groups.

$L_{33}$ is a substituted or unsubstituted monocyclic hydrocarbon group having 6 or less ring carbon atoms or a substituted or unsubstituted monocyclic heterocyclic group having 6 or less ring atoms.

w is an integer of 0 to 3. When w is 0, at least one of $X_{35}$ to $X_{38}$ is directly bonded to at least one of $Y_{31}$ to $Y_{34}$.

At least one of $A_{31}$ and $B_{31}$ is a cyano-substituted aromatic hydrocarbon group having 6 to 30 ring carbon atoms or a cyano-substituted heterocyclic group having 6 to 30 ring atoms.

The substituted or unsubstituted amino group for $R^E$ is preferably represented by $-N(R_{200})$, in which $R_{200}$ is preferably a substituted or unsubstituted alkyl group having 1 to 30 carbon atoms or a substituted or unsubstituted aromatic hydrocarbon group having 6 to 30 ring carbon atoms. The alkyl group for $R_{200}$ preferably has 1 to 10 carbon atoms, more preferably 1 to 6 carbon atoms. The aromatic hydrocarbon group preferably has 6 to 20 ring carbon atoms, more preferably 6 to 12 ring carbon atoms.

The examples of the substituent for $R^E$ in the second material of the third exemplary embodiment are different from the examples of the substituent for $R^D$ in the second material of the second exemplary embodiment. The third exemplary embodiment is the same as the second exemplary embodiment with respect to other points. Preferable examples of the second material in the third exemplary embodiment are the same as the preferable examples of the second material in the second exemplary embodiment.

The second material of the exemplary embodiment is preferably a luminescent material, particularly a luminescent material emitting TADF.

In the organic EL device of the exemplary embodiment, the second material contained in the emitting layer preferably emits light. In the organic EL device of the exemplary embodiment, the emitting layer preferably contains no metal complex.

Specific examples of the second material of the exemplary embodiment are shown below. It should be noted that the second material according to the invention is not limited to these specific examples.

[Formula 101]

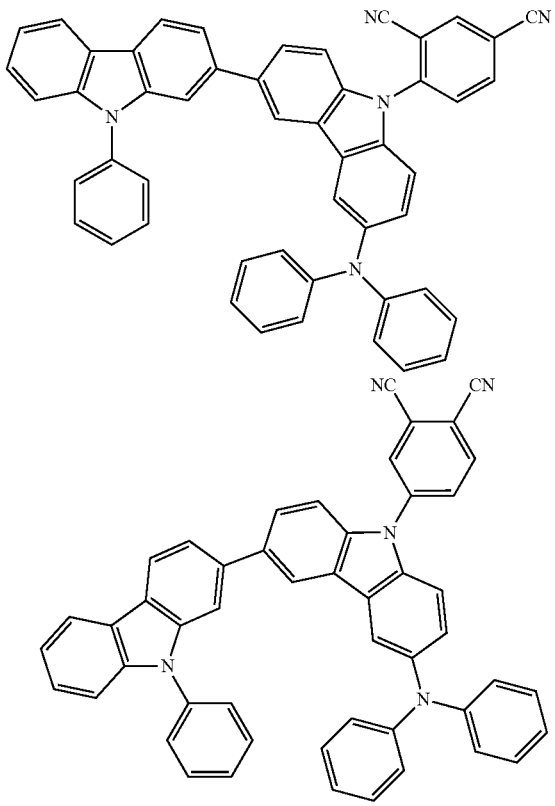

[Formula 102]

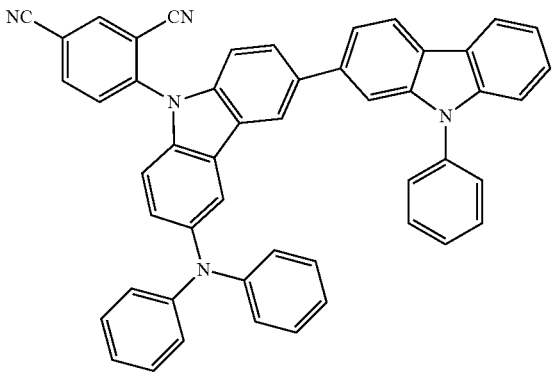

-continued
189
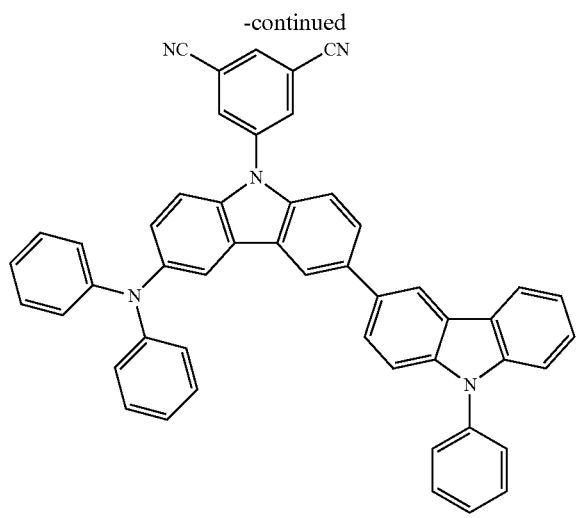
190
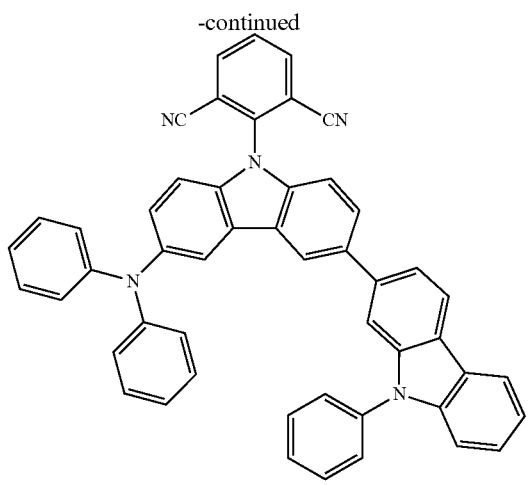
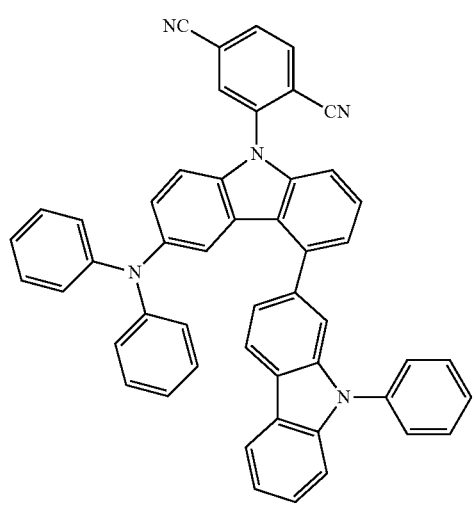
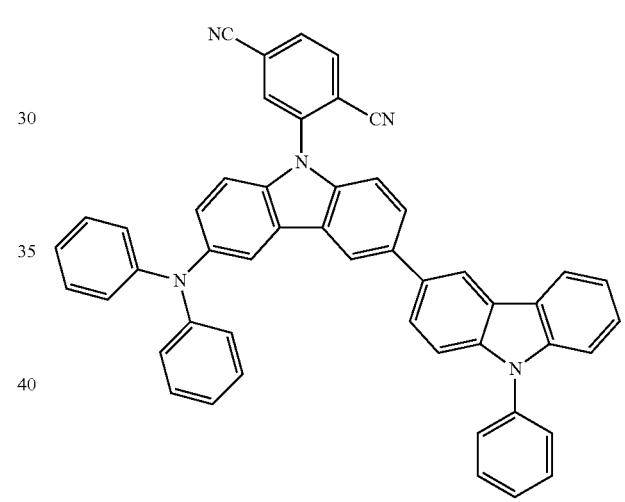
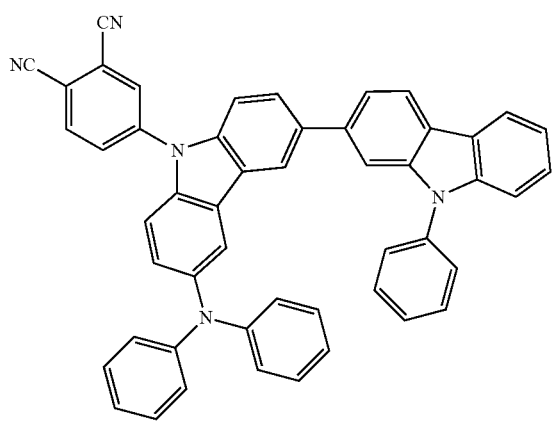
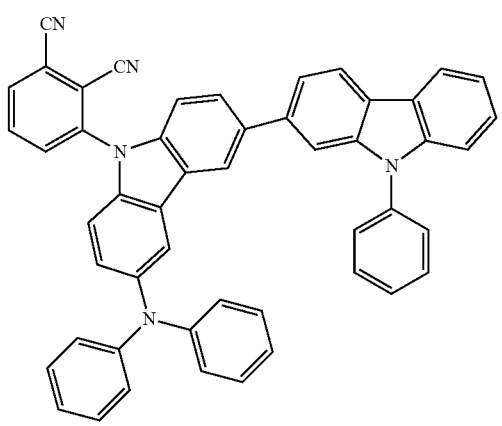

[Formula 103]
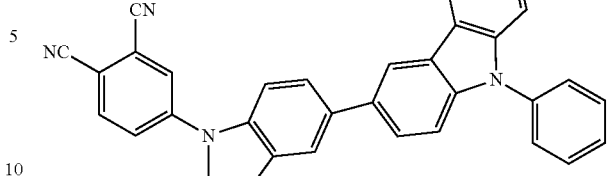
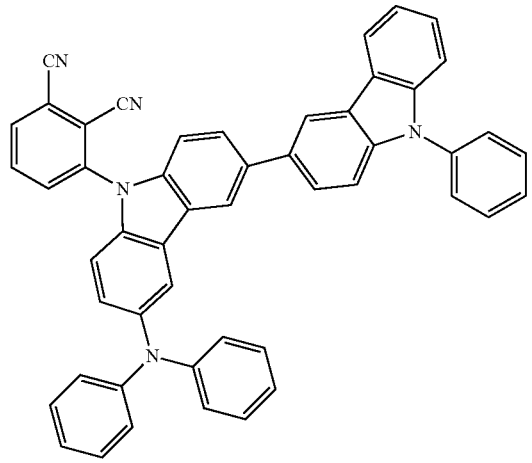
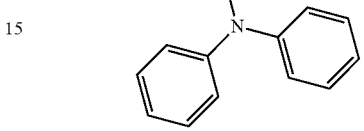
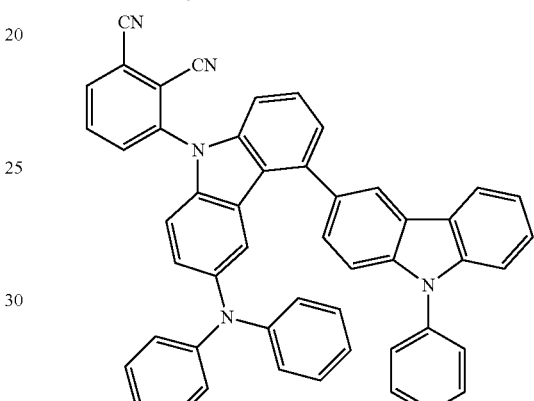
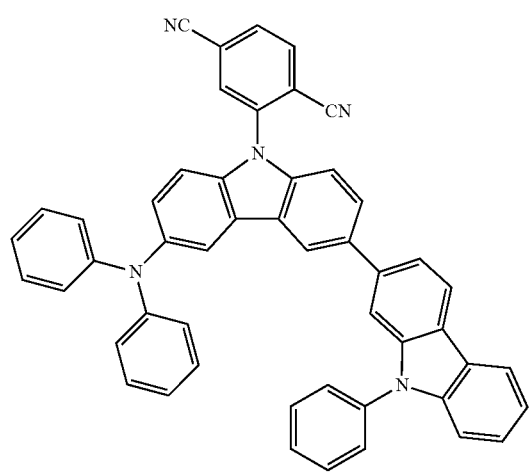
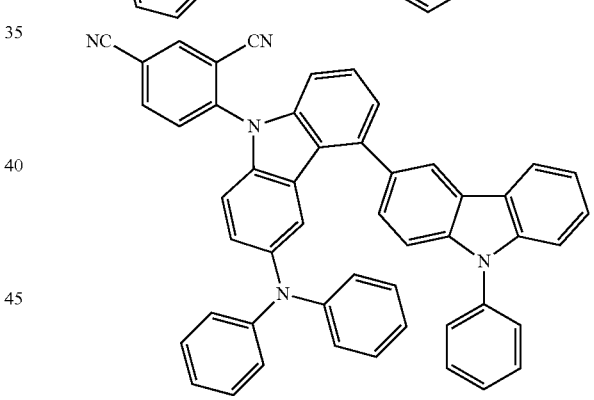
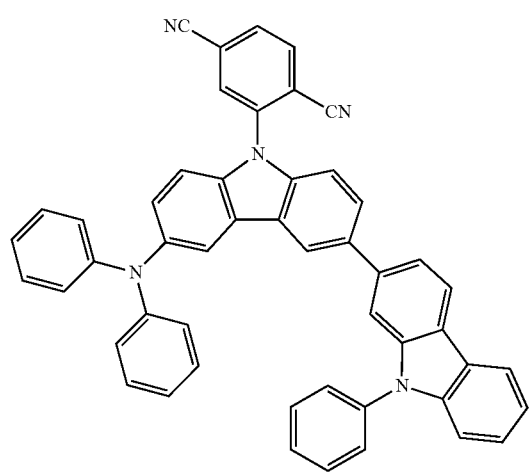
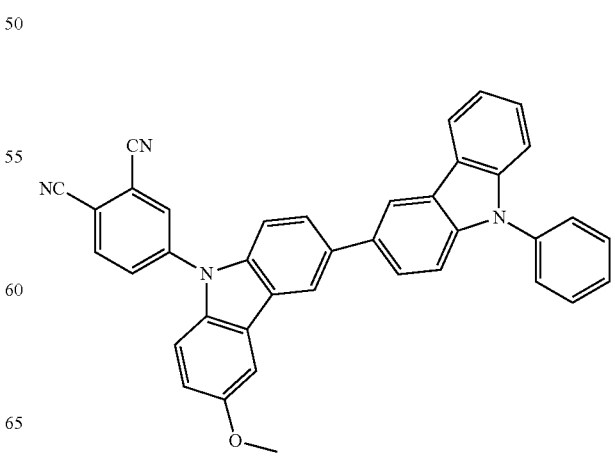

193
-continued
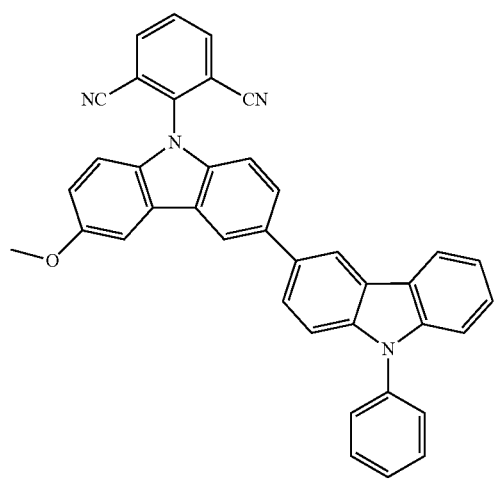
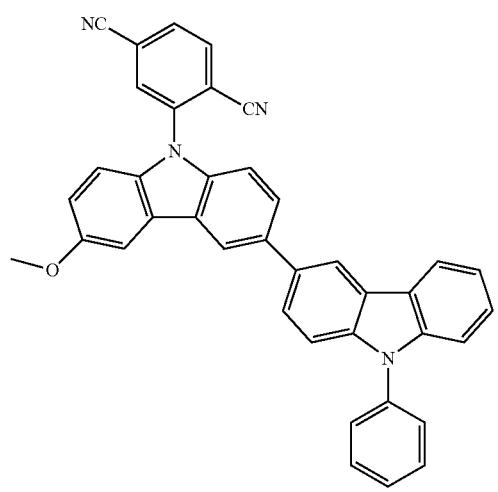
[Formula 104]
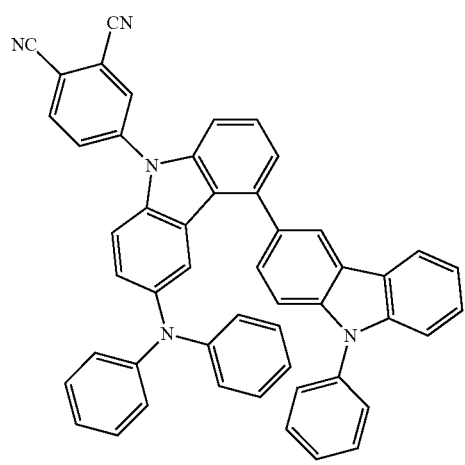
194
-continued
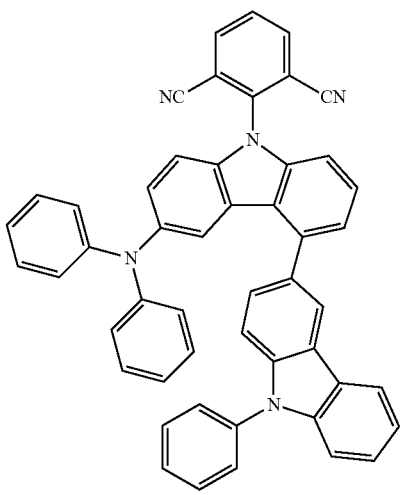
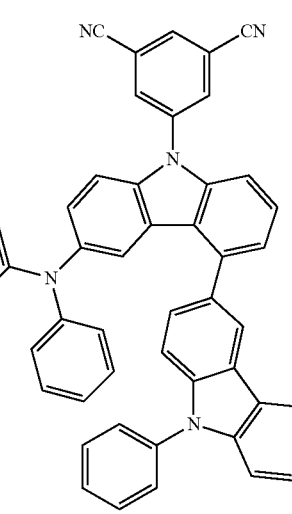
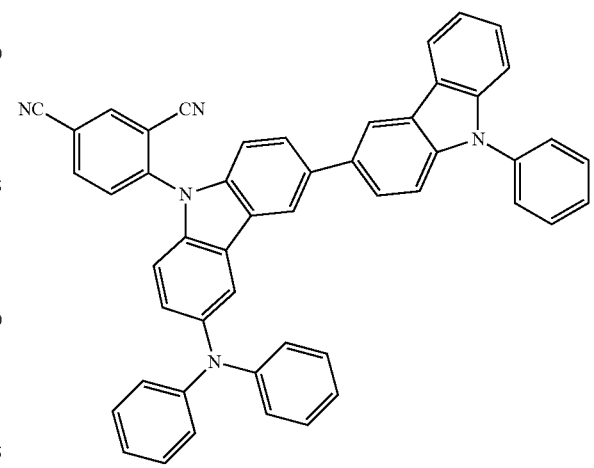

195
-continued
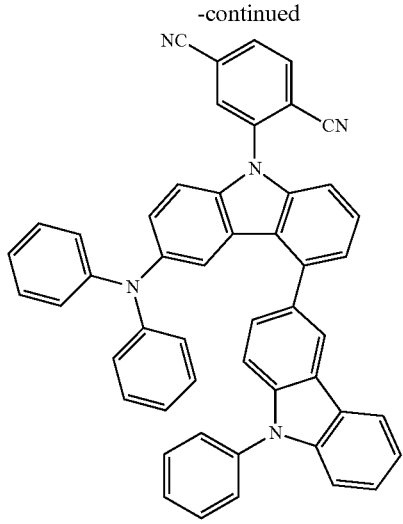
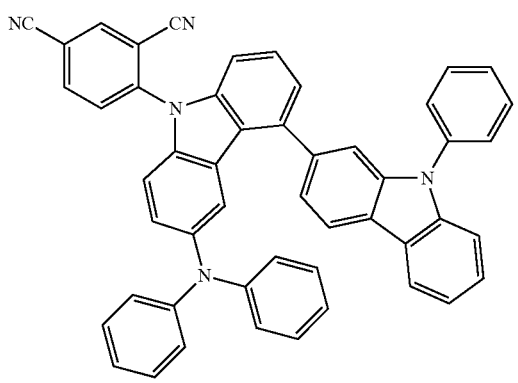
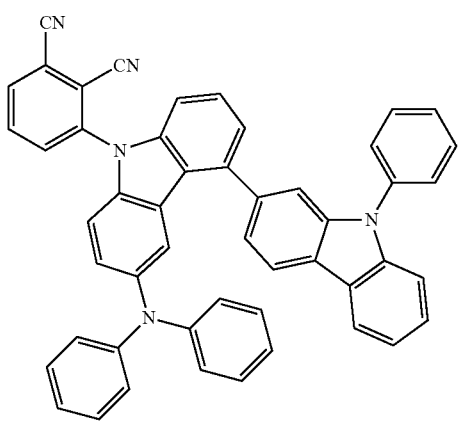
196
-continued
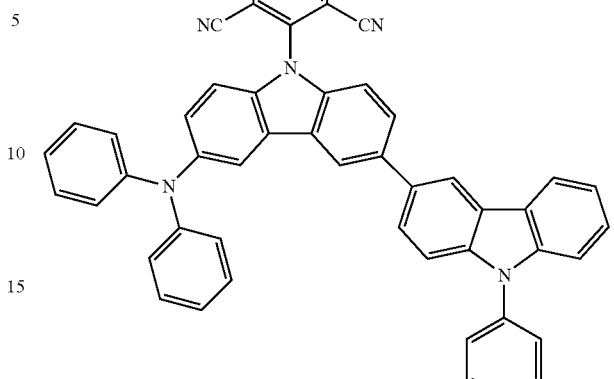
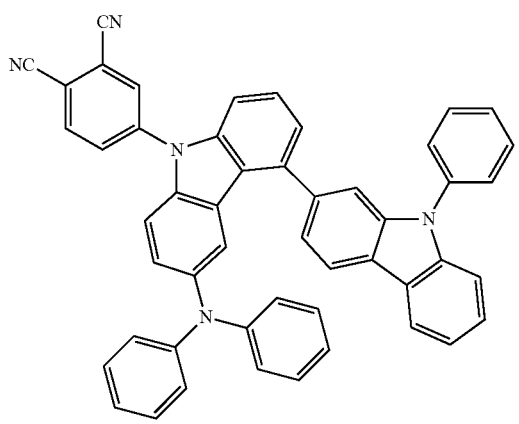
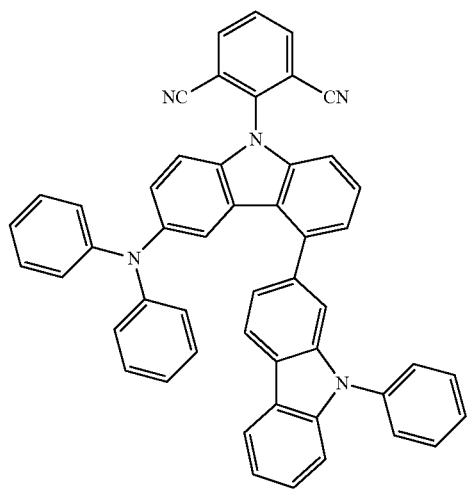

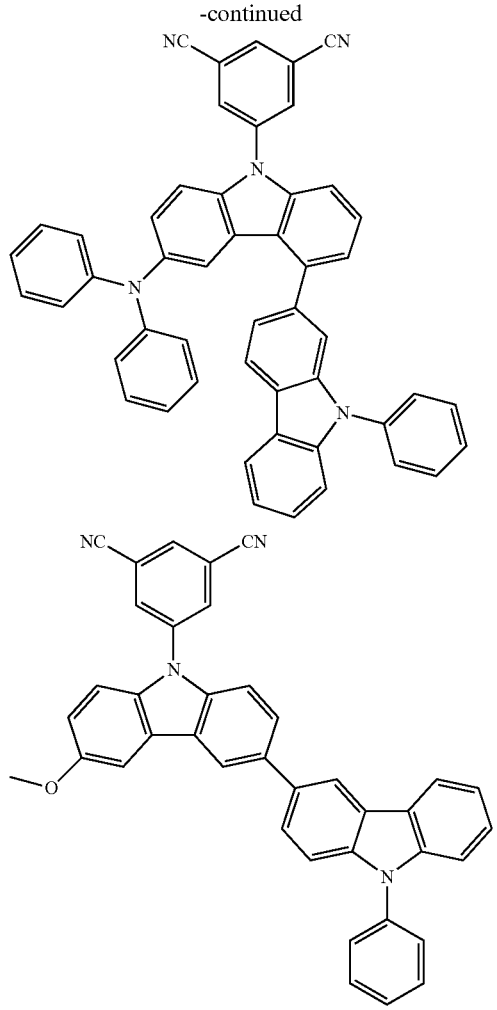
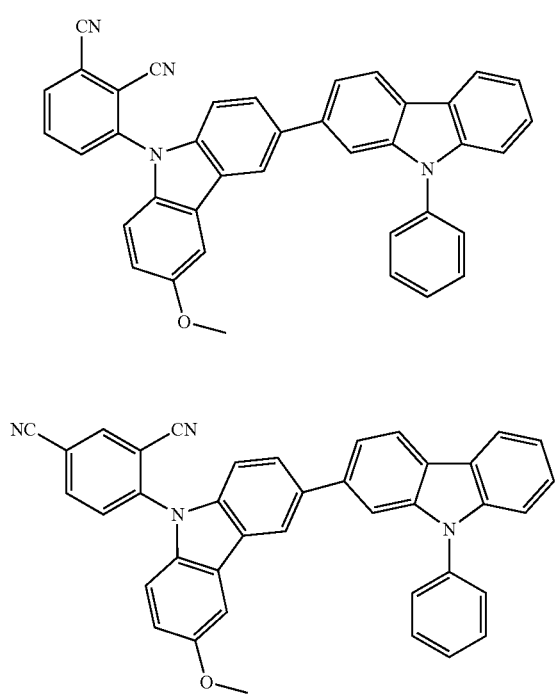
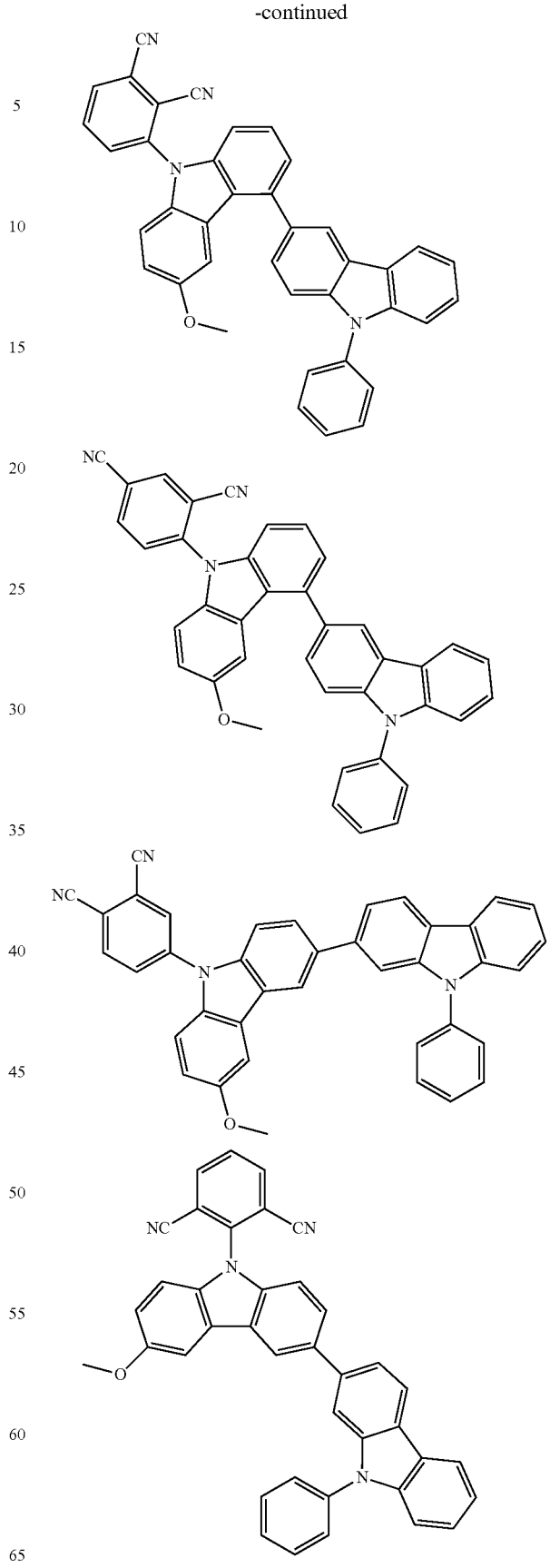
[Formula 105]

199
-continued
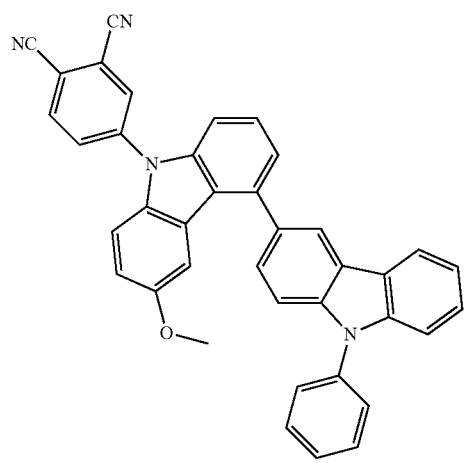
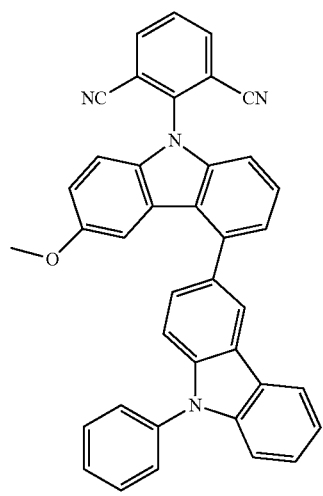
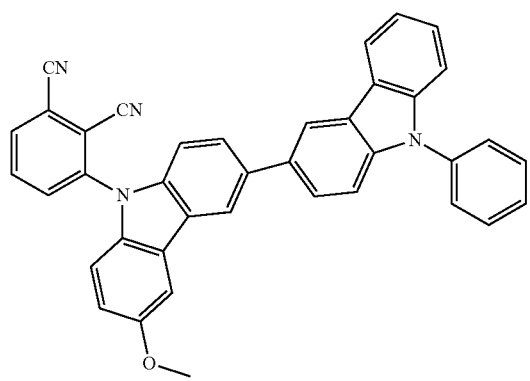
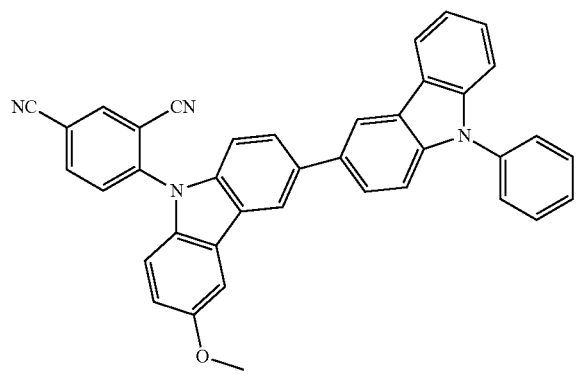
200
-continued
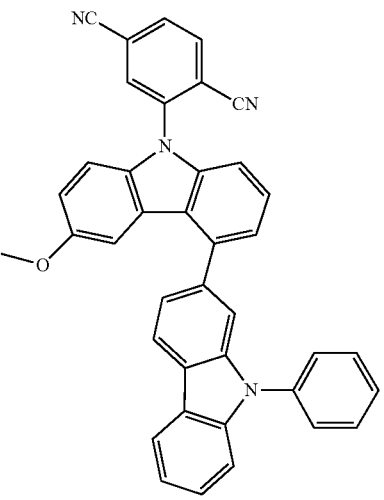
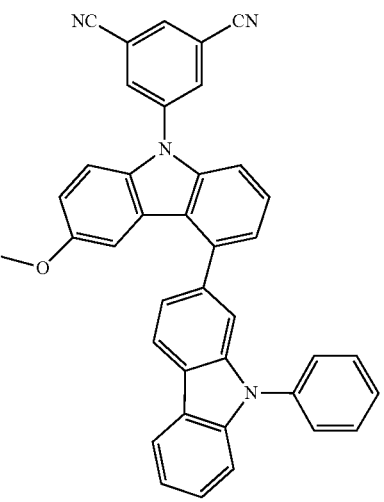
[Formula 106]
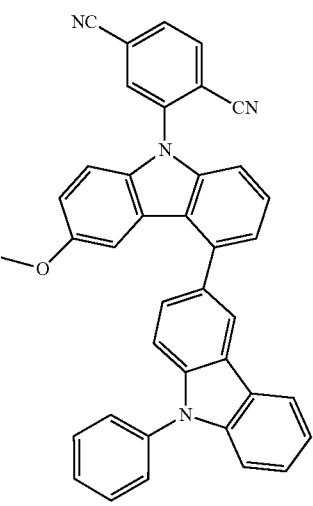

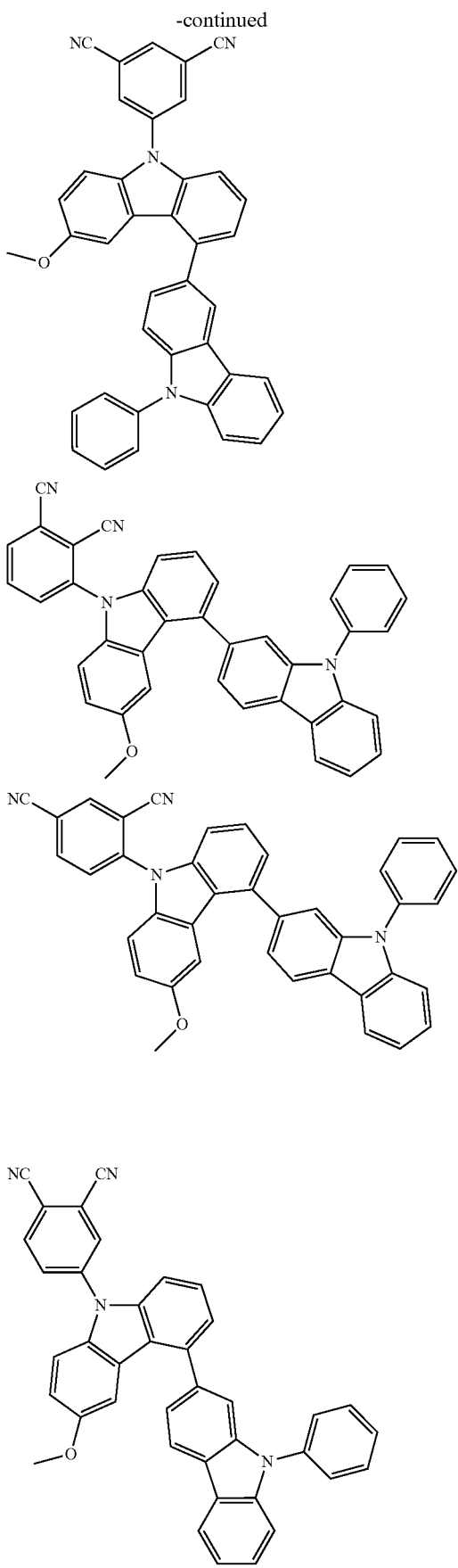

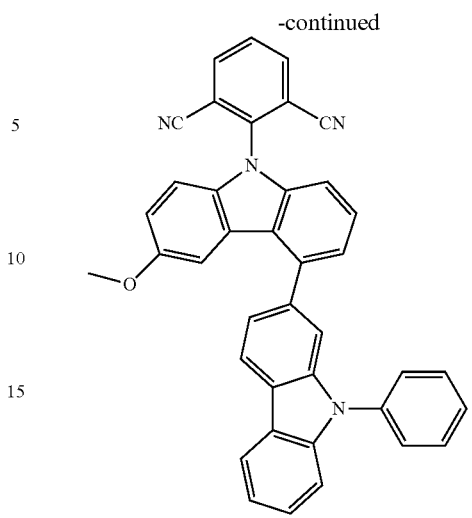

Combination of First Material and Second Material

Also in the third exemplary embodiment, the first material and the second material may be combined in the same view as in the first exemplary embodiment. Also in the third exemplary embodiment, the first material and the second material preferably satisfy the relationship represented by Numerical Formula 1. Also in the third exemplary embodiment, the first material and the second material preferably satisfy the relationship represented by Numerical Formula 2. Also in the third exemplary embodiment, the first material and the second material preferably satisfy the relationship represented by Numerical Formula 3.

According to the third exemplary embodiment, an organic electroluminescence device configured to emit TADF and an electronic device including the organic electroluminescence device can be provided.

Modifications of Embodiment(s)

It should be noted that the invention is not limited to the above exemplary embodiments but may include any modification and improvement as long as such modification and improvement are compatible with the invention.

The emitting layer is not limited to a single layer, but may be provided as laminate by a plurality of emitting layers. When the organic EL device includes the plurality of emitting layers, it is only required that at least one of the emitting layers includes the second material according to the above exemplary embodiments. The others of the emitting layers may be a fluorescent emitting layer or a phosphorescent emitting layer.

When the organic EL device includes the plurality of emitting layers, the plurality of emitting layers may be adjacent to each other, or may be laminated on each other via an intermediate layer, a so-called tandem organic EL device.

Figure 5:
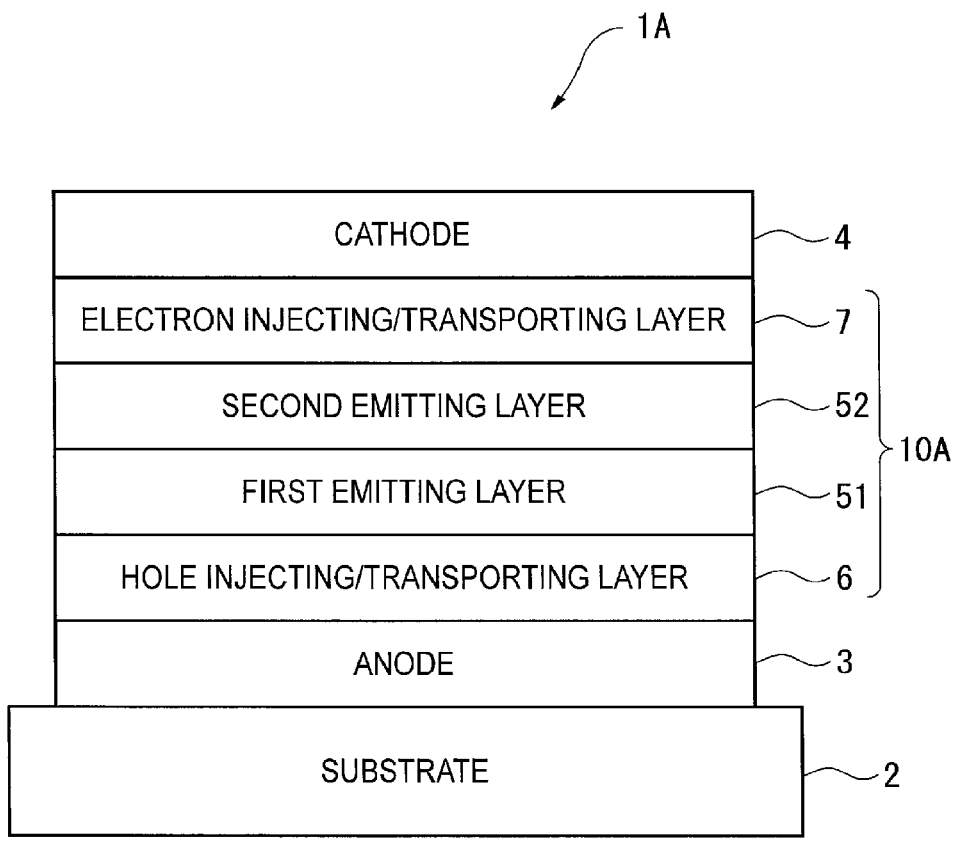
FIG. 5 schematically shows an exemplary arrangement of an organic electroluminescence device according to a modification of the invention.

When the plurality of emitting layers are laminated, an organic EL device 1A is exemplarily shown in FIG. 5. The organic EL device 1A includes an organic layer 10A. The organic EL device 1A is different from organic EL device 1 shown in FIG. 1 in that the organic layer 10A has a first emitting layer 51 and a second emitting layer 52 between the hole injecting/transporting layer 6 and the electron injecting/transporting layer 7. At least one of the first emitting layer 51 and the second emitting layer 52 contains the compound represented by the formula (1). As for other points, the organic EL device 1A is formed in the same manner as the organic EL device 1.

For instance, the electron blocking layer may be provided to the emitting layer adjacent to the anode while the hole blocking layer may be provided adjacent to the emitting layer near the cathode. With this arrangement, the electrons and the holes can be trapped in the emitting layer, thereby enhancing probability of exciton generation in the emitting layer.

Further, the specific arrangement and disposition for practicing the invention may be altered to other arrangements and treatments as long as such other arrangements and dispositions are compatible with the invention.

EXAMPLES

Examples of the invention will be described below. However, the invention is not limited by these Examples.

Compounds used in Examples are as follows.

[Formula 107]

HI

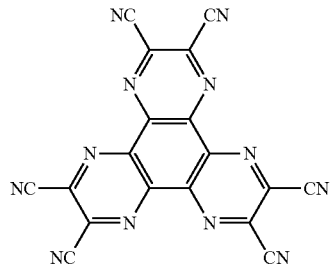

HT-1

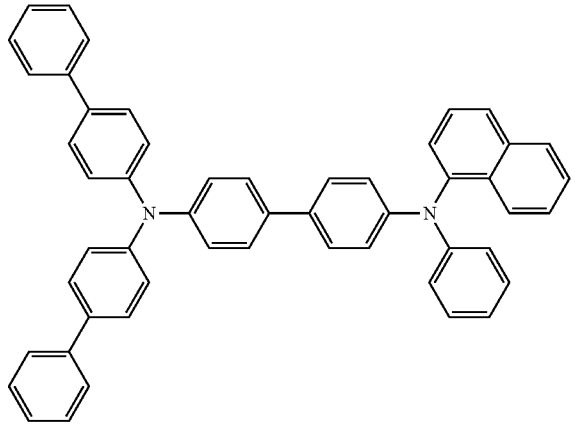

HT-2

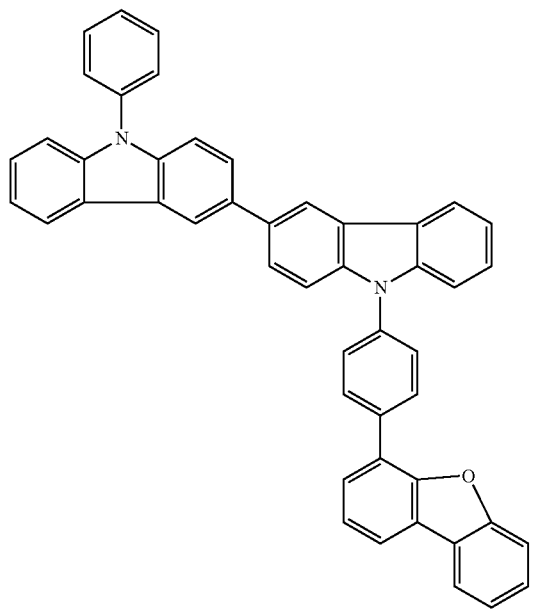

-continued
[Formula 108]
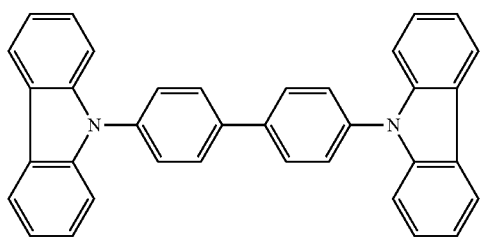
CBP
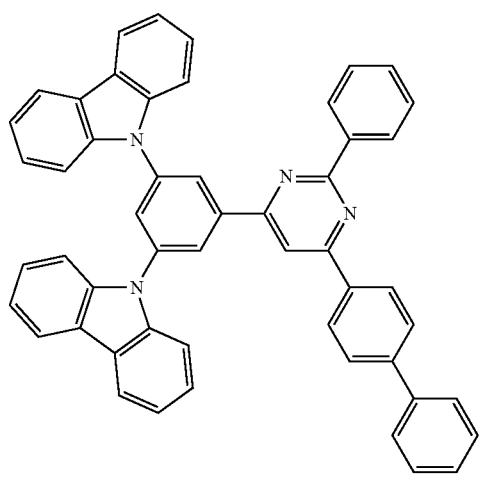
EB-1
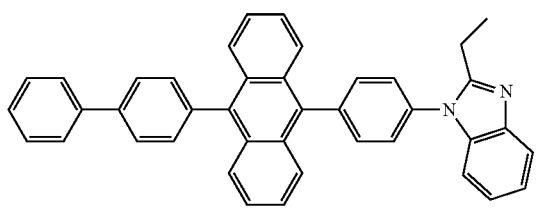
ET-1
[Formula 109]
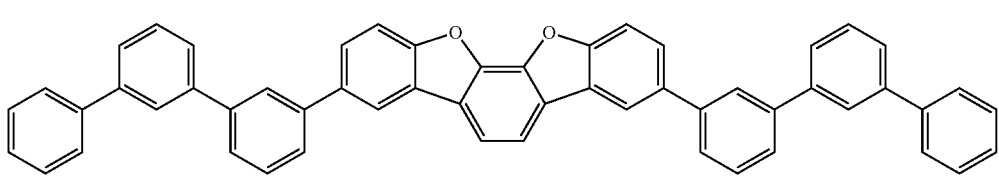
TH-1
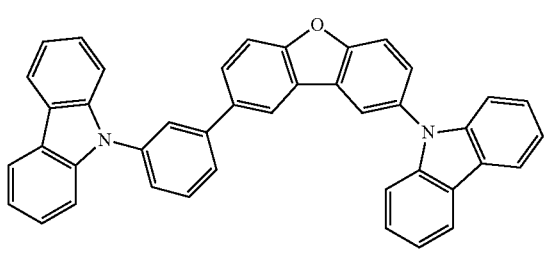
TH-2
[Formula 110]
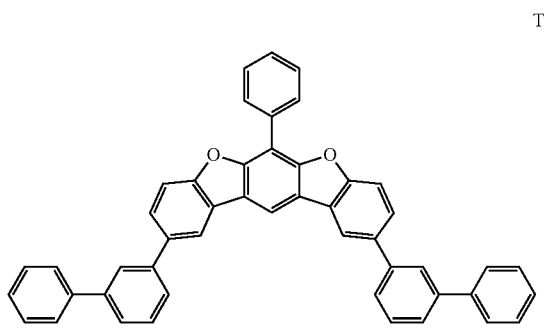
TH-3
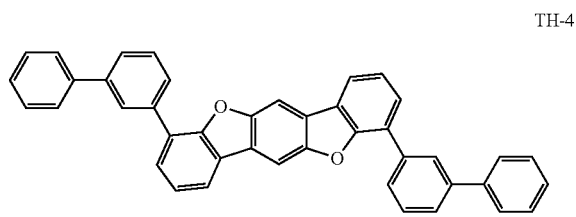
TH-4

[Formula 111]

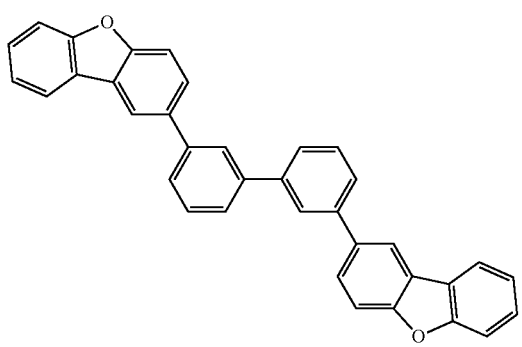
TH-5

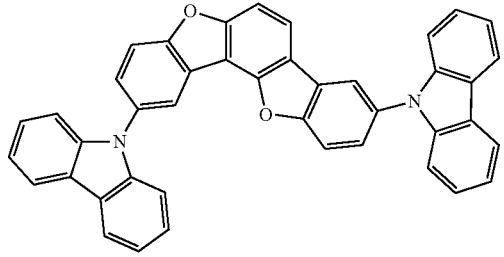
TH-6

[Formula 112]

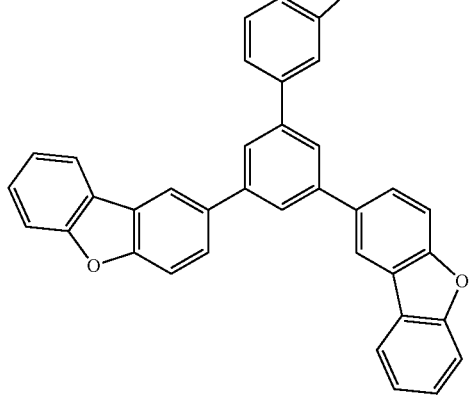
TH-7

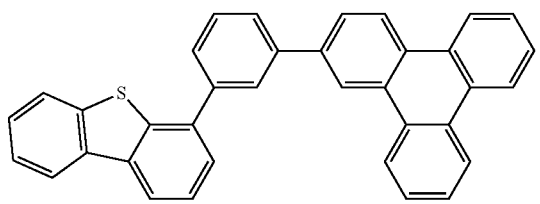
TH-8

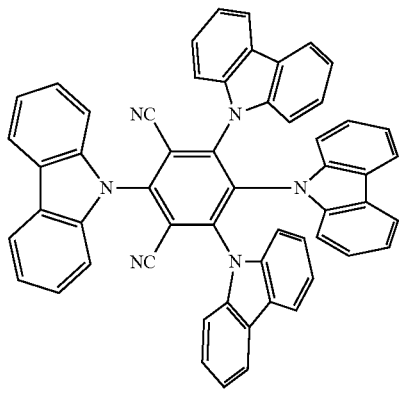
TD-1

Evaluation of Compounds

Next, properties of the compounds used in Example were measured. A measurement method and a calculation method are described below. Measurement results and calculation results are shown in Table 5.

Singlet Energy S

A 10 μmol/L toluene solution of a compound TD-1 was prepared and put in a quartz cell. A luminescence spectrum (ordinate axis: luminous intensity, abscissa axis: wavelength) of the thus-obtained sample was measured at a normal temperature (300K). A tangent was drawn to the rise of the luminescence spectrum on the short-wavelength side. A singlet energy S was calculated by substituting a wavelength value $\lambda_{edge}$ [nm] of an intersection between the tangent and the abscissa axis into the following conversion equation 2.

$$S(eV) = 1239.85/\lambda_{edge} \quad \text{Conversion Equation 2:}$$

In Example, the luminescence spectrum was measured using a spectrophotometer manufactured by Hitachi, Ltd. (device name: U3310).

The tangent to the rise of the emission spectrum on the short-wavelength side was drawn as follows. While moving on a curve of the emission spectrum from the short-wavelength side to the maximum spectral value closest to the short-wavelength side among the maximum spectral values, a tangent was checked at each point on the curve toward the long-wavelength of the emission spectrum. An inclination of the tangent was increased as the curve rose (i.e., a value of the ordinate axis was increased). A tangent drawn at a point of the maximum inclination (i.e., a tangent at an inflection point) was defined as the tangent to the rise of the luminescence spectrum on the short-wavelength side.

The maximum with peak intensity being 15% or less of the maximum peak intensity of the spectrum was not included in the above-mentioned maximum closest to the short-wavelength side of the spectrum. The tangent drawn at a point of the maximum spectral value being closest to the short-wavelength side and having the maximum inclination was defined as a tangent to the rise of the emission spectrum on the short-wavelength side.

Delayed Fluorescence

A sample was prepared by co-depositing the compound TD-1 and a compound TH-2 on a quartz substrate at a ratio of the compound TD-1 of 12 mass % to form a 100-nm thick thin film.

When the sample was irradiated with pulse exciting light, emission from the compound TD-1 was observed. A time-dependent change in the luminous intensity after the light irradiation (transient PL spectrum) was measured. Since the integrated value of a time-dependent luminous intensity at and after the elapse of 1 micro second after photo-excitation in the transient PL spectrum was 5% or more of an integrated value of a time-dependent luminous intensity within 1 micro second after photo-excitation, the compound TD-1 was confirmed to exhibit delayed fluorescence.

Energy Gap $T_{77K}$

A measurement sample was prepared in the following manner.

With respect to a compound other than the compound TD-1, the compound to be measured was dissolved in a solvent EPA (diethylether:isopentane:ethanol=5:5:2 in volume ratio) at a concentration of 10 μmol/L, and the resulting solution was set in a quartz cell to provide a measurement sample.

The compound TD-1 was replaced since exhibiting delayed fluorescence as described above to prepare a measurement sample. Specifically, the measurement sample was prepared by co-depositing the compound TD-1 and the compound TH-2 on a quartz substrate at a ratio of the compound TD-1 of 12 mass % to form a 100-nm thick thin film.

A phosphorescent spectrum (ordinate axis: phosphorescent luminous intensity, abscissa axis: wavelength) of the measurement sample was measured at a low temperature (77K). A tangent was drawn to the rise of the phosphorescent spectrum on the short-wavelength side. An energy amount was calculated as the energy gap $T_{77K}$ at 77K according to a conversion equation 1 below based on a wavelength value $\lambda_{edge}$ (nm) at an intersection of the tangent and the abscissa axis.

$$T_{77K}[eV]=1239.85/\lambda_{edge} \quad \text{Conversion Equation 1:}$$

The tangent to the rise of the phosphorescence spectrum on the short-wavelength side was drawn as described above. For phosphorescence measurement, a spectrophotofluorometer body F-4500 (manufactured by Hitachi High-Technologies Corporation) was used.

ΔST

ΔST of the compound TD-1 was calculated as a difference between S and $T_{77K}$ measured by the above method, and the result was 0.16 eV.

Ionization Potential Ip

A photoelectron spectroscopy device (AC-3, manufactured by Riken Keiki Co., Ltd.) was used for the measurement of an ionization potential under atmosphere. Specifically, a compound to be measured was irradiated with light and the amount of electrons generated by charge separation during the light irradiation was measured.

TABLE 5

|      | $T_{77K}$ [eV] | Ip [eV] |
|------|----------------|---------|
| TH-1 | 2.85           | 6.11    |
| TH-2 | 3.00           | 6.13    |
| TH-3 | 2.80           | 6.14    |
| TH-4 | 2.67           | 6.19    |
| TH-5 | 2.92           | 6.45    |
| TH-6 | 2.98           | 6.07    |
| TH-7 | 2.93           | >6.50   |
| TH-8 | 2.74           | 6.10    |
| CBP  | 2.80           | 6.05    |
| TD-1 | 2.56           | 5.91    |

Table 5 shows that a measurement value of an ionization potential Ip of TH-7 exceeds 6.50 eV.

Preparation and Evaluation of Organic EL Device

The organic EL device was prepared and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound HI was deposited on a surface of the glass substrate where the transparent electrode line was provided in a manner to cover the transparent electrode, thereby forming a 5-nm-thick hole injecting layer.

Subsequently, the compound HT-1 was deposited on the hole injecting layer to form a 20-nm-thick first hole transporting layer on the HI film.

Next, the compound HT-2 was deposited on the first hole transporting layer to form a 5-nm-thick second hole transporting layer.

Next, a compound CBP was deposited on the second hole transporting layer to form a 5-nm-thick third hole transporting layer.

Further, a compound TH-1 (the first material) and the compound TD-1 were co-deposited on the third hole transporting layer to form a 25-nm-thick emitting layer. A mass ratio between the compound TH-1 and the compound TD-1 was set at 1:1.

Next, a compound EB-1 was deposited on the emitting layer to form a 5-nm-thick hole blocking layer.

A compound ET-1 was then deposited on the hole blocking layer to form a 50-nm-thick electron transporting layer.

Lithium fluoride (LiF) was then deposited on the electron transporting layer to form a 1-nm-thick electron injecting electrode (cathode).

A metal aluminum (Al) was then deposited on the electron injecting electrode to form an 80-nm-thick metal Al cathode. A device arrangement of the organic EL device in Example 1 is shown in symbols as follows.

ITO(130)/HI(5)/HT-1(20)/HT-2(5)/CBP(5)/TH-1:TD-1 (25, 50%)/EB-1(5)/ET-1(50)/LiF(1)/Al(80)

Numerals in parentheses represent a film thickness (unit: nm). Numerals represented by percentage in the same parentheses represent a ratio (mass %) of an added component such as the dopant material in the emitting layer.

Examples 2 to 8

Organic EL devices in Examples 2 to 8 were manufactured in the same manner as in Example 1 except that, as the first material of the emitting layer in Example 1, the compound TH-1 was replaced by compounds shown in Table 2.

A device arrangement of the organic EL device in Example 2 is shown in symbols as follows.

ITO(130)/HI(5)/HT-1(20)/HT-2(5)/CBP(5)/TH-2:TD-1 (25, 50%)/EB-1(5)/ET-1(50)/LiF(1)/Al(80)

A device arrangement of the organic EL device in Example 3 is shown in symbols as follows.

ITO(130)/HI(5)/HT-1(20)/HT-2(5)/CBP(5)/TH-3:TD-1 (25, 50%)/EB-1(5)/ET-1(50)/LiF(1)/Al(80)

A device arrangement of the organic EL device in Example 4 is shown in symbols as follows.

ITO(130)/HI(5)/HT-1(20)/HT-2(5)/CBP(5)/TH-4:TD-1 (25, 50%)/EB-1(5)/ET-1(50)/LiF(1)/Al(80)

A device arrangement of the organic EL device in Example 5 is shown in symbols as follows.

ITO(130)/HI(5)/HT-1(20)/HT-2(5)/CBP(5)/TH-5:TD-1 (25, 50%)/EB-1(5)/ET-1(50)/LiF(1)/Al(80)

A device arrangement of the organic EL device in Example 6 is shown in symbols as follows.

ITO(130)/HI(5)/HT-1(20)/HT-2(5)/CBP(5)/TH-6:TD-1 (25, 50%)/EB-1(5)/ET-1(50)/LiF(1)/Al(80)

A device arrangement of the organic EL device in Example 7 is shown in symbols as follows.

ITO(130)/HI(5)/HT-1(20)/HT-2(5)/CBP(5)/TH-7:TD-1 (25, 50%)/EB-1(5)/ET-1(50)/LiF(1)/Al(80)

A device arrangement of the organic EL device in Example 8 is shown in symbols as follows.

ITO(130)/HI(5)/HT-1(20)/HT-2(5)/CBP(5)/TH-8:TD-1 (25, 50%)/EB-1(5)/ET-1(50)/LiF(1)/Al(80)

Comparative 1

An organic EL device in Comparative 1 was manufactured in the same manner as in Example 1 except that, as the first material of the emitting layer in Example 1, the compound TH-1 was replaced by a compound shown in Table 2. A device arrangement of the organic EL device in Comparative 1 is shown in symbols as follows.

ITO(130)/HI(5)/HT-1(20)/HT-2(5)/CBP(5)/CBP:TD-1 (25, 50%)/EB-1(5)/ET-1(50)/LiF(1)/Al(80)

Evaluation of Organic EL Devices

The prepared organic EL devices of Examples 1 to 8 and Comparative 1 were evaluated as follows. The evaluation results are shown in Table 6.

Drive Voltage

Voltage was applied between ITO electrode and Al metal cathode such that a current density was 10.0 mA/cm², where the voltage (unit: V) was measured.

Current Efficiency L/J

Voltage was applied on each of the organic EL devices such that the current density was 10.0 mA/cm², where spectral radiance spectra were measured by a spectroradiometer CS-1000 (Manufactured by Konica Minolta, Inc.). Based on the obtained spectral radiance spectra, the current efficiency (unit: cd/A) was calculated.

Lifetime

A voltage was applied on the organic EL devices such that a current density was 50.00 mA/cm², where a time (unit: h) elapsed before a luminance was reduced to 80% of an initial luminance intensity was measured.

TABLE 6

| | First material | Drive voltage [V] | Current efficiency [cd/A] | Lifetime [h] |
|---|---|---|---|---|
| Example 1 | TH-1 | 3.9 | 54.6 | 60 |
| Example 2 | TH-2 | 4.0 | 51.2 | 47 |
| Example 3 | TH-3 | 3.8 | 51.3 | 29 |
| Example 4 | TH-4 | 3.9 | 51.1 | 46 |
| Example 5 | TH-5 | 4.4 | 51.6 | 61 |
| Example 6 | TH-6 | 4.1 | 50.2 | 35 |
| Example 7 | TH-7 | 3.8 | 50.0 | 35 |
| Example 8 | TH-8 | 4.0 | 55.5 | 52 |
| Comparative 1 | CBP | 4.2 | 48.4 | 28 |

The organic electroluminescence devices in Examples 1 to 8 emitted TADF. Moreover, since the compound TD-1 (the second material) and the compounds TH-1 to TH-8 (the first material) were combined in use in the organic EL devices of Examples 1 to 8, the current efficiency was improved and the lifetime was prolonged as compared with the organic EL device of Comparative 1 in which the compounds TD-1 and CBP were combined.

Further, compounds below were used in Examples below.

[Formula 113]

Compound 1

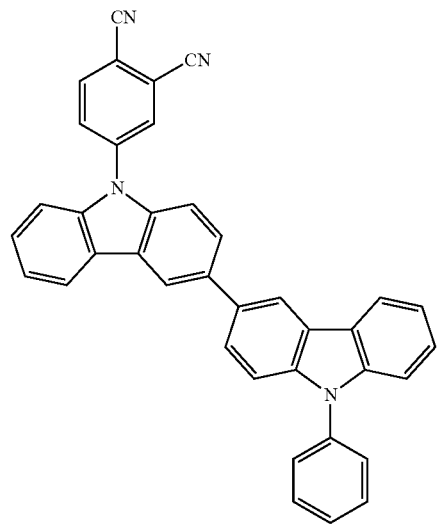

Compound 2
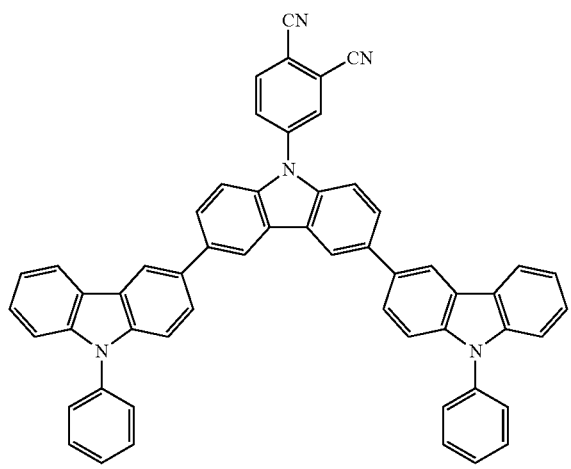
[Formula 114]
Compound 3
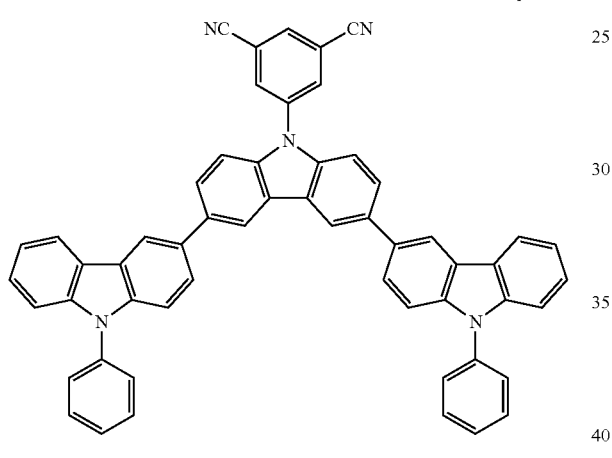
Compound 4
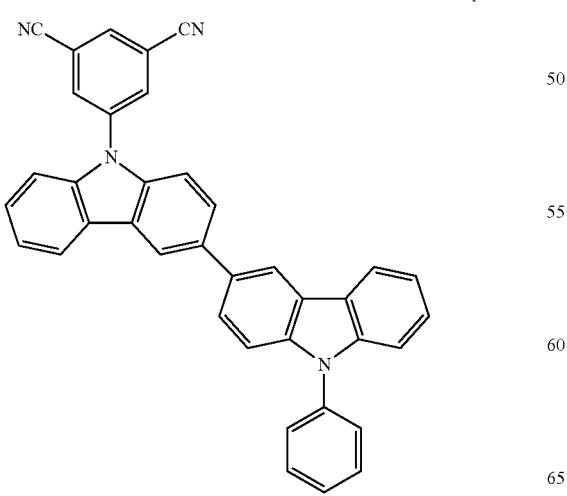
Compound 5
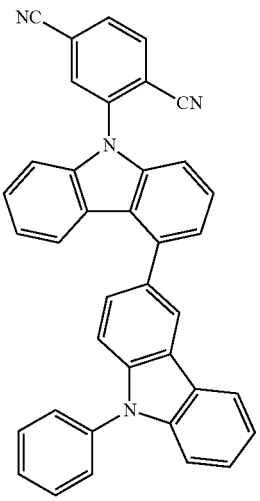
[Formula 115]
Compound 6
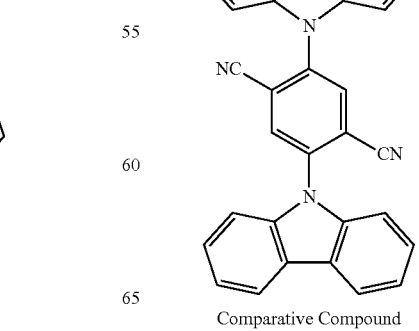
Comparative Compound

215

-continued

EB-2

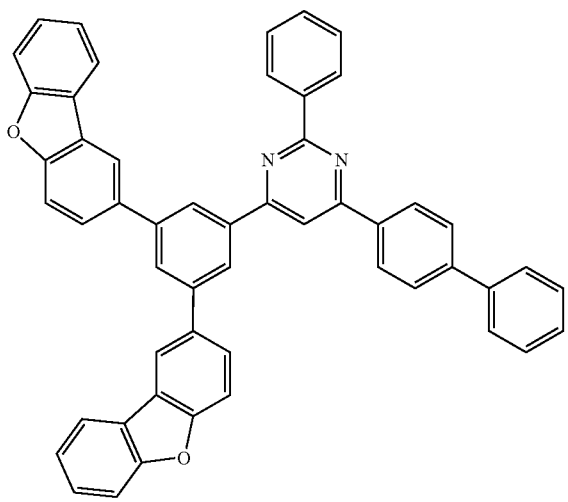

SYNTHESIS EXAMPLES

Synthesis Example 1

In synthesizing a compound 1, initially, an intermediate 1 was synthesized according to a scheme below.

[Formula 116]

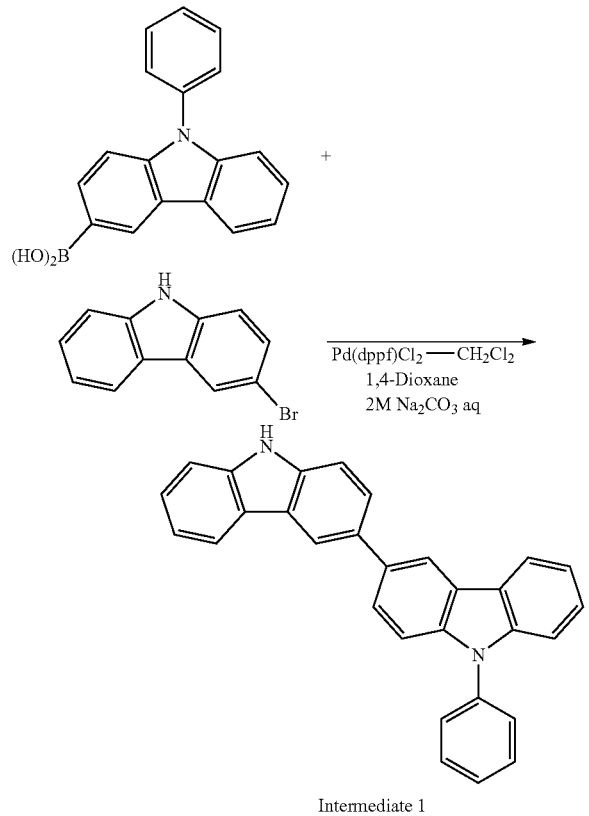

Intermediate 1

216

Under an argon gas atmosphere, 9-phenylcarbazole-3-boronic acid (2.41 g, 8.4 mmol), 3-bromocarbazole (1.71 g, 6.9 mmol), palladium-methylene chloride complex (Pd(dppf)Cl$_2$—CH$_2$Cl$_2$) (0.057 g, 0.07 mmol), and 1,4-dioxane (21 mL), and 2 M sodium carbonate aqueous solution (10.5 mL) were sequentially added and heated to reflux for eight hours. After the reaction solution was cooled down to the room temperature, the deposited solid was collected by filtration, washed with 1,4-dioxane and water, and dried under reduced pressure. The obtained residue was refined by silica-gel column chromatography, so that an intermediate 1 (2.49 g, a yield of 88%) was obtained.

Next, the compound 1 was synthesized according to a scheme below.

[Formula 117]

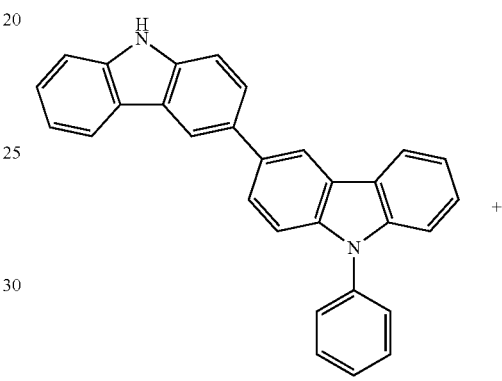

Compound 1

Under an argon gas atmosphere, the intermediate 1 (3.35 g, 8.2 mmol), 4-fluorophthalonitrile (1.00 g, 6.8 mmol), potassium carbonate (1.42 g, 10 mmol), and N,N-dimethylformamide (15 mL) were sequentially added and stirred at 80 degrees C. for eight hours. N,N-dimethylformamide is occasionally referred to as DMF. After the reaction solution was cooled down to the room temperature, the reaction solution was washed with methanol and water. The deposited solid was collected by filtration and dried under reduced pressure. The obtained residue was refined by silica-gel column chromatography, so that the compound 1 (2.84 g, a yield of 78%) was obtained.

Synthesis Example 2

In synthesizing a compound 2, initially, an intermediate 2 was synthesized according to a scheme below.

[Formula 118]

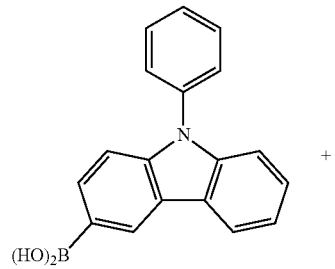

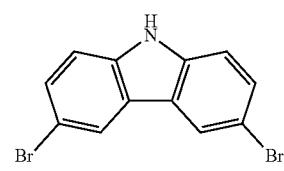

Intermediate 2

Under an argon gas atmosphere, 3,6-dibromocarbazole (8.16 g, 25 mmol), 9-phenylcarbazole-3-boronic acid (15.8 g, 55 mmol), tetrakis(triphenylphosphine)palladium (0.230 g, 0.20 mmol), toluene (25 mL), 1,2-dimethoxyethane (25 mL), and 2 M sodium carbonate aqueous solution (12.5 mL) were sequentially added and heated to reflux for 10 hours. 1,2-dimethoxyethane is occasionally referred to as DME.

Immediately after the reaction was over, the reaction solution was subjected to filtration. The obtained aqueous phase of the reaction solution was removed. After an organic phase of the reaction solution was dried with sodium sulfate, the organic phase was condensed. The obtained residue was refined by silica-gel column chromatography, so that the intermediate 2 (11.4 g, a yield of 70%) was obtained.

Next, the compound 2 was synthesized according to a scheme below.

[Formula 119]

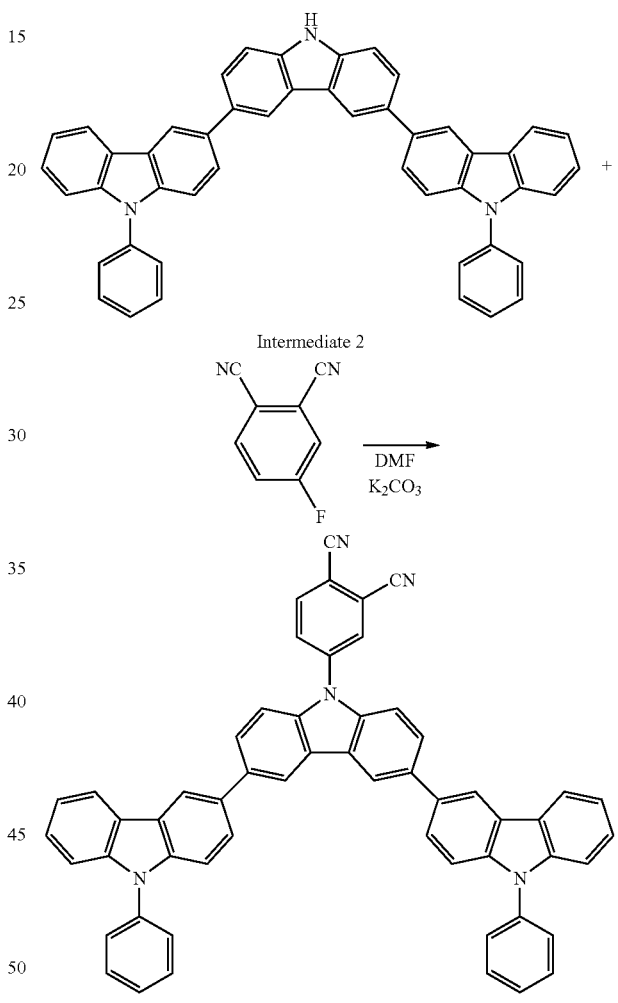

Compound 2

Under an argon gas atmosphere, the intermediate 2 (3.40 g, 5.2 mmol), 4-fluorophthalonitrile (0.701 g, 4.8 mmol), potassium carbonate (0.992 g, 7.2 mmol), and N,N-dimethylformamide (12 mL) were sequentially added and stirred at 80 degrees C. for eight hours. After the reaction solution was cooled down to the room temperature, the reaction solution was washed with methanol and water. The deposited solid was collected by filtration and dried under reduced pressure.

The obtained residue was refined by silica-gel column chromatography, so that the compound 2 (2.98 g, a yield of 80%) was obtained.

Synthesis Example 3

A compound 3 was synthesized according to a scheme below.

Synthesis Example 4

A compound 4 was synthesized according to a scheme below.

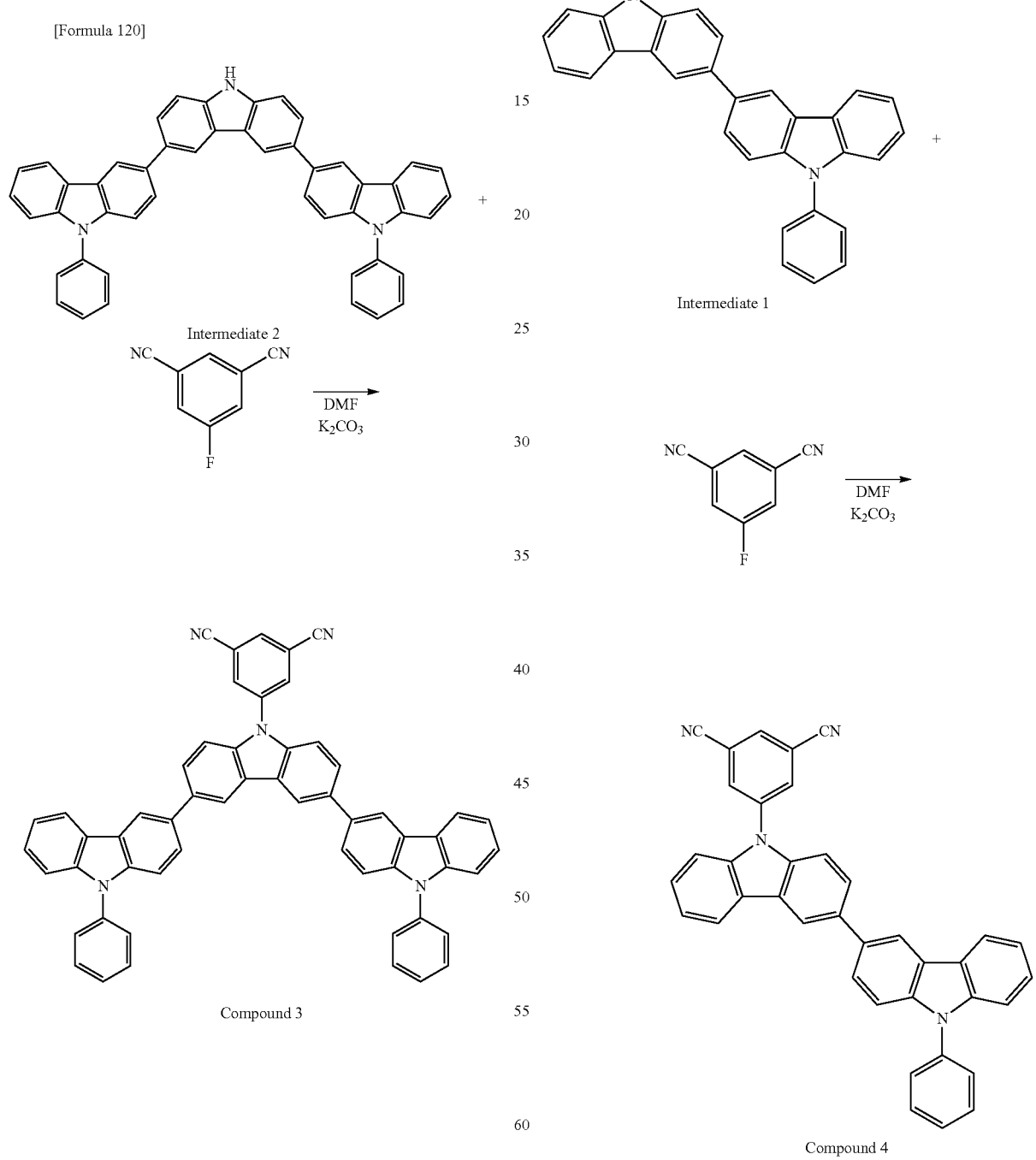

The compound 3 was synthesized by the same method as the compound 2 in Synthesis Example 2 except that 5-fluoroisophthalonitrile was used in place of 4-fluorophthalonitrile.

The compound 4 was synthesized by the same method as the compound 1 in Synthesis Example 1 except that 5-fluoroisophthalonitrile was used in place of 4-fluorophthalonitrile.

Synthesis Example 5

In synthesizing a compound 5, initially, an intermediate 3 was synthesized according to a scheme below.

[Formula 122]

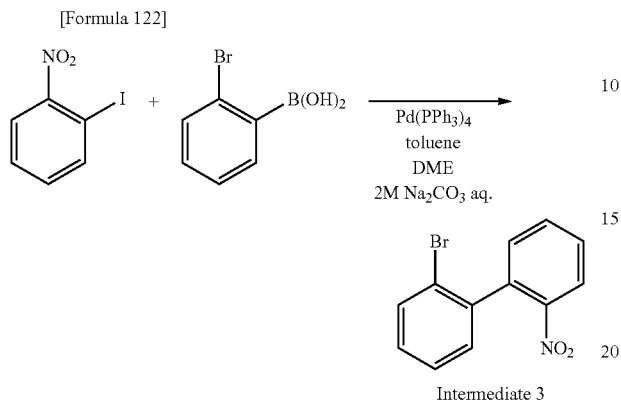

Intermediate 3

Under an argon gas atmosphere, 2-nitroiodobenzene (62.0 g, 249 mmol), 2-bromophenylboron acid (50.0 g, 249 mmol), toluene (345 mL), 1,2-dimethoxyethane (345 mL), and 2 M sodium carbonate aqueous solution (344 mL) were sequentially added and stirred at 76 degrees C. for 20 hours. After the reaction solution was cooled down to the room temperature, a toluene layer was separated, dried with magnesium sulfate, and dried under reduced pressure. The obtained residue was refined by silica-gel column chromatography, so that the intermediate 3 (64.8 g, a yield of 94%) was obtained.

Next, an intermediate 4 was synthesized according to a scheme below.

[Formula 123]

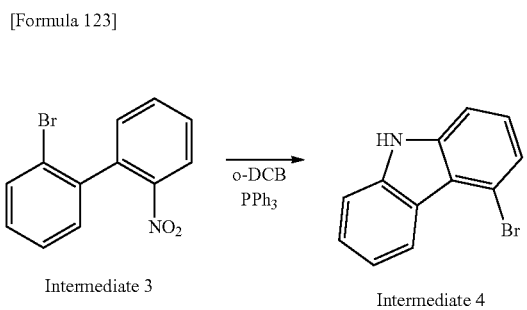 [SMILES: O=[N+]([O-])c1ccccc1-c1ccccc1Br ; Brc1cccc2[nH]c3ccccc3c12]

Intermediate 3          Intermediate 4

Under an argon gas atmosphere, the intermediate 3 (64.8 g, 233 mmol), triphenylphosphine (152 g, 583 mmol), and o-dichlorobenzene (500 mL) were sequentially added and stirred at 186 degrees C. for 13 hours. o-dichlorobenzene is occasionally referred to as o-DCB. After cooled down to the room temperature, the reaction solution was refined by silica-gel column chromatography twice and recrystallization, so that the intermediate 4 (21.2 g, a yield of 37%) was obtained.

Next, an intermediate 5 was synthesized according to a scheme below.

[Formula 124]

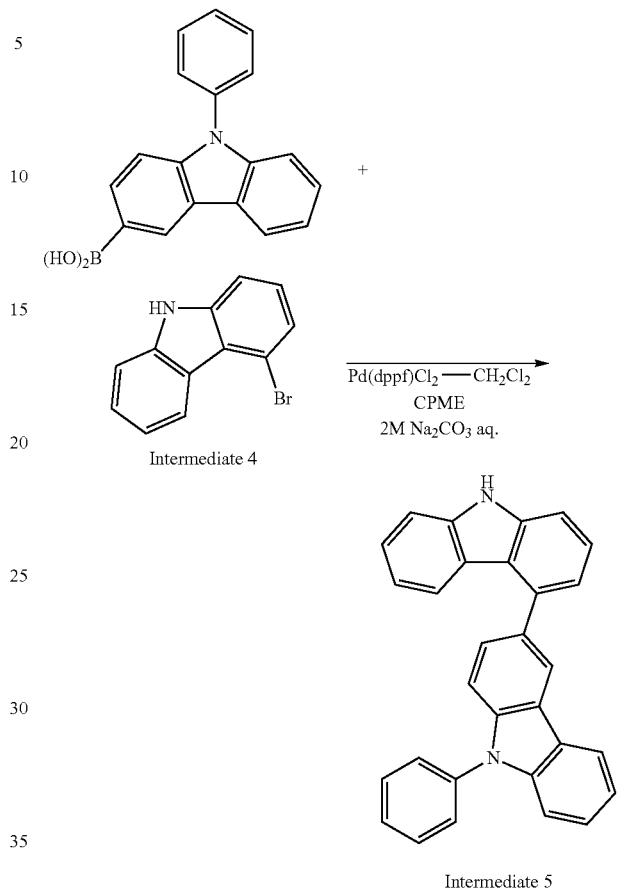

Intermediate 5

Under an argon gas atmosphere, 9-phenylcarbazole-3-boronic acid (24.7 g, 86.0 mmol), the intermediate 4 (21.2 g, 86.0 mmol), palladium-methylene chloride complex (Pd(dppf)Cl$_2$—CH$_2$Cl$_2$) (0.988 g, 1.21 mmol), cyclopentylmethylether (458 mL), and 2 M sodium carbonate aqueous solution (130 mL) were sequentially added and stirred at 80 degrees C. for five hours. Cyclopentylmethylether is occasionally referred to as CPME. After the reaction solution was cooled down to the room temperature, a CPME layer was separated, dried with magnesium sulfate, and dried under reduced pressure. The obtained residue was refined twice by silica-gel column chromatography and further refined by recrystallization, so that the intermediate 5 (27.1 g, a yield of 77%) was obtained.

Next, an intermediate 6 was synthesized according to a scheme below.

[Formula 125]

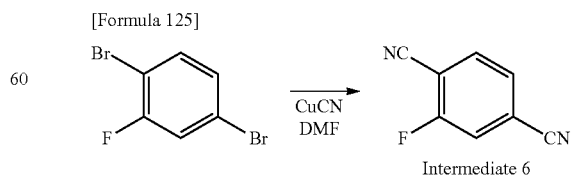

Intermediate 6

Under an argon gas atmosphere, 1,4-dibromo-2-fluorobenzene (30.0 g, 118 mmol), copper cyanide (42.1 g, 470 mmol), and N,N-dimethylformamide (200 mL) were sequentially added and heated to reflux for 16 hours. After the reaction solution was cooled down to the room temperature, the reaction solution was dried under reduced pressure. The obtained residue was separated by dichloromethane, dried with magnesium sulfate, and dried under reduced pressure, so that the intermediate 6 (9.12 g, a yield of 53%) was obtained.

Next, the compound 5 was synthesized according to a scheme below.

[Formula 126]

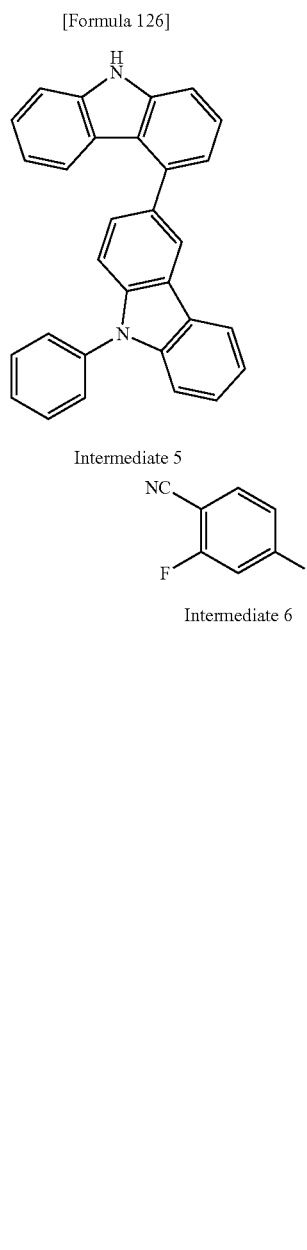

Intermediate 5

Intermediate 6

Compound 5

The compound 5 was synthesized by the same method as the compound 1 in Synthesis Example 1 except that the intermediate 5 was used in place of the intermediate 1 and the intermediate 6 was used in place of 4-fluorophthalonitrile.

Synthesis Example 6

In synthesizing a compound 6, initially, an intermediate 7 was synthesized according to a scheme below.

[Formula 127]

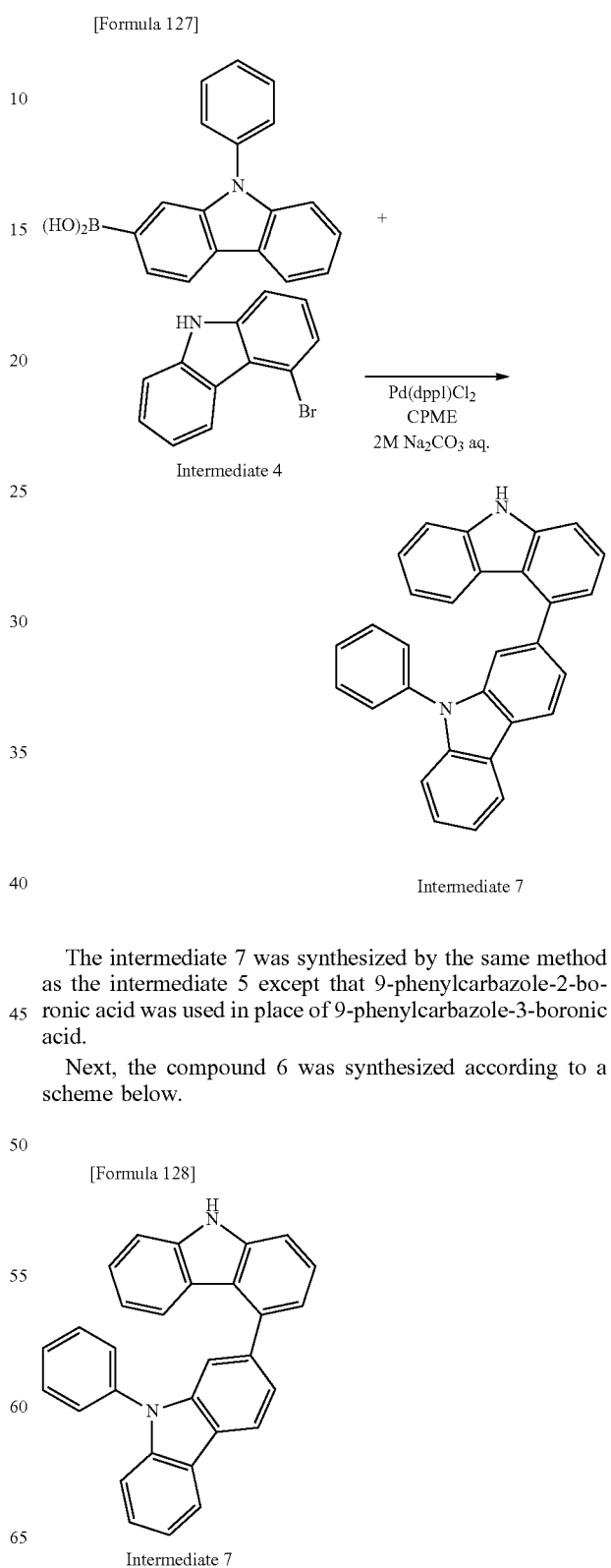

Intermediate 4

Intermediate 7

The intermediate 7 was synthesized by the same method as the intermediate 5 except that 9-phenylcarbazole-2-boronic acid was used in place of 9-phenylcarbazole-3-boronic acid.

Next, the compound 6 was synthesized according to a scheme below.

[Formula 128]

Intermediate 7

-continued

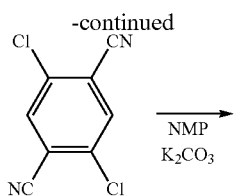

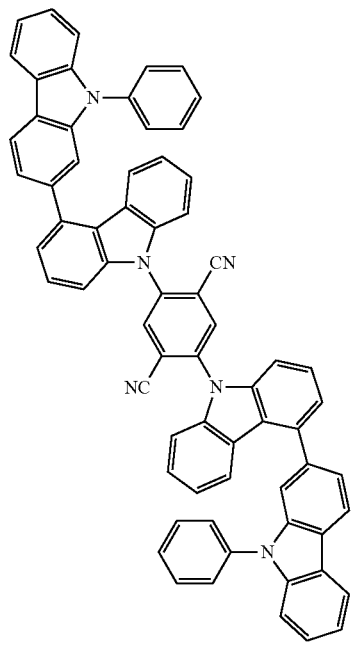

Compound 6

Under an argon gas atmosphere, the intermediate 7 (2.57 g, 6.3 mmol), 2,5-dichloroterephthalonitrile (0.591 g, 3.0 mmol), potassium carbonate (0.912 g, 6.6 mmol), and 1-methyl-2-pyrrolidone (12 mL) were sequentially added and stirred at 110 degrees C. for eight hours and at 150 degrees C. for eight hours. 1-methyl-2-pyrrolidone is occasionally referred to as NMP. After the reaction solution was cooled down to the room temperature, the reaction solution was washed with methanol and water. The deposited solid was collected by filtration and dried under reduced pressure. The obtained residue was refined by silica-gel column chromatography, so that the compound 6 (1.00 g, a yield of 35%) was obtained.

Properties Measurement of Compounds

An orientation parameter S of each of the compound 1, the compound 2, the compound TD-1, and the comparative compound was measured. The measurement results are shown in Table 7.

A measurement method of the orientation parameter S in a thin film is known and specifically described in Organic-Electronics (in 2009, page 127, vol. 10). Provided that an angle formed between a molecular axis and a substrate normal direction in a thin film formed on a substrate is defined as θ and extinction coefficients of a substrate parallel direction and a substrate vertical direction obtained by measuring the thin film by a multi-incident angle spectroscopic ellipsometry are respectively defined $k_o$ and $k_e$, the orientation parameter S is represented by a formula (A) below.

$$S = (1/2)\langle 3\cos^2\theta - 1\rangle \quad \text{(A)}$$
$$= (k_e - k_o)/(k_e + 2k_o)$$

As a method for forming the thin film, known methods such as vacuum deposition, spin coating and casting are applicable.

The compound 1 and the compound 2 in Examples are materials easily molecularly orientable in the thin film. When the easily orientable compound 1 is used at a high concentration in the emitting layer as in Examples, the orientation parameter of the thin film of the emitting layer is presumed to be in a range from −0.5 to −0.2. Further, since the compound 1 and the compound 2 are delayed fluorescent materials, an improvement in the luminous efficiency can be expected by forming a thin film of these materials.

In general, emission from the organic compound is mainly produced in a direction vertical to transition dipole moment of molecules. The transition dipole moment means an amount representing probability of electron transition. A direction of the transition dipole moment means a direction along which electrons are transferred in association with the electron transition. Accordingly, when the orientation of the organic compound is horizontal relative to the substrate, the emission from the organic compound is in a direction vertical to the substrate to be not trapped in a device, so that an external luminous efficiency of the organic EL device is improved. On the other hand, when the molecules are oriented at random or vertically relative to the substrate, the emission from the organic compound is likely to be trapped in the organic EL device, so that the external luminous efficiency cannot be improved. In other words, it was confirmed that the compound 1 and the compound 2 are delayed fluorescent materials capable of improving an internal quantum efficiency up to 100% in theory and also materials capable of simultaneously improving an external quantum efficiency because the compound 1 and the compound 2 are easily oriented in the thin film.

TABLE 7

|  | Orientation Parameter S |
| --- | --- |
| Compound 1 | −0.28 |
| Compound 2 | −0.30 |
| Compound TD-1 | −0.07 |
| Comparative Compound | 0.01 |

Preparation and Evaluation of Organic EL Device

The organic EL device was prepared and evaluated as follows.

Example 9

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound HI was deposited on a surface of the glass substrate where the transparent electrode line was provided in a manner to cover the transparent electrode, thereby forming a 5-nm-thick hole injecting layer.

Subsequently, the compound HT-1 was deposited on the hole injecting layer to form a 20-nm-thick first hole transporting layer on the HI film.

Next, the compound HT-2 was deposited on the first hole transporting layer to form a 5-nm-thick second hole transporting layer.

Next, a compound CBP was deposited on the second hole transporting layer to form a 5-nm-thick third hole transporting layer.

Further, on the third hole transporting layer, the compound TH-8 (the first material) and the compound 1 (the second material) were co-deposited on the third hole transporting layer to form a 25-nm-thick emitting layer. A ratio of the first material in the emitting layer was set at 76 mass % and a ratio of the second material in the emitting layer was set at 24 mass %.

Next, a compound EB-2 was deposited on the emitting layer to form a 5-nm-thick hole blocking layer.

A compound ET-1 was then deposited on the hole blocking layer to form a 50-nm-thick electron transporting layer.

Lithium fluoride (LiF) was then deposited on the electron transporting layer to form a 1-nm-thick electron injecting electrode (cathode).

A metal aluminum (Al) was then deposited on the electron injecting electrode to form an 80-nm-thick metal Al cathode. A device arrangement of the organic EL device in Example 9 is shown in symbols as follows.

ITO(130)/HI(5)/HT-1(20)/HT-2(5)/CBP(5)/TH-8: Compound 1 (25, 50%)/EB-2(5)/ET-1(50)/LiF(1)/Al(80)

Numerals in parentheses represent a film thickness (unit: nm). Numerals represented by percentage in the same parentheses represent a ratio (mass %) of an added component such as the dopant material in the emitting layer.

In the organic EL device manufactured in Example 9, voltage was applied at 4.87 V between ITO electrode and Al metal cathode such that a current density was 10 mA/cm². When the voltage was applied on the organic EL device such that the current density was 10 mA/cm², luminance was measured by a spectroradiometer (CS-1000 manufactured by Konica Minolta, Inc.) and the result was 2398.0 nit. A main peak wavelength $\lambda_p$ was calculated based on the spectral-radiance spectra measured by the spectroradiometer CS-1000 and the result was 547 nm. A peak wavelength at which a luminous intensity was maximum in a spectrum was defined as main peak wavelength $\lambda_p$.

Further, a delayed fluorescence lifetime was measured and calculated using a lifetime fluorescence spectrofluorometer (TemPro: manufactured by HORIBA, Ltd.). A semiconductor pulse LED light source NanoLED-340 or a semiconductor pulse LED light source SpectralLED-355 was used as an excitation light source. The excitation light source was used depending on the delayed fluorescence lifetime. Spectroscopic wavelength in a detector PPD-850 of the lifetime fluorescence spectrofluorometer was defined as the main peak wavelength $\lambda_p$ of the organic EL device. The measurement was conducted at the room temperature. As a result, in the organic EL devices of Example 9, the delayed fluorescence lifetime was 25.8 μs.

Example 10

An organic EL device in Example 10 was manufactured in the same manner as in Example 9 except that the compound 1 was replaced by the compound 2 as the second material of the emitting layer in Example 9. A device arrangement of the organic EL device in Example 10 is shown in symbols as follows.

ITO(130)/HI(5)/HT-1(20)/HT-2(5)/CBP(5)/TH-8: Compound 2 (25, 50%)/EB-2(5)/ET-1(50)/LiF(1)/Al(80)

The organic EL device of Example 10 was evaluated in the same manner as in Example 9. As results, the voltage was 4.77 V, the luminance was 2892.1 nit, the main peak wavelength $\lambda_p$ was 547 nm, and the delayed fluorescence lifetime was 30.4 μs.

Example 11

An organic EL device in Example 11 was manufactured in the same manner as in Example 9 except that the compound 1 was replaced by the compound 3 as the second material of the emitting layer in Example 9. A device arrangement of the organic EL device in Example 11 is shown in symbols as follows.

ITO(130)/HI(5)/HT-1(20)/HT-2(5)/CBP(5)/TH-8: Compound 3 (25, 50%)/EB-2(5)/ET-1(50)/LiF(1)/Al(80)

The organic EL device of Example 11 was evaluated in the same manner as in Example 9. As results, the voltage was 4.44 V, the luminance was 1597.1 nit, the main peak wavelength $\lambda_p$ was 551 nm, and the delayed fluorescence lifetime was 8.29 μs.

Example 12

An organic EL device in Example 12 was manufactured in the same manner as in Example 9 except that the compound 1 was replaced by the compound 4 as the second material of the emitting layer in Example 9. A device arrangement of the organic EL device in Example 12 is shown in symbols as follows.

ITO(130)/HI(5)/HT-1(20)/HT-2(5)/CBP(5)/TH-8: Compound 4 (25, 50%)/EB-2(5)/ET-1(50)/LiF(1)/Al(80)

The organic EL device of Example 12 was evaluated in the same manner as in Example 9. As results, the voltage was 4.36 V, the luminance was 821.2 nit, the main peak wavelength $\lambda_p$ was 539 nm, and the delayed fluorescence lifetime was 11.9 μs.

Example 13

An organic EL device in Example 13 was manufactured in the same manner as in Example 9 except that the compound 1 was replaced by the compound 6 as the second material of the emitting layer in Example 9. A device arrangement of the organic EL device in Example 13 is shown in symbols as follows.

ITO(130)/HI(5)/HT-1(20)/HT-2(5)/CBP(5)/TH-8: Compound 6 (25, 50%)/EB-2(5)/ET-1(50)/LiF(1)/Al(80)

The organic EL device of Example 13 was evaluated in the same manner as in Example 9. As results, the voltage was 4.71 V, the luminance was 4314.5 nit, the main peak wavelength $\lambda_p$ was 529 nm, and the delayed fluorescence lifetime was 19.2 μs.

It was confirmed that the compounds 1 to 4 and 6 are delayed fluorescent materials based on the evaluation results regarding the delayed fluorescence lifetimes of the organic EL devices in Examples 9 to 13.

The invention claimed is:
1. An organic electroluminescence device, comprising:
an anode;
an emitting layer which contains no metal complex; and
a cathode, wherein
the emitting layer comprises a first material and a second material, wherein said first material and said second material are contained in the same layer, the first material has a partial structure represented by a formula (1) below, and the second material has a partial structure represented by a formula (2) below, a partial structure represented by a formula (3f), and optionally further, a partial structure represented by a formula (3e), below in one molecule,

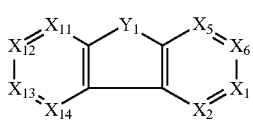
(1)

where: $X_1$, $X_2$, $X_5$, $X_6$ and $X_{11}$ to $X_{14}$ are each independently a carbon atom bonded to $R^A$, or a carbon atom bonded to $H_B$, with a proviso that 1 set to 4 sets among a set of $X_1$ and $X_2$, a set of $X_5$ and $X_6$, a set of $X_1$ and $X_6$, a set of $Xu$ and $X_{12}$, a set of $X_{13}$ and $X_{14}$, and a set of $X_{12}$ and $X_{13}$ are carbon atoms to be bonded to a structure represented by a formula (1a) below, $Y_1$ is a sulfur atom or an oxygen atom,

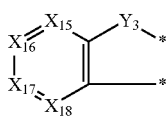
(1a)

where: $X_{15}$ to $X_{18}$ are each independently a carbon atom bonded to $R^A$ or a carbon atom bonded to $H_B$; $Y_3$ is a sulfur atom, an oxygen atom, or a nitrogen atom; * shows a bonding position to the carbon atom in the set selected from the set of $X_1$ and $X_2$, the set of $X_5$ and $X_6$, the set of $X_1$ and $X_6$, the set of $X_{11}$ and $X_{12}$, the set of $X_{13}$ and $X_{14}$, and the set of $X_{12}$ and $X_{13}$ in the formula (1); $Y_1$ and $Y_3$ are optionally mutually the same or different; and a plurality of $Y_3$ are optionally mutually the same or different, $R^A$ is a hydrogen atom, substituted or unsubstituted aryl group having 6 to 30 ring carbon atoms, or substituted or unsubstituted heterocyclic group having 5 to 30 ring atoms, wherein $R^A$ is not an anthryl group, a benz[a]anthryl group, a perylenyl group, an aryloxy group or a pyrenyl group, $H_B$ is a substituted or unsubstituted aryl group having 6 to 30 ring carbon atoms, a substituted or unsubstituted heterocyclic group having 5 to 30 ring atoms, a group derived from the structure of formula (1), or a group formed by bonding any 2 to 4 groups selected from these groups, wherein $H_B$ is not an anthryl group, benz[a]anthryl group, perylenyl group, or pyrenyl group, a substituent for a substituted group in the first material is selected from the group consisting of an aryl group, heterocyclic group, and alkyl group, wherein the aryl group as the substituent in the first material is not an anthryl group, benz[a]anthryl group, perylenyl group, or pyrenyl group,

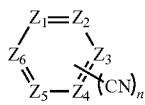
(2)

where: CN is a cyano group; n is 2; $Z_1$ is a carbon atom bonded to CN; one of $Z_3$ and $Z_5$ is a carbon atom bonded to CN, with the other of $Z_3$ and $Z$ being a carbon atom bonded to another atom in the molecule of the second material; $Z_2$, $Z_4$, and $Z_6$ are each independently a carbon atom bonded to another atom in the molecule of the second material; and a six-membered ring represented by the formula (2) of the second material is a six membered ring including $Z_1$ to $Z_6$ or a fused ring including the six-membered ring that is further fused with a ring,

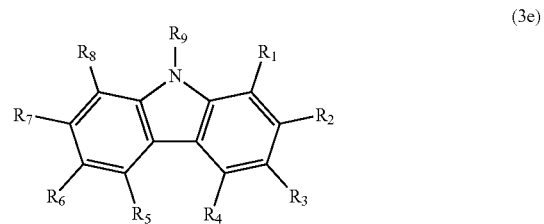
(3e)

where, in the formula (3e):

$R_1$ to $R_8$ are each independently a hydrogen atom, substituted or unsubstituted aryl group having 6 to 30 ring carbon atoms, substituted or unsubstituted heterocyclic group having 5 to 30 ring atoms, substituted or unsubstituted alkyl group having 1 to 30 carbon atoms, or a single bond to be bonded to another atom in the molecule of the second material, $R_9$ is a single bond to be bonded to another atom in the molecule of the second material,

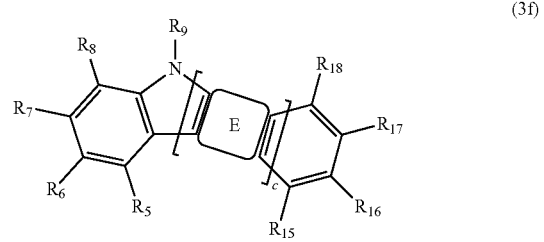
(3f)

where, in the formula (3f):

$R_{11}$ to $R_{18}$ are each independently the same as $R_1$ to $R_8$ in the formula (3e), $R_{19}$ is a single bond to be bonded to another atom in the molecule of the second material, at least one of combinations of substituents selected from Rn to Rig is optionally bonded to each other to form a cyclic structure, E represents a cyclic structure represented by a formula (3g) below or a cyclic structure represented by a formula (3h) below, the cyclic structure E being fused to an adjacent cyclic structure at any position, c indicates the number of the cyclic structure E and is an integer in a range of 2 to 4, a plurality of cyclic structures E are mutually the same or different, the plurality of cyclic structures E contain at least one cyclic structure of the formula (3g) and at least one cyclic structure of the formula (3h),

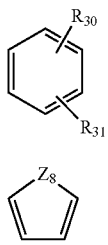

(3g)

(3h)

where, in the formula (3g), $R_{30}$ and $R_{31}$ each independently represent the same as $R_1$ to $R_8$, $R_{30}$ and $R_{31}$ are optionally bonded to each other to form a cyclic structure, $R_{30}$ and $R_{31}$ are respectively bonded to carbon atoms forming the six-membered ring of the formula (3g), where, in the formula (3h), $Z_8$ is a sulfur atom, a substituent for a substituted group in the second material is selected from the group consisting of an aryl group, heterocyclic group, and alkyl group.

2. The organic electroluminescence device according to claim 1, wherein the second material is represented by a formula (20) below,

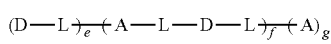

(20)

where: A is represented by the formula (2), in which: CN is a cyano group; n is 2;

$Z_1$ is a carbon atom bonded to CN;

one of $Z_3$ and $Z_5$ is a carbon atom bonded to CN, with the other of $Z_3$ and $Z_5$ being carbon atom bonded to R, a carbon atom bonded to L, or a carbon atom bonded to D;

$Z_2$, $Z_4$, and $Z_6$ are each independently a carbon atom bonded to R, a carbon atom bonded to L, or a carbon atom bonded to D;

at least one of $Z_2$, $Z_3$, $Z_4$, $Z_5$, and $Z_6$ is the carbon atom bonded to L or D;

R is each independently a hydrogen atom, substituted or unsubstituted aryl group having 6 to 30 ring carbon atoms, or substituted or unsubstituted heterocyclic group having 5 to 30 ring atoms;

D is the partial structure represented by the formula (3f) and optionally further, the partial structure represented by the formula (3e);

(i) when L intervenes between A and D: L is a single bond, substituted or unsubstituted aromatic hydrocarbon group having 6 to 14 ring carbon atoms, substituted or unsubstituted heterocyclic group having 5 to 14 ring atoms, $CR_{81}R_{82}$, $NR_{83}$, O, S, $SiR_{84}R_{85}$, $CR_{86}R_{87}$—$CR_{88}R_{89}$, $CR_{90}=CR_{91}$, substituted or unsubstituted aliphatic hydrocarbon cyclic group, or substituted or unsubstituted aliphatic heterocyclic group, in which $R_{81}$ to $R_{91}$ each independently represent the same as the groups for R; and (ii) when L is positioned at a terminal end in the molecule of the second material, L represents the same as R;

f is an integer of 1 or more;

e and g are each independently an integer of 0 or more;

a plurality of A are optionally mutually the same or different;

a plurality of D are optionally mutually the same or different; and a plurality of L are optionally mutually the same or different.

3. The organic electroluminescence device according to claim 1, wherein the first material is represented by a formula (10a) or (10b) below,

(10a)

(10b)

in the formula (10a), ka is an integer of 1 to 4;

in the formula (10b), kb is an integer of 1 to 4;

in the formulae (10a) and (10b), $H_A$ represents a structure represented by the formula (1), wherein $X_1$, $X_2$, $X_5$, $X_6$ and $X_{11}$ to $X_{14}$ are each independently a carbon atom to be bonded to $R^A$ or a carbon atom to be bonded to $H_B$, with a proviso that 1 set to 4 sets among the set of $X_1$ and $X_2$, the set of $X_5$ and $X_6$, the set of $X_1$ and $X_6$, the set of $X_{11}$ and $X_{12}$, the set of $X_{13}$ and $X_{14}$, and the set of $X_{12}$ and $X_{13}$ are carbon atoms to be bonded to the structure represented by the formula (1a);

in the formula (1a); $X_{15}$ to $X_{18}$ are each independently a carbon atom to be bonded to $R^A$ or a carbon atom to be bonded to $H_B$;

$Y_1$ is a sulfur atom or an oxygen atom;

$Y_3$ is a sulfur atom, an oxygen atom, or $NR^B$;

* shows a bonding position to the carbon atom in the set selected from the set of $X_1$ and $X_2$, the set of $X_5$ and $X_6$, the set of $X_1$ and $X_6$, the set of $X_{11}$ and $X_{12}$, the set of $X_{13}$ and $X_{14}$, and the set of $X_{12}$ and $X_{13}$ in the formula (1);

$Y_1$ and $Y_3$ are optionally mutually the same or different and a plurality of $Y_3$ are optionally mutually the same or different;

$R^A$ and $R^B$ are each independently a hydrogen atom, substituted or unsubstituted aryl group having 6 to 30 ring carbon atoms, or substituted or unsubstituted heterocyclic group having 5 to 30 ring atoms, wherein $R^A$ is not an anthryl group, benz[a]anthryl group, perylenyl group, aryloxy group or pyrenyl group;

a plurality of $R^A$ are optionally mutually the same or different and a plurality of $R^B$ are optionally mutually the same or different; and in the formula (10a) and (10b), $H_B$ is a substituted or unsubstituted aryl group having 6 to 30 ring carbon atoms, a substituted or unsubstituted heterocyclic group having 5 to 30 ring atoms, a group derived from the structure $H_A$, or a group formed by bonding any 2 to 4 groups selected from these groups, wherein $H_B$ is not an anthryl group, benz[a]anthryl group, perylenyl group, or pyrenyl group.

4. An organic electroluminescence device, comprising:

an anode;

an emitting layer which contains no metal complex; and a cathode, wherein the emitting layer comprises a first material and a second material, wherein said first material and said second material are contained in the same layer, the first material is represented by a formula (11a) or (11b) below, and the second material has a partial structure represented by a formula (2) below, a partial structure represented by a formula (3f), and optionally further, a partial structure represented by a formula (3e), below in one molecule,

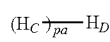 (11a)

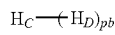 (11b)

in the formula (11a), pa is an integer of 1 to 4; in the formula (11b), pb is an integer of 1 to 4; and in the formulae (11a) and (11b), $H_C$ represents a structure represented by formula (111) or (112),

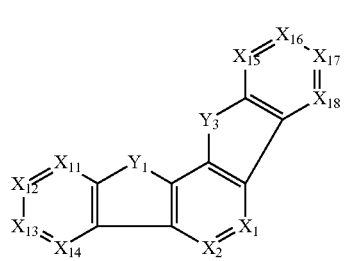 (111)

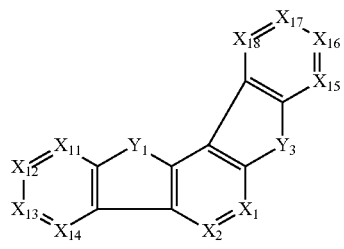 (112)

in the formulae (111) and (112), $X_1$, $X_2$, $X_{11}$ to $X_{14}$, and $X_{15}$ to $X_{18}$ are each independently a carbon atom to be bonded to $R^A$ or a carbon atom to be bonded to $H_D$; $Y_1$ is a sulfur atom or an oxygen atom; $Y_3$ is a sulfur atom, an oxygen atom, or $NR^B$; $Y_1$ and $Y_3$ are optionally mutually the same or different; $R^A$ and $R^B$ are each independently a hydrogen atom, substituted or unsubstituted aryl group having 6 to 30 ring carbon atoms, or substituted or unsubstituted heterocyclic group having 5 to 30 ring atoms, wherein $R^A$ and $R^B$ are not an anthryl group, benz[a]anthryl group, perylenyl group, aryloxy group or pyrenyl group;
  a plurality of $R^A$ are optionally mutually the same or different and a plurality of $R^B$ are optionally mutually the same or different; and
  in the formula (11a) and (11b), $H_B$ is a substituted or unsubstituted aryl group having 6 to 30 ring carbon atoms, a substituted or unsubstituted heterocyclic group having 5 to 30 ring atoms, a group derived from the structure $H_C$, or a group formed by bonding any 2 to 4 groups selected from these groups, wherein $H_B$ is not an anthryl group, benz[a]anthryl group, perylenyl group, or pyrenyl group,
a substituent for a substituted group in the first material is selected from the group consisting of an aryl group, heterocyclic group, and alkyl group, wherein the aryl group as the substituent in the first material is not an anthryl group, benz[a]anthryl group, perylenyl group, or pyrenyl group

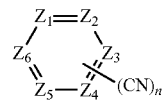 (2)

where: CN is a cyano group; n is 2; $Z_1$ is a carbon atom bonded to CN; one of $Z_3$ and $Z_5$ is a carbon atom bonded to CN, with the other of $Z_3$ and $Z_5$ being a carbon atom bonded to another atom in the molecule of the second material; $Z_2$, $Z_4$, and $Z_6$ are each independently a carbon atom bonded to another atom in the molecule of the second material; and a six-membered ring represented by the formula (2) of the second material is a six membered ring including $Z_1$ to $Z_6$ or a fused ring including the six-membered ring that is further fused with a ring,

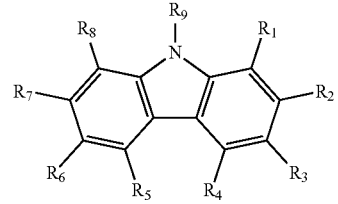 (3e)

where, in the formula (3e):
  $R_1$ to $R_8$ are each independently a hydrogen atom, substituted or unsubstituted aryl group having 6 to 30 ring carbon atoms, substituted or unsubstituted heterocyclic group having 5 to 30 ring atoms, substituted or unsubstituted alkyl group having 1 to 30 carbon atoms, or a single bond to be bonded to another atom in the molecule of the second material,
  $R_9$ is a single bond to be bonded to another atom in the molecule of the second material,

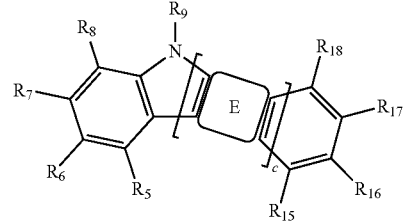 (3f)

where, in the formula (3f):
  $R_{11}$ to $R_{18}$ are each independently the same as $R_1$ to $R_8$ in the formula (3e),
  $R_{19}$ is a single bond to be bonded to another atom in the molecule of the second material,
  at least one of combinations of substituents selected from $R_{11}$ to $R_{18}$ is optionally bonded to each other to form a cyclic structure,
  E represents a cyclic structure represented by a formula (3g) below or a cyclic structure represented by a formula (3h) below, the cyclic structure E being fused to an adjacent cyclic structure at any position,
  c indicates the number of the cyclic structure E and is an integer in a range of 2 to 4, a plurality of cyclic structures E are mutually the same or different, the plurality of cyclic structures E contain at least one cyclic structure of the formula (3g) and at least one cyclic structure of the formula (3h),

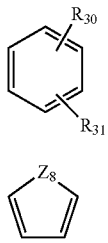

(3g)

(3h)

where, in the formula (3g), $R_{30}$ and $R_{31}$ each independently represent the same as $R_1$ to $R_8$, $R_{30}$ and $R_{31}$ are optionally bonded to each other to form a cyclic structure, $R_{30}$ and $R_{31}$ are respectively bonded to carbon atoms forming the six-membered ring of the formula (3g), where, in the formula (3h), $Z_8$ is a sulfur atom, a substituent for a substituted group in the second material is selected from the group consisting of an aryl group, heterocyclic group, and alkyl group.

5. The organic electroluminescence device according to claim 4, wherein $Y_1$ and $Y_3$ are each independently a sulfur atom or an oxygen atom.

6. The organic electroluminescence device according to claim 4, wherein $X_1, X_2, X_{11}$ to $X_{14}$, and $X_{15}$ to $X_{18}$ are each independently a carbon atom to be bonded to $R^A$ or a carbon atom to be bonded to $H_D$.

7. The organic electroluminescence device according to claim 1, wherein at least one of $X_1, X_2, X_5, X_6, X_{11}$ to $X_{14}$ and $X_{15}$ to $X_{18}$ is a carbon atom to be bonded to $R^A$ represented by a formula (1b) below,

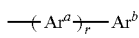

(1b)

where: r is an integer of 0 to 5;

$Ar^\alpha$ is a substituted or unsubstituted arylene group having 6 to 15 ring carbon atoms or a substituted or unsubstituted heteroarylene group having 5 to 15 ring atoms;

a plurality of $Ar^\alpha$ are optionally mutually the same or different; $Ar^\alpha$ is not an anthryl group, benz[a]anthryl group, perylenyl group or pyrenyl group; and $Ar^b$ is a substituted or unsubstituted aryl group having 6 to 20 ring carbon atoms or a substituted or unsubstituted heterocyclic group having 5 to 20 ring atoms, wherein $Ar^b$ is not an anthryl group, benz[a]anthryl group, perylenyl group, or pyrenyl group.

8. The organic electroluminescence device according to claim 4, wherein at least one of $X_1, X_2, X_{11}$ to $X_{14}$, and $X_{15}$ to $X_{18}$ is a carbon atom to be bonded to $R^A$ represented by a formula (1b) below,

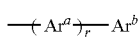

(1b)

where: r is an integer of 0 to 5;

$Ar^\alpha$ is a substituted or unsubstituted arylene group having 6 to 15 ring carbon atoms or a substituted or unsubstituted heteroarylene group having 5 to 15 ring atoms;

a plurality of $Ar^\alpha$ are optionally mutually the same or different; $Ar^\alpha$ is not an anthryl group, benz[a]anthryl group, perylenyl group or pyrenyl group; and $Ar^b$ is a substituted or unsubstituted aryl group having 6 to 20 ring carbon atoms or a substituted or unsubstituted heterocyclic group having 5 to 20 ring atoms, wherein $Ar^b$ is not an anthryl group, benz[a]anthryl group, perylenyl group, or pyrenyl group.

9. The organic electroluminescence device according to claim 7, wherein $Ar^\alpha$ in the formula (1b) is a phenylene group.

10. The organic electroluminescence device according to claim 3, wherein the structure $H_B$ is represented by a formula (1c) below,

(1c)

where: s is an integer of 0 to 5;

$Ar^c$ is a substituted or unsubstituted aryl group having 6 to 20 ring carbon atoms or a substituted or unsubstituted heterocyclic group having 5 to 20 ring atoms, wherein Are is not an anthryl group, benz[a]anthryl group, perylenyl group, or pyrenyl group;

$Ar^d$ is a substituted or unsubstituted arylene group having 6 to 15 ring carbon atoms or a substituted or unsubstituted heteroarylene group having 5 to 15 ring atoms;

a plurality of $Ar^d$ are optionally mutually the same or different; and $Ar^d$ is not an anthryl group, benz[a]anthryl group, perylenyl group or pyrenyl group.

11. The organic electroluminescence device according to claim 3, wherein the structure $H_A$ is represented by one of formulae (122) to (127) below,

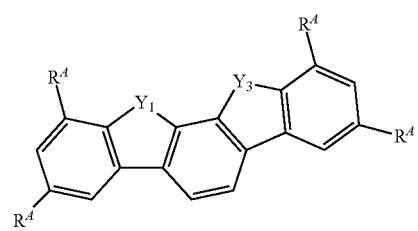

(122)

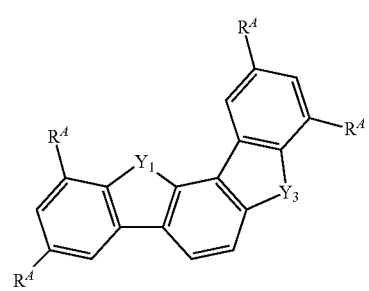

(123)

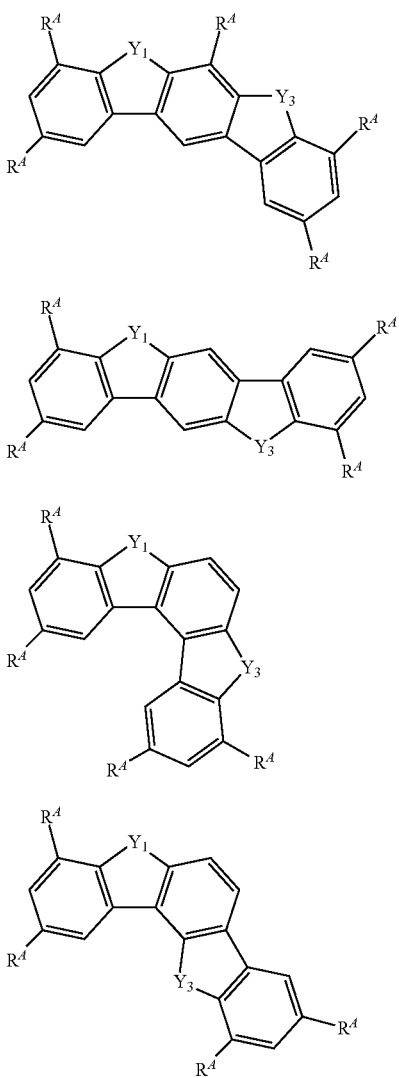

in the formulae (122) to (127):
Y₁ is a sulfur atom or an oxygen atom;
Y₃ is a sulfur atom, an oxygen atom, or NR^B;
at least one of a plurality of R^A is a single bond to the structure H_B; at least one of the plurality of R^A is represented by a formula (1b) below; the rest of the plurality of R^A is each independently a hydrogen atom, substituted or unsubstituted aryl group having 6 to 30 ring carbon atoms, substituted or unsubstituted heterocyclic group having 5 to 30 ring atoms, or a single bond to the structure H_A, wherein R^A is not an anthryl group, benz[a]anthryl group, perylenyl group, aryloxy group or pyrenyl group; and R^B is a hydrogen atom, substituted or unsubstituted aryl group having 6 to 30 ring carbon atoms, or substituted or unsubstituted heterocyclic group having 5 to 30 ring atoms; wherein R^B is not an anthryl group, benz[a]anthryl group, perylenyl group, aryloxy group or pyrenyl group;

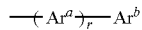

(Ib)

where: r is an integer of 0 to 5;
Ar^α is a substituted or unsubstituted arylene group having 6 to 15 ring carbon atoms or a substituted or unsubstituted heteroarylene group having 5 to 15 ring atoms;
a plurality of Ar^α are optionally mutually the same or different;
Ar^α is not an anthryl group, benz[a]anthryl group, perylenyl group or pyrenyl group; and
Ar^b is a substituted or unsubstituted aryl group having 6 to 20 ring carbon atoms or a substituted or unsubstituted heterocyclic group having 5 to 20 ring atoms, wherein Ar^b is not an anthryl group, benz[a]anthryl group, perylenyl group or pyrenyl group.

12. The organic electroluminescence device according to claim 1, wherein a difference ΔST (M2) between a singlet energy S (M2) of the second material and an energy gap $T_{77K}(M2)$ at 77 [K] of the second material satisfies a relationship of a numerical formula (Numerical Formula 2) below, $$\Delta ST(M2)=S(M2)-T_{77K}(M2)<0.3\ [eV] \qquad \text{(Numerical Formula 2)}.$$

13. The organic electroluminescence device according to claim 1, wherein the second material exhibits delayed fluorescence.

14. The organic electroluminescence device according to claim 1, wherein an ionization potential Ip (M1) of the first material and an ionization potential Ip (M2) of the second material satisfy a relationship of a numerical formula (Numerical Formula 3) below, $$Ip(M1)>Ip(M2) \qquad \text{(Numerical Formula 3)}.$$

15. The organic electroluminescence device according to claim 1, wherein the ionization potential Ip (M1) of the first material is 5.9 eV or more.

16. The organic electroluminescence device according to claim 1, wherein an energy gap $T_{77K}(M1)$ at 77 [K] of the first material and the energy gap $T_{77K}(M2)$ at 77 [K] of the second material satisfy a relationship of a numerical formula (Numerical Formula 1) below, $$T_{77K}(M1)>T_{77K}(M2) \qquad \text{(Numerical Formula 1)}.$$

17. The organic electroluminescence device according to claim 1, wherein the second material emits light.

18. The organic electroluminescence device according to claim 1, wherein the emitting layer comprises 20 mass % or more of the second material.

19. The organic electroluminescence device according to claim 1, wherein an orientation parameter of the emitting layer is in a range from −0.5 to −0.2.

20. The organic electroluminescence device according to claim 1, further comprising:
a hole transporting layer provided between the anode and the emitting layer.

21. The organic electroluminescence device according to claim 1, further comprising:
an electron transporting layer provided between the cathode and the emitting layer.

22. An electronic device comprising the organic electroluminescence device according to claim 1.

23. The organic electroluminescence device according to claim 1, wherein Y₃ of the first material is not a nitrogen atom.

24. The organic electroluminescence device according to claim 1, wherein Y₃ of the first material is a nitrogen atom.

25. The organic electroluminescence device according to claim 4, wherein Y₃ of the first material is NR^B.

26. The organic electroluminescence device according to claim 1, wherein $Y_1$ and $Y_3$ are each independently a sulfur atom or an oxygen atom.

27. The organic electroluminescence device according to claim 1, wherein at least one of combinations of substituents selected from $R_{11}$ to $R_{14}$ are bonded to each other to form a cyclic structure.

28. The organic electroluminescence device according to claim 4, wherein at least one of combinations of substituents selected from $R_{11}$ to $R_{14}$ are bonded to each other to form a cyclic structure.

29. The organic electroluminescence device according to claim 1, wherein the second material does not have the partial structure represented by the formula (3e) or has one partial structure represented by the formula (3e).

30. The organic electroluminescence device according to claim 4, wherein the second material does not have the partial structure represented by the formula (3e) or has one partial structure represented by the formula (3e).

* * * * *